(12) United States Patent
Call et al.

(10) Patent No.: US 10,022,423 B2
(45) Date of Patent: *Jul. 17, 2018

(54) MICROCIN AND USES THEREOF

(71) Applicant: WASHINGTON STATE UNIVERSITY, Pullman, WA (US)

(72) Inventors: Douglas R. Call, Pullman, WA (US); Lisa Orfe, Pullman, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/268,666

(22) Filed: Sep. 19, 2016

(65) Prior Publication Data

US 2017/0028017 A1    Feb. 2, 2017

Related U.S. Application Data

(63) Continuation-in-part of application No. 14/407,975, filed as application No. PCT/US2013/045937 on Jun. 14, 2013, now Pat. No. 9,492,500.

(60) Provisional application No. 61/660,616, filed on Jun. 15, 2012.

(51) Int. Cl.
| | |
|---|---|
| *C12N 1/12* | (2006.01) |
| *C12N 1/20* | (2006.01) |
| *A61K 38/16* | (2006.01) |
| *A61K 35/74* | (2015.01) |
| *A01N 63/00* | (2006.01) |
| *A01N 37/46* | (2006.01) |
| *A01N 63/02* | (2006.01) |

(52) U.S. Cl.
CPC ............ *A61K 38/164* (2013.01); *A01N 37/46* (2013.01); *A01N 63/00* (2013.01); *A01N 63/02* (2013.01); *A61K 35/74* (2013.01)

(58) Field of Classification Search
CPC .................................................... A61K 38/164
See application file for complete search history.

(56) References Cited

U.S. PATENT DOCUMENTS

| 5,512,282 A | 4/1996 | Krivan et al. |
| 9,492,500 B2 * | 11/2016 | Call ................. C07K 14/245 |
| 2008/0200374 A1 | 8/2008 | Severinov et al. |

OTHER PUBLICATIONS

Eberhart et al, "Characterization of a Novel Microcin that kills Enterohemorrhagic *Escherichia coli* O157:H7 and O26", Appl. Environ. Microbiol., Jul. 6, 2012, vol. 78, No. 18, pp. 6592-6599.
NCBI, GenBank Accession No. YP_006954414.1, "microcin protein [*Escherichia coli*]", Jun. 9, 2013.
Zschuttig et al, "Identification and characterization of microcin S, a new antibacterial peptide produced by probiotic *Escherichia coli* G3/10", PloS One, Mar. 30, 2012, vol. 7, No. 3, pp. 1-9.
Sawant et at., Proximity-dependent inhibition in *Escherichia coli* isolates from cattle:, Appl. Environ. Microbial., Feb. 4, 2011, vol. 77, No. 7, pp. 2345-2351.
Azpiroz et al., "Microcin H47 system: an *Escherichia coli* small genomic island with novel features", PloS One, Oct. 11, 2011, vol. 6, No. 10, pp. 1-7.
Ashkenazi et al (Therapeutic Advances in Vaccines, vol. 1 (3) pp. 113-123, 2013).
Plotkin et al. (Vaccines WB Saunders Company, p. 571, 1988).

* cited by examiner

*Primary Examiner* — Albert M Navarro
(74) *Attorney, Agent, or Firm* — W & C, IP

(57) ABSTRACT

Microcin MccPDI and bacteria harboring the mcpM gene which encodes MccPDI limit growth of and/or kill pathogenic bacteria such as pathogenic *Escherichia coli* (*E. coli*) and/or *Shigella* bacteria via proximity-dependent inhibition (PDI).

9 Claims, 17 Drawing Sheets

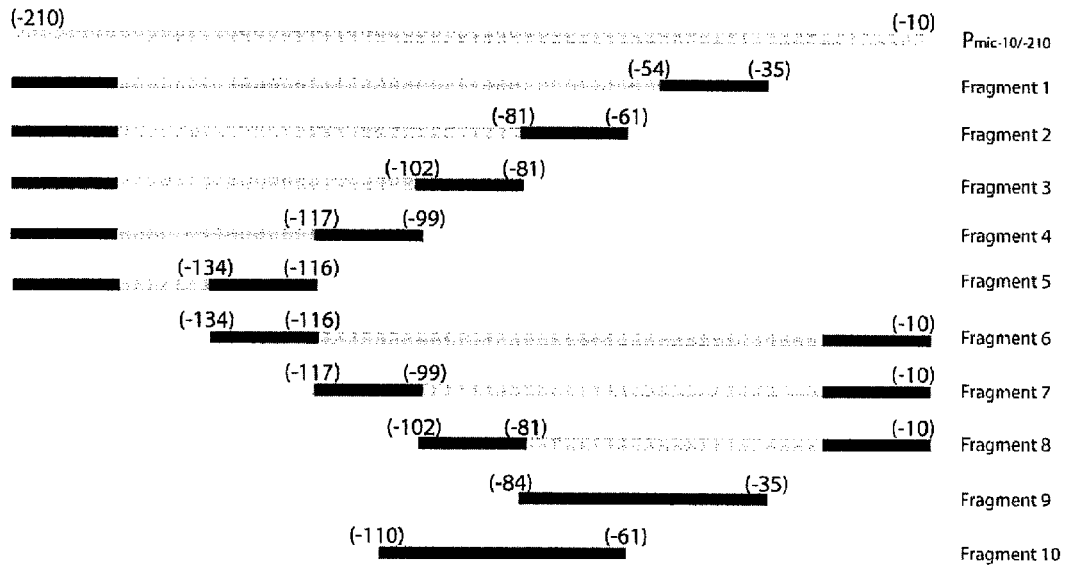

Figure 11A

```
       -115         B3        -97              B1          -77            B2         -58
GAAAACATACAAATTTTTTCACATATTTACATTTAATCACACAATTTCACTTTCATTACATTTTG
                                                                         SEQ ID NO:62
F1    TTTACTTTTGGTTACATATT   SEQ ID NO:63
F2    TTTTCTTTTTGAAACCAAAT   SEQ ID NO:64
F3    TTATCTTTGTAGCACTTTCA   SEQ ID NO:65
F4    GTTACGGAATATTACATTGC   SEQ ID NO:66
C1    TTTACATTTTGAAACATCTA   SEQ ID NO:67
B1    TTTACATTTAATCACACAAT   SEQ ID NO:68
B2    TTCAC-TTTCATTACATTTT   SEQ ID NO:69
B3    TACAAATTTTTTCACATA     SEQ ID NO:70
```

Figure 11B

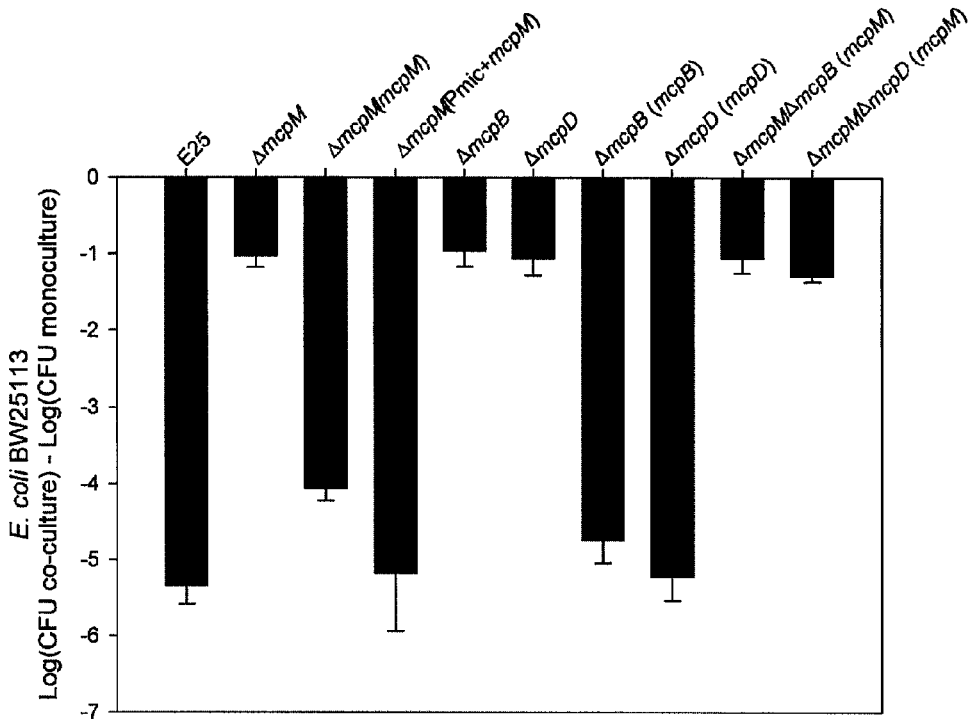

Figure 12

```
                      Cleavage site I      Cleavage site II
                            ↓                   ↓                            ▽
mccPDI    MANIRELTLDEITLVSGGNANSNFEGGPRNDRSSGARNSLGRNAPTHIYSDPSTVKCANAV      (61)
mcsS      MSNIRELSFDEIALVSGGNANSNYEGGGSRSRNTGARNSLGRNAPTHIYSDPSTVKCANAV      (61)
colV      ---MRTLTLNELDSVSGG--AS----------GRDIAMAIGTLSGQFVAG--GIGAAAGGV       (11)
mccL      ---MREITLNEMNNVSGAGDVN----------WVDVGKTVATNGAGVIGG--AFGAGLCGP       (46)
mcc24     -MYMRELDREELNCVGGAGDPL----------ADPNSQIVRQIMSNAAWG--PPL-VPERF       (47)
mccE492   ----MREISQKDLNLAFGAGE-----------TDPNTQLLNDLGNNMAWG--AALGAPGGL       (41)
mccH47    ---MREITESQLRYISGAGG------------APAT-SANAAGAAAIVG--ALAGIPGGP       (42)

▽          ▽      ▽
mccPDI    FSGMIGGAIKGGPIGMARGTIGGAVVGQCLSDHGSGNGSG-NRCSSSSCSGNNVGGTCNR      (120)
mcsS      FSGMVGGAIKGGPVGMTRGTIGGAVIGQCLSGGGNGNGGG-NRAGSSNCSGSNVGGTCSR      (120)
colV      AGGAIYDYASTHKPNPAMSPSGLGGTIKQKPEGIPSEAWNYAACRLCNWSPNNLSDVCL-      (103)
mccL      VCAGAFAVGSSAAVAALYDAAGNSNSAKQKPEGLPPEAWNYAECRMCNWSPNNLSDVCL-      (105)
mcc24     R-GMAVGAAGGVTQTVLQGAAAHMPVNVPIPKVPMGPSW---NCS-KG------------      (90)
mccE492   G-SAALGAAGGALQTVGQQGLIDHGPVNVPIP-VLIGPSW---NCSGSGYNSATSSSGSGS     (99)
mccH47    L-GVVVGAVSAGLTTAIGSTVGSGSASSSAG----------GCS---------------       (75)
```

Figure 13

MICROCIN AND USES THEREOF

CROSS-REFERENCE TO RELATED APPLICATIONS

This application is a Continuation-in-Part of Ser. No. 14/407,975 which is a National Stage Application based on the International Application No. PCT/US2013/045937 filed Jun. 14, 2013 which claims priority to U.S. Provisional Application 61/660,616 filed Jun. 15, 2012. The complete contents thereof are herein incorporated by reference.

ACKNOWLEDGEMENT OF FEDERAL FUNDING

Particular aspects of the present invention were, at least in part, supported by Grant Number 2010-04487 from the United States Department of Agriculture (USDA-AFRI-NIFA) and Grant Number 10-086 from the National Pork Board. The United States government and National Pork Board therefore may have certain rights in the invention.

FIELD OF THE INVENTION

Aspects of the invention relate generally to bacteria, bacteriocins (e.g., colicins or microcins) and proximity-dependent inhibition (PDI), and in more particular embodiments to compositions and methods for controlling and/or killing pathogenic bacteria (e.g., enterohemorrhagic and/or enterotoxigenic strains of E. coli), comprising use of a novel microcin.

BACKGROUND

Escherichia coli are commonly found in the gut of both humans and animals. Most E. coli are considered symbiotic; however, pathogenic strains have been isolated that are associated with foodborne illness in people and animals e.g., pathogenic E. coli K88 and K99 affect swine and calves, respectively. Transmission of pathogenic E. coli occurs through fecal contamination of food or water, and is commonly associated with the consumption of under-cooked meat, raw milk, or contaminated vegetables.

Pathogenic E. coli includes the Shiga-toxin producing strains known as STEC. Shiga-toxin is named for its resemblance to the Shiga-toxin produced by Shigella dysenteriae. STEC infection can be asymptomatic, or include symptoms of fever, watery diarrhea, severe abdominal pain, hemolytic uremic syndrome (HUS) and even death, with more severe cases typically being reported in young children or the elderly. Enterohaemorrhagic E. coli (EHEC) are a subset of STEC, characterized by their ability to form attaching and effacing intestinal lesions. Cattle are the main reservoir for EHEC, the bacteria living asymptotically in the cow intestine, although these bacteria have also been isolated from the intestinal tract of other domestic animals including sheep, pigs, goats, and dogs. These EHEC predominantly colonize the recto-anal junction of cattle, thereby increasing the risk of transmission to humans through fecal contamination. Numerous EHEC have been isolated including serotypes O111, O145, O103, O26, and O157. According to the Centers for Disease Control and Prevention, O157:H7 is the most common serotype that causing E. coli-linked food poisoning in the United States. The infectious dose is estimated to be as low as 10-100 bacteria. EHEC infections can be difficult to treat and some antibiotics actually worsen symptoms of an EHEC infection by inducing Shiga-toxin production and increasing the risk of HUS.

The introduction of antibiotics as therapeutics in the mid-1940s was an important advancement for medicine in terms of reducing human morbidity and mortality. The subsequent emergence of antibiotic resistant bacteria, however, indicates that bacteria adapt to antibiotic pressure. Resistance can be acquired and maintained within a population through horizontal transfer of resistant genes, and/or through selection for mutations that confer resistance. Unfortunately, the use of antibiotics is widespread and invariably selects for resistance as continual exposure to the drugs inhibit susceptible strains and allows resistant strains to emerge and dominate a population. Selection for resistance occurs for all bacteria exposed to antibiotics, not just the specific pathogens that are being targeted. For example, when enrofloxacin was used to treat E. coli infections in poultry, it simultaneously selected for resistance in Campylobacter jejuni, which is another important food-borne pathogen. The increasing prevalence of resistant bacterial pathogens threatens the effectiveness of currently available antibiotics and presents a difficult challenge in human and animal medicine. The development of novel strategies to control pathogenic bacteria is necessary to 1) combat infection by existing strains and 2) provide alternatives so that antibiotic use, and hence the emergence of resistant strains, can be decreased.

Some bacteria have developed the ability to inhibit other bacteria, and further characterization of how this occurs could be helpful in the design of new anti-bacterial strategies. For example, cell-cell inhibition mechanisms have been documented in the literature and range from contact-dependent inhibition (1, 20) to production of narrow-spectrum antimicrobial proteins called bacteriocins. Bacteriocins typically restrict the growth of closely related bacteria (reviewed in (28, 31)). E. coli produce numerous bacteriocins (31), classified as either colicins or microcins (2, 11). Colicins are high-molecular weight, whereas microcins are typically <10 kDa. Microcins can be either chromosomally or plasmid encoded, whereas colicins have only been found on plasmids (13, 29, 30). Colicin production is usually correlated with an SOS response to stress (22, 34) and release of the colicin typically occurs through cell lysis. Microcins are secreted from intact cells (8, 27). Bacteriocins have been identified that kill competitors through pore formation, nuclease activity, or by inhibiting protein synthesis (3, 23-25).

Sawant et al. recently described a novel bacterial inhibition phenotype whereby defined strains of E. coli from cattle are able to inhibit growth of other E. coli strains including several strains of enterohemorrhagic E. coli (EHEC) and enterotoxigenic E. coli (ETEC) (32). During in vitro competition assays, susceptible strains declined an average 4-6 log in population size relative to their expected population density when grown as monocultures. The inhibition phenotype was called "proximity-dependent inhibition" (PDI) because of the apparent need for inhibitor and susceptible strains to be located in close physical proximity for the phenotype to be observed. Two different E. coli strains were described as expressing this trait (PDI+); multidrug resistant E. coli-25 and antibiotic susceptible E. coli-264. E. coli-25 and E. coli-264 do not affect the growth of each other, indicating that immunity is either conferred actively through the presence of an immunity mechanism, or passively through the absence of a receptor ligand found on susceptible cells.

Certain characteristics of the PDI phenotype resemble that of microcin production. For example, inhibition is effective against closely related species; PDI is not dependent on an SOS response; and production presumably does not kill the inhibitor strain (32). Nevertheless, microcins are soluble proteins and when Sawant et al. (32) employed a split-well experiment they demonstrated that close cell-cell proximity is required for the PDI phenotype to function. These findings suggest that the inhibition mechanism is not due to a soluble molecule unless the concentration is so low as to require close proximity to be effective (32).

The initial report of PDI provided a detailed description of the phenotype and a similar phenotype has been described between *Bibersteinia trehalosi* and *Mannheimia haemolytica* (4). Nevertheless, the exact mechanism of PDI and requisite genes for inhibition and immunity were not known at the time that the PDI was originally described. Progress in this field could aid the development of strategies to combat the emergence and spread of pathogenic bacteria, and to provide treatments for infection with pathogenic bacteria.

SUMMARY OF EXEMPLARY ASPECTS

Particular embodiments of the invention demonstrate, for the first time, that "proximity-dependent inhibition" (hereinafter "PDI") results in death of the susceptible cells, and that PDI can be used for killing pathogenic *E. coli* in vitro on surfaces and materials of interest, and in vivo, and further the PDI can be used prophylactically and therapeutically.

Additional embodiments of the invention identify the PDI gene cluster, which resembles that of a class IIa microcin. The gene cluster includes ORFs putatively encoding proteins for microcin synthesis, immunity, and export. In addition, tolC is required for inhibition, thereby confirming that the microcin is secreted by a type I secretion system (T1SS).

According to further embodiments of the invention, the PDI phenotype is caused by a novel microcin, designated herein as MccPDI, and MccPDI is utilized in a number of different and beneficial applications. In some instances, the use of MccPDI and/or bacteria that produce MccPDI advantageously replaces the use of antibiotics.

Every strain from a genetically diverse panel of *E. coli* O157:H7 (n=25) and additional strains of *E. coli* serovar O26 were susceptible to the PDI phenotype. Live-dead staining was consistent with inhibition by killing of susceptible cells. Comparative genome analysis identified the genetic component of PDI, which is composed of a plasmid-borne (Incl1) operon encoding a putative microcin and associated genes for transport, immunity, and microcin activation. Transfer of the plasmid to a PDI⁻ strain resulted in transfer of the phenotype and deletion of the genes within the operon resulted in loss of the inhibition phenotype. Deletion of chromosomally encoded tolC also resulted in loss of the inhibitory phenotype and this confirmed that the putative microcin is most likely secreted via a type I secretion pathway. Deletion of an unrelated plasmid gene had no effect on the PDI phenotype. Quantitative RT-PCR demonstrated that microcin expression is correlated with logarithmic-phase growth.

According to yet further embodiments of the invention, the ability to inhibit a diversity of *E. coli* strains indicates that this microcin has utility to influence gut community composition (Eberhart, L J, J N Ochoa, T E Besser, and D R Call. 2014. Microcin mccPDI reduces the prevalence of susceptible *Escherichia coli* in neonatal calves. Journal of Applied Microbiology doi: 10.1111/jam.12535), and substantial utility for control of important enteric pathogens.

In some aspects, the bacteria that are killed (lysed, inhibited, damaged, etc.) are any that have (carry, bear, include, contain, etc.) the OmpF protein in or as a component of their outer membrane. OmpF or "outer membrane protein F", (or OmpF porin), is an integral membrane protein located in the outer membrane of *E. coli* bacteria. OmpF porin is found in a trimer formation and is a non-specific transport channel that allows passive diffusion of small, polar molecules (600-700 Da in size) through the cell's outer membrane, e.g. water, ions, glucose, and other nutrients as well as waste products. Without being bound by theory, the microcin described herein appears to bind to OmpF when exerting its lethal effects.

BRIEF DESCRIPTION OF THE DRAWINGS

FIGS. 11A and B. McpM promoter region has multiple binding sites for phosphorylated OmpR. (A) Diagram of the 10 DNA fragments that were selected from within the promoter region of mcpM. Fragments 1-8 were obtained by PCR amplification with bars indicating the primer position. Fragments 9-10 were obtained by annealing complementary oligonucleotides. (B) Three putative OmpR binding sites (B1, B2 and B3) are shown. F1, F2, F3 and F4 are the OmpR binding sites from the promoter region of *E. coli* ompF and C1 is the OmpR binding site identified with the promoter region of *E. coli* ompC.

FIG. 12. CFU counts for *E. coli* BW25113 following competition with microcinproducing *E. coli*-25 and associated gene knockout and complemented strains. Results are expressed as the difference in CFUs of the sensitive strain grown in co-culture and monoculture (error bars=SEM; 3 independent experiments).

FIG. 13. Amino acid sequence alignment of class II microcin precursors. MccPDEI (SEQ ID NO:24); McsS, microcin S (YP_006954535; SEQ ID NO:71): ColV, colicin V (CAA40746: SEQ ID NO:72); MccL microcin L (AAP03989; SEQ ID NO:73); Mcc24, microcin 24 (AAA88772; SEQ ID NO:74); MccE492, microcin E492 (AAD04332; SEQ ID NO:75); MccH47, MchB protein (CAB54534; SEQ ID NO:76). The arrows indicate the cleavage sites corresponding to McpM that we identified in this study. The inverted triangles indicate the position of the four cysteines of McpM. Sequence alignments were generated using ClustalX 1.83. Parenthetical numbers on the right indicate the amino acid position relative to the N terminus of each sequence.

DETAILED DESCRIPTION

Figure 1:
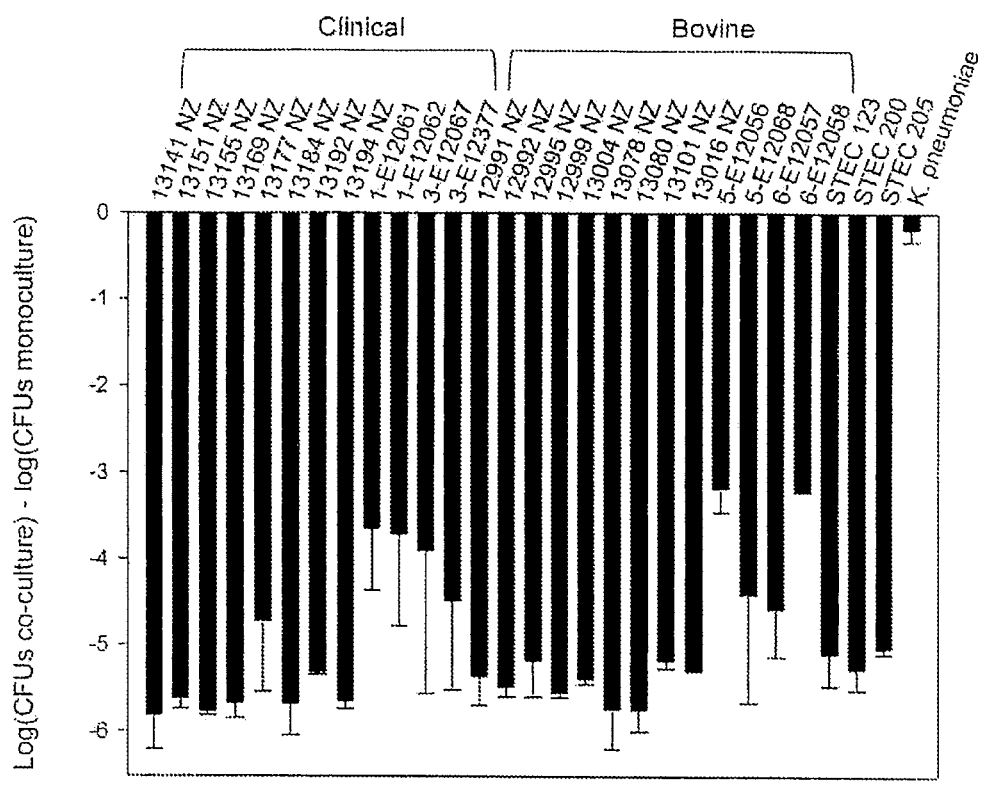
FIG. 1. PDI is effective against a broad panel of O157:H7 and STEC O26 *E. coli* isolates. On average, susceptible populations were reduced greater than 5-logs following 24 h co-culture with *E. coli*-25. Clinical and bovine-biased O157 genotypes are indicated (33). *Klebsiella pneumnonia* was not inhibited by PDI and is included as a negative control. Error bars correspond to the standard error of the mean based on duplicate experiments.

The genetic components that are responsible for the PDI phenotype observed from *E. coli*-25 and *E. coli*-264 are, for the first time, identified herein. This 4.8-kb cassette is present on pPDI (see Example 10 below) and is comprised of the genes mcpM, mcpI, mcpA, mcpD, and mcpB (see Example 9 below).

According to particular aspects, inhibition is mediated by the microcin encoded by mcpM, whose mature gene product is designated herein as MccPDI. The inventors demonstrate that a non-mccPDI strain called *E. coli*-82 is genetically very similar to *E. coli*-25 based on a technique called XbaI macrorestriction digest and pulsed-field gel electrophoresis. These two strains were sequenced using a 454 sequencing platform. The resulting sequences showed that the primary difference between the two strains was the presence of a large IncI1 plasmid. From this sequence, the inventors identified the mccPDI gene cassette, pPDI was subsequently marked with a kanamycin resistant cassette while simultaneously knocking out an unrelated genes, traM (ΔtraM). This plasmid was subsequently transferred to the PDI⁻ strain, *E. coli*-4. Wild-type *E. coli*-4 does not exhibit the inhibitory phenotype, as indicated by competition assays with the susceptible *E. coli*-186 (Table 2; and see Example 6 herein below). *E. coli*-4 also exhibits susceptibility to PDI, based on CFU counts following co-culture with PDI⁺ *E. coli*-264. Following transformation with pPDIΔtraM, *E. coli*-4 acquired the inhibitory phenotype and immunity (Table 2; and see Example 6). Together these results indicate PDI and self-immunity are encoded by the 98.8 kb plasmid (see Example 10 below).

To demonstrate the necessity for each gene in the operon for PDI function, genetic knockouts were constructed and used herein to show that disrupting any gene within the PDI operon blocked the inhibitory phenotype and, additionally, immunity to PDI was lost in the mcpM and mcpI mutants (FIG. 3). According to particular aspects, this indicated that all the genes were important for PDI, but immunity was dependent on only one or two genes. Due to the direct downstream location of mcpI, loss of immunity in the mcpM mutant was likely caused by a polar effect from ΔmcpM. This is consistent with the ability shown herein to complement immunity by the expression of mcpI alone. Although mcpI likely does not play a direct role in killing, it is necessary for self-immunity and for this reason is required for PDI. Deleting traM, a gene located ~20 Kb upstream of the PDI operon, did not affect either inhibition or immunity indicating that the methods used herein did not interfere with PDI. Furthermore, the tolC mcpB, and mcpD mutants lost the ability to inhibit but retained immunity, consistent with a role in toxin transport.

According to particular aspects, and based on gene cluster and sequence analysis, MccPDI is best characterized as a Gram-negative class IIa microcin. The PDI gene cluster is relatively simple, consisting of two genes for export, one for immunity, one presumptively for microcin activation, and the microcin gene itself. Unlike class I and IIb microcins, which have several genes for post-translational modification, MccPDI only has one recognizable gene that is putatively required for microcin activation. The dedicated transport system involves the products of two plasmid-encoded genes, mcpB and mcpD. These two PDI genes have homology with hlyB and hlyD of the *E. coli* α-hemolysin T1SS (9). This multicomponent export system has similar organization to transport systems for other class II microcins, including MccE492, MccL, and MccV (10, 18, 26). McpB contains the transmembrane domains and nucleotide-binding domains, including the highly conserved Walker A and B motifs and ABC signature, characteristic of the ABC-transporter superfamily of proteins (21). McpD is thought to act as a membrane fusion protein, forming a channel through the periplasm and connecting to the outer membrane protein TolC, the third component of class II microcin export machinery (7, 10, 18, 26). In total, these proteins form the export system allowing secretion of protein from the cytoplasm across the periplasmic space and into the extracellular medium. McpM has homology to other microcin precursors within the N-terminal sequence, which encodes a putative signal peptide (6) that is consistent with T1SS transport. The presence of a conserved double glycine suggests the McpM precursor contains an 18-residue signal peptide that is cleaved to produce a mature MccPDI. There is no apparent sequence identity with other microcins in the activity region (C-terminal sequence) (6).

This indicates that a unique receptor is probably involved with the uptake of MccPDI and that the mechanism of killing is different from other microcins. The fact that only *E. coli* and *Shigella* (data not shown) are currently known to be susceptible to this PDI (MccPDI) suggests target cell recognition occurs through a specific receptor, possibly only expressed in these species.

Class IIa microcin gene clusters are typically composed of only four genes: two necessary for microcin export, one for immunity, and one encoding the microcin. The PDI operon is unique because it also includes a gene presumably involved with microcin processing or export. Deleting mcpA in *E. coli*-25 interrupts the inhibitory phenotype but does not affect immunity. It is possible this mutant has downstream effects on the microcin transport system (i.e. a polar effect); however, not to be bound by theory, bioinformatic analysis suggests the protein product is likely to be involved with post-translational modification of McpM. McpA has similarity to McmM and MceF (both 29% identity) of the MccM and MccE492 gene clusters, respectively. Wilkens et al. (36) showed an mceF mutant had a non-inhibitory phenotype and the microcin product collected from cell lysate was found at a higher molecular weight than mature MccE492, suggesting the presence of an inactive microcin precursor. Consistent with a role in protein modification, McpA contains a CaaX amino terminal protease domain (PF02517) that functions in post-translation modification of proteins with the CaaX sequence motif (35). Furthermore, the McpM C-terminus putatively contains a modified terminal CaaX sequence, suggesting McpM may be processed either before or during transport, resulting in the fully mature MccPDI.

Although microcins are released extracellularly to inhibit competing bacteria, no antimicrobial compounds were detected through membrane-divided competitions or spent media assays in previous work (32). It is possible the PDI microcin requires contact between competing cells or some other signal to become active in the media. Alternatively, the methods used in the Examples section herein may interfere with the detection of a soluble microcin in these assays, or the concentration of secreted microcin is too low to have a biological effect except when inhibitor cells express the microcin in close proximity to susceptible strains. Without being bound by theory, it is likely that MccPDI interacts with an outer membrane protein OmpF, which is highly conserved in all sequenced *E. coli* and *Shigella*. Data presented in Example 12 below shows that six genes (atpA, atpF, dsbA, dsbB, ompF, and ompR) were required for susceptibility to PDI, suggesting that OmpF acts as the receptor for MccPDI and the other genes required for sensitivity are necessary for expression and folding of OmpF, and/or they are required to translocate MccPDI across the cellular membrane.

Figure 4:
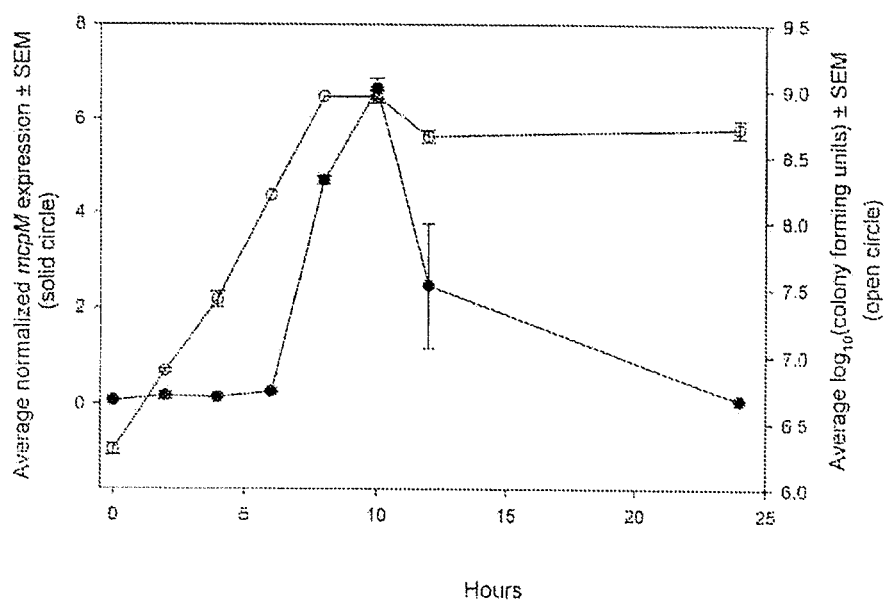
FIG. 4. Expression of mcpM by *E. coli*-25 is correlated with growth phase. Expression of mcpM was measured during 24 hr culture in M9. Closed circles are the mean normalized mcpM expression ±SEM (n=2 replicates). Open circles are the mean colony forming units (CFU) ±SEM (n=2 replicates).

Like other microcins, MccPDI is a low molecular weight protein that inhibits the growth of closely related species. Whereas the activity of some microcins extends to a range of Gram-negative bacteria including *Escherichia, Klebsiella, Salmonella*, and *Pseudonionas* (6), MccPDI has only been observed to inhibit *Escherichia*, and testing has also shown inhibition of *Shigella* but not *Salmonella* or *Klebsiella* (data not shown). In Examples presented below, the PDI$^+$ strain *E. coli*-25 was competed against a panel of pathogenic *E. coli* O157:H7 (n=25) and *E. coli* O26 (n=3). All the strains were susceptible to killing (FIG. 1) and the average reduction following co-culture was greater than 5 logs. The degree of killing may actually be much greater as our methods to determine cell counts were limited to $2 \times 10^3$ CFU/ml. Calculations for the degree of killing were determined using $2 \times 10^3$ CFU/ml for instances where the susceptible population was undetectable. Nonetheless, PDI effectively kills greater than 99% of the competing population. Because many of these pathogens are significant in diseases of both animals and humans (33), McPDI has application in clinical medicine, food safety and other fields. FIG. 4 shows that native mcpM transcription occurs primarily during rapid growth of the inhibitor population.

The invention provides methods and compositions for killing and/or for preventing or decreasing the adverse effects of pathogenic bacteria such as pathogenic *Escherichia coli* (*E. coli*). The methods involve contacting the pathogenic bacteria with the novel microcin described herein, microcin McPDI, the amino acid sequence of which is presented in SEQ ID NO: 24. In some embodiments, the microcin McPDI has undergone one or more cleavage events and comprises a sequence comprising residues 37-120 of SEQ ID NO: 24. The cleaved product may form multimers containing two, three, four, five, six, or more cleaved products as part of a disulfide-bonded complex. In exemplary embodiments, the product forms a dimer. The contact may be via a preparation of the microcin itself, or via a preparation of a bacterium encoding the microcin, as described in detail below.

A further aspect of the invention provides a composition comprising microcin McPDI having one or more of a sequence of SEQ ID NO: 77 or a functional variant thereof and/or SEQ ID NO:24 or a functional variant thereof, wherein said functional variant has a sequence at least 95% identical to SEQ ID NO: 77 or SEQ ID NO:24; and an oxidizing agent. The composition may contain 5-30% oxidizing agent. In some embodiments, the composition contains 10% oxidizing agent or 20% oxidizing agent. An oxidizing agent is a compound that is capable removing an electron (e.g., addition of a hydrogen) from another chemical species in a redox reaction. Exemplary oxidizing agents include, but are not limited to, dimethyl sulfoxide (DMSO), sodium perborate, permanganate, hypochlorite, and hydrogen peroxide.

Hosts, Pathogens and Sources of Contamination

While most *E. coli* strains are harmless, some serotypes can cause serious and even deadly diseases in a host, either as the result of exposure to the pathogenic bacteria via direct transmission from another infected host or by ingestion of or exposure to (e.g. handling) contaminated food products or from other sources of the bacteria (e.g. fomites). In particular, the targeted pathogenic bacteria include *E. coli* strains expressing the OmpF protein, which are known to be vulnerable to the MccPDI microcin. The methods and compositions are also effective for killing (e.g. lysing) or preventing or decreasing the adverse effects of pathogenic *Shigella* sp. Those of skill in the art will recognize that phylogenetic studies indicate that *Shigella* is more appropriately treated as a subgenus of *Escherichia*, and that certain strains generally considered *E. coli* (e.g. *E. coli* O157:H7) could be classified as *Shigella*. Herein, the phrases "pathogenic bacteria" and "pathogenic *E. coli*" encompasses both pathogenic *E. coli* and pathogenic *Shigella*, although the two may be discussed separately, for clarity and to accord with historic designations.

The term "pathogenic" refers to the ability of the bacterium to cause disease symptoms in one or more hosts. The targeted bacterium need not cause disease in all hosts that is it capable of colonizing. Successful colonization of some hosts by the bacterium may be entirely benign (asymptomatic, harmless, etc.). However, such non-susceptible hosts may serve as reservoirs of the pathogenic bacteria which, when transmitted to a susceptible host, cause disease. Herein, these two genera of hosts may be referred to as "disease susceptible hosts" and "non-disease susceptible hosts", respectively, or simply as "susceptible hosts" and "non-susceptible hosts". It will be understood that the methods of treatment described herein may be advantageously applied to both susceptible and non-susceptible hosts. For the susceptible hosts, treatment may prevent, cure (fully or partially) or ameliorate disease symptoms, or prevent or decrease adverse effects that would otherwise be caused by pathogenic bacteria. These beneficial effects are brought about by killing and/or damaging established pathogenic bacteria, or by preventing, slowing or minimizing the growth of pathogenic bacteria to which the host is newly exposed. For non-susceptible hosts, treatment may destroy or lessen the number of pathogenic bacteria that can colonize the host or that might otherwise colonize the host, but for intervention using the methods and compositions described herein, thereby lessening or eliminating transmission of the pathogenic bacteria to other disease susceptible and non-susceptible hosts.

Susceptible hosts that may be subject to diseases caused by pathogenic *E. coli* are usually endotherms and may be mammals. Such mammals include but are not limited to: primates (e.g. humans), livestock e.g. cattle, pigs, sheep goats, etc., especially neonates, juveniles, elderly or immune compromised individuals; etc. Alternatively, various avian species may also be subject to such infections, including but not limited to: chickens, turkeys, ducks, etc. Non-susceptible hosts that may act as reservoirs of pathogenic bacteria that are passed to susceptible hosts include substantially the same endotherms described above as susceptible hosts.

Further, pathogenic bacteria may be transmitted among members of a particular host group (e.g. from person to person, among cows in a herd, etc.) or even from one area of an individual host organism to another area of the same organism, e.g. pathogenic bacteria may be transmitted from the anus to the urethra via fecal contamination, causing urethral infection.

Particular combinations of susceptible hosts and pathogenic bacteria include the following exemplary animal pathogens of interest:
Poultry—avian pathogenic *E. coli* (APEC)
Calves—*E. coli* K99 (which causes calf diarrhea)
Swine—*E. coli* K88 (which causes post-weaning diarrhea)
For food safety:
*E. coli* O157:H7
The United States Department of Agriculture (USDA) "Big 6" STEC *E. coli* pathogens: *E. coli* serovars O26, O45, O103, O111, O121 and O145.
Diarrhoeagenic *E. coli* human pathovars:
various enteropathogenic *E. coli* (EPEC)
various enterohaemorrhagic *E. coli* (EHEC)
various enterotoxigenic *E. coli* (ETEC)
various enteroinvasive *E. coli* (EIEC; including *Shigella*)
various enteroaggregative *E. coli* (EAEC)
various so-called diffusely adherent *E. coli* (DAEC)
Extraintestinal *E. coli* (ExPEC) human pathovars:
uropathogenic *E. coli* (UPEC)
neonatal meningitis *E. coli* (NMEC)
Exemplary pathogenic *Shigella* species of interest which may be killed by the compositions and methods of the invention include but are not limited to: Serogroup A: *S. dysenteriae*. Serogroup B: *S. flexneri*, and Serogroup D: *S. sonnei*, and serotypes and serovars thereof.

In addition, contamination with pathogenic bacteria can occur via other routes of transmission such via fomites, (inanimate objects such as countertops, cutting boards, utensils, towels, money, clothing, dishes, toys, dirt, excreted feces, diapers, surfaces in barns and stockyards, etc.), or via unpasteurized milk, dairy products, juices, etc.; or via contaminated water (e.g. drinking water, ponds and lakes, swimming pools, etc.), or via contaminated animals, meat, or produce; or fruits, etc.

In some aspects, the methods of the invention involve contacting pathogenic bacteria with the microcin MccPDI. Accordingly, the invention provides i) substantially purified MccPDI microcin protein; and ii) substantially pure cultures of bacteria that produce the microcin protein.

Proteins and Nucleic Acids

In some aspects the invention provides MccPDI microcin protein and/or a gene that encodes the protein (e.g. SEQ ID NOS: 23 or 33 and 24) as well as proteins/polypeptides of the operon disclosed herein, and the genes which encode them (e.g. SEQ ID NOS: 25-32). In some embodiments, the microcin MccPDI has undergone one or more cleavage events and comprises a sequence comprising residues 37-120 of SEQ ID NO: 24 which is represented by SEQ ID NO:77. The cleaved product may form multimers containing two, three, four, five, six, or more cleaved products as part of a disulfide-bonded complex. In exemplary embodiments, the product forms a dimer.

Substantially purified MccPDI microcin protein may be produced either recombinantly, or from a native or naturally occurring source such as the bacteria described herein. Those of skill in the art are familiar with techniques for genetically engineering organisms to recombinantly produce or overproduce a protein of interest such as MccPDI. Generally, such techniques involve excision of a gene encoding the protein from a natural source e.g. using nucleases or by amplifying the gene e.g. via PCR using primers complementary to sequences that flank the gene of interest. The gene can then be inserted into and positioned within a vector (e.g. an expression vector such as a plasmid or virus) so that it is able to be expressed (transcribed into translatable mRNA). Typically, the gene that is to be transcribed is juxtaposed to one or more suitable control elements such as promoters, enhancers, etc. that drive expression of the gene. Suitable vectors include but are not limited to: plasmids, adenoviral vectors, baculovirus vectors (e.g. so-called shuttle or "bacmid" vectors, and the like). Suitable vectors may be chosen or constructed to contain appropriate regulatory sequences, including promoter sequences, terminator sequences, polyadenylation sequences, enhancer sequences, marker genes, and other sequences. The vectors may also contain a plasmid or viral backbone.

Typically, the vector is used to genetically engineer or infect a host organism where the gene is transcribed and translated into protein. In the host, the gene may be expressed from the vector (transcribed extrachromosomally, also called "in trans") and may be overexpressed. i.e. expressed at a level that is higher than normally occurs in its native bacterial host. Alternatively, the gene may be inserted into the chromosome of the host ("in cis"). Exemplary expression systems that may be utilized include but are not limited to bacteria (such as *E. coli*), yeast, baculovirus, plant, mammalian, and cell-free systems. Host bacteria may be heterologous, i.e. they may be non-native bacteria in which the gene is not present in nature. Alternatively, they may be native bacteria that are natural hosts, but which are genetically engineered to produce the microcin in greater abundance (at higher levels or concentrations) than in the native, non-engineered host. Exemplary heterologous bacterial hosts include but are not limited to: various *lactobacillus* species such as *Lactobacillus casei, Lactobacillus acidophilus, Lactobacillus fermentum, Lactobacillus gasseri, Lactobacillus pentosus, Lactobacillus plantarum, Lactobacillus sporogenes, Lactobacillus brevis, Lactobacillus delbrueckii, Lactobacillus salivarius, Lactobacillus hilgardii, Lactobacillus lactis, Lactobacillus rhamnosus, Lactobacillus johnsonii, Lactobacillus leishnmanis, Lactobacillus jensenii, Lactobacillus reuteri, Lactobacillus sakei, Lactobacillus cellobiosus, Lactobacillus crispatus, Lactobacillus curvatus, Lactobacillus caucasicus*, and *Lactobacillus helveticus*, and others taught, for example, in United States patent application 20090169582 (Chua), the complete contents of which is hereby incorporated by reference in entirety; and other types of bacterial, fungal and/or viral recombinant hosts. Mammalian cells available in the art for heterologous protein expression include lymphocytic cell lines (e.g., NSO), HEK293 cells, Chinese hamster ovary (CHO) cells, COS cells, HeLa cells, baby hamster kidney cells, oocyte cells, and cells from a transgenic animal, e.g., mammary epithelial cell. For details, see Sambrook et al., Molecular Cloning: A Laboratory Manual. 2nd ed., Cold Spring Harbor Laboratory Press (1989). Many established techniques used with vectors, including the manipulation, preparation, mutagenesis sequencing, and transfection of DNA, are described in Current Protocols in Molecular Biology, Second Edition, Ausubel et al. eds., John Wiley & Sons (1992).

The vector or chromosome from which the microcin is transcribed includes at least a genetic sequence encoding the microcin described herein and may comprise one or more additional genes of the operon described herein. i.e. genes mcpM (SEQ ID NO: 23), mcpI (SEQ ID NO: 25), mcpA (SEQ ID NO: 27), mcpD (SEQ ID NO: 29), and mcpB (SEQ ID NO: 31), each of which encodes a respective protein or functional variant thereof (see below for explanation of "variant". The one or more (at least one) gene(s) in the vector or chromosome is/are expressable and are operably (functionally, expressibly) linked to one or more control or expression elements, e.g. promoters, enhancers, etc. in a manner that facilitates, causes or allows expression of the gene(s). In some aspects, the genes are present on a plasmid such as the plasmid with the nucleotide sequence shown in SEQ ID NO: 33), or a plasmid with at least about 55, 60, 65, 70, 75, 80, 85, 90, or 95% or more (e.g. 96, 97, 98, 99%) identity. The plasmid may be located in a native host bacterium, e.g. E-25 (which is resistant to tetracycline, streptomycin and sulfa drugs) and/or E-264 (which is not antibiotic resistant).

The protein that is produced is the microcin MccPDI (or another protein encode by the operon as described above) or a physiologically active variant thereof. By "physiologically active variant" or "active variant" or "functional variant", we mean a protein sequence that is able to kill pathogenic bacteria as described herein. The protein may have the sequence shown in SEQ ID NO: 24, or may include this sequence, or a sequence that shares at least about 95% identity to SEQ ID NO: 24 (e.g. that is about 95, 96, 97, 98 or 99% identical thereto, as determined by alignment methods that are well-known), but that retains the ability to kill and/or impede growth/reproduction of and/or colonization by pathogenic bacteria. Compared to the wild type microcin, such variants are at least about 50%, and usually about 55, 60, 65, 70, 75, 80, 85, 90, or 95% or more as potent re killing, impeding growth and/or colonization, etc. In some embodiments, the variant may be more potent than the native microcin.

The variants of McPDI that may be used in the practice of the invention may include those in which one or more amino acids are substituted by conservative or non-conservative amino acids, as is understood in the art. Further, deletions or insertions may also be tolerated without impairing the function. In addition, the microcin may be included in a chimeric or fusion protein that includes other useful sequences, e.g. tagging sequences (e.g. histidine tags), various targeting sequences (e.g. sequences that promote secretion or target the protein to a subcellular apartment or to the membrane), other antimicrobial sequences (e.g. other microcins), and the like, as well as spacer or linking sequences. The sequence of the microcin may be altered to prevent or discourage proteolysis, to promote solubility, or in any other suitable manner.

Some aspects of the invention provide a microcin with a sequence such as that shown in SEQ ID NO: 24, but which is foreshortened by 18 amino acids at the amino terminus, i.e. the 18 amino terminal residues present in SEQ ID NO: 24 are absent in this sequence, which is shown below as SEQ ID NO: 35. As described above for SEQ ID 24, active variants of the sequence represented by SEQ ID NO: 35 are also encompassed by the invention.

(SEQ ID NO: 35)
N A N S N F E G G P R N D R S S G A R N S L G R N

A P T H I Y S D P S T V K C A N A V F S G M I G G

A I K G G P I G M A R G T I G G A V V G Q C L S D

H G S G N G S G N R G S S S S C S G N N V G G I C

N R.

Some aspects of the invention provide a microcin with a sequence such as that shown in SEQ ID NO: 24, but which is foreshortened by 36 amino acids at the amino terminus, i.e. the 36 amino terminal residues present in SEQ ID NO: 24 are absent in this sequence, which is shown below as SEQ ID NO: 77. As described above for SEQ ID 24, active variants of the sequence represented by SEQ ID NO: 77 are also encompassed by the invention. The protein may have the sequence shown in SEQ ID NO: 77, or may include this sequence, or a sequence that shares at least about 95% identity to SEQ ID NO: 24 (e.g. that is about 95, 96, 97, 98 or 99% identical thereto).

(SEQ ID NO: 77)
R N S L G R N A P T H I Y S D P S T V K C A N A V

F S G M I G G A I K G G P I G M A R G T I G G A V

V G Q C L S D H G S G N G S G N R G S S S S C S G

N N V G G I C N R.

The invention also encompasses nucleic acid sequences that encode the microcin and active variants thereof as described herein. For example, the encoding sequence may be that which is represented in SEQ ID NO: 23, but this is not always the case. Variants of SEQ ID NO: 23, usually having at least about 95, 96, 97, 98, or 99% identity thereto, are also contemplated. However, those of skill in the art will recognize that the identity may be much lower (e.g. about 50, 55, 60, 65, 70, 75, 80, 85 or 90%) and the sequence may still encode a fully functional microcin, e.g. due to the redundancy of the genetic code.

Calculations of "homology" and/or "sequence identity" between two sequences may be performed as follows: The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference (native) sequence. The amino acid residues or nucleotides at corresponding amino acid positions or nucleotide positions are then compared. When a position the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In an exemplary embodiment, the percent identity between two amino acid sequences is determined using the Needleman and Wunsch (1970, J. Mol. Biol. 48:444-453) algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In an exemplary embodiment, the percent homology/identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that may be used if the practitioner is uncertain about what parameters may be applied to determine if a molecule is within a sequence identity, or homology limitation of the invention) are a Blossum 62 scoring matrix with a gap penalty of 12, a gap extend penalty of 4, and a frame shift gap penalty of 5. The percent identity/homology between two amino acid or nucleotide sequences can also be determined using the algorithm of E. Meyers and W. Miller ((1988) CABIOS, 4:11-17) that has been incorporated into the ALIGN program (version 2:0); using a PAM120 weight residue table, a gap length penalty of 12 and a gap penalty of 4.

The culturing and the maintenance of cultures of microorganisms such as the bacteria of the invention is carried out e.g. as described herein in the Examples section. Bacterial preparations may be lyophilized or freeze-dried.

The production of the substantially purified microcin protein is carried out by methods known to those of skill in the art, e.g. by collecting unpurified protein from a source such as the bacteria (or other expression system) that make the protein, and purifying and characterizing the protein using known steps, e.g. various separation techniques and identification techniques which include but are not limited to: centrifugation, column chromatography, affinity chromatography, electrophoresis, precipitation, sequencing, spectroscopy, etc. Preparations may be lyophilized or freeze-dried. By "substantially purified" we mean that the microcin is provided in a form that is at least about 75 wt %, preferably at least about 80 wt %, more preferably at least about 90 wt %, and most preferably at least about 95 wt % or more free from other macromolecules such as other peptides, proteins, nucleic acids, lipids, membrane fragments, etc., as is understood by those of skill in the art.

Compositions

The microcins and/or bacteria producing microcins (both of which may be referred to herein as "active agent(s) or "active ingredient(s))" of this invention will generally be used as a bactericidal active ingredient in a composition, i.e. a formulation, with at least one additional component such as a surfactant, a solid or liquid diluent, etc., which serves as a carrier. The formulation or composition ingredients are selected to be consistent with the physical properties of the active ingredient, the mode of application and environmental factors at the site of use, e.g. such as surface type, (e.g. soil or solid substrate, etc.), moisture, temperature, etc. If the composition is to be administered to a host, the ingredients are selected so as to be physiologically compatible with the host. Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspoemulsion. The general types of nonaqueous liquid compositions are emulsifiable concentrate, microemulsifiable concentrate, dispersible concentrate and oil dispersion.

The general types of solid compositions are dusts, powders, granules, pellets, pills, pastilles, tablets, films, filled or layered films, coatings, impregnations, gels, cakes, and the like, which can be water-dispersible ("wettable") or water-soluble. Films and coatings formed from film-forming solutions or flowable suspensions may be useful for some applications. Active ingredients can be (micro) encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions may be used as intermediates for further formulation.

Sprayable formulations are typically extended in a suitable medium before spraying. Liquid and solid formulations are formulated to be readily diluted in the spray medium, which may be aqueous-based, e.g. water. Spray volumes can range from about one to several thousand liters, sprayable formulations may be tank mixed with water or another suitable medium for treatment by aerial or ground application, e.g. of stockyards, barns, stables, stalls, bins containing produce, etc. Smaller volume spray formulations for use on smaller surfaces (e.g. countertops, for application to small quantities of food stuffs, etc.) are also contemplated.

The formulations will typically contain effective amounts of active ingredient in the range of about 1 to about 99 percent by weight.

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., Handbook of Insecticide Dust Diluents and Carriers, 2nd Ed., Dorland Books, Caldwell, N.J., the complete contents of which is hereby incorporated by reference in entirety.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and .gamma.-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, Solvents Guide, 2nd Ed., Interscience, New York, 1950, the complete contents of which is hereby incorporated by reference in entirety.

The solid and liquid compositions of the present invention may include one or more surfactants. When added to a liquid, surfactants (also known as "surface-active agents")

generally modify, most often reduce, the surface tension of the liquid. Depending on the nature of the hydrophilic and lipophilic groups in a surfactant molecule, surfactants can be useful as wetting agents, dispersants, emulsifiers or defoaming agents. Surfactants can be classified as nonionic, anionic or cationic. Exemplary suitable surfactants can be found, for example, in United States patent application 20130143940 to Long, the entire contents of which is hereby incorporated by reference. Also useful for the present compositions are mixtures of nonionic and anionic surfactants or mixtures of nonionic and cationic surfactants. Nonionic, anionic and cationic surfactants and their recommended uses are disclosed in a variety of published references including McCutcheon's Emulsifiers and Detergents, annual American and International Editions published by McCutcheon's Division, The Manufacturing Confectioner Publishing Co.; Sisely and Wood, Encyclopedia of Surface Active Agents, Chemical Publ. Co., Inc., New York, 1964; and A. S. Davidson and B. Milwidsky, Synthetic Detergents, Seventh Edition, John Wiley and Sons, New York, 1987, the complete contents of each of which is hereby incorporated by reference in entirety.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co., the complete contents of which is hereby incorporated by reference in entirety.

The active agents described herein and any other active ingredients are typically incorporated into the present compositions by dissolving or suspending the active ingredient in a solvent or by grinding in a liquid or dry diluent. Solutions, including emulsifiable concentrates, can be prepared by simply mixing the ingredients. The preparation may be lyophilized (freeze dried). If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084, the complete contents of which is hereby incorporated by reference in entirety) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", Chemical Engineering, Dec. 4, 1967, pp 147-48, Perry's Chemical Engineer's Handbook, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566. For further information regarding the art of formulation, see T. S. Woods, "The Formulator's Toolbox—Product Forms for Modern Agriculture" in Pesticide Chemistry and Bioscience. The Food-Environment Challenge, T. Brooks and T. R. Roberts. Eds., Proceedings of the 9th International Congress on Pesticide Chemistry, The Royal Society of Chemistry, Cambridge, 1999, pp. 120-133. See also U.S. Pat. No. 3,235,361. Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, Weed Control as a Science, John Wiley and Sons, Inc., New York, 1961, pp 81-96; Hance et al., Weed Control Handbook, 8th Ed., Blackwell Scientific Publications, Oxford, 1989; and Developments in formulation technology, PJB Publications, Richmond, U K, 2000. The complete contents of each of these references is hereby incorporated by reference in entirety.

In addition, the formulations may include other suitable active agents, e.g. other antimicrobial agents such as other microcins, antibiotics, etc.; or broadly defined antimicrobials such as antiseptics or heavy metals, etc.

Incorporation into Various Products

The active agents described herein may be incorporated into and/or used as an amendment to many different products, e.g. substrates and media which include but are not limited to: so-called "hand-sanitizing" preparations and soaps, gels, etc.: various sprays and washes; detergents and various cleaning agents; fabrics e.g. linings for materials such as diapers and other garments that may be contacted by feces: "booties" that are used to cover and protect shoes; disposable or non-disposable gloves; disposable or non-disposable food preparation surfaces, e.g. as sheets of material that can be placed on a cutting surface, or in a cutting surface itself: in storage apparatuses for implements used in food preparation (e.g. knife blocks, or holders, etc.); and others.

In some aspects, the active agents described herein are incorporated into packaging materials, e.g. packaging materials designed to contain meat or meat products or produce. For example, the packaging material may be impregnated with the active agent either during or after manufacture, or may be coated onto one or more surfaces of the material. The packaging material may be a film e.g. formed from a flexible polymer that may be transparent, or may be a rigid or semi-rigid container formed from e.g. plastic resin, styrofoam, wood, cardboard or pasteboard or other molded cellulose product, or made from some other so-called "natural" material. The packaging material may be in the form of "peanuts". The material may be biodegradable. United States patent applications 20120259295 (Bonutti) and 20030234466 (Rasmussen) and references cited therein, the complete contents of all of which are hereby incorporated by reference in entirety, discuss the preparation of various types of packaging materials.

The active agents may be incorporated into probiotic formulations. Such formulations may be designed or tailored to suit the mode of administration and the host to which the probiotic is administered. For example, if the targeted host is a human, the active agents may be added to other known probiotic products (kefir, yogurts, "smoothies", etc.) and/or other ingredients that increase palatability may be added (e.g. flavorings, thickeners, coloring agents, etc.). The formulation may be chewable (e.g. a gum or tablet) or taken as a pill. Other organisms may also be present in the probiotic preparation e.g. lactic acid bacteria (LAB), bifidobacteria, yeasts and various bacilli. If the recipient host is a juvenile such as a calf, the probiotic may be a milk substitute formulation. If the recipient is a bird or fowl, the probiotic may be a formulation of drinking water. Probiotics may also be formulated as suppositories.

Methods and Uses

In some aspects, the invention provides methods of using the microcins and bacteria that produce the microcins described herein, for preventing or decreasing the transmission of pathogenic *Escherichia coli* (*E. coli*) bacteria from a first location to a second location, e.g. from a first host (that may or not be a susceptible host) or first contaminated area, to a second host or previously uncontaminated area. The second host may or may not be susceptible. The first location may be a "reservoir" host or area/location that is already colonized by the pathogenic bacteria. Alternatively, the first host or location may be likely to be colonized or possible to colonize.

Administration to Hosts

If the first location is a susceptible (or non-susceptible) first host, the method comprises administering to the first host the microcin described herein or a bacterium that contains and expresses a nucleotide sequence encoding the microcin. By "administering" we mean the deliberate, intentional, active introduction of the bacterium into the first host (i.e. the purposeful inoculation of the first host), usually by a human or by a device, instrument or machine designed and operated by a human. In other words, the bacterium is not inadvertently, passively or accidentally transmitted, or is not transmitted as the result of an act of nature, or as the result of contamination of a source of the bacteria. Generally, the "bacterium" that is deliberately administered is a substantially pure, genetically homogenous population of substantially identical bacteria, or part of a mixture of several types of such substantially pure bacteria (e.g. several different serotypes, serovars, or strains. The bacteria that are so administered are generally cultured in vitro for a time prior to administration, and the method may involve culturing the bacteria from a natural source, selecting a single colony for propagation, and propagating the bacteria to form a culture that is sufficiently large or populous to successfully inoculate a host.

Administration results in contact between pathogenic bacteria that reside in/on the first host and the killing or damaging, etc. of the pathogens. Alternatively, administration may be prophylactic, i.e. the first host is not already infected with the pathogen, and infection is prevented or decreased. If bacteria are administered, the step of administering may also result in colonization of a host that is treated with the administered bacteria, i.e. bacteria that have the gene encoding the microcin. Thus, in some aspects, the step of administering results in an alteration of the microflora (e.g. "gut" or "digestive tract" microflora) of the recipient host, and the bacteria thus are a "probiotic" as discussed elsewhere herein, competing for nutrition and attachment sites to within the host. "Digestive tract" includes e.g. the mouth, esophagus, stomach, small intestine and large intestine (which includes the cecum, colon and rectum). In general, the amount of microcin that is administered in order to be effective is in the range of from about the amount of microcin would range between about 1 ug and 100 mg depending on the application and dilution factor; and the amount of bacteria that is administered in order to be effective is in the range of from about $10^3$ to about $10^{12}$; and is preferably in the range of from about $10^6$ to about $10^9$. Those of skill in the art will recognize that variations may occur, depending e.g. on how much microcin is produced by the bacterial strain in question, by the species, size, age. etc. of the subject to whom the microcin and/or the bacteria (or other recombinant host that produces the microcin) is administered.

When the microcin is administered, it may be in any suitable form or incorporated into any suitable vehicle. Exemplary vehicles for administering the microcin include but are not limited to: liquids such as drinking water, formula, and the like; and solid or semi-solid forms such as suppositories, pills, tablets, etc. The vehicle may be a solid "slow release" vehicle. The vehicle may include or be contained within e.g. a permeable or semi-permeable bag or pouch which can be suspended or retained indefinitely in the gut of a host organism (e.g. a cow), from which the active agent leaches or is released over time. The bag or pouch may be biodegradable.

For avian hosts (e.g. chickens), an exemplary mode of administration is addition of microcin-producing bacteria to drinking water or feed. Administration in this manner may be termed "probiotic" because the goal is to encourage colonization of the bird's digestive system with the harmless, protective bacteria, although colonization is not a requirement for positive effects to accrue. The protective microcin-producing bacteria can destroy or kill and thus outcompete pathogenic bacteria encountered by the bird, preventing colonization by the pathogens, or a least decreasing the level of colonization of, and hence transmission from, the bird. If the microcin itself is added to the drinking water or feed, it will destroy or kill pathogenic bacteria encountered by the bird, preventing colonization by the pathogens, or a least decreasing the level of colonization of, and hence transmission from, the bird, and possibly allow other non-pathogenic bacteria to flourish.

Similar strategies may be employed for bovine hosts, e.g. addition of microcin-producing bacteria or the microcin itself to drinking water, feed, salt licks, calf formula, etc., or administration of the bacteria as a probiotic to encourage the establishment of microcin-producing bacteria as described herein, or to provide a protective shield against infection by pathogenic bacteria.

Application to Surfaces

Those of skill in the art will recognize that it is also beneficial to prevent (discourage, impede, lessen, decrease, etc.) transmission of pathogenic bacteria from non-host sources to possible hosts. e.g. to prevent transmission from surfaces or areas which harbor the pathogens. The invention also comprises methods of doing so by applying the microcin of the invention and/or bacteria encoding the microcin, to surfaces which harbor the pathogens, or which are suspected or harboring the pathogens, or which could become contaminated with pathogens. Applying or treating such surfaces may be accomplished by any of many methods, e.g. by spraying a preparation of the microcin or bacteria, by applying a composition comprising a powder or granules, etc. Suitable compositions are described above. In general, the amount of microcin that is applied to a surface in order to be effective is in the range of from between about 1 ug and 100 mg; and the amount of bacteria that is applied is in the range of from about $10^3$ to about $10^{12}$, and is preferably in the range of from about $10^6$ to about $10^9$.

Areas that are particularly prone to contamination with pathogenic bacteria include those which house of livestock or fowl. Such areas, especially commercial areas, may be treated using the compositions of the invention, especially spray formulations. The areas may or may not be associated with a commercial enterprise, e.g. they may be associated with for profit or non-profit farms, stables, etc. The areas may also be set aside for animals e.g. as reserves, zoos, stockyards etc., or may be located at veterinary facilities. The compositions of the invention may be applied to any suitable surface where the microcin may be useful to kill pathogenic bacteria, e.g. soil or grass, flooring, stalls, pens, milking carousels, feed lot surfaces, drinking and/or feeding containers, cages, crates, truck beds, etc. Exemplary animals which are housed in such areas and are potential hosts of pathogenic bacteria include but are not limited to: livestock e.g. horses, mares, mules, jacks, jennies, colts, cows, calves, yearlings, bulls, oxen, sheep, goats, lambs, kids, hogs, shoats, pigs, bison, and others; and avian species such as land and water fowl e.g. chickens, turkeys, ducks, geese, ostriches, guinea fowl, etc. The preparations of the invention may be applied to the animals themselves, or to specific areas of the animals, e.g. to feet, the anal area, etc.

In addition, the preparations of the invention may be applied to various products, especially products derived from animals that are susceptible to infection with and/or to disease caused by pathogenic bacteria. The preparations may be applied to or included in (mixed into), for example, meats or meat products (including both raw and so-called "ready to eat" meat and poultry products), eggs, hides, carcasses, horns, hooves, feathers, etc.

Diseases Prevented or Treated

The types of diseases and conditions that may be prevented or treated using the methods and compositions disclosed herein include any of those which are caused by pathogenic *E. coli*, including but not limited to: food poisoning (e.g. in humans), gastroenteritis, diarrhea, urinary tract infections, neonatal meningitis, hemolytic-uremic syndrome, peritonitis, mastitis, septicemia and Gram-negative pneumonia, shigellosis, dysentery, etc. In some aspects, probiotic preparations are contemplated, e.g. liquid or solid preparations that are taken prophylactically to prevent or treat disease symptoms or so-called Traveler's diarrhea prior to or during travel.

Herein, where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

EXAMPLES

Example 1. Materials and Methods

Bacterial Strains, Media, and Culture Conditions.

*E. coli* strains (Table 1) were cultured in Luria-Bertani (LB) media (Fisher Scientific, Pittsburgh, Pa.) or in M9 minimal media (6 g/L $Na_2HPO_4$. 3 g/L $KH_2PO_4$, 0.5 g/L NaCl, 1 g/l $NH_4Cl$, 2 mg/L thiamine, 1 mM $MgSO_4$ 0.1 mM $CaCl_2$ and 0.2% glucose) at 37° C. with shaking (200 rpm), unless stated otherwise. Components for the M9 media were purchased from Fisher Scientific (Pittsburgh, Pa.), Sigma-Aldrich (St. Louis, Mo.) and J.T. Baker Reagents and Chemicals (Phillipsburg, N.J.). Antibiotics were added to media at the following concentrations: ampicillin (amp) 100 µg/ml (Fisher Biotech, Fair Lawn, N.J.); kanamycin (kan) 50 µg/ml (Fisher Scientific, Pittsburgh, Pa.); nalidixic acid (nal) 30 µg/ml (MP Biomedicals, Solon, Ohio); and tetracycline (tet) 50 µg/ml (Fisher Scientific, Pittsburgh, Pa.). Strains that would otherwise be antibiotic susceptible were selected for nalidixic acid resistance through successive passage in LB media with increasing nalidixic acid concentrations until the strains were capable of growth at 30 µg/ml.

TABLE 1

E. coli strains and PCR primer sequences used in this work.

| Strain | Genotype/phenotype | Primers: Homologous extensions (H1[a] and H2[b]); PDI, rpoD, and mcpM loci | Ref. |
|---|---|---|---|
| E. coli-25 | Wild-type, SSuT$^R$, PDI$^+$ | PDI fwd: TAGTTGCAGGGGCATAAGAA (SEQ ID NO: 1)<br>PDI rev: AGGAAACGCAAACAGCAACT (SEQ ID NO: 2)<br>rpoD fwd: CAGGTTCAATGCTCCGTTGC (SEQ ID NO: 3)<br>rpoD rev: GCGACCTTTCGCTTTGATGG SEQ ID NO: 4)<br>mcpM fwd: CCGTAATGACCGTTCCAGT (SEQ ID NO: 5)<br>mcpM rev: CCATTTCCACTACCATGATCT (SEQ ID NO: 6) | (17) |
| E. coli-25ΔtolC | SSuT$^R$, Kan$^R$, ΔtolC, PDI$^-$ | H1: ATAACCCGTATCTTTACGTTGC CT TACGTTCA (SEQ ID NO:7)<br>H2: CTAGAATCCGCAATAATTTTAC AGTTTGAT (SEQ ID NO: 8) | This work |
| E. coli-25ΔtraM | SSuT$^R$, Kan$^R$, ΔtraM, PDI$^-$ | H1: AATAACGTGATTGCATATTACT TATCTCAGGAGTTC (SEQ ID NO: 9)<br>FP: ATCCCTGGAAGGACTACAACC TATGACCGAAAATAC (SEQ ID NO: 10) | This work |
| E. coli-25ΔmcpM | SSuT$^R$, Kan$^R$, ΔmcpM, PDI$^-$ | H1: GTAATTTAATAAACATAGTAG CGCCCTCCATTATATCTAT (SEQ ID NO: 11)<br>H2: AACGCACAAAATAACAAACAA CCGATAGGGGAAATATGAT (SEQ ID NO:12) | This work |
| E. coli-25ΔmcpMΔmcpI | SSuT$^R$, Kan$^R$, ΔmcpMΔmcpI, PDI$^-$ | H1: ATTATCTTTACTATATTTATAT ATGTTATCATTCATAATG (SEQ ID NO: 13)<br>H2: AACGCACAAAATAACAAACAA CCGATAGGGGAAATATGAT (SEQ ID NO: 14) | This work |
| E. coli-25ΔmcpMΔmcpI+ pMcpI | SSuT$^R$, Kan$^R$, ΔmcpMΔmcpI, PDI$^-$, immune to PDI | H1: TGGTGATGAATTCCTGTCAAA (SEQ ID NO: 15) | This work |
| E. coli-25ΔmcpB | SSuT$^R$, Kan$^R$, ΔmcpB, PDI$^-$ | H2: TACCAGTTTCACCCGTCACA (SEQ ID NO: 16) | |
| E. coli-25ΔmcpD | SSuT$^R$, Kan$^R$, ΔmcpD, PDI$^-$ | H1: TCAGCCATTCCCATAAATGAC GAGTATCAAGGTTGACG (SEQID NO: 17)<br>H2: TTGACGGAAAGGTTACTTATTG TATTAAAAATAATG (SEQ ID NO: 18) | This work |

TABLE 1 -continued

E. coli strains and PCR primer sequences used in this work.

| Strain | Genotype/phenotype | Primers: Homologous extensions (H1[a] and H2[b]); PDI, rpoD, and mcpM loci | Ref. |
|---|---|---|---|
| E. coli-25ΔmcpA | SSuT[R], Kan[R], ΔmcpA, PDI[-] | H1: GATATACATCTGACCTGTGTGA TGTTAAAGTTTTATACTA (SEQ ID NO: 19) H2: ATAGAAAAAATAAGAACAATC TCCGCGAAATAGCATTATG (SEQ ID NO: 20) | This work |
| E. coli-4 | Wild-type, SSuT[R], PDI[-] | | (32) |
| E. coli-4pPDI | SSuT[R], Kan[R], pPDI, PDI[+] | | This work |
| E. coli-6 | Wild-type, SSuT[R], PDI[-] | | (32) |
| E. coli-82 | Wild-type, SSuT[R], PDI[-] | | This work |
| E. coli-186 | Wild-type, Nal[R], PDI[-] | | (32) |
| E. coli-264 | Wild-type. Nal[R], PDI[+] | | (32) |
| O157:H7 Sakai | Wild-type | | (15) |
| E. coli K12 | Nal[R] | | (19) |

[a] E. coli-25 gene-specific sequences are shown. For gene deletion mutants, homologous extensions also had the kanamycin primer site: TGTGTAGGCTGGAGCTGCTTCG (SEQ ID NO: 21), 3' to the E. coli-25 specific sequence.
[b] E. coli-25 gene-specific sequences are shown. For gene deletion mutants, homologous extensions also had the kanamycin primer site: CATATGAATATCCTCCTTA (SEQ ID NO: 22), 3' to the E. coli-25 specific sequence.

Competition Assays to Measure Inhibition Phenotype.

Bacterial strains were grown individually overnight in LB. Equal volumes of each competing strain were inoculated into fresh M9 media at a 1:200 dilution, for a final 1:100 dilution of total cells. Cultures were then incubated at 37° C. for 8 to 24 h. It was previously shown that the PDI phenotype does not differ significantly between 8 and 24 h competitions (32). Mixed cultures were then serially diluted, plated on LB supplemented with the appropriate antibiotic to select for each competing strain, and enumerated.

Live/Dead Staining and Flow Cytometry.

Viability assays were conducted using the Live/Dead® BacLight™ Bacterial Viability Kit (L34856, Molecular Probes, Invitrogen, Eugene, Oreg.). Cell cultures were grown in M9 media for six hours at 37° C. and then 1 ml of each culture was collected by centrifugation, washed in 0.85% NaCl, and resuspended in 0.85% NaCl. Cells were then diluted 1:10 in 0.85% NaCl that contained 1.5 μl of 3.34 mM SYTO 9 and 1.5 μl of 30 mM propidium iodide. Samples were incubated at room temperature in the dark for 15 min. Flow cytometry was performed on a FACCalibur flow cytometer (BD Biosciences) and data was analyzed using FCS Express software (De Novo software, Thornton, Ontario, Canada). Initial parameters were established by analyzing cell suspensions with known live- and dead-cell populations. These bacterial suspensions were prepared as follows: cells were grown in M9 minimal media to late-log phase and 1 ml aliquots of the cultures were collected by centrifugation, washed in 0.85% NaCl, and resuspended in either 0.85% NaCl (live portion) or 70% isopropyl alcohol (dead portion). Samples were incubated at room temperature for 30 min, then processed and analyzed by flow cytometry as described above. Ratios of live to dead cells used for the standard were (live:dead): 0:100, 50:50, and 100:0. Gates specific to our E. coli (based on side and forward light scatter) were used to collect data on 50,000 cell events. Green versus red fluorescence was measured to distinguish between SYTO 9 stained live cells and propidium iodide-SYTO 9 stained dead cells. Nonspecific signal was excluded at the time of data acquisition.

Sequencing and Analysis.

Genomic extractions of E. coli-25, E. coli-82, and E. coli-264 were prepared using the DNeasy Blood & Tissue kit (Qiagen, Valencia, Calif.) according to the manufacturer's instructions. Sequencing was conducted at the Genomics Core Lab at Washington State University using a Roche 454 FLX Titanium Genome Sequencer to a depth of 24× represented by 399,076 reads. Sequences were assembled using Newbler (version 2.5.3). Annotation employed Glimmer version 3.02 for gene calling, and then the data was piped into CLC Genomics Workbench (CLC Bio, Cambridge, Mass.) where the resulting genes were screened against the current BLAST. SignalP and Pfam databases for functional predictions. The annotated sequence has been deposited in GenBank under (note: sequence submitted, accession number pending).

Site-Directed Gene Deletion.

Gene-specific knockouts were generated using the methods described by Datsenko and Wanner (5). Briefly, the gene of interest was replaced with a PCR-generated kanamycin resistance marker. PCR primers were designed to amplify the kanamycin resistance gene from the template plasmid pKD4. Each primer incorporated 36-50 nt of the region flanking the gene of interest (Table 1). PCR products were column purified (Qiagen, Valencia, Calif.), digested overnight at 37° C. with DpnI (New England Biolabs, Ipswich, Mass.), purified again, and suspended in 30 μl 10 mM Tris, pH 8.0. E. coli-25 carrying the λ Red plasmid pKD46

(Amp®) were grown in SOB (2% bactotryptone, 0.5% yeast extract, 10 mM NaCl, 2.5 mM KCl, 10 mM $MgCl_2$, 10 mM $MgSO_4$) with 1 mM L-arabinose at 30° C. to an $OD_{600}$ of ~0.6. The cells were then made electrocompetent by washing twice with ice-cold water, once with 10% glycerol, and concentrating the cells 100-fold in 10% glycerol. Electrocompetent cells (50 µl) were pulsed with ~100 ng of PCR product using the Gene Pulsar 1 (Bio-Rad, Hercules, Calif.). SOC media (12) was immediately added to the cells that were then incubated 2 h at 30° C. Cells were plated on LB with kanamycin and incubated overnight at 30° C. to select for transformants. PCR amplification using primers within the kanamycin resistance gene combined with genomic primers adjacent to the sequence of interest were used to verify that the resistance cassette integrated at the desired location.

Complementation of mcpI Knockout.

A pET100 TOPO® vector (Invitrogen, Grand Island, N.Y.) was used for inducible expression of the putative immunity gene. This gene was PCR amplified from *E. coli*-25 using primers that produce a 3' single-stranded overhang identical to the 5' end of the pET100 vector, allowing directional joining of our gene of interest and the vector. Ligation and transformation was conducted according to the instructions of the Champion™ pET Directional TOPO® Expression kit. Briefly, 2 µl of PCR product was added to 1 µl Salt Solution (provided in kit), 1 µl TOPO vector, and 2 µl sterile water. This reaction incubated at room temperature for 25 min and then was placed on ice for 30 min. An aliquot (3 µl) was added into 50 µl chemically competent Top10 *E. coli* and incubated on ice for 2 min. Cells were heat shocked for 30 sec at 42° C. then transferred to ice. SOC media (250 µl) was added and the cells were incubated 1 h at 37° C. Cells were then plated on LB agar containing ampicillin and incubated overnight at 37° C. Transformants were screened by PCR using the universal T7 forward and reverse primers to identify clones containing the pET100 vector with an insert. Five transformants were selected for sequencing to verify they contained the correct insert. Plasmid was then isolated using the PureYield™ Plasmid Miniprep System (Promega, Madison, Wis.) and transferred to a host cell by electroporation as described above. Transformants were selected by their growth on LB with ampicillin.

Transforming *E. coli*-4 with the PDI Plasmid.

The pPDIΔtraM plasmid was purified using the MiniPrep Express™ Matrix (MP Biomedicals, Solon, Ohio). *E. coli*-4 was then made electrocompetent and transformed (as described above for the gene deletion mutants) with pPDIΔtraM. Successful transformants were selected on LB with kanamycin and PCR verified for the presence of the PDI region.

Plasmid Mating Experiments.

*E. coli*-25ΔmcpM and *E. coli* K12 were grown overnight in LB media with kanamycin or nalidixic acid, respectively. Equal amounts of plasmid-bearing strain *E. coli*-25ΔmcpM were mixed with non-plasmid-bearing *E. coli* K12 and centrifuged for 3 min at 16,000×g. The cells were washed and concentrated 100-fold in 10 mM $MgSO_4$. Cell suspensions were then pipetted onto a nitrocellulose membrane placed on a non-selective LB-agar plate. Following 24 h incubation at 30° C., the cells were resuspended in sterile PBS and dilutions plated on LB-agar containing nalidixic acid and/or kanamycin. The conjugation efficiency was calculated by dividing the CFU of transconjugants by the CFU of donor cells. Plasmid profiles were prepared for a subset of transconjugants to confirm the presence of plasmid. Profiles were conducted as described by Kado and Liu (14). The same experiments, using kanamycin and tetracycline for selection, were then repeated using the K12 pPDIΔmcpM transconjugant and *E. coli*-6 to determine whether the plasmid is self-mobilizable.

RNA Isolation, First-Strand cDNA Synthesis, and Microcin RT-qPCR.

*E. coli*-25 encoding McpM was inoculated into 5 ml M9 minimal media containing tetracycline and incubated overnight at 37° C. One ml of overnight culture was inoculated into 300 ml of room temperature M9 media and incubated at 37° C. Aliquots containing approximately $10^8$-$10^9$ cells were removed immediately after inoculation (0 h), and 2 h, 4 h, 6 h, 8 h, 10 h, 12 h, and 24 h post-inoculation. Cells were pelleted by centrifugation at 4° C. and total RNA was isolated and DNase treated using RiboPure-bacteria kit (Ambion) according to manufacturer instructions. RNA concentrations were determined using a NanoDrop ND-1000 spectrophotometer. RNA samples from a given time course experiment were diluted to the same concentration as the least concentrated sample. To assess DNA contamination in RNA samples prior to cDNA synthesis and expression analysis, equivalent RNA concentrations to be used in the corresponding cDNA RT-qPCR reactions were run under identical conditions used for RT-qPCR analysis using polymerase sigma subunit rpoD primers (Table 1). RNA samples with cycle threshold (Ct) values less than 37.5 cycles were again treated with DNase and Ct values reanalyzed prior to cDNA synthesis. First-strand cDNA synthesis was completed using 8 µl of RNA (2-20 ng/µl), random hexamers and SuperScript III reverse transcriptase (Invitrogen) in a final reaction volume of 20 µl according to manufacturer instructions. To verify the specificity of the mcpM primers (Table 1), a single PCR product of the correct size (213 bp) was detected in PDI$^+$ strains but not in PDI$^-$ strains when analyzed on agarose gels. rpoD primers, described above, amplified a single PCR product of the correct size (336 bp) when analyzed on agarose gels from all PDI$^+$ and PDI$^-$ *E. coli* strains tested. The amplification efficiency of primer sets was then determined using plasmid DNA encoding their respective targets under identical conditions used for RT-qPCR.

All RT-qPCR reactions were performed as a single-plex reaction in triplicate in 96-well plates. Positive controls and no template controls were included in duplicate for each primer set. Each reaction was performed using 2 µl of cDNA, 500 nM final concentration per primer, and SsoFastEva Green Supermix (Bio-Rad) in a final volume of 20 µl. All PCR reactions were performed on a CFX96 Real-Time PCR Detection System with version 2.1 software (Bio-Rad) with the following cycling conditions: 95° C. for 30 s, 40 cycles of 95° C. for 1 s, 55° C. for 5 s, and 72° C. for 15 s. Normalized (ΔΔCt) microcin expression was automatically computed using the Bio-Rad CFX Manager Software version 2.1 using rpoD as the reference gene.

Example 2. PDI is Effective Against a Broad Range of *E. coli*

In this Example, PDI was shown to be effective against a broad range of *E. coli*. Because *E. coli* O157:H7 is represented by a diversity of genetic types (33) we first determined if the PDI phenotype was effective against the representative panel of strains. Strains representing bovine-biased and clinical-biased genotypes (33) from both the U.S. and New Zealand were highly susceptible to the PDI phenotype with an average reduction >5 log compared to the population for their respective monocultures (FIG. 1). Three strains of *E. coli* O26 were also tested, and similar reductions were found in population numbers (FIG. 1).

Example 3. Live/Dead Staining Indicated that PDI is Bactericidal

In this example, Live/dead staining indicated that PDI is bactericidal. Although susceptible cells show a substantial reduction in their CFU/ml following competition with PDI$^+$ strains, it was not clear if the effect is bacteriostatic or bactericidal. Live/dead staining was used in conjunction with flow-cytometry to address this question using *E. coli*-25 and *E. coli* O157:H7 Sakai in mono- or co-culture. The percent of dead cells detected from the two mono-cultures was 0.50±0.06% and 0.11±0.01%, respectively (mean±SEM). When co-cultured for six hours the percent of dead cells increased to 1.27±0.09% consistent with killing of *E. coli* O157:H7 Sakai. When this susceptible strain was co-cultured with a PDI$^-$ strain (*E. coli*-6), the percentage of dead cells was 0.33±0.03%. These results, which were based on 3 independently replicated assays, indicate that PDI functions by killing susceptible cells.

Example 4. The Microcin-Encoding Gene Cluster was Identified

In this example, the microcin-encoding gene cluster was identified. In addition to the two PDI$^+$ strains, *E. coli*-82 was identified from earlier work (16) as genetically similar (no differences) to *E. coli*-25 based on Xba-I macro-restriction, pulsed-field gel electrophoresis (PFGE) profile (unpublished data). Despite having a comparable genetic profile, *E. coli*-82 does not express the PDI phenotype. Genome sequencing of these two strains allowed an in-depth comparison that identified one relatively large region of sequence difference that was located on a large plasmid in *E. coli*-25. Although previous work using a different method did not detect the presence of plasmids in *E. coli*-25 (32), these results were verified by plasmid purification (14) and subsequent Southern analysis probing for mcpA (data not shown). PCR amplification of the PDI locus (primers available in Table 1) confirmed this region is present in the PDI$^+$ strains *E. coli*-25 and *E. coli*-264, but not the PDI$^-$ strains *E. coli*-6, *E. coli*-82, or *E. coli*-186.

Figure 2:
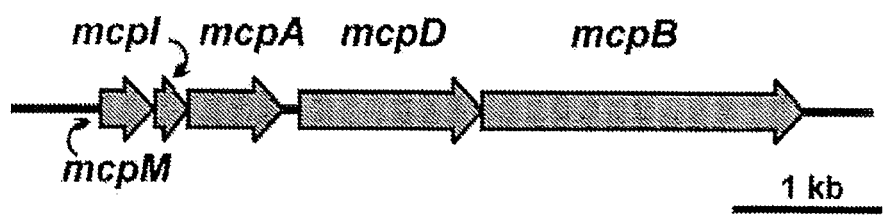
FIG. 2. Schematic of the putative PDI sequence (~5 kb). Whole genome sequencing identified a large plasmid containing a unique region that is present in PDI⁺ strains but not PDI⁻ strains (GenBank accession JQ901381) (SEQ ID NO:). Bioinformatics identified five open reading frames putatively corresponding to genes for microcin synthesis (mcpM and mcpA), immunity (mcpI), and export (mcpD and mcpB).

The *E. coli*-25 IncI1 microcin-containing plasmid is 98,809 bp with a G+C content of 49% and a coding density of 88%. Annotation of the 132 coding sequences revealed that most of the plasmid content is devoted to genes involved in transfer, including a Ira system and a pil system, or encodes proteins of unknown function. The novel region of interest is a locus of approximately 4,800 bp that encodes five genes (FIG. 2). Two genes, which we have designated mcpB and mcpD, encode homologs of HlyB and HlyD that are known to be the structural components of a microcin transfer system along with chromosomally encoded tolC (7, 10, 18, 26). McpA, which contains a CaaX protease domain (PF02517), is thought to be the "activity" protein that processes the microcin, encoded by mcpM, to its mature form prior to transfer from the cell. mcpI likely encodes an immunity protein. This novel sequence was also found in a recent GenBank submission of *E. coli* DEC10F (Accession AIGU01000076; version: AIGU01000076.1 GI:378122919; incorporated by reference herein in its entirety).

Example 5. Knockout Mutations from *E. coli*-25 Blocked PDI

Figure 3A:
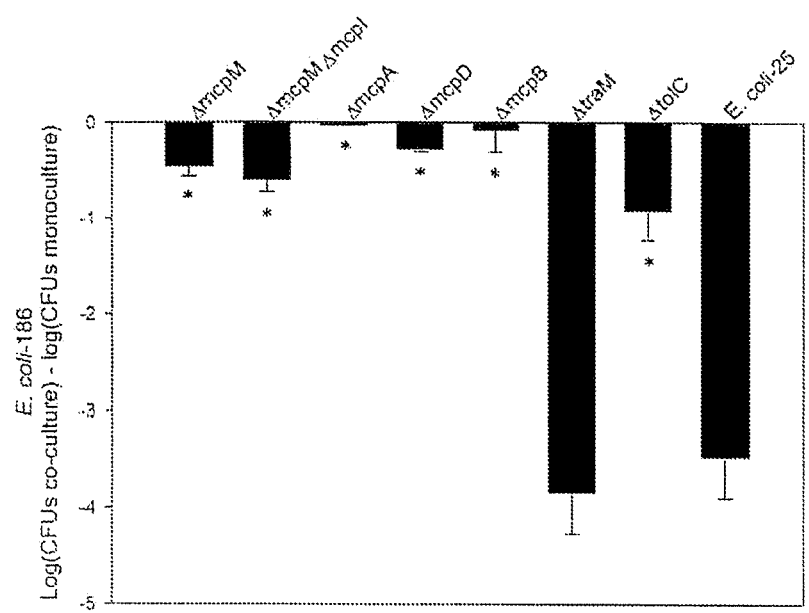
FIGS. 3A-B. Targeted gene deletion results in the loss of the PDI phenotype. A. CFUs of PDI⁻ *E. coli*-186 following co-culture with wild-type *E. coli*-25 or *E. coli*-25 knockout mutants. Results are expressed as the difference in CFUs of the sensitive strain grown in co-culture and monoculture. B. Competitions with PDI⁺ *E. coli*-264 indicate which knockout mutants no longer exhibit immunity to PDI. Immunity to PDI is restored in the mcpI complemented clone. Results are expressed as the difference of log CFUs during co-culture and individual culture. Experiments were conducted in triplicate with error bars representing the standard error of the mean. *, statistically significant ANOVA (p-value <0.01 with Dunnett's upper one-sided multiple-comparison test with control).
Figure 3B:
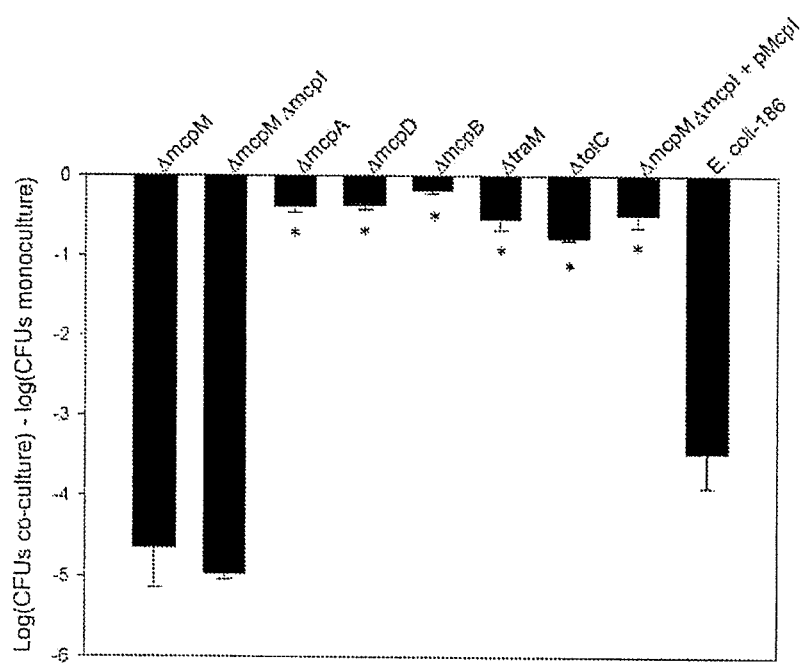

This example shows that knockout mutations from *E. coli*-25 blocked PDI. Four of the five putative microcin genes (FIG. 2) were individually knocked out in *E. coli*-25 to analyze their role in PDI. The mcpI gene knockout was constructed as a double knockout, ΔmcpM ΔmcpI. Each region of interest was replaced with a kanamycin resistant cassette and verified by PCR for the correct insertion site. Subsequently each knockout mutant was put into competition with the PDI$^-$ *E. coli*-186 to determine whether the deletion affected the PDI phenotype. CFU counts following co-culture in M9 minimal media showed that *E. coli*-186 was greatly inhibited by *E. coli*-25 but was no longer inhibited by the ΔmcpD, ΔmcpB, ΔmcpM, ΔmcpMΔmcpI, and ΔmcpA mutants (FIG. 3A). Conversely, each mutant was also competed with *E. coli*-264 to determine how each knockout affected immunity to PDI (FIG. 3B). Only the ΔmcpM and ΔmcpMΔmcpI strains became susceptible to PDI indicating that the other knockout strains retained immunity. Immunity was fully restored when mcpI was complemented back into the ΔmcpMΔmcpI strain, verifying that this gene is required for resistance to killing by PDI$^+$ strains (FIG. 3B). Expression of mcpI in a PDI$^-$ strain does not confer immunity, indicating this gene alone is insufficient to prevent inhibition from the microcin (data not shown).

Class II microcins are typically secreted by a T1SS and the presence of the putative ABC transporter and membrane-fusion genes, mcpB and mcpD, is consistent with this structure in *E. coli*-25. These secretion systems require co-expression of a chromosomally encoded TolC protein on the cell surface (7, 10, 18, 26). Consequently, a ΔtolC strain was constructed and this disrupted the ability of *E. coli*-25 to inhibit *E. coli*-186 (FIG. 3A) but it did not influence immunity (FIG. 3B). These results are consistent with the requirement for a T1SS for PDI function. To verify that the gene knockout procedure was not producing artifacts, a gene deletion in an unrelated region of the plasmid was also generated. As expected, deleting traM did not affect inhibition or immunity (FIG. 3).

Example 6. Transferring the PDI Plasmid to a Non-Inhibitor *E. coli* Conferred the Inhibitory Phenotype This example shows that transferring the PDI plasmid to a non-inhibitor *E. coli* conferred the inhibitory phenotype. Although the above knockout mutants verified that the genes involved with PDI had been identified, it was desirable to confirm from the mutants that all the genes unique to PDI were included on pPDI. Generating the traM mutant in *E. coli*-25 provided a selectable marker on pPDI that did not interfere with the PDI phenotype (see above). Following transformation with pPDIΔtraM, *E. coli*-4 acquired the ability to inhibit susceptible strains, and immunity to inhibition by *E. coli*-264 (Table 2).

Table 2 shows competition results of wild-type *E. coli*-4 and *E. coli*-4 carrying the PDI plasmid verifies the PDI genes are present on the plasmid. CFUs of PDI$^-$ *E. coli*-186 following co-culture with wild-type *E. coli*-4 or *E. coli*-4+ pPDI verifies the plasmid confers the inhibitory phenotype. Immunity to PDI is also maintained on the plasmid, as indicated by the ability of *E. coli*-4+pPDI to survive co-culture with the PDI$^+$ strain *E. coli*-264. Results are expressed as log CFUs/ml±the SEM of 3 replicates.

This data indicates that all the PDI-specific genes are present on pPDI. Nevertheless, there is a possibility that other chromosomally-encoded genes common to *E. coli*-25 and *E. coli*-264 are involved with PDI expression or function.

TABLE 2

Competition results of wild-type *E. coli*-4 and *E. coli*-4 carrying the PDI plasmid verified the PDI genes are present on the plasmid.

| Competition | Log$_{10}$(CFU)/ml | |
|---|---|---|
| | *E. coli*-4 | Competitor |
| *E. coli*-4 (PDI⁻) | | |
| vs. *E. coli*-186 (PDI⁻) | 8.83 ± 0.05 | 8.64 ± 0.06 |
| vs. *E. coli*-264 (PDI⁺) | 4.70 ± 0.28 | 9.14 ± 0.02 |
| *E. coli*-4 + pPDI | | |
| vs. *E. coli*-186 (PDI⁻) | 9.18 ± 0.06 | 4.03 ± 0.61 |
| vs. *E. coli*-264 (PDI⁺) | 8.88 ± 0.03 | 8.76 ± 0.02 |

Example 7. The PDI ΔmcpM Plasmid was Shown to be Self-Transmissible

This example shows that the PDI ΔmcpM plasmid is self-transmissible. Filter mating experiments between the ΔmcpA mutant and *E. coli* K12 showed the PDI plasmid is mobile with a conjugation efficiency ranging between $4.81 \times 10^{-6}$ and $3.66 \times 10^{-6}$. Plasmid profiles of K12 Kan® verified the presence of a single plasmid of ~100 Kb, consistent with the PDI plasmid. Another series of conjugation experiments between the K12 transformants and *E. coli*-6 confirmed that the plasmid is self-transmissible. Using this assay conjugation of the PDI plasmid was not detected when there was a functional microcin system, presumably because recipient cells are killed.

Example 8. The Kinetics of the Expression of mcpM were Determined

This example shows the kinetics of the expression of mcpM. Expression of the PDI phenotype has been observed throughout log-phase growth, but this function appears to subside when cells enter stationary phase (32). This earlier work was limited by the analytic sensitivity of the phenotypic assay and thus to better describe the kinetics of microcin expression we employed a quantitative PCR assay. RT-qPCR data confirmed that expression of the microcin increases rapidly during the log-phase growth and drops off rapidly in stationary phase (FIG. 4).

Example 9. cDNA Sequences and Protein Sequences for mcpM, mcpI, mcpA, mcpD, and mcpB were Determined This example shows the cDNA sequences and protein sequences encoded by mcpM, mcpI, mcpA, mcpD, and mcpB:

cDNA sequence and protein sequence for mcpM
(SEQ ID NOS: 23 and 24)

```
ATGGCAAATATAAGAGAATTAACTTTAGATGAGATAACGCTTGTCAGCGGAGGAAC

AGCAACTTTGAAGGTGGCCCCCGTAATGACCGTTCCAGTGGGGCTCGTAACTCACTG

GGTCGAAACGCACCAACTCATATTTATAGTGATCCAAGCACTGTAAAATGCGCTAAC

GCTGTATTTAGTGGAATGATTGGTGGTGCGATCAAAGGAGGTCCCATAGGAATGGC

AAGAGGTACCATTGGTGGAGCCGTTGTTGGTCAATGTCTCTCAGATCATGGTAGTGG

AAATGGAAGTGGTAACAGAGGAAGTTCCAGTAGTTGTTCAGGTAATAATGTTGGCG

GAACATGTAACCGATAA

M A N I R E L T L D E I T L V S G G N A N S N F E G G P R N D R S S G A R N S L G R N

A P T H I Y S D P S T V K C A N A V F S G M I G G A I K G G P I G M A R G T I G G A V

V G Q C L S D H G S G N G S G N R G S S S S C S G N N V G G T C N R Stop
``` cDNA sequence and protein sequence for mcpI
(SEQ ID NOS: 25 and 26)

```
ATGGAGGGCGCTACTATGTTTATTAAATTACTTTCCTTTATATGTGGTTTGTTACTGG

GATTTGCACTATTGAGTGGCTCCTCTGTTATTGATTTATACTGGTTTTCACTACCTTCC

GAGTTTTCAAAGATTGTAGTCATGCTGATCACTCTTTTTTCCACGGCAAGATTCATGG

ACTATATCATAGAAAAAATAAGAACAATCTCCGCGAAATAG

M E G A T M F I K L L S F I C G L L L G F A L L S G S S V I D L Y W F S L P S E F S K I

V V M L I T L F S T A R F M D Y I I E K I R T I S A K Stop
``` cDNA sequence and protein sequence for mcpA
(SEQ ID NOS: 7 and 28)

```
ATGAATGATAACATATATAAATATAGTAAAGATAATGCGATAGCGaTCTTCTACTTG

TTGTTATATCAACAGTTGTGATATTCACACCGGCATTCACCATACAATATATTGGTTT

GGATCTGGCATTTTCCTTTGTCTTTATTACTGAAATTTTAATGTCAACTTCATTTTATA

TTTTTTACTTAAGAAGAATACCAGGTTGTAAAATCACCATAAAGACAAATGCGAAA

ACATTAAAGCTATTAGTAATATCATTTGCTGTGATTGCTCTCATGCAACTGCTTATTT
```

```
TTGCTTATAGAGACAATTTGAACAATAGTGAATCAACTTCACTTAATTGGATTGAAA
TATTTATACTGGTCCTGACAGTTCCGTATTATGAAGAAATTGTTTACCGAACATGTCT
ATTCGGTCTTCTATGTACGACTTATaAAAAAGAATTATTTAcCCCCTGCGTGTGTACA
TCTTTAtTTTTCTGCCTGATGCATCCGCAGTATTATAATGTGGCTGATCAAATTATTCT
GTTTATTATGTCAATGTTATTGTTGAATATAAGGATTTGCAGTAAGGGGATTTTCTAT
CCAATGCTGTTACATGCGGGAATAAACGGCTTTGTTATATTGTTAAATATATTATAG
```

M N D N I Y K Y S K D N A I A F L L L V V I S T V V I F T P A F T I Q Y I G L D L A F S F
V F I T E I L M S T S F Y I F Y L R R I P G C K I T I K T N A K T L K L L V I S F A V I A L
M Q L L I F A Y R D N L N N S E S T S L N W I E I F I L V L I V P Y Y E E I V Y R I C L
F G L L C T T Y K K E L F T P C V C T S L F F C L M H P Q Y Y N V A D Q I I L F I M S
M L L L N I R I C S K G I F Y P M L L H A G I N G F V I L L N I L Stop cDNA sequence and protein sequence for mcpD (SEQ ID NOS: 29 and 30)

```
ATGAATATATTCAGAAGTGAAGCAATAGAACATCATAATGACACTGAATATGGTGA
CATTATTTTACCAACATCATTTAGCCTATCCGTATGTGCAACAGTTACATTATTCATT
ATGTTAAGTCTGACTGTATTCATATATTACGGTAGCTATACAAGGAAAGCGCATCTT
ACAGGTATCGTCATGCCCTCATCAGGACTGGTAAAAATAATTCCTCAATATGCAGGA
TATGTAACACAACTGACTGTATCCGAAGGAGAACACGTAACTGCAGGGACACAACT
CTATCATATAAGTGGAGAACATTATAACGGTAACGGAACTGGCACATTAGCAACGA
TGAGTATTTCCCTGAAGACTCAGTATATTATGTTGGCCTCCCAGCAATCCTTTGAGTC
GCGAGATAATAGTCAACAACAGGAAGCCATACGGCAAAGGATGATATCACTTGAGC
CGCAAATAAGAAGTGCAGAACAAAGACTTCAGCTTGCTGAACGTCAGGCAGAACTG
GCTATATCCGTCATGGAACGCTATAAAAAATTGGCTGGTACGCATTATGTGTCAGAT
ATCGAATTCCAACAGAAACAAATTGATGTTTCTGCCGCTCAACAAAACGTTGAAGAT
CAGCGTCAGGGGCTTCTCCAGTTACATACTGCAATGGACACAGCCAAAGATGAACT
AAATCATCTTATTGTTCAGGGGAAAAGCCGTAAAGCAGAACTCGACAGACAATTGC
AGGTGCTAAAACAACAACAGGATGAACTCGCCGGACAAGAAAAATTTACACTGAGG
GCTCCAGTATCCGGGACTATTGCTGCTGTACTGATCAAACAGGGGCAGTCTGTGAAA
GCATCTGAACCGGTCATGACTCTCATTCCCGATAATGCTCATTTACAAATTGAGCTTT
ATGCTACCAGCCAGAAAGCCGGTTTTATCCGACCAGGTCAACGGGTATCTCTGAAGT
TTTCGGCCTTCCCTTATCAGAAATTTGGTATCCAGTACGGCACAATTCGTAAAATCA
GTCATACGACTCTGGCTCCTTCCGACTTATTACCAGTTTCACCCGTCACATGGAAAG
AAAACGAAGGGCATTATCGCGTTATTGTTGAACCTGAAAATACATTTATATTTGCAT
ACGGaAAAAAAGAACCGCTAAGACCAGGCATGACTCTGGAAGGAGACGTCAACCTT
GATACTCGTCATTTATGGGAATGGCTGACAGAGCCCCTATGGAGCATGAAAGGAAA
TCTGTAA
```

M N I F R S E A I E H H N D I E Y G D I I L P T S F S L S V C A T V I L F I M L S L T V F
I Y Y G S Y T R K A H L T G I V M P S S G L V K I I P Q Y A G Y V T Q L T V S E G E H
V T A G T Q L Y H I S G E H Y N G N G T G T L A T M S I S L K T Q Y I M L A S Q Q S F
E S R D N S Q Q Q E A I R Q R M I S L E P Q I R S A E Q R L Q L A E R Q A E L A I S V M
E R Y K K L A G T H Y V S D I E F Q Q K Q I D V S A A Q Q N V E D Q R Q G L L Q L H

T A M D T A K D E L N H L I V Q G K S R K A E L D R Q L Q V L K Q Q Q D E L A G Q E

K F T L R A P V S G T I A A V L I K Q G Q S V K A S E P V M T L I P D N A H L Q I E L Y

A T S Q K A G F I R P G Q R V S L K F S A F P Y Q K F G I Q Y G T I R K I S H T T L A P

S D L L P V S P V T W K E N E G H Y R V I V E P E N T F I F A Y G K K E P L R P G M T

L E G D V N L D T R H L W E W L T E P L W S M K G N L Stop cDNA sequence and protein sequence for mcpB (SEQ ID NOS: 31 and 32)

ATGGAATCAATAAACTGGAAAGTAAGGAAACAACTACCCGTTATCCGTCAAACCGA

ATCAGCTGAATGCGGTCTGGCGTGTCTGGCTATGATTGCCTGCTGGCATGGACTGAA

AACAGATTTATCGACATTACGGGAACGTTTCAATATAGGTATTCAGGGAATGACGCT

ACAAAGGTTGATCGAATGTGCAGCGTCCATCCATTTATCATCACGTGCAGTTCGTCT

GGAACCCGAAGATCTGAGGTGTCTTAATCTTCCATCTATTCTGCACTGGGATATGAA

CCATTTCGTCGTTCTCCATAAAGTTCGGGGAAACCGGTTATACATCCATGATCCGGA

CAGAGGAAAAATTACAATAAGTCTGTTGGACGCAGGTAAGCATTTTACAGGAGTGG

CACTGGAATTAACTCCAGCCAGTGATTTCACCCCCCGGAACGAGAGAAAAAAATCC

ACCTGCGTCAACTGACAGGGAAAACCCCGGGGCTTTTAGCATCAATGACaAAAATTA

TTATTTTTGCTCTGGCCCTTGAGATTCTGGCTTTAGGTGGTCCACTTCTTAATCAACT

GGTAATTGATGAAGTTCTGGTCGCAGCAGACAGAAGTCTATTGTATGTCATTATAGT

GGCACTACTGTTGTTATCACTCATACAATTATTACTCTCCCTAGCACGACAATGGGC

AACGATCAGTTTATCCGTCAATTTTAACATGCAATGGACTGCCAGAGTTTTCCATCA

TCTTGTAAGACTCCCTCTTGCATGGTTCGATGCCCGAAGTAAAGGAAGTATTAATGC

CCGTTTTGAAGCAGTAGATATAATCCAGCAGGCGCTGACAACGCAGGTTCTTGAAG

GCATTCTGGATATGCTACTTATTGTGACTGCTCTTTGCATGATGCTGTTGTATAGCCC

AGGAATGACATTAATCGCAGTAATTGCAGCTATTATATATGGCGCACTGAGAGCATT

GTGGTATCCGGCTTTACGGCAATCTGTTGAAGATGTCTGGGATGCAGGAACTAAGGA

GTCGGGGCATTTTCTCGAAACCCTTAACGGCATTCAGAGTCTGAGAATCAACGGTGT

AACTATTCACAGAGAAGCGGCCTGGCTGAACCTCAACGTTACCCGCAGAAACACAC

AGCTACGCCAGAATCGTTTACAAATGAGCTATGAACTGACGCATACACTGACGGAA

AGTGTAGTTTCAGCCATTATTTTGTGGCAGGGAGCAGTAGAAGTGCTGGATGGGACA

TTTACCGTGGGTATGTTGGTTGCTTACTTATCCTATCAGATGCGTTTTTCATCCAGTA

TAAGCAATCTGACTGATAACTTTTTTTCCTGGCGCATGCTTGATGTTTATAACGAGAG

ACTTGCCGATATTGTGCTAACACCACAGGAAGGTCACCAGAATCAGCACCATTGGG

CAAACCATAATGAAACAATATCTGCAAGCCAGTACAGAGAACATAAATATGATAAT

ACCCATCCACCATTACTTATCGaAAAAATAACATTTAGCCATAAGGGCGCAGATAAA

CCCATATTGGATAACGCGTCACTAATGCTCTTTCCTGGAGAAATATTAGCAATAACA

GGTAAATCAGGATGTGGCAAATCAACATTGGTAAAGCTTATTCTTGGAATTCATACA

CCAAGTGAAGGAAGAATTAATGCATTTGGCATACCACATACACATTCTGATTATTTT

CAGGTTCGTCAACGAATTGGCACTGTATTGCAAGATGACTATCTTTTCAAAGGTTCT

ATAGCTGATAATATAATGTTTTTTAGCGAAATTAGAGATCATGAACACATGCGTAAA

TGCGCAAGTCTGGCACTTATAGACAGTGATATTATGGCAATGCCAATGGGCTATCAA

CATTACTTGGAGAAACCGGAGGGGGACTTTCAGGTGGTCAGAAGCAACGTATTCTA

CTGGCAAGAGCACTGTATAAAAAACCCGGTCTATTATTACTGGACGAAGCAACCAG

-continued

TCATCTTGATGTGGAAAGTGAAATAGAAATAAGCCAGACATTACGCCAACTCGGAT

TCCTGTTCTGTTAATAGCTCATCGACCAGAAACAATAGCATCCGCAGACAGAGTTCT

ATCTGAGAGATGGTCACTTTTCGGAAATAACATATCGACCTGCCAGAACTCATAATA

TAAATAATCACCCCAACAGGAGGTGA

M E S I N W K V R K Q L P V I R Q T E S A E C G L A C L A M I A C W H G L K T D L S

T L R E R F N I G I Q G M T L Q R L I E C A A S I H L S S R A V R L E P E D L R C L N L

P S I L H W D M N H F V V L H K V R G N R L Y I H D P D R G K I T I S L L D A G K H F

T G V A L E L T P A S D F T P R N E R K K I H L R Q L I G K I P G L L A S M T K I I I F

A L A L E I L A L G G P L L N Q L V I D E V L V A A D R S L L Y V I I V A L L L L S L I

Q L L L S L A R Q W A T I S L S V N F N M Q W T A R V F H H L V R L P L A W F D A R

S K G S I N A R F E A V D I I Q Q A L T T Q V L E G I L D M L L I V T A L C M M L L Y

S P G M T L I A V I A A N Y G A L R A L W Y P A L R Q S V E D V W D A G T K E S G H

F L E T L N G I Q S L R I N G V T I H R E A A W L N L N V T R R N T Q L R Q N R L Q M

S Y E L T H T L T E S V V S A I I L W Q G A V E V L D G T F T V G M L V A Y L S Y Q

M R F S S S I S N L T D N F F S W R M L D V Y N E R L A D I V L T P Q E G H Q N Q H H

W A N H N E T I S A S Q Y R E H K Y D N T H P P L L I E K I T F S H K G A D K P I L D N

A S L M L F P G E I L A I T G K S G C G K S T L V K L I L G I H T P S E G R I N A F G I P

H T H S D Y F Q V R Q R I G T V L Q D D Y L F K G S I A D N I M F F S E I R D H E H M

R K C A S L A L I D S D I M A M P M G Y Q T L L G E T G G G L S G G Q K Q R I L L A

R A L Y K K P G L L L L D E A T S H L D V E S E I E I S Q T L R Q L G I P V L L I A H R P

E T I A S A D R V L Y L R D G H F S E I T Y R P A R T H N I N N H P N R R

Example 10. Sequence for Plasmid Containing the Unique 4.8-Kb Operon Region that is Present in PDI+ Strains but not PDI− Strains (GenBank Accession: JQ901381)

This sequence for the plasmid containing the unique 4.8-kb operon region that is present in PDI+ strains but not PDI− strains was determined (GenBank accession JQ901381) and is presented as SEQ ID NO: 33. The region covering mcpM, mcpI, mcpA, mcpD, and mcpB is presented as SEQ ID NO: 34. Within SEQ ID NO: 34, the nucleotide positions of individual operon components are as follows: mcpM (41253-43442); mcpI (43443-44695): mcpA (44798-45433); mcpD (45438-45654); and mcpB (45663-46026).

REFERENCES FOR BACKGROUND AND EXAMPLES 1-10

1. Aoki, S. K., R. Pamma, A. D. Hemday, J. E. Bickham, B. A. Braaten, and D. A. Low. 2005. Science 309:1245-8.
2. Asensio, C., and J. C. Perez-Diaz. 1976. Biochem Biophys Res Commun 69:7-14.
3. Bullock, J. O., F. S. Cohen, J. R. Dankert, and W. A. Cramer. 1983. J Biol Chem 258:9908-12.
4. Dassanayake, R. P., D. R. Call, A. A. Sawant, N. C. Casavant, G. C. Weiser, D. P. Knowles, and S. Srikumaran. 2010. Appl Environ Microbiol 76:1008-13.
5. Datsenko, K. A., and B. L. Wanner. 2000. Proc Natl Acad Sci USA 97:6640-5.
6. Duquesne, S., D. Destoumieux-Garzon, J. Peduzzi, and S. Rebuffat. 2007. Nat Prod Rep 24:708-34.
7. Gaggero, C., F. Moreno, and M. Lavina. 1993. J Bacteriol 175:5420-7.
8. Garrido, M. C., M. Herrero, R. Kolter, and F. Moreno. 1988. EMBO J 7:1853-62.
9. Gentschev, I., G. Dietrich, and W. Goebel. 2002. Trends Microbiol 10:39-45.
10. Gilson, L., H. K. Mahanty, and R. Kolter. 1990. EMBO J 9:3875-84.
11. Gratia, A. 1925. C. R. Soc. Biol. (Paris) 93:1040-1041.
12. Hanahan, D. 1983. J Mol Biol 166:557-80.
13. Hardy, K. G., G. G. Meynell, J. E. Dowman, and B. G. Spratt. 1973. Mol Gen Genet 125:217-30.
14. Kado, C. I., and S. T. Liu. 1981. J Bacteriol 145:1365-73.
15. Kawamura, T. 1997. Rinsho Byori 45:865-8.
16. Khachatryan, A. R., T. E. Besser, and D. R. Call. 2008. Appl Environ Microbiol 74:391-5.
17. Khachatryan, A. R., D. D. Hancock, T. E. Besser, and D. R. Call. 2006. Appl Environ Microbiol 72:443-8.
18. Lagos, R., M. Baeza, G. Corsini, C. Hetz, E. Strahsburger, J. A. Castillo, C. Vergara, and O. Monasterio. 2001. Mol Microbiol 42:229-43.
19. Lederberg, J., and E. L. Tatum. 1946. Nature 158:558.
20. Lemonnier, M., B. R. Levin, T. Romeo, K. Garner, M. R. Baquero, J. Mercante, E. Lemichez, F. Baquero, and J. Blazquez. 2008. Proc Biol Sci 275:3-10.
21. Linton, K. J., and C. F. Higgins. 1998. Mol Microbiol 28:5-13.
22. Lwoff, A., F. Jacob, E. Ritz, and M. Gage. 1952. C R Hebd Seances Acad Sci 234:2308-10.
23. Martinez, M. C., C. Lazdunski, and F. Pattus. 1983. EMBO J 2:1501-7.

24. Nomura, M., and M. Nakamura. 1962. 7:306-9.
25. Ohno-Iwashita, Y., and K. Imahori. 1982. J Biol Chem 257:6446-51.
26. Pons, A. M., F. Delalande, M. Duarte, S. Benoit, I. Lanneluc, S. Sable, A. Van Dorsselaer, and G. Cottenceau. 2004. Chemother 48:505-13.
27. Pugsley, A. P., and S. T. Cole. 1986. J Gen Microbiol 132:2297-307.
28. Reeves, P. 1965. The Bacteriocins. Bacteriol Rev 29:24-45.
29. Riley, M. A., and D. M. Gordon. 1992. J Gen Microbiol 138:1345-52.
30. Riley, M. A., Y. Tan, and J. Wang. 1994. Proc Natl Acad Sci USA 91:11276-80.
31. Riley, M. A., and J. E. Wertz. 2002. Annu Rev Microbiol 56:117-37.
32. Sawant, A. A., N. C. Casavant, D. R. Call, and T. E. Besser. 2011. Appl Environ Microbiol 77:2345-51.
33. Shringi, S., A. Garcia, K. K. Lahmers, K. A. Potter, S. Muthupalani, A. G. Swennes, C. J. Hovde, D. R. Call, J. G. Fox, and T. E. Besser. 2012. Infect Immun 80:369-80.
34. Smarda, J. 1962. Experientia 18:271-3.
35. Trueblood, C. E., V. L. Boyartchuk, E. A. Picologlou, D. Rozema, C. D. Poulter, and J. Rine. 2000. Mol Cell Biol 20:4381-92.
36. Wilkens, M., J. E. Villanueva, J. Cofre, J. Chnaiderman, and R. Lagos. 1997. J Bacteriol 179:4789-94.

Example 11. Microcin MccPDI Reduces the Prevalence of Susceptible *Escherichia coli* in Neonatal Calves MccPDI microcin producing *E. coli*-25 or the equivalent knockout strains were co-inoculated into calves with susceptible *E. coli*-186 to investigate the function of MccPDI in vivo. MccPDI-producing *E. coli*-25 out-competed *E. coli*-186 (P=0.003), consistent with MccPDI being responsible for antibiotic resistant *E. coli*-25 competitive advantage in calves. The increasing prevalence of antibiotic resistant bacteria presents a major challenge for both human and animal health. High levels of antimicrobial usage in livestock potentially plays an important role in amplifying and retaining antibiotic resistance genes in bacterial populations (6, 7, 13). Nevertheless, even in the absence of antibiotic use resistant bacteria can persist (2, 5, 8). A previous study showed that *E. coli* strains with resistance to streptomycin, sulfadiazine, and tetracycline (SSuT) were the dominant *E. coli* found in calves at the Washington State University (WSU) dairy (10). Mixtures of these SSuT *E. coli* isolates, including strain *E. coli*-25, demonstrated a fitness advantage in dairy calves and in broth culture over antibiotic susceptible strains (10). The mechanism allowing these strains to dominate in calves was unknown, but was not associated with antimicrobial resistance traits (9). Recently we showed *E. coli*-25 produces the novel microcin, MccPDI, that is responsible for killing susceptible *E. coli* in vitro. MccPDI-production allows *E. coli*-25 to inhibit a diversity of *E. coli*, including olates enterohemorrhagic (EHEC) and enterotoxigenic (ETEC) strains (4, 11). The spectrum of MccPDI activity makes *E. coli*-25 attractive as a probiotic against pathogenic bacteria with potential for prophylactic, therapeutic, and food safety applications. Consequently, we tested the hypothesis that an MccPDI-producing *E. coli*-25ΔtraM strain will limit colonization of dairy calves by the MccPDI-susceptible *E. coli*-186, while MccPDI-knockout strain, *E. coli*-25ΔmcpMΔmcpI would exhibit no selective advantage in vivo (4).

This study was conducted in the large animal isolation facilities at WSU under a WSU Institutional Animal Care and Use Committee approved protocol. Calves inoculated with the same strains were housed in groups when possible. Bulk milk was fed two to three times daily with one feeding containing 1 tbsp. of milk non-antibiotic containing supplement (10). Calves were pre-screened for nalidixic acid-, kanamycin-, and chloramphenicol-resistant *E. coli* using methods described below. If resistant bacteria were detected the calf was not used in the study. Kanamycin- and chloramphenicol-resistant *E. coli*-25 mutants were generated (Table 1) to allow the use of calves that carried either kanamycin or chloramphenicol resistant flora, but did not carry both. Each calf (<3 days old) was orally inoculated with $10^9$ CFU of each competing *E. coli* strain. Inoculum was prepared by pelleting overnight cultures of each strain, resuspending the cells in fresh LB, and mixing the cultures immediately before inoculation. If the inoculated strains were not detected at one day post-inoculation, a second dose was administered on day two. Day one refers to the day following the final inoculation. The trial included two groups of calves with group one (n=4) receiving MccPDI knockout *E. coli*-25ΔmcpMΔmcpI and *E. coli*-186 and group two (n=7) receiving MccPDI-producing *E. coli*-25ΔtraM and *E. coli*-186; chance enrollment of calves with incompatible antibiotic resistant flora led to rejection of more calves from group one.

Figure 5:
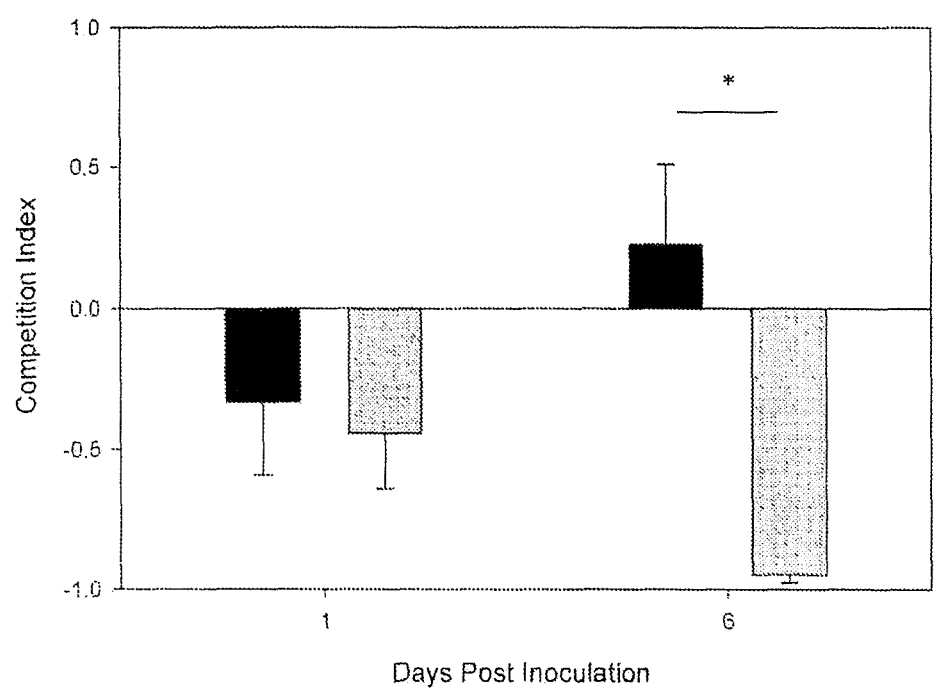
FIG. 5. MccPDI-producing *E. coli*-25 inhibits the growth of susceptible *E. coli*-186 in neonatal calves. A competition index (CI) was calculated as (X−Y)/(X+Y), where X is the CFU of *E. coli*-25ΔmcpMΔmcpI or *E. coli*-25ΔtraM colonies and Y is the CFU of *E. coli*-186 colonies. A CI approaching +1 indicates the *E. coli*-25 mutant is the dominant strain and a CI approaching −1 indicates *E. coli*-186 is dominant. The mean CI for the positive (black bars; *E. coli*-25ΔtraM and *E. coli*-186; n=7)) and negative control (white bars; *E. coli*-25ΔmcpMΔmcpI and *E. coli*-186; n=4) calves on day one and day six. Error bars correspond to the standard error of the mean and the asterisk shows significant difference between MccPDI-producing and non-producing groups (P=0.003).

Fecal samples were collected directly from the rectum of each calf immediately following inoculation (day 0) and each day for six days (10). Within 4 h of collection ten-fold serial dilutions of each sample were prepared in sterile PBS and plated on MacConkey agar to determine total colony forming units (CFUs) of lactose fermenting enteric bacteria with colony morphology consistent with *E. coli*. MacConkey agar supplemented with kanamycin (50 μg/ml), tetracycline (50 μg/ml), chloramphenicol (34 μg/ml) and tetracycline (50 μg/ml), or nalidixic acid (30 μg/ml) was used to enumerate the test strains present in the fecal samples. A competition index (CI) was calculated to compare the fitness of competing strains (FIG. 5). PCR was used to confirm the identity of the *E. coli*-25 mutants by pairing primers within the resistance cassette (3) with locus-specific primers (Table 3; n=368). The putative *E. coli*-186 isolates (n=172) recovered from the fecal samples were confirmed by pulsed-field gel electrophoresis analysis (1).

TABLE 3

E. coli strains and PCR primer sequences used in this work.

| E. coli Strain | Genotype/phenotype | Strain-specific primer | Ref. |
|---|---|---|---|
| 25ΔmcpMΔmcpI | SSuT$^r$ Chlor$^r$ ΔmcpMΔmcpI PDI$^-$ | mcpM_mcpI fwd: CAAACAACCGATAGGGGAAA (SEQ ID NO: 36) c2: GATCTTCCGTCACAGGTAGG (SEQ ID NO: 37) | This work |

TABLE 3 -continued

E. coli strains and PCR primer sequences used in this work.

| E. coli Strain | Genotype/phenotype | Strain-specific primer | Ref. |
|---|---|---|---|
| 25ΔmcpMΔmcpI | SSuT<sup>r</sup> Kan<sup>r</sup> ΔmcpMΔmcpI PDI<sup>−</sup> | mcpM_mcpI<br>fwd: CAAACAACCGATAGGGGAAA (SEQ ID NO: 38)<br>k2: CGGTGCCCTGAATGAATGAACTGC (SEQ ID NO: 39) | (4) |
| 25ΔtraM | SSuT<sup>r</sup> Chlor<sup>r</sup> ΔtraM PDI<sup>−</sup> | traM<br>fwd: GTTCTGCCATCCTGCGTTAT (SEQ ID NO: 40)<br>c1: TTATACGCAAGGCGACAAGG (SEQ ID NO: 41) | This work |
| 25ΔtraM | SSuT<sup>r</sup> Kan<sup>r</sup> ΔtraM PDI<sup>−</sup> | traM<br>fwd: GTTCTGCCATCCTGCGTTAT (SEQ ID NO: 42)<br>k1: CAGTCATAGCCGAATAGCCT (SEQ ID NO: 43) | (4) |
| 186 | Wild-type; Nal<sup>r</sup> PDI<sup>−</sup> | | (11) |
| O157:H7 6-E12057 | Wild-type: Nal<sup>r</sup> Cip<sup>r</sup> | rfb fwd: AAGATTGCGCTGAAGCCTTT (SEQ ID NO: 36)<br>rfb rvs: CATTGGCATCGTGTGGACAG (SEQ ID NO: 36) | (12) |

At six days post-inoculation calves were euthanized and five to ten centimeter lengths of the cecum, spiral colon, descending colon, and rectal-anal junction (RAJ) were collected. All fecal matter was removed by rinsing the tissue in sterile PBS. A 6 mm sterile biopsy punch was used to collect a sample and make a 1:10 dilution (sa/vol) in PBS. The tissue was homogenized, serially diluted, and plated onto MacConkey agar supplemented with antibiotics.

A previous study with E. coli-25 indicated the microcin-producing strain E. coli-25ΔtraM should have a distinct advantage over the susceptible strain E. coli-186 (10). As expected, by day six, E. coli-25ΔtraM dominated E. coli-186 (CI=0.22, P=0.003; FIG. 1). In contrast, the microcin-knockout strain E. coli-25ΔmcpMΔmcpI was significantly less fit than E. coli-186 (CI=−0.95; FIG. 5). Notably, different treatment outcomes were asymmetric with the CI for E. coli-25ΔtraM (0.22) being a smaller magnitude than the competition index for E. coli-25ΔmcpMΔmcpI (−0.95). This could possibly be explained by the presence of native MccPDI-expressing strains that would also compete with E. coli-25ΔtraM while enhancing inhibition of the susceptible E. coli-25ΔmcpMΔmcpI.

Figure 6:
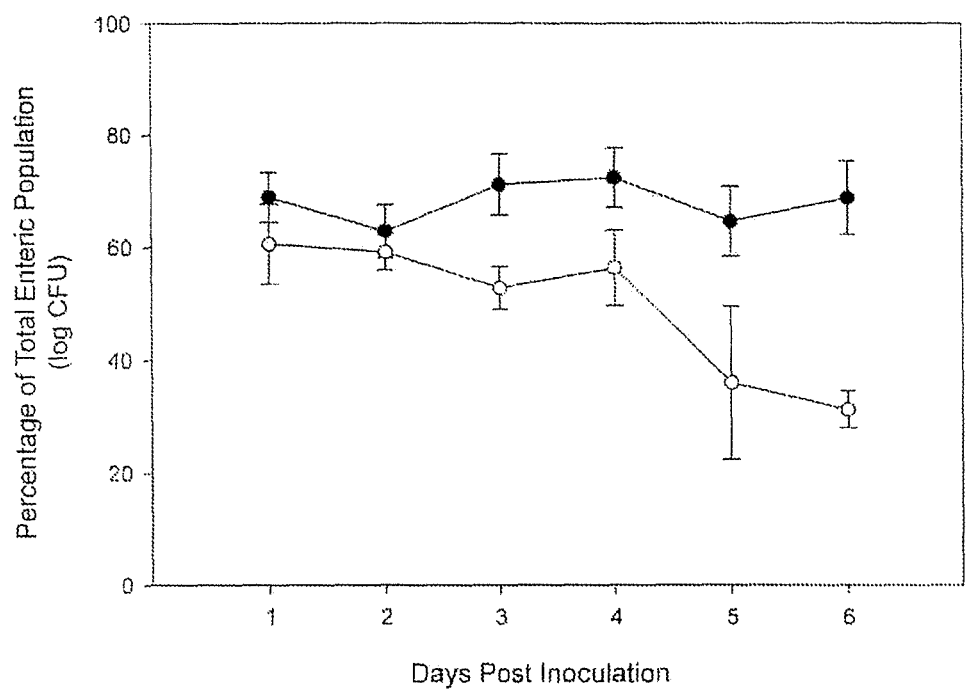
FIG. 6. The production of MccPDI contributes to the fitness of *E. coli*-25 within a calf. Each data point represents the percentage of the *E. coli*-25 mutant relative to the total lactose fermenting enteric CFU at the corresponding day post inoculation. Closed circles represent *E. coli*-25ΔtraM (n=7 calves) and open circles correspond to *E. coli*-25ΔmcpMΔmcpI (n=4 calves). Error bars represent the standard error of the mean.

If most native E. coli strains are susceptible to MccPDI, and if the MccPDI producing strain has a fitness advantage relative to non-producing strains of E. coli, then the MccPDI-producing strain should be found in greater numbers relative to the total E. coli population. We enumerated the CFU for the E. coli-25 mutants relative to the CFU lactose-fermenting enteric bacteria in the fecal samples. E. coli-25ΔmcpMΔmcpI accounted for <0.2% of the total lactose-fermenting enteric bacteria by day six, whereas E. coli-25ΔtraM consistently comprised >2% of this population throughout the trial (repeated measures ANOVA, P=0.01; FIG. 6). There was no difference between the total number of lactose-fermenting bacteria between the two groups (P=0.96). These results confirm the MccPDI-producing strain has a selective advantage over the non-producing strain in this model.

Figure 7A:
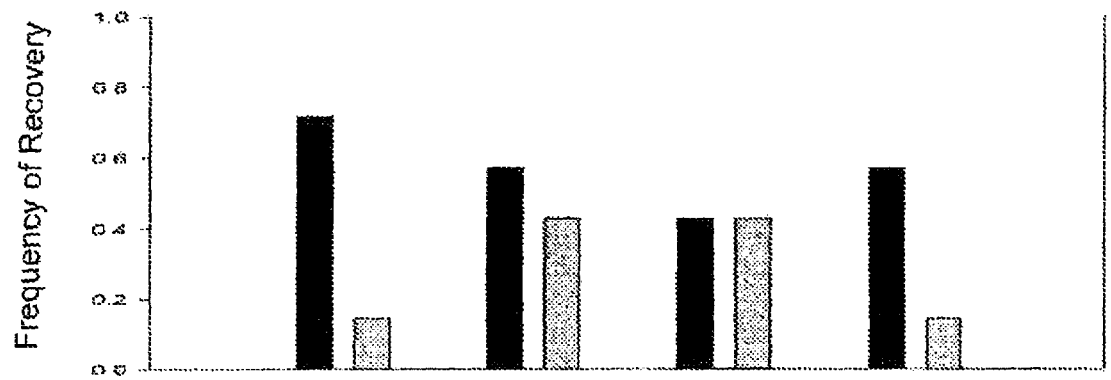
FIGS. 7A and B. MccPDI-producing *E. coli*-25 is recovered more frequently from GI tissues. Bars represent the frequency of recovery for competing strains in each trial at four segments of the GI tract: A. MccPDI-producing *E. coli*-25ΔtraM (black) and *E. coli*-186 (grey), B. MccPDI-knockout *E. coli*-25ΔmcpMΔmcpI (black) and *E. coli*-186 (grey).
Figure 7B:
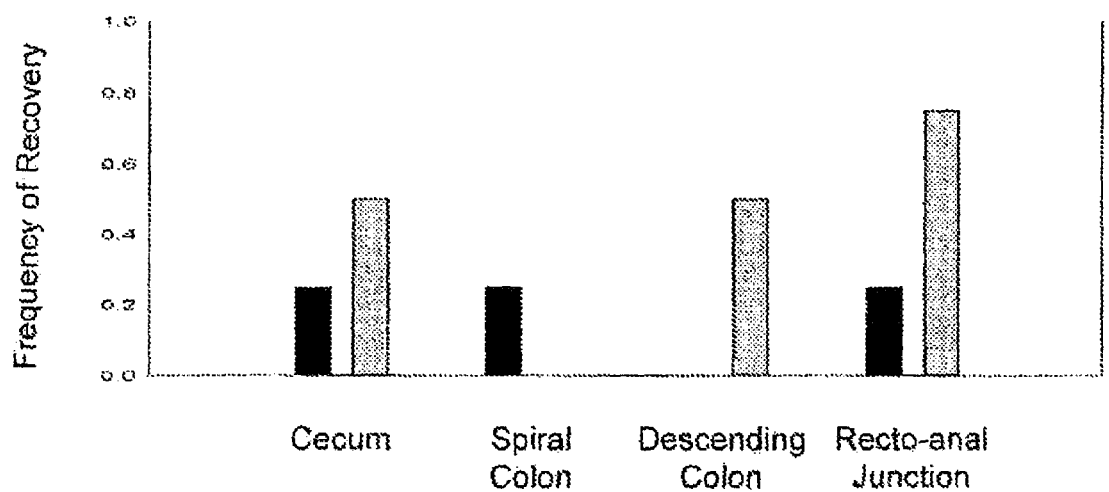
Figure 8A:
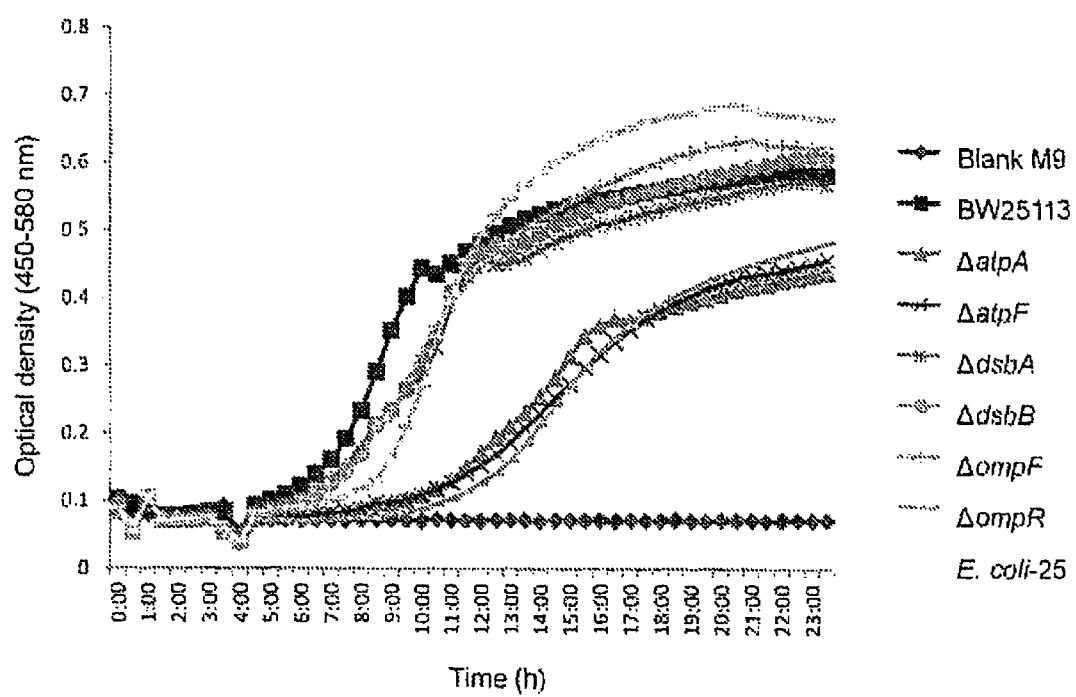
FIGS. 8A and B. Growth curves of *E. coli*-25, *E. coli* BW25113, and the MccPDI-resistant mutants ΔatpA, ΔatpF, ΔdsbA, ΔdsbB, ΔompF, and ΔompR when cultured in M9 minimal media (A) or LB media (B).
Figure 8B:
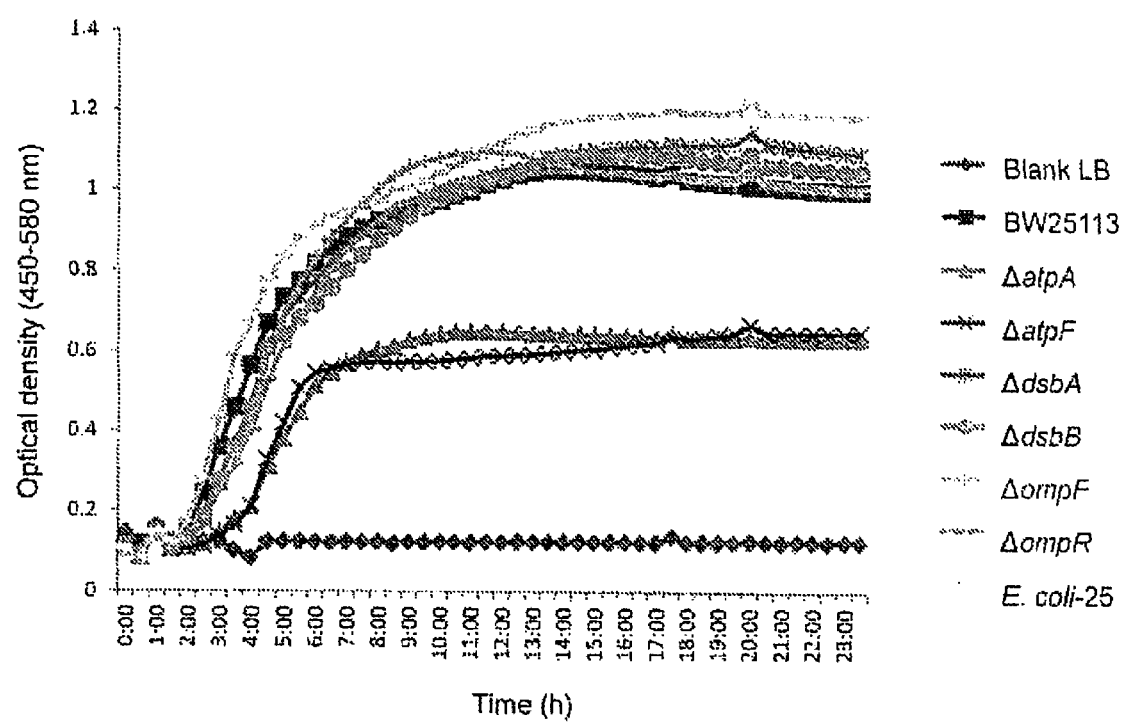

E. coli was consistently recovered from tissues of the lower gastrointestinal tract (GI). The inoculated strains, however, were typically only detected at counts just above the detection level. E. coli-25ΔtraM strain was recovered more frequently compared to E. coli-186, whereas E. coli-25ΔmcpMΔmcpI was recovered at a frequency similar to the E. coli-186 strain (P=0.01 and P=0.052, respectively; paired t-test; FIGS. 7A and B). There were no apparent differences in the frequency of detection between tissues (ANOVA, P=0.41). These results are consistent with E. coli-25ΔtraM having an in vivo fitness advantage allowing better colonization within calves.

Sixteen arbitrarily selected E. coli from each calf were tested for strain identity. Of calves inoculated with E. coli-25ΔtraM and E. coli-186, we detected the expected strains in 5 and 6 calves, respectively. We only recovered the expected strains from 1 of 4 calves for the non-microcin treatment group.

Bacteriocin-producing bacteria present an attractive means to control pathogens in food animal production. E. coli-25ΔtraM reduces the shedding of E. coli-186 confirming that MccPDI is functional in vivo. Changing the timing and doses of E. coli-25ΔtraM may potentially improve the treatment effect because it is unknown when or at what concentration MccPDI functions in vivo. Future research should investigate the use of multiple bacteriocinogenic strains, increased doses, or pre-inoculation of E. coli-25ΔtraM to limit pathogenic E. coli populations in cattle.

REFERENCES FOR EXAMPLE 11

1. Broschat, S. L., D. R. Call, M. A. Davis, D. Meng, S. Lockwood, R. Ahmed, and T. E. Besser. 2010. J Clin Microbiol 48:4072-82.
2. Chaslus-Dancla, E., G. Gerbaud, M. Lagorce, J. P. Lafont, and P. Courvalin. 1987. Antimicrob Agents Chemother 31:784-8.
3. Datsenko, K. A., and B. L. Wanner. 2000. Proc Natl Acad Sci USA 97:6640-5.

4. Eberhart, L. J., J. R. Deringer, K. A. Brayton, A. A. Sawant, T. E. Besser, and D. R. Call. 2012. Appl Environ Microbiol 78:6592-9.
5. Enne, V. I., D. M. Livermore, P. Stephens, and L. M. Hall. 2001. Lancet 357:1325-8.
6. Hinton, M., D. J. Hampson, E. Hampson, and A. H. Linton. 1985. J Hyg (Lond) 95:77-85.
7. Jackson, C. R., P. J. Fedorka-Cray, J. B. Barrett, and S. R. Ladely. 2004. Appl Environ Microbiol 70:4205-10.
8. Khachatryan, A. R., T. E. Besser, D. D. Hancock, and D. R. Call. 2006 Appl Environ Microbiol 72:4583-8.
9. Khachatryan, A. R., D. D. Hancock, T. E. Besser, and D. R. Call. 2006. Appl Environ Microbiol 72:443-8.
10. Khachatryan, A. R., D. D. Hancock, T. E. Besser, and D. R. Call. 2004. Appl Environ Microbiol 70:752-7.
11. Sawant, A. A., N. C. Casavant, D. R. Call, and T. E. Besser. 2011. Appl Environ Microbiol 77:2345-51.
12. Shringi, S., A. Garcia, K. K. Lahmers, K. A. Potter, S. Muthupalani, A. G. Swennes, C. J. Hovde, D. R. Call, J. G. Fox, and T. E. Besser. 2012. Infect Immun 80:369-80.
13. Singer, R. S., R. Finch, H. C. Wegener, R. Bywater, J. Walters, and M. Lipsitch. 2003. Lancet Infect Dis 3:47-51.

Example 12. Identification of a Receptor and Associated Proteins Required for MccPDI to Recognize and Inhibit Susceptible *E. coli*

The *E. coli* Keio Collection, a single-gene deletion library, was screened for mutants able to grow in the presence of the MccPDI producing strain *E. coli*-25. The Keio Collection includes individual gene knockouts for all non-essential genes that are expressed by *E. coli* strain BW25113, which is also sensitive to PDI. Screening of the full library followed by verification experiments demonstrated that mutants of atpA, atpF, dsbA, dsbB, ompF, or ompR were no longer sensitive to PDI, indicating these genes are required for MccPDI function.

Materials and Methods
Strains and Culture Conditions.

*E. coli*-25 [streptomycinR, sulfadiazineR, tetracyclineR, (SSuTR)] (26), *E. coli* S17, *E. coli* BW25113 and the *E. coli* BW25113 gene-deletion library (Keio Collection, kanamycinR, Thermo Scientific) were used in this study. *E. coli* BW25113 was purchased from the *Coli* Genetic Stock Center (CGSC, Yale) and it is susceptible to antibiotics employed in the current study. To isolate this strain in a mixed culture, *E. coli* BW25113 was made nalidixic acid resistant by passaging 5 times with increasing concentrations until it was capable of growing in 30 µg/ml nalidixic acid. Unless stated otherwise, all strains were cultured in either Luria Broth (LB) or M9 Minimal Media at 37° C. shaking 250 rpm. Antibiotics were used at the following concentrations: tetracycline (50 µg/ml), chloramphenicol (34 µg/ml), kanamycin (50 µg/ml), nalidixic acid (30 µg/ml) and ampicillin (100 µg/ml).

Screening the Keio Collection for Loss of PDI.

The Keio collection of *E. coli* knockouts (Thermo Scientific) was employed to identify genes associated with susceptibility to MccPDI. Each mutant was grown overnight at 37° C. without shaking in a 96-well plate containing 150 µl fresh LB (50 µg/ml kanamycin) per well. A 10 ml culture of *E. coli*-25 was also started at this time in LB (50 µg/ml tetracycline) and incubated at 37 C with shaking (250 rpm). The following day each mutant was individually placed into co-culture with *E. coli*-25 in a sterile, U-bottom 96-well plate with 200 µl M9 minimal media per well. A 96-pin replicator (Boekel Scientific) was used to transfer overnight cultures (~1 µl) of each strain for competition experiments. The replicator was sterilized 3× between each use by submerging pins into 70% ethanol and flaming. The *E. coli*-25 culture was poured into a sterile plastic trough and transferred in the same manner. Competition cultures were incubated overnight at 37° C., shaking at 100 rpm. Approximately 24 h later co-cultures (~1 µl) were transferred onto LB agar containing kanamycin or tetracycline to select for the Keio strains or *E. coli*-25, respectively. The plates were incubated at 37° C. for at least 6 h. Growth on tetracycline verified the presence of *E. coli*-25 in the culture. No growth on kanamycin indicated that the Keio knockout strain being tested was still susceptible to PDI. Growth of a Keio mutant strain on the kanamycin plate indicated putative identification of gene knockouts that were no longer susceptible to PDI.

Competition Assays and Enumeration of Resistant *E. coli* Mutants.

To confirm detection of PDI-resistant strains from the Keio collection, prospective strains were grown overnight in LB with antibiotic selection. Each mutant strain culture was then added (10 µl) with *E. coli*-25 culture (10 µl) to 2 ml M9 media. These co-cultures were incubated at 37° C. for 8 to 24 h. To determine the CFUs of each strain following competition, serial dilutions of the co-cultures were prepared in a 96-well plate containing sterile PBS and then spotted (5 µl) onto LB agar supplemented with kanamycin or tetracycline. Agar plates (3 per enumerated dilution) were incubated overnight at 37° C. and colonies were tallied for total colony forming units (cfu).

PCR Verification of the Knockout Mutants.

Primers corresponding to sequence up- and downstream the deleted gene (Table 3) were designed to verify the location of the kanamycin cassette insertion. Reactions were carried out with an initial denaturing step at 95° C. for 4 min, followed by 30 cycles of 95° C. for 20 s, 55° C. for 20 s, 72° C. for 1 min 20 s, and a final extension at 72° C. for 5 min. The PCR products were evaluated using electrophoresis alongside an O'gene Ruler 1 Kb plus ladder (Thermo Scientific) to determine the amplicon sizes. The wild-type (non-mutant) *E. coli* BW25113 was included as a control in addition to a no-template negative control.

Regenerating Resistant Mutants in *E. coli* S17.

To validate the findings from the Keio library screen, we generated independent mutants in a PDI sensitive strain, *E. coli* S17. The methods used to create these mutants were previously described by Datsenko and Wanner (2000; Proc Natl Acad Sci USA 97:6640-5) and were the same used to create the Keio Collection (Baba et al. Mol Syst Biol 2:2006 0008). The new gene-deletion mutants were generated with the insertion of chloramphenicol resistance (cat) instead of a kanamycin cassette as was used for the Keio Collection. PCR primers were designed to amplify the chloramphenicol cassette from plasmid pKD3 and contained extensions identical to the sequence flanking the gene of interest (Table 3). *E. coli* S17 was transformed with the pKD46 plasmid, which facilitates homologous recombination between the gene of interest and the PCR amplicon. *E. coli* S17+pKD46 was grown in super optimal broth (2% bacto-trypton, 0.5% yeast extract, 8.56 mM NaCl, 2.5 mM KCL, 10 mM $MgCl_2$) with ampicillin and 0.1 mM arabinose to induce the proteins necessary for homologous recombination. These induced cells were then made competent and electroporated with the chloramphenicol amplicon containing the requisite flanking sequences. Transformed cells were recovered at 30° C. and were plated onto LB agar with chloramphenicol to select for successful deletion mutants. PCR was used to verify the insertion site of the chloramphenicol cassette (Table 3) using PCR conditions as describe above.

Growth Curves.

All strains, including the gene knockout mutants, were assessed for their ability to grow in M9 and LB media. Growth curves were run on a BioScreen C (Oy Growth Curves Ab Ltd). Each strain was grown individually overnight in LB media with antibiotic selection. These cultures were used to inoculate (1:1.000 dilution) M9 minimal media or LB broth without antibiotics. Cultures incubated for 24 h at 37° C. with continuous shaking and optical density (450-580 nm) measured every 30 min.

Fluorescent Labeling and Microscopy.

E. coli-25ΔmcpMΔmcpI, E. coli-25ΔtraM, and E. coli-186 were each transformed with a vector expressing cherry red fluorescent protein (pFPV-mCherry) or GFP (pFPV25). Competition assays (described above) were conducted with the fluorescently labeled cells; one with McPDI-producing E. coli-25ΔtraM+pFPV-mCherry and PDI-susceptible E. coli-186+pFPV25, and another with McPDI-nonproducing E. coli-25ΔmcpMΔmcpI+pFPV-mCherry and PDI-susceptible E. coli-186+pFPV25. Additionally, these competitions were repeated where each strain carried the opposite plasmid to ensure the results were not caused by either strain differentially expressing either fluorescent protein. Individual cultures were run as controls. Each culture was visualized at 24 h using a fluorescent scope at 60× magnification.

Results

Six E. coli mutants in the Keio Collection were resistant to PDI. The single gene deletion E. coli mutant library, called the Keio Collection, was used to identify genes putatively associated with susceptibility to McPDI. Approximately 3,985 mutants were screened using a high-throughput 96-well plate method. Following two rounds of screening using these methods, six mutants were identified as potentially being resistant to inhibition by E. coli-25. These mutants were then placed into a 2 ml competition experiment (M9 media) with E. coli-25 and CFUs were subsequently enumerated after 24 h co-culture. Mutants that were able to grow to a population density >$10^5$ CFU were considered resistant to PDI and these included the mutants with a deletion in atpA, atpF, dsbA, dsbB, ompF, or ompR (Table 4).

TABLE 4

Gene-knockout mutants that are no longer susceptible to killing by E. coli-25. PCR primer sequences amplify the gene of interest and were used to verify the specific knockouts. The CFUs represent the average of triplicate competition assays.

| Gene Disrupted | Primers: Gene-specific primers and flanking sequences (H1$^a$ and H2$^b$) | Gene Function | Co-culture with E. coli-25 (CFU) |
| --- | --- | --- | --- |
| atpA | atpA fwd: TGCTGCGATGGAAAAACGTC (SEQ ID NO: 36) atpA rvs: TTCTGGACGCTTGCGATCTT (SEQ ID NO: 37) H1: CTTGCAGACGTCTTGCAGTCTTAAGGGGACTGGAGC (SEQ ID NO: 38) H2: GCCTTGCGGCCTGCCCTAAGGCAAGCCGCCAGACGT (SEQ ID NO: 39) | ATP synthase, F1 complex, α subunit; also called papA | $4.10 \times 10^5$ |
| atpF | atpF fwd: ATCGCTGTAGGTCTGGGTCT (SEQ ID NO: 40) alpF rvs: ATGTCCTGCCAGCGTTCTAC (SEQ ID NO: 41) H1: AATATCAGAACGTTAACTAAATAGAGGCATTGTGCT (SEQ ID NO: 42) H2: CTACCGTAATAAATTCAGACATCAGCCCCTCCCTCC (SEQ ID NO: 43) | ATP synthase, F0 complex, b subunit; also called papF | $6.51 \times 10^6$ |
| dshA | dsbA fwd: AGCGGCAGGATGCATTATCA (SEQ ID NO: 44) dsbA rvs: GGGAAGATTACTGGCTGCGA (SEQ ID NO: 45) H1: GTGAATATTTCACGGGCTTTATGTAATTTACATTGAA (SEQ ID NO: 46) H2: AATTAACACCTATGTATTAATCGGAGAGAGTAGATC (SEQ ID NO: 47) | Periplasmic protein disulfide isomerase (disulfide bond formation) | $2.37 \times 10^7$ |
| dsbB | dsbB fwd: CAATGGCAGATGAAGCGAGC (SEQ ID NO: 48) dsbB rvs: TGCAAATGGGCTGGATAGCA (SEQ ID NO: 49) H1: AACTGCGCACTCTATGCATATTGCAGGGAAATGATT (SEQ ID NO: 50) H2: CAGGAAAAAGCGCTCCCGCAGGAGCGCTGAAGGGA (SEQ ID NO: 51) | Disulfide oxidoreductase (disulfide bond formation) membrane protein; oxidizes periplasmic DsbA | $3.97 \times 10^7$ |

TABLE 4 -continued

Gene-knockout mutants that are no longer susceptible to killing by E. coli-25. PCR primer sequences amplify the gene of interest and were used to verify the specific knockouts. The CFUs represent the average of triplicate competition assays.

| Gene Disrupted | Primers: Gene-specific primers and flanking sequences (H1[a] and H2[b]) | Gene Function | Co-culture with E. coli-25 (CFU) |
|---|---|---|---|
| ompF | ompF fwd: CGCTATCAGGGTAACGGGAG (SEQ ID NO: 52) ompF rvs: AGCACTTTCACGGTAGCGAA (SEQ ID NO: 53) H1: GTTGTCAGAATCGATCTGGTTGATGATGTAGTCAAC (SEQ ID NO: 54) H2: GTGATCGTCCCTGCTGTTAGTAGCAGGTACTGCA (SEQ ID NO: 55) | Outer membrane protein, porin | $9.50 \times 10^6$ |
| ompR | ompR fwd: TGTTGCGAACCTTTGGGAGT (SEQ ID NO: 56) ompR rvs: AGCAAGGTGACGATGAGCAA (SEQ ID NO: 57) H1: GGGCAAATGAACTTCGTGGCGAGAAGCGCAATCGCC (SEQ ID NO: 58) H2: CTTACAAATTGTTGCGAACCTTTGGGAGTACAAACA (SEQ ID NO: 59) | Transcriptional regulatory protein OmpR; Response regulator for osmoregulation | $2.12 \times 10^6$ |

[a]E. coli S17 gene-specific sequences are shown. For gene deletion mutants, flanking sequences also included the chloramphenicol primer site: TGTGTAGGCTGGAGCTGCTTCG, (SEQ ID NO: 60)3' to the E. coli S17 specific sequence.
[b]E. coli-25 gene-specific sequences are shown. For gene deletion mutants, flanking sequences also included the chloramphenicol primer site: CATATGAATATCCTCCTTA, (SEQ ID NO: 61)3' to the E. coli S17 specific sequence.

Example 13. Microcin PDI Regulation and Post-Translational Modifications are Unique Among Known Microcins In this study, we used competition assays with gene knockout and complemented strains, QPCR assays, western blots and electrophoretic mobility assays to demonstrate that expression of the microcin PDI is induced in low osmolarity conditions and is regulated by the EnvZ/OmpR system through the binding of the phosphorylated OmpR to the mcpM promoter region. The phosphorylated OmpR may recognize three different binding sites within this promoter region. This system of regulation is similar to that of OmpF and unique from other described microcins. Site-directed mutagenesis revealed that the McpM precursor peptide includes two leader peptides that undergo sequential cleavage (positions G17/G18 and G35/A36) during export through the type I secretion system. Competition assays showed that these cleaved products are required for the PDI phenotype. McpM has four cysteines within the mature peptide and experimental data showed that the first two cysteines are necessary for the microcin PDI inhibition of susceptible cells. DAPI staining of fluorescently-labeled strains showed that the microcin PDI likely induces membrane permeability of susceptible cells. Without being bound by theory, the data suggests that McpM forms a multimer within the periplasm of susceptible cells where it damages membrane integrity. Together these data combined with previous work indicates that MccPDI is unique amongst the microcins that have been described to date.

Introduction

Like bacteriocins from Gram-positive bacteria, microcins are generally derived from precursor peptides that are composed of a C-terminal core region and an N-terminal leader peptide. The leader peptide is typically cleaved during the process of export (Kolter & Moreno, 1992. Duquesne et al., 2007). For example, the Colicin V precursor protein (a class IIa microcin) includes a double-glycine leader peptide, consisting of 15 amino acid residues, which is cleaved during export by the CvaA/CvaB/TolC export machinery (Gilson et al., 1990) (Havarstein et al., 1994; Zhong et al., 1996).

Microcin PDI (MccPDI), a newly identified microcin, is of particular interest because it inhibits the growth of a broad diversity of E. coli including EHEC serotypes O157:H7 and O26 (Sawant et al., 2011). The inhibitory phenotype has been called "proximity-dependent inhibition" (PDI) because inhibition only occurs when the microcin-producing cells are located in close proximity to sensitive cells (Sawant et al., 2011). Whole-genome sequence analysis has identified five open-reading frames: mcpM and mcpA (microcin synthesis), mcpI (immunity) and mcpD and mcpB (export) (Eberhart et al., 2012). The number and organization of the genes resembles that of the class IIa microcins. Gene deletions verified that five plasmid encoded genes and the chromosomally located to/C are responsible for the PDI phenotype. To date, however, gene regulation, protein maturation and protein function have not been determined for MccPDI.

In this study, we demonstrate that the expression of microcin MccPDI is responsive to extracellular osmolarity and is regulated by the EnvZ/OmpR system. Maturation of the MccPDI effector protein, McpM, involves two sequential cleavage events, and once exported it appears that McpM interacts with susceptible cells resulting in increased cell membrane permeability.

Material and Methods

Bacterial strains, media and growth conditions.

E. coli strains were cultured in LB-Lennox medium (LB broth) (Difco) or in M9 minimal medium (6 g/L Na2HPO4, 3 g/L KH2PO4, 0.5 g/L NaCl, 1 g/L NH4Cl, 2 mg/L thiamine, 1 mM MgSO4, 0.1 mM CaCl2, and 0.2% glucose) at 37° C. with shaking (200 rpm). Unless otherwise indicated, antibiotics were added to media at the following concentrations: tetracycline (Tet), 50 µg/ml; chloramphenicol (Cm), 34 µg/ml; kanamycin (Kan), 50 µg/ml; nalidixic acid (Nal), 30 µg/ml; and ampicillin (Amp), 100 µg/ml. LB broth with different salt concentrations were made by mixing 10 g/L Bacto-tryptone, 5 g/L yeast extract and NaCl at indicated concentrations.

DNA Manipulation and Mutant Construction.

Extraction of E. coli genomic DNA was accomplished using a Dneasy® Blood & Tissue kit following the manufacturer's instruction (Qiagen). Plasmid DNA was purified using a QIAprep® Spin Miniprep Kit (Qiagen). Conventional PCR included DreamTaq® Green PCR Master Mix (Thermo Scientific) while preparative PCR was used for plasmid construction using Platinum PCR SuperMix High Fidelity (Invitrogen) according to the manufacturer's protocol. Deletion cassettes for chromosomal in-frame deletions were first generated using the splice-overlap-extension method (Heckman & Pease, 2007), which joins two 400-600 bp PCR fragments corresponding to genomic sequences flanking the gene(s) of interest. The deletion cassettes were subsequently cloned into a suicide plasmid (pDM4) by using standard cloning procedures (Milton et al., 1996) followed by confirmation with DNA sequencing. The resulting constructs were individually electroporated into E. coli S17-1 λpir, after which they were introduced by conjugation into MccPDI-producing E. coli-25. Mutant strains were selected on LB plates containing Cm and Tet followed by a 10% sucrose selection process. Gene deletion was confirmed by PCR using primers located just outside of the deleted sequence. Plasmids for complementation (pMMB207 and pCR2.1) and overexpression (pPAL7) were constructed by using standard cloning procedures and all inserts were fully sequenced to confirm construct assembly. For site-directed mutagenesis, primers were designed by using (EbaseChanger and were then used to generate point mutation plasmids with a Q5 Site-Directed Mutagenesis Kit (New England Biolabs) following the manufacturer's protocol. These constructs were introduced into their target strains by electroporation.

Competition Assays.

Bacterial strains were grown individually overnight in LB media with appropriate antibiotics. Equal volumes of each competing strain were inoculated at 1:200 into either fresh LB medium with different salt concentrations or M9 medium. The cultures were mixed and incubated at 37° C. for 12 h. When necessary. IPTG (100 µM unless specified otherwise) and antibiotics (chloramphenicol or ampicillin) were added during the competition. Monocultures of each competing strain were also prepared as controls by inoculation into the appropriate media at the same dilution. To estimate the number of colony forming units (CFUs) for each strain following competition, a 6×6 drop-plate method was employed (Chen et al., 2003) with triplicate counts for each competition experiment (technical replicates were averaged before analysis).

RNA Isolation and qPCR.

Expression was quantified for mcpA, mcpB, mcpM, mcpI and tolC at 4, 8, 12 and 24 h. Briefly, a cell pellet was collected by centrifugation from 1.0-1.5 Ml broth culture. This was resuspended in RNAwiz® reagent (350 µL; Bacteria Ribopure kit; Ambion). Primary organic extraction was carried out as per manufacturer's instructions. The RNA was treated with RQ1-RNase-free DNase (Promega) for 30 min at 37° C., followed by a second organic extraction using TRIzol LS (Invitrogen) as per manufacturer's instructions. The final RNA was quantified using a NanoDrop™ 2000 Spectrophotometer (Thermo Scientific). All RNA extractions were confirmed as "DNA free" by subjecting them to a qPCR reaction with primers for rpoD (without cDNA synthesis). Any samples for which a Ct value of <38 cycles was generated were treated a second time with DNase and were re-extracted as described above. RT reactions were performed utilizing iScript Supermix (BioRad) as per manufacturer's instructions with 500 ng of RNA in a total volume of 20 µL. The resultant cDNA was diluted 1:10 with the addition of 180 µL of ultra-pure water. Diluted cDNA (5 µL) was used as template in each qPCR reaction. qPCR reactions included SsoAdvance SYBR Mastermix (2×) (BioRad). Mastermix (10 µL) was combined with 5 µL of cDNA template and 200 nM of each primer in a final volume of 20 µL. All primer pairs were run using the same cycling parameters: initial denaturation at 95° C. for 2 min, followed by 40 cycles of 55° C. for 1 min and 95° C. for 15 s. Fluorescent signal was recorded during the annealing/extension step (55° C.). A melt-curve analysis was performed on all reactions starting at 75° C. and increasing 0.5° C./cycle, with a pause and fluorescence detection at each temperature for 5 s. All assays were run in triplicate and each condition was run in biological duplicate. rpoD served as the housekeeping gene for normalization purposes.

Electrophoretic Mobility Shift Assays (EMSA).

DNA fragments 1-8 (see results) were prepared by PCR and were then purified by using a QIAquick® PCR purification kit (Qiagen). Fragments 9-10 were obtained by annealing oligonucleotides in annealing buffer (10 mM Tris pH 8.0, 50 mM NaCl, 1 mM EDTA). Briefly, equal volumes of complementary oligonucleotides (at equimolar concentration) were mixed in a 1.5 ml microfuge tube and placed in a heat block at 95° C. for 5 min. The heat block along, with the samples, was removed from the apparatus and allowed to cool for 1 h to room temperature. The resulting double-stranded DNA was separated on a 2.0% agarose gel and purified using QIAquick gel extraction kit (Qiagen). All fragments were quantified using a NanoDrop™ 2000 Spectrophotometer before EMSA experiments. The OmpR and XRE (control) proteins were expressed and purified using the Profinity eXact System. Concentration of purified proteins was estimated using a micro-BCA protein assay kit (Thermo Scientific). The purified proteins were mixed with the DNA fragments at different concentrations in 20 µL of binding buffer [10 mM Tris (pH 7.5), 100 mM KCl, 10 mM MgCl2, 1 mM DTT, 5% glycerol]. Binding reactions were incubated at room temperature for 30 min before adding 5 µL of 5× loading buffer. The samples were electrophoresed on 5% native TBE gels (BioRad) for 45 min at 100 V followed by staining with ethidium bromide.

Western Blot Analysis.

Protein samples from bacterial pellets and cell fractions were denatured in boiling water for 5 min in tricine sample buffer (BioRad). SDS-PAGE was used to separate proteins with either Any kD Tris-glycine precast gels or a 16.5% Tris-Tricine precast gels (BioRad) prior to western blotting. The Tris-Tricine gels were used to improve resolution for McpM. A Trans-Blot turbo transfer starter system (BioRad) was used to transfer proteins to a low-fluorescence polyvinylidene fluoride (LF-PVDF) membrane. Primary antibodies anti-Histag (1:2500, Novagen), anti-DnaK (1:5000, Abcam) were used with secondary goat anti-mouse antibody (1:5000, DyLight 488 conjugate) to visualize proteins on western blots. A ChemiDoc MP Imaging System (BioRad) was used to detect fluorescent signal.

Supernatant Protein Precipitation.

Bacterial strains were grown 10 h at 37° C. (200 rpm) in M9 broth (50 ml) supplemented with appropriate antibiotics. Supernatants were filtered through 0.45-µm PVDF syringe filters, and the proteins in the supernatant were precipitated by adding 20% (vol/vol) trichloroacetic acid (TCA) followed by incubation on ice for 1 h. Precipitated protein was pelleted by centrifugation (12,000×g for 1 h), washed with acetone for 15 min, dried, and suspended in Tricine sample buffer.

Fluorescent Labeling and DAPI Staining.

To construct pFPV-tdTomato, the gfpmut3 gene in pFPV25.1 (Valdivia & Falkow, 1996) was replaced with the tdTomato gene (Clontech) using primers tdtomato_XbaI and tdtomato_SphI. Standard cloning procedures were used and sequencing was used to verify results. E25ΔtraM:kan and E25ΔmcpMΔmcpI:kan were transformed with the pFPV25.1-gfpmut3 expressing green fluorescent protein (GFP), while target strain BW25113 was transformed with the pFPV-tdtomato expressing red fluorescent protein (tomato red). Competition assays (described above) were conducted with the fluorescently labeled cells, and individual monocultures were run as controls. After 2 h and 6 h incubations, 1 ml samples were taken from each of the cultures and 4,6-Diamidino-2-phenylindole dihydrochloride (DAPI) (Thermo Scientific) stain was added at a final concentration of 0.25 μg/ml for 10 min at room temperature. The stained bacteria were pelleted by centrifugation for 1 min at 12,000×g and re-suspended into the same volume of PBS buffer. Cells were then immobilized onto poly-L-lysine coated glass slides (Sigma) for 20 min and covered with glass coverslips. Cells were observed and images were captured by using an inverted fluorescence microscope (EVOS, Advanced Microscopy Group).

Statistical Analysis.

All qPCR results were processed using the Δ-Δ Ct method (Livak & Schmittgen, 2001) with the resultant fold change/biological replicate analyzed using an ANOVA with a Bonferroni multiple comparison post-hoc test (NCSS 2007; LLC. Kaysville, Utah). Other comparisons were made by using ANOVA with a Dunnett's one-way multiple comparisons posthoc test (SigmaPlot version 12.5; Systat Software, Inc., San Jose, Calif.).

Results

McPDI is Regulated by the EnvZ/OmpR Two-Component Regulatory System.

Figure 9A:
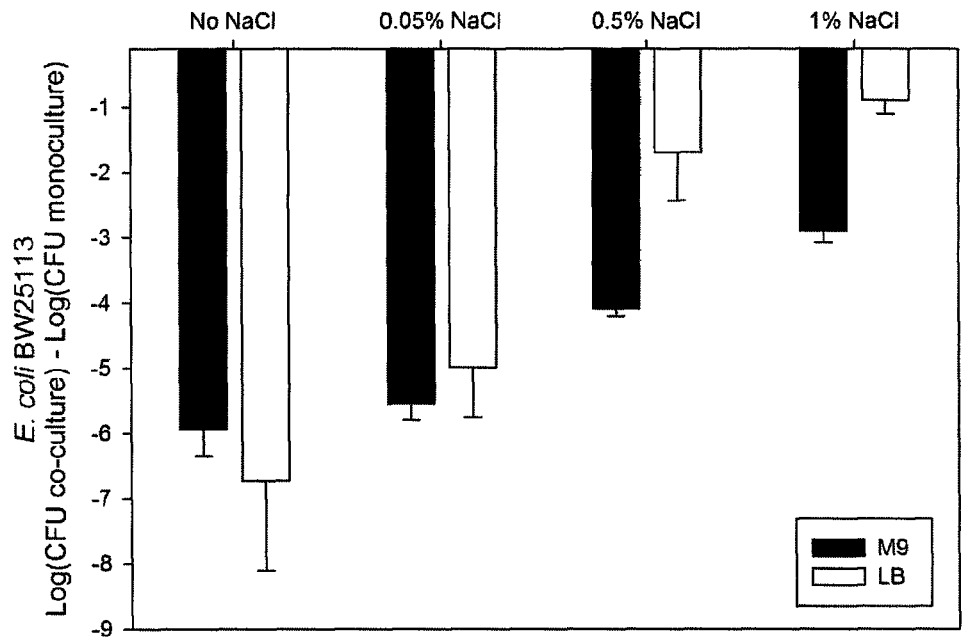
FIGS. 9A and B. The EnvZ/OmpR two-component regulatory system controls the MccPDI phenotype. (A) Competition assays between an MccPDI-producing strain (*E. coli*-25) and a target strain (BW25113) in M9 and LB with different concentrations of NaCl for 12 h. Results are expressed as the difference of mean log CFU during co-culture and mono-culture (n=3 independent replicates; error bars=SEM). (B) ΔenbZ or ΔompR strains no longer exhibit the MccPDI phenotype. Results are shown for competition assays between different knockouts or their complemented strains and BW25113 or BW25113 (vector control). Results are expressed as the difference of BW25113 log CFUs during co-culture and mono-culture for 12 h (error bars=SEM; 3 independent replicates). For complementation experiments the competition assays were performed in M9 with 34 ug/ml chloramphenicol and 0.5 mM IPTG. *, significant ANOVA followed by a Dunnett's one-way multiple comparisons test versus control group (E25) (P<0.001).
Figure 10A:
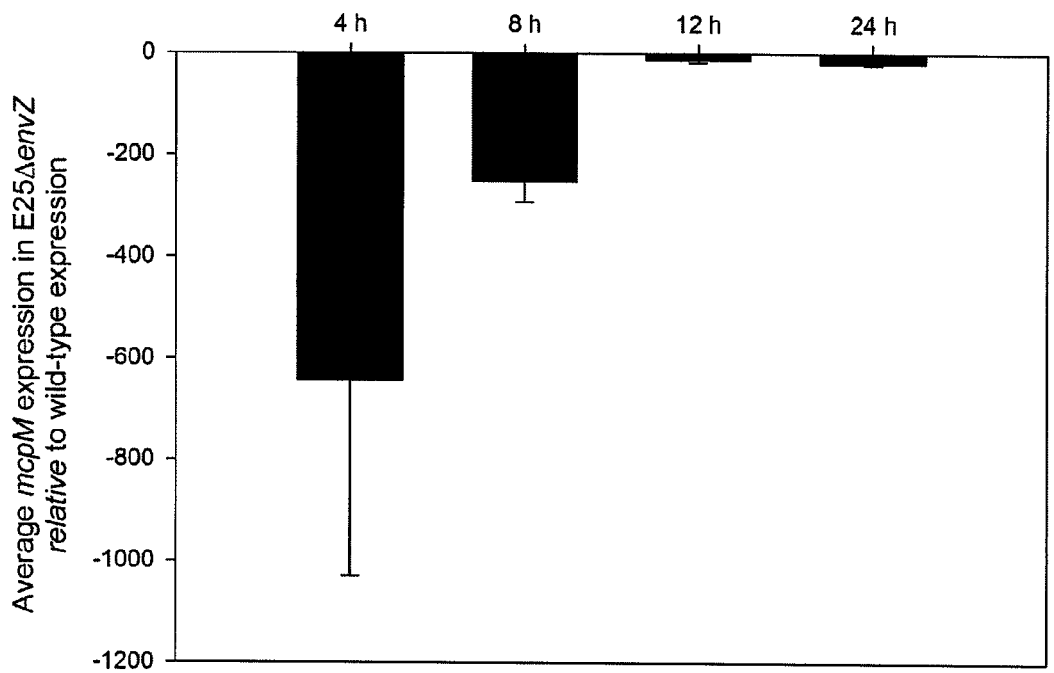
FIGS. 10A and B. (A) Transcriptional analysis (qPCR) of mcpM for *E. coli*-25 and ΔenvZ strains in M9 media (error bars=SEM; 2 independent replicates). P<0.05 for all time points E25ΔenvZ versus WT at 8 h. GLM ANOVA followed by a Bonferroni multiple-comparison test. (B) Transcriptional analysis (qPCR) of mcpM for *E. coli*-25 cultured in LB or M9 media. Fold change is expressed relative to mcpM expression in LB at 24 h (error bars=SEM; 3 independent replicates).*P<0.01 based on ANOVA.
Figure 10B:
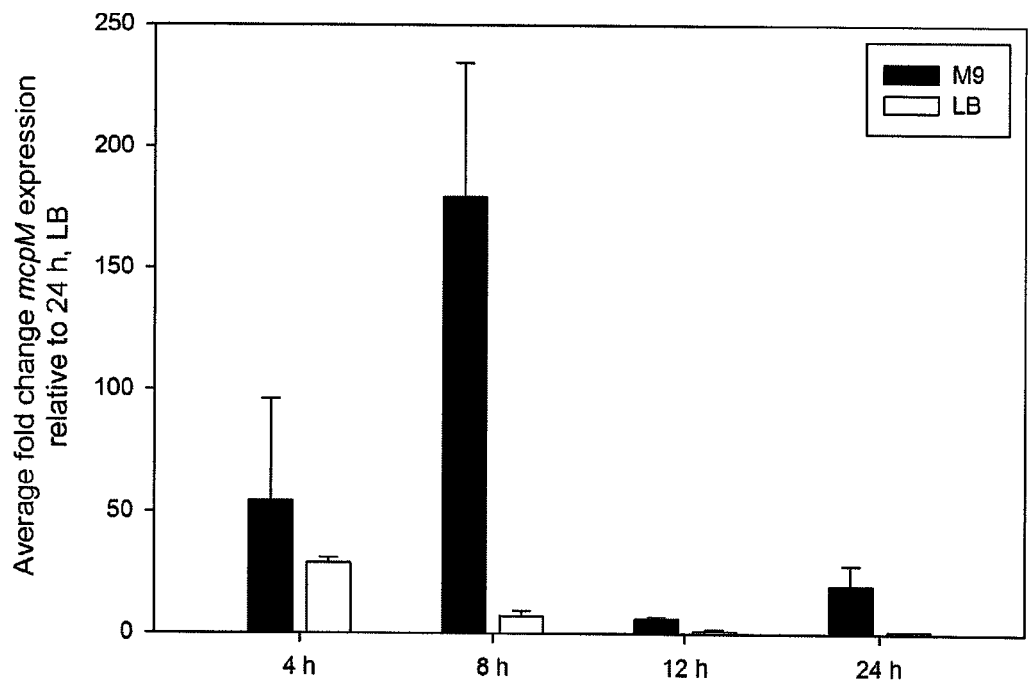

A previous study reported that inhibition by MccPDI was phenotypically obvious when strains were co-cultured in M9 medium (0.05% NaCl) but muted when co-cultured in LB medium (0.5% NaCl) (Sawant et al., 2011). Competition assays were performed here between a ccPDI producing strain (E. coli-25) and a target strain (BW25113) in M9 and LB with different concentrations of NaCl. We found that the McPDI phenotype was significantly enhanced in LB containing low (0.05% NaCl) or no added salt (FIG. 9A). In contrast, when the concentration of NaCl in LB or M9 was increased (0.5% and 1%), inhibition was reduced correspondingly, indicating that McPDI function or synthesis is responsive to changes in osmolarity. Consistent with the phenotype, qPCR analysis revealed that transcription of mcpM was significantly upregulated at 8 h in M9 when compared to LB (FIG. 10B). Transcription of other genes (mcpI, mcpA, and mcpB) within McPDI gene cluster showed a similar pattern when cultured in LB and M9 media.

Figure 9B:
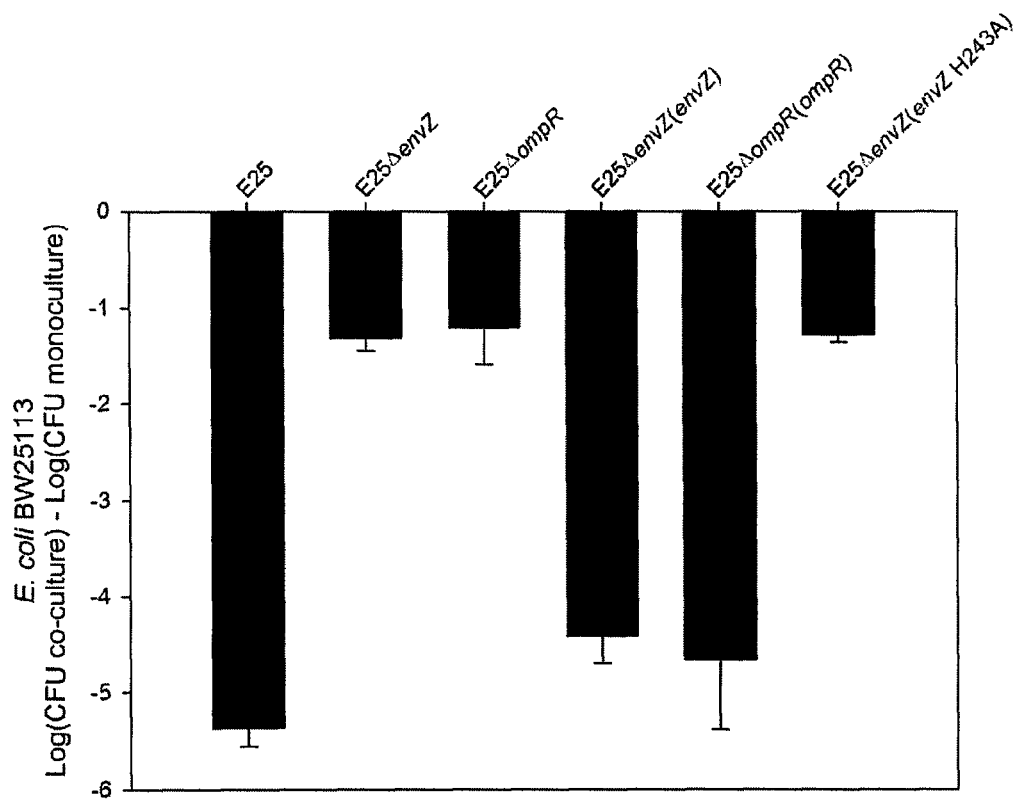

The E. coli EnvZ/OmpR two-component system responds to osmolarity changes in broth media (Forst & Roberts, 1994, Cai & Inouye, 2002). To determine if this system is involved with McPDI regulation, envZ and ompR deletion strains were constructed in E. coli-25. Transcription of mcpM was down-regulated significantly, particularly at 4 h. for the E25ΔenvZ strain when compared to the isogenic control (FIG. 10A). Competition assays showed that the envZ or ompR gene knockouts abolished inhibition from McPDI whereas complementation of each gene in the corresponding mutant restored the PDI phenotype (FIG. 9B). Furthermore, when the functionally important histidine residue (H243) of EnvZ was mutated to alanine, complementation using this mutant envZ sequence did not restore the inhibition phenotype (FIG. 10B). This data is consistent with McPDI being regulated by osmolarity that is signaled through the EnvZ/OmpR two-component system.

Phosphorylated OmpR Binds to the Promoter Region of mcpM.

EnvZ is an Osmotic Sensor that regulates the phosphorylation state of the transcriptional factor OmpR (Qin et al., 2000). Phosphorylated OmpR controls the expression levels of outer membrane porin genes (ompF and ompC) and other virulence and fimbriae genes by binding their promoter region (Cai & Inouye, 2002, Feng et al., 2003, Jubelin et al., 2005). To determine if the OmpR binds to the promoter sequence of mcpM, a 200 bp DNA fragment located at position −10 bp to −210 bp (Pmic-10/-210) relative to the start codon of mcpM was mixed with recombinant OmpR and subjected to a mobility-shift assay. A concentration-dependent shift of the OmpR/DNA mixture was clearly evident and is consistent with OmpR binding to the mcpM promoter region. The negative control protein, XRE (expressed and purified identically to recombinant OmpR) did not bind the promoter of mcpM. A secondary control involving an unrelated DNA fragment (270 bp, atpE) displayed no gel shift after addition of purified OmpR. Sequence analysis showed that there is a non-coding region upstream from the ABC transporter genes (mcpD and mcpB) that could serve as another promoter sequence within the McPDI gene cluster. No gel shift was observed for this 143 bp DNA fragment (PmicD-20/-163; relative to mcpD start codon), implying that the fragment PmicB-20/-163 does not contain a promoter cassette that can be recognized by OmpR. Additionally, no gel shift was observed for another 201 bp DNA sequence (Pmic-233/-433; relative to mcpM start codon).

To determine if OmpR phosphorylation is required for binding to the mcpM promoter region, we mutated a conserved D55 residue of OmpR that is known to undergo transphosphorylation by EnvZ (Forst et al., 1994). This mutated OmpR recombinant protein was mixed with Pmic-10/-210 and the gel mobility shift assay showed no evidence of binding even when 900 ng of protein was added. Consistent with the data, the OmpR, purified from M9 media, which contained a reduced amount of phosphorylated OmpR, displayed reduced binding to the mcpM promoter region compared to the OmpR purified from LB media. Taken together, this data indicates that phosphorylated OmpR binds to the promoter region of mcpM.

mcpM promoter region includes more than one OmpR recognition site. To identify the sequence motif(s) that OmpR binds to within Pmic-10/-210, a series of truncated DNA fragments were prepared (FIG. 11A). OmpR bound DNA fragments 1-3, but not fragments 4 and 5, indicating that the region between −81 to −102 is necessary for OmpR binding. This is consistent for the gel shifts that were evident for fragments 6-8 and fragment 10, which contain the region between −81 to −102, whereas fragment 9 did not bind as expected. From a qualitative perspective, binding was reduced for fragments 3, 7 and 8 compared with fragments 1, 2, and 6 (the same batch of recombinant OmpR was used for all of these mixtures). This could be a staining artefact (less ethidium bromide intercalated into shorter strands of DNA), but this is also consistent with sequences −61 to −81 and −102 to −134 providing additional binding sites or stabilizing OmpR binding. The mcpM promoter region is rich in adenines and thymines and three possible binding sites (B1, B2 and B3) are highlighted based on the above data (FIG. 11B). A multiple sequence alignment showed that the three possible binding sites, especially B1, resemble the consensus OmpR binding sites for ompF and ompC (F1, F2, F3, F4 and C1) and include conserved nucleotides that are important for OmpR binding (Harlocker et al., 1995). Collectively, these data are consistent with the mcpM promoter region having multiple binding sites and that region B1 is likely the primary binding site for the OmpR protein.

McpM is Cleared into Three Peptides.

Eberhart et al. (2012) could not recover the MccPDI inhibition phenotype with complementation of ΔmcpM: Kan. They assumed this was due to a polar effect on the immunity protein, mcpI, owing to the proximal insertion of a kanamycin resistance gene. For this reason, we generated a new scarless knock-out of mcpM using the suicide vector pDM4 in the wild-type E. coli-25 strain. As expected, the inhibition phenotype was lost for the new knockout strain, but we were able to restore the phenotype upon in trans expression of mcpI driven by an IPTG-induced promoter (Ptac) in pMMB207 vector (FIG. 12). Importantly, western blot analysis showed three distinct protein products in the mcpM complemented strains. The upper band is the presumptive full length protein because its mass is consistent with the mass of the recombinant protein (also visible when synthesized in two MccPDI-susceptible strains. E. coli BW25113 and 186). Presumably, the middle and lower bands are cleaved forms of the full length protein. To exclude the possibility that the promoter (Ptac) affects the observed phenotype, we generated a recombinant mcpM construct with the native promoter (Pmic-1/-210+mcpM). The new construct displayed the same phenotype as the previous construct (p207::mcpM) that was driven by Ptac promoter (FIG. 12).

McpM Undergoes Two Cleavage Events.

Figure 14:
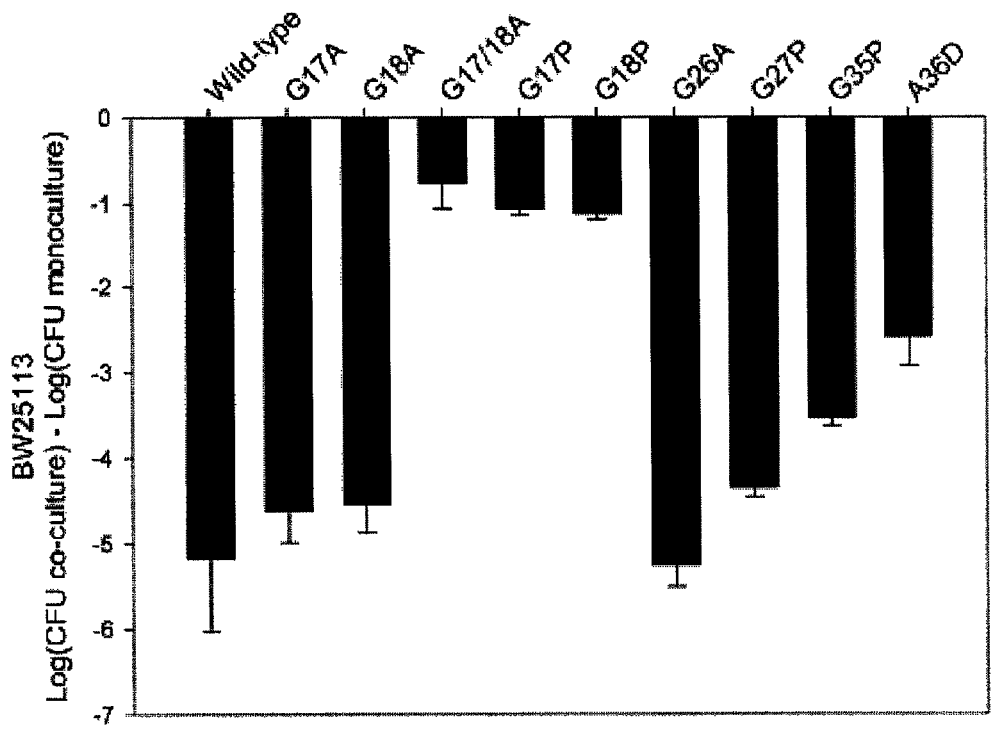
FIG. 14. Identification of McpM cleavage sites. Competition assays between the different site-specific mutants and BW25113 (vector ctrl). Results are expressed as the mean difference in CFU of the sensitive strain grown in co-culture and monoculture (error bars=SEM; 3 independent replicates). *, statistically significant ANOVA (P<0.01 with Dunnett's upper one-sided multiple-comparison test with control).

Class II microcins are typically generated from a precursor protein that harbors conserved leader peptides (Duquesne et al., 2007). Alignment of class IIa microcin precursors showed that a conserved double glycine is present in positions 17 and 18 of mcpM, consistent with the presence of an 18-residue leader peptide (FIG. 13). When the glycine residues were changed to proline (G17P and G18P) this resulted in loss of two protein bands relative to the wild-type strain. Changing only one glycine to alanine (G17A or G18A) did not prevent cleavage although the faint-low mass protein bands are consistent with reduced cleavage efficiency for the G17A mutation. Double mutations from glycine to alanine
(G17A/G18A) abolished cleavage. Competition assays showed that these mutants are unable to inhibit sensitive strains (FIG. 14).

If changes to the double-glycine site (G17/G18) results in loss of a cleavage site, this would only explain one of the two proteins band differences. One possibility is that the smallest protein band is the cleaved product while the middle band is modified form of the cleaved product. Peptide sequencing after different protease treatments (trypsin, chymotrypsin, and elastase) and analysis using UPLC-MS/MS on an Q-Exactive Orbitrap instrument showed no evidence for post-translational modifications (Bioproximity), arguing that the middle band is not a modified form of the smaller protein (data not shown). Alternatively, a second double glycine (positions 26 and 27) or a glycine-alanine motif at positions 35 and 36 could be the second cleavage sites for McpM (FIG. 13). Mutations G26P and G27P had no effect on the cleavage while mutations G35P and A36D resulted in loss of the lower-mass protein band.

Figure 15:
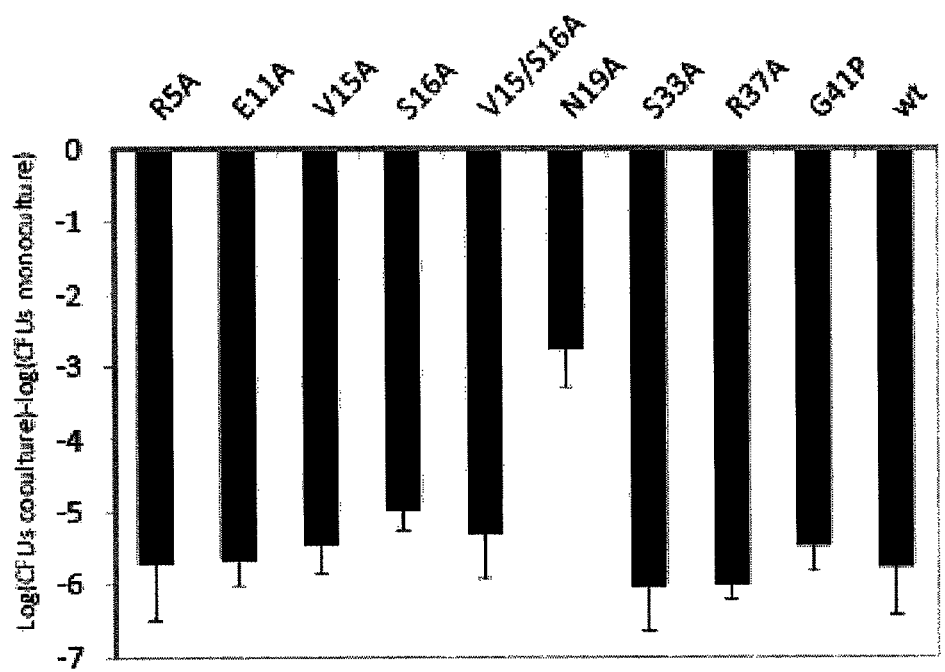
FIG. 15. Competition assays between the different residue-specific mutants and BW25113 (vector ctrl). Competition was performed in M9 medium with chloramphenicol (34 ug/ml) and 0.5 mM IPTG for 12 h. Results are expressed as the difference in CFUs of the sensitive strain grown in co-culture and monoculture.

These data indicate that MccPDI has two leader peptides (1-18 and 19-36) and the protein undergoes two cleavage events during maturation which are likely sequential. A competition assay employing the mutated secondary cleavage site (G35P or A36D) displayed only partial inhibitory activity when compared with wild-type strain (FIG. 14). We also mutated other residues (R5, E11, V15, S16, N19, S33, R37 and G41) located within the two leader peptides and around the cleavage sites. Western blots showed that each mutant was processed normally, although E11A and V15A may have resulted in reduced synthesis of MccPDI. All mutants, except N19 exhibited comparable inhibition of a susceptible strain (FIG. 15).

Cleavage of McpM is Insufficient to Produce a Functional Protein.

Figure 16A:
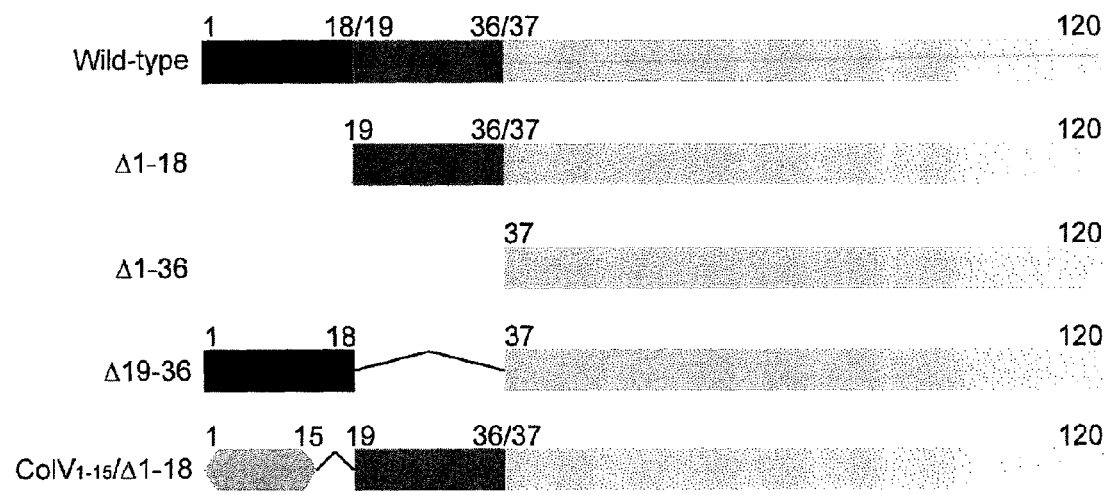
FIGS. 16A and B. Loss of leader sequences blocks function of McpM. (A) Schematic diagram of different deleted constructs where residue numbering corresponds to amino acids in the full length McpM (wt). ColV1-15 is the signal peptide sequence from colicin V. (B) Competition assays between the different deleted mutants and BW25113 (vector control). Results are expressed as the mean difference in CFU of the sensitive strain grown in co-culture and monoculture (error bars=SEM; 3 independent replicates).
Figure 16B:
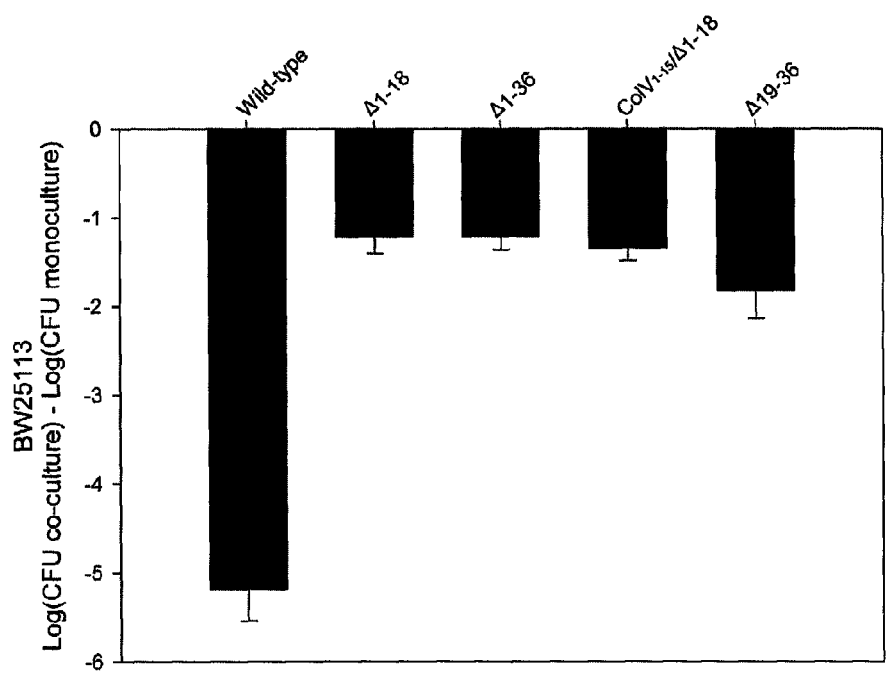

We generated different constructs of mcpM that lack individual leader peptides (Δ1-18 or Δ19-36) or both (Δ1-36; FIG. 16A). Neither the Δ1-18 or Δ1-36 strains inhibited sensitive strains (FIG. 16B). Furthermore, western blots showed very limited quantities of McpM from these strains compared to the wild-type strain. The Colicin V leader peptide shares ~50% amino acid identity with the primary leader sequence of McpM (FIG. 13). Consequently, we therefore replaced the primary leader peptide with the Colicin V leader peptide (ColV1-15/Δ1-18) (FIG. 16A), but this was not sufficient to recover wild-type phenotype (FIG. 16B) and very limited quantities of McpM were again detected by western blot.

Interestingly, the Δ19-36 strain appeared to have a similar concentration of protein as the wild-type strain, but its inhibitory activity was severely reduced (FIG. 16B). It is possible that the reduced activity is due to loss of export owing to the missing second leader sequence. Nevertheless, a western blot demonstrated that the product was present in TCA-precipitated culture supernatant. Both of the cleaved McpM products appeared to be present for the wild-type strain whereas no products were present for the secretion-negative ΔmcpB strain. While the Δ19-36 construct of McpM is exported, it appears to have lost most of its functional activity (FIG. 16B, last bar).

McpM Cleavage is Concomitant with Export.

Class II microcin export machinery displays a canonical structure consisting of three components. The ABC transporter and an accessory protein are encoded in the microcin gene cluster while the third component is the chromosome-encoded TolC (Vassiliadis et al., 2011). We verified that ΔmcpB and ΔmcpD strains lose the PDI phenotype and complementation restores it (FIG. 12). Sequence alignment shows that McpB contains three conserved domains including an N-terminal peptidase C39 domain, an ABC transporter transmembrane domain, and a C-terminal ABC transporter ATP-binding domain, which is consistent with the ABC transporter family. In trans expression of mcpM in a double knockout (ΔmcpMΔmcpB) demonstrated that deletion of mcpB leads to the loss of McpM cleavage, confirming that the ABC transporter is responsible for cleavage of this protein. McpD is homologous to proteins of class II microcin export machinery and it likely serves as a connector between the ABC transporter and TolC (Gilson et al., 1990, Pons et al., 2004). In trans expression of mcpM in the double knockout ΔmcpMΔmcpD did not affect production of full-length McpM, but cleavage was blocked as with the ΔmcpB strain, indicating that cleavage of McpM is concomitant with export.

The First Two Cysteines within the McpM are Necessary for Function.

Figure 17:
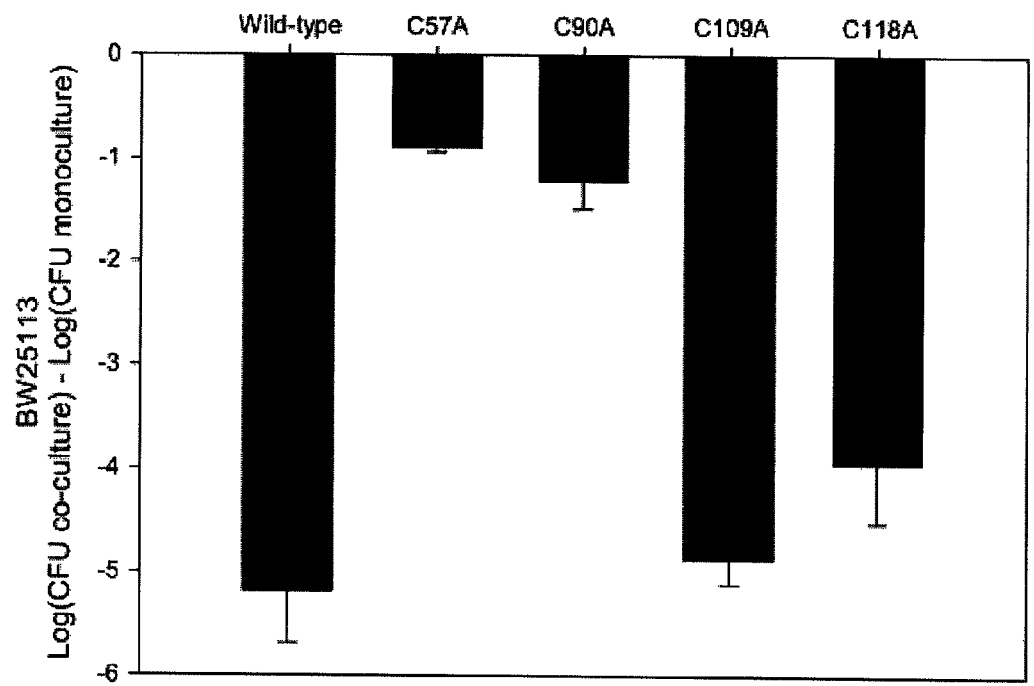
FIG. 17. Cysteine residues 57 and 90 are required for McpM function. Competition assays between the 4 cysteine-residue mutants and BW25113 (vector control). Results are expressed as the difference in CFU of the sensitive strain grown in co-culture and monoculture (bars=SEM; 3 independent replicates). *, statistically significant ANOVA (P<0.01 with Dunnett's upper one-sided multiple-comparison test with control).
Figure 18:
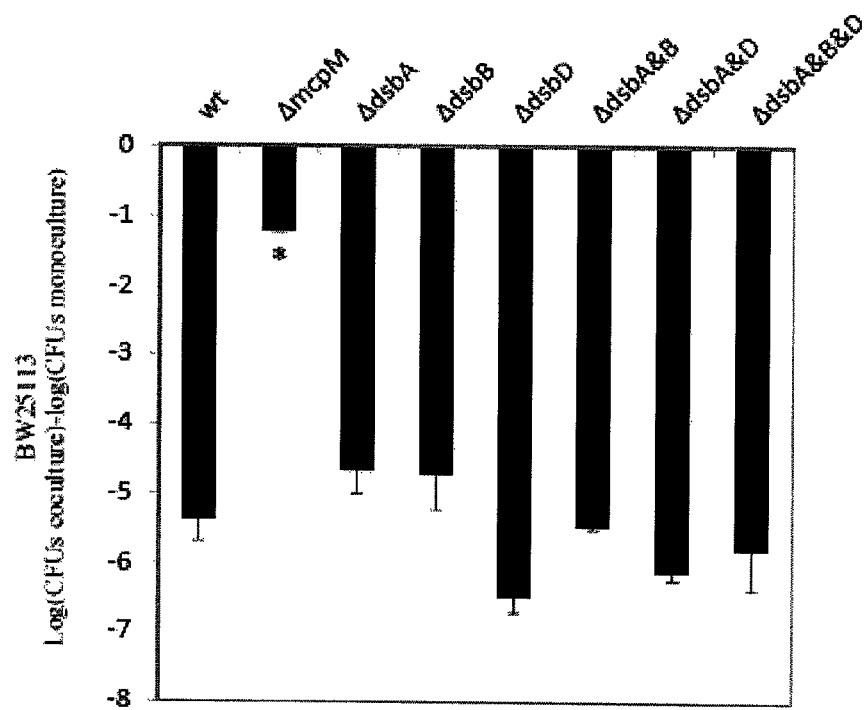
FIG. 18. Disulfide bond formation system in *E. coli* is not involved into the mccPDI activity. CFUs of *E. coli* BW25113 following competition with wild-type E25 and different knockouts strains in the E25 background (single and double). Results are expressed as the difference in CFUs of the sensitive strain grown in co-culture and monoculture. Experiments were done in duplicate with error bars representing the standard error of the mean (SEM). *, statistically significant ANOVA (P<0.01 with Dunnett's upper one-sided multiple-comparison test with control).

In class IIa microcins, cysteine pairs are commonly associated with the formation of disulfide bonds (Duquesne et al., 2007). The McpM protein includes four cysteine residues (positions 57, 90, 109 and 118) and all are located within the mature peptide sequence (FIG. 13). To determine if these cysteine residues are involved in post-translational modifications, each was individually mutated to alanine using site-directed mutagenesis. Western blots demonstrated that these point mutations did not affect McpM synthesis or post-translational cleavage, but the PDI inhibitory phenotype was eliminated for C57A and C90A, whereas mutation of cysteines 3 and 4 (C109A and C118A) had no affect on function (FIG. 17). These results are consistent with the possibility that a disulfide bond is required between the cysteine residues located at positions 57 and 90 for McpM to be functional. DsbA and DsbB are thiol-redox enzymes that are responsible for disulfide-bond formation in $E.\ coli$ (Inaba, 2009). Knockouts of dsbA and dsbB (ΔdsbA and ΔdsbB) in the wild-type E-25 strain did not result in loss of PDI phenotype (FIG. 18). Furthermore, a series of double-knockouts (ΔdsbAΔdshB and ΔdsbAΔdsbD) or triple-knockout (ΔdsbAΔdsbBΔdsbD) eliminated the possible redundancy between the DsbA/DsbB and DsbC/DsbD pathways, but did not impact the killing phenotype strain (FIG. 18).

MccPDI Induces Membrane Permeability.

Figure 19:
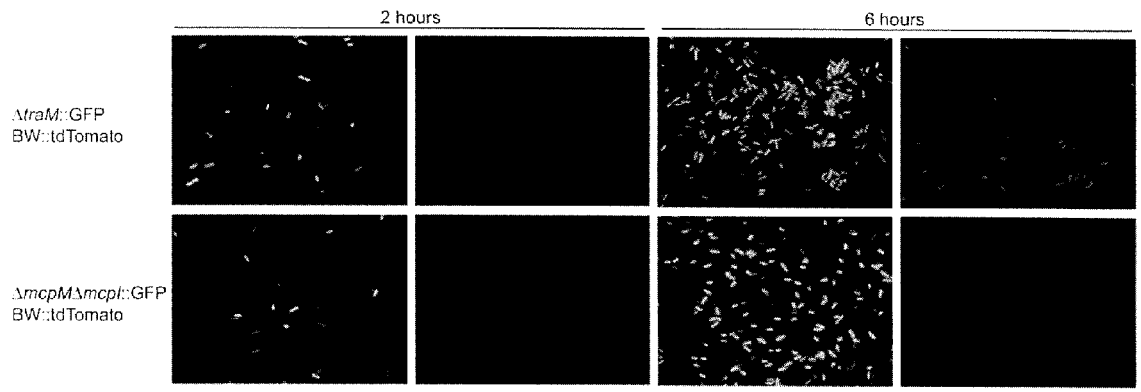
FIG. 19. MccPDI induces membrane permeability in susceptible cells. DAPI staining of the fluorescent-labeled strains in mono-culture and co-culture for 2 h and 6 h. The strains were derived from E25 (E25ΔtraM and E25ΔmcpMΔmcpI), and the MccPDI target strain BW25113. The DAPI staining was consistent with increased membrane permeability given exposure to MccPDI.

To probe how MccPDI exerts its inhibitory activity on target cells, we fluorescently labeled the mccPDI-producing strain (GFP-labeled E25ΔtraM and E25ΔmcpMΔmcp I) and target strain (tdTomato-labeled $E.\ coli$ BW25113) to distinguish the two populations. After co-culture for 2 and 6 h, the cell mixtures were stained with a low concentration of DAPI (0.25 µg/ml). DAPI is normally used to stain fixed cells that have a permeabalized cell membrane. Although high concentration of DAPI can also be used to stain live cells, the effectiveness of the stain is lower (Zink et al., 2003). MccPDI-susceptible cells were co-cultured with E25ΔtraM for 6 hours after which they were easily stained by using a low concentration of DAPI (FIG. 19, top right panel). As a control, the susceptible cells were co-cultured with E25ΔmcpMΔmcpI for 6 hours and after applying the same staining protocol, there was no DAPI staining observed (FIG. 19, bottom right panel). DAPI also did not stain either strain in monoculture (data not shown).

Discussion

Regulation of Microcin PDI.

Bacteriocin production is an inducible process that is affected by different environmental and nutritional factors (Drider et al., 2006). For example, expression of colicin genes is regulated by the SOS response regulon that responds to DNA damage (Walker, 1995, Gillor et al., 2008). Alternatively, regulation of microcin synthesis is more related to nutrient depletion or anoxic conditions (Duquesne et al., 2007). For example, production of many class I microcins (MccB17, MccC7/C51 and MccJ25) are upregulated when cells reach the stationary growth phase (Moreno et al., 2002). One notable exception is MccE492, which is only produced during the exponential growth phase (Corsini et al., 2002). Nitrogen starvation induces MccB17 production (Connell et al., 1987) and MccV production is initiated under iron-limiting conditions (Gilson et al., 1990).

MccPDI gene expression increases rapidly during log-phase growth and drops off as the population enters stationary phase (Eberhart et al., 2012). The PDI phenotype is enhanced significantly when these experiments are conducted in M9 media compared to LB media, arguing that differences between the media (e.g., salt concentrations) might affect microcin synthesis or function (Sawant et al., 2011). We demonstrated that osmolarity in the growth media regulates expression of the mcpM. This is a novel regulatory mechanism with respect to what is known about microcins, although osmolarity can influence bacteriocin production in Gram-positive bacteria (Uguen et al., 1999).

The EnvZ/OmpR two-component regulatory system plays a central role in mediating the response to osmotic stress in $E.\ coli$ (Stock et al., 2000). Consequently, it was not surprising to find that osmolarity-sensitive expression of MccPDI is dependent on the EnvZ/OmpR system where the phosphorylated transcriptional regulator, OmpR, binds to the mcpM promoter region. Similarly. Hernandez-Chico et al (1986) reported that expression of MccB17 gene cluster was dependent on the OmpR transcriptional factor, but this regulation is growth-phase dependent. RNA polymerase sigma 70 factor (570) is involved in MccB17 expression (Bohannon et al., 1991) while RNA polymerase sigma S (SS) appears to regulate MccJ25 and mccC7/C51. The histone like protein H-NS acted as a repressor of MccB17 and mccC7/C51 expression (Fomenko et al. 2001; Moreno et al., 2002).

The EnvZ/OmpR system also regulates synthesis of the outer membrane proteins OmpF and OmpC that enable bacteria to cope with fluctuations in osmolarity (Forst et al., 1989). Under high osmolarity conditions, EnvZ auto-phosphorylates and transfers the phosphoryl group to OmpR, producing the phosphorylated form OmpR-P. At low osmolarity OmpR-P is present in low concentrations. OmpR-P binds to the promoter regions of outer membrane porin genes ompF and ompC and differentially modulates their expression according to the concentration of cellular OmpR-P (Yoshida et al., 2002). There are several binding sites for OmpR-P within the promoter region of ompF. When present in low concentrations, OmpR-P only binds to the high-affinity sites. Under high osmolarity conditions, OmpR-P concentration increases and binding occurs at low-affinity sites that result in reduced expression of ompF (Harlocker et al., 1995). Here, we show that regulation of mcpI is negatively correlated with osmolarity of the growth media (greater in M9 than LB). OmpR-P clearly binds the promoter region of mcpM whereas unphosphorylated OmpR does not. Consequently, the EnvZ/OmpR system is required for activation of MccPDI and we propose that mcpM transcriptional regulation mirrors that of ompF regulation. This conclusion is further supported by the finding of at least three putative binding sites in the MccPDI promoter region that resembles the consensus OmpR binding site for ompF.

Furthermore, Zhao et al. (2015) recently demonstrated that McpM interacts with OmpF and consequently, the concurrent expression of these traits in producer and susceptible cells likely maximizes the ability of the MccPDI-producing strains to inhibit susceptible competitors.

McpM Maturation.

Functional microcins are usually derived from a precursor protein that is composed of a C-terminal structural region and an N-terminal leader peptide (Kolter Moreno, 1992). Enzymatic cleavage removes the leader peptide and the microcin may or may not undergo further post-translational modification. The Class II microcins have conserved leader peptides that range in size from 15 to 19 residues and harbor a double-glycine or glycinealanine cleavage site (Duquesne et al., 2007). In contrast, there is little sequence similarity between the leader peptides of Class I microcins. For example, the MccB17 precursor, a class I microcins, is processed at G26, but this cleavage site is not a typical sequence of the doubleglycine-type leader peptides as described for class II microcins (Davagnino et al., 1986).

McPDI most closely resembles a Class IIa microcin based on its genetic organization (Eberhart et al., 2012). The complete microcin protein, McpM, contains a typical double-glycine cleavage site (G17G18) and a conserved leader peptide (residues 1-18) similar to other Class II microcins. McpM also harbors a second cleavage site (G35A36) corresponding to a second leader peptide sequence. To our knowledge, this is the first report of a microcin containing two leader peptides (1-18 and 19-36).

Leader peptides typically prevent microcin function (e.g., in the cytoplasm of the producing strain) or serve as a recognition site for export (Drider et al., 2006). For McpM, experimental evidence suggests that the first leader peptide, but not the second, is required for export. The first leader sequence may also serve to inhibit protein degradation because when absent we find only very small quantities of the modified McpM protein in the cell. We assume that the second cleavage event takes place during or after export. If the latter, this would be consistent with the hypothesis that the fully functional microcin is composed of a dimer or multimer of the two cleaved products.

Cysteine is the least abundant amino acid found in proteins (Brooks & Fresco, 2002) and it performs a variety of essential functions including binding metal ions and forming disulfide bonds that produce three-dimensional protein structures (Giles et al., 2003). For these reasons, if a protein contains an "even" number of cysteines and is predicted to function outside the cytoplasm, it is likely that cysteines form disulfide bonds (Berkmen, 2012). McpM has four cysteines within the mature protein, consistent with the prediction that disulfide bond formation occurs. Our experimental data showed that the first two cysteines are necessary for MccPDI inhibition. We also conducted competition assays in the presence of 5 mM DTT, a reducing agent that breaks disulfide bonds. Under these conditions, no inhibition was observed (data not shown) although this type of experiment could have multiple confounding effects. There was no evidence in this study that Dsb-based enzymatic activity in the McpM-producing strain contributes to disulfide-bond formation, but other works shows that strains lacking DsbA or DsbB are less susceptible to MccPDI (Zhao et al., 2015). While a computational three dimensional model for McpM did not support the formation of an intra-molecular disulfide bond between cysteine 57 and cysteine 90 due to the physical distance between these sites (data not shown), the reduced killing activity observed when only one of the two cleaved forms is present suggests the possibility of inter-molecular disulfide-bond formation. If disulfide bonds are required for function, we surmise that they form after the mature McpM protein enters the susceptible cell where folding likely occurs in the periplasm.

For class IIa microcins, cysteines commonly form disulfide bonds in the mature peptide. The full-length MccB17 protein has four cysteine residues that form heterocyclic rings by an unusual post-translational modification of the mature microcin (Bayer et al., 1995), and mutational analysis suggests that the mature form of MccV has a disulfide bond between the cysteine residues at positions 76 and 87 (Zhang et al., 1995). In addition, using mass spectrometry Pons et al. (2004) detected the presence of two intramolecular disulfide bridges in the mature MccL.

After maturation and export, microcins inhibit susceptible bacteria through a variety of mechanisms. MccJ25 recognizes the outer membrane protein FhuA and requires the inner membrane proteins TonB, ExbB, ExbD and SbmA, for translocation (Destoumieux-Garzon et al., 2005, Salomon & Farias, 1993, Salomon & Farias, 1995). Once it reaches the cytoplasm, MccJ25 inhibits transcription by obstructing the RNA polymerase secondary channel (Wilson et al., 2003). MccB17 binds OmpF on the outer membrane and the inner protein SbmA mediates uptake into the cytoplasm, where MccB17 inhibits the DNA gyrase (Lavina et al., 1986).

Microcin C7/C51 requires OmpF and the inner-membrane ABC-transporter, Yej, to be actively transported through the inner membrane (Novikova et al., 2007). Within the target cell MccC7/C51 is cleaved to form a modified aspartyl adenylate that inhibits Asp-tRNA synthetase, thus blocking protein synthesis at the translation level (Kazakov et al., 2008, Metlitskaya et al., 2006). MccE492, MccM, and MccH47, all Class IIb microcins, are unable to inhibit the growth of strains carrying mutations in the fepA, cir, and fiu genes, consistent with the requirement for these iron-catecholate receptors (Thomas et al., 2004, Patzer et al., 2003).

The transport of class IIb microcins across the outer membrane is also TonB-dependent (Destoumieux-Garzon et al., 2006. Thomas et al., 2004). Once in the periplasm, MccE492 functions by inserting into the inner membrane and interfering with membrane potential (Lagos et al., 1993, Destoumieux-Garzon et al., 2003). This activity is facilitated by the inner membrane proteins ManY and ManZ (Bieler et al., 2006). MccH47 exerts its activity by inhibiting the ATP synthase (Trujillo et al., 2001). MccV causes channel formation and disruption of membrane potential by binding to the inner membrane receptor SdaC (Yang & Konisky, 1984, Gerard et al., 2005). Recently, it was shown that MccPDI interacts with the sole receptor OmpF (Zhao et al., 2015). In this study we further demonstrate that MccPDI undergoes two sequential cleavage events, with the mature microcin inducing membrane permeability in susceptible cells. Without being bound by theory, the following model is representative of MccPDI function. First, McpM precursor protein undergoes two cleavage events to produce two cleaved forms during and possibly after export. The two cleaved peptides interact with OmpF of susceptible cells, cross the outer membrane using an unknown mechanism to access the periplasm where disulfide bridges facilitate the formation of multimers. The disulfide bonds are formed utilizing the target cells thio-redox systems, DsbA/B and/or DsbC/D, and once fully mature, the multimers permeabilize the susceptible-cells membrane leading to cell death.

REFERENCES FOR EXAMPLE 13

Asensio, C. & J. C. Perez-Diaz, (1976) A new family of low molecular weight antibiotics from enterobacteria. *Biochem Biophys Res Commun* 69: 7-14.

Baquero. F. & F. Moreno, (1984) The microcins. *FEMS Microbiology Letters* 23: 117-124.

Bayer, A., S. Freund & G. Jung, (1995) Post-translational heterocyclic backbone modifications in the 43-peptide antibiotic microcin B17. Structure elucidation and NMR study of a 13C,15N-labelled gyrase inhibitor. *Eur J Biochem* 234: 414-426.

Berkmen, M., (2012) Production of disulfide-bonded proteins in *Escherichia coli*. *Protein Expr Purif* 82: 240-251.

Bieler, S., F. Silva. C. Soto & D. Belin, (2006) Bactericidal activity of both secreted and nonsecreted microcin E492 requires the mannose permease. *J Bacteriol* 188: 7049-7061.

Bohannon, D. E., N. Connell, J. Keener, A. Tormo, M. Espinosa-Urgel, M. M. Zambrano & R. Kolter, (1991) Stationary-phase-inducible "gearbox" promoters: differential effects of katF mutations and role of sigma 70. *J Bacteriol* 173: 4482-4492.

Brooks, D. J. & J. R. Fresco, (2002) Increased frequency of cysteine, tyrosine, and phenylalanine residues since the last universal ancestor. *Mol Cell Proteomics* 1: 125-131.

Cai, S. J. & M. Inouye, (2002) EnvZ-OmpR interaction and osmoregulation in *Escherichia coli*. *J Biol Chem* 277: 24155-24161.

Chen, C. Y., G. W. Nace & P. L. Irwin, (2003) A 6×6 drop plate method for simultaneous colony counting and MPN enumeration of *Campylobacter jejuni, Listeria monocytogenes,* and *Escherichia coli*. *J Microbiol Methods* 55: 475-479.

Connell, N., Z. Han, F. Moreno & R. Kolter, (1987) An *E. coli* promoter induced by the cessation of growth. *Mol Microbiol* 1: 195-201.

Corsini, G., M. Baeza, O. Monasterio & R. Lagos, (2002) The expression of genes involved in microcin maturation regulates the production of active microcin E492. *Biochimie* 84: 539-544.

Davagnino, J., M. Herrero, D. Furlong, F. Moreno & R. Kolter, (1986) The DNA replication inhibitor microcin B17 is a forty-three-amino-acid protein containing sixty percent glycine. *Proteins* 1: 230-238.

Destoumieux-Garzon, D., S. Duquesne, J. Peduzzi, C. Goulard, M. Desmadril, L. Letellier, S. Rebuffat & P. Boulanger, (2005) The iron-siderophore transporter FhuA is the receptor for the antimicrobial peptide microcin J25: role of the microcin Val11-Pro16 beta-hairpin region in the recognition mechanism. *Biochem J* 389: 869-876.

Destoumieux-Garzon, D., J. Peduzzi, X. Thomas, C. Djediat & S. Rebuffat, (2006) Parasitism of iron-siderophore receptors of *Escherichia coli* by the siderophore-peptide microcin E492m and its unmodified counterpart, *Biometals* 19: 181-191.

Destoumieux-Garzon, D., X. Thomas, M. Santamaria, C. Goulard, M. Barthelemy, B. Boscher, Y. Bessin, G. Molle, A. M. Pons, L. Letellier, J. Peduzzi & S. Rebuffat, (2003) Microcin E492 antibacterial activity: evidence for a TonB-dependent inner membrane permeabilization on *Escherichia coli*. *Mol Microbiol* 49: 1031-1041.

Drider, D., G. Fimland, Y. Hechard, L. M. McMullen & H. Prevost, (2006) The continuing story of class IIa bacteriocins. *Microbiol Mol Biol Rev* 70: 564-582.

Duquesne, S., D. Destoumieux-Garzon, J. Peduzzi & S. Rebuffat, (2007) Microcins, geneencoded antibacterial peptides from enterobacteria. *Nat Prod Rep* 24: 708-734.

Eberhart. L. J., J. R. Deringer, K. A. Brayton, A. A. Sawant, T. E. Besser & D. R. Call, (2012) Characterization of a novel microcin that kills enterohemorrhagic *Escherichia coli* O157:H7 and O26. *Appl Environ Microbiol* 78: 6592-6599.

Feng. X., R. Oropeza & L. J. Kenney, (2003) Dual regulation by phospho-OmpR of ssrA/B gene expression in *Salmonella* pathogenicity island 2. *Mol Microbiol* 48: 1131-1143.

Fomenko, D., A. Veselovskii & I. Khmel, (2001) Regulation of microcin C51 operon expression: the role of global regulators of transcription. *Res Microbiol* 152: 469-479.

Forst, S., J. Delgado & M. Inouye, (1989) Phosphorylation of OmpR by the osmosensor EnvZ modulates expression of the ompF and ompC genes in *Escherichia coli*. *Proc Natl Acad Sci USA* 86: 6052-6056.

Forst, S. A. & D. L. Roberts, (1994) Signal transduction by the EnvZ-OmpR phosphotransfer system in bacteria. *Res Microbiol* 145: 363-373.

Gerard, F., N. Pradel & L. F. Wu, (2005) Bactericidal activity of colicin V is mediated by an innermembrane protein, SdaC, of *Escherichia coli*. *J Bacteriol* 187: 1945-1950.

Giles, N. M., G. I. Giles & C. Jacob, (2003) Multiple roles of cysteine in biocatalysis. *Biochem Biophys Res Commun* 300: 1-4.

Gillor, O., J. A. Vriezen & M. A. Riley, (2008) The role of SOS boxes in enteric bacteriocin regulation. *Microbiology* 154: 1783-1792.

Gilson, L., H. K. Mahanty & R. Kolter, (1990) Genetic analysis of an MDR-like export system: the secretion of colicin V. *Embo J* 9: 3875-3884.

Harlocker, S. L., L. Bergstrom & M. Inouye, (1995) Tandem binding of six OmpR proteins to the ompF upstream regulatory sequence of *Escherichia coli*. *J Biol Chem* 270: 26849-26856.

Havarstein. L. S., H. Holo & I. F. Nes, (1994) The leader peptide of colicin V shares consensus sequences with leader peptides that are common among peptide bacteriocins produced by gram-positive bacteria. *Microbiology* 140 (Pt 9): 2383-2389.

Heckman, K. L. & L. R. Pease, (2007) Gene splicing and mutagenesis by PCR-driven overlap extension. *Nat Protoc* 2: 924-932.

Hernandez-Chico, C., J. L. San Millan, R. Kolter & F. Moreno, (1986) Growth phase and ompR regulation of transcription of microcin B17 genes. *J Bacteriol* 167: 1058-1065.

Hibbing. M. E., C. Fuqua, M. R. Parsek & S. B. Peterson, (2010) Bacterial competition: surviving and thriving in the microbial jungle. *Nat Rev Microbiol* 8: 15-25.

Inaba, K., (2009) Disulfide bond formation system in *Escherichia coli*. *J Biochem* 146: 591-597.

Jubelin. G., A. Vianney, C. Beloin, J. M. Ghigo, J. C. Lazzaroni, P. Lejeune & C. Dorel, (2005) CpxR/OmpR interplay regulates curli gene expression in response to osmolarity in *Escherichia coli*. *J Bacteriol* 187: 2038-2049.

Kazakov, T., G. H. Vondenhoff, K. A. Datsenko, M. Novikova, A. Metlitskaya, B. L. Wanner & K. Severinov, (2008) *Escherichia coli* peptidase A, B, or N can process translation inhibitor microcin C. *J Bacteriol* 190: 2607-2610.

Kolter, R. & F. Moreno, (1992) Genetics of ribosomally synthesized peptide antibiotics. *Annu Rev Microbiol* 46: 141-163.

Lagos, R., M. Wilkens, C. Vergara, X. Cecchi & O. Monasterio, (1993) Microcin E492 forms ion channels in phospholipid bilayer membrane. *FEBS Lett* 321: 145-148.

Lavina, M., A. P. Pugsley & F. Moreno, (1986) Identification, mapping, cloning and characterization of a gene (sbmA) required for microcin B17 action on *Escherichia coli* K12. *J Gen Microbiol* 132: 1685-1693.

Livak. K. J. & T. D. Schmittgen, (2001) Analysis of relative gene expression data using real-time quantitative PCR and the 2(-Delta Delta C(T)) Method. *Methods* 25: 402-408.

Metlitskaya, A., T. Kazakov, A. Kommer, O. Pavlova, M. Praetorius-Ibba. M. Ibba, I. Krasheninnikov, V. Kolb, I.

Khmel & K. Severinov, (2006) Aspartyl-tRNA synthetase is the target of peptide nucleotide antibiotic Microcin C. *J Biol Chem* 281: 18033-18042.

Milton, D. L., R. O'Toole, P. Horstedt & H. Wolf-Watz, (1996) Flagellin A is essential for the virulence of *Vibrio anguillarum*. *J Bacteriol* 178: 1310-1319.

Moreno, F., J. E. Gonzalez-Pastor, M. R. Baquero & D. Bravo, (2002) The regulation of microcin B, C and J operons. *Biochimie* 84: 521-529.

Novikova, M., A. Metlitskaya, K. Datsenko, T. Kazakov, A. Kazakov, B. Wanner & K. Severinov, (2007) The *Escherichia coli* Yej transporter is required for the uptake of translation inhibitor microcin C. *J Bacteriol* 189: 8361-8365.

Patzer, S. I., M. R. Baquero, D. Bravo, F. Moreno & K. Hantke, (2003) The colicin G, H and X determinants encode microcins M and H47, which might utilize the catecholatesiderophore receptors FepA, Cir, Fiu and IroN. *Microbiology* 149: 2557-2570.

Pons. A. M., F. Delalande, M. Duarte, S. Benoit, I. Lanneluc. S. Sable, A. Van Dorsselaer & G. Cottenceau, (2004) Genetic analysis and complete primary structure of microcin L. *Antimicrob Agents Chemother* 48: 505-513.

Qin, L., R. Dutta. H. Kurokawa, M. Ikura & M. Inouye, (2000) A monomeric histidine kinase derived from EnvZ, an *Escherichia coli* osmosensor. *Mol Microbiol* 36: 24-32.

Rebuffat, S., (2011) Bacteriocins from Gram-Negative Bacteria: A Classification? In: Prokaryotic Antimicrobial Peptides. D. Drider & S. Rebuffat (eds). Springer New York, pp. 55-72.

Riley, M. A. (2011) Bacteriocin-mediated competitive interactions of bacterial populations and communities. In: Prokaryotic antimicrobial peptides. D. Drider & S. Rebuffat (eds). Springer New York, pp. 13-26.

Riley M. A. & J. E. Wertz, (2002) Bacteriocins: evolution, ecology, and application. *Annu Rev Microbiol* 56:117-137.

Salomon, R. A. & R. N. Farias, (1993) The FhuA protein is involved in microcin 25 uptake. *J Bacteriol* 175: 7741-7742.

Salomon, R. A. & R. N. Farias, (1995) The peptide antibiotic microcin 25 is imported through the TonB pathway and the SbmA protein. *J Bacteriol* 177: 3323-3325.

Sawant, A. A., N. C. Casavant, D. R. Call & T. E. Besser, (2011) Proximity-dependent inhibition in *Escherichia coli* isolates from cattle. *Appl Environ Microbiol* 77: 2345-2351.

Severinov, K., E. Semenova, A. Kazakov, T. Kazakov & M. S. Gelfand, (2007) Low-molecular weight post-translationally modified microcins. *Mol Microbiol* 65: 1380-1394.

Severinov, K., E. Semenova & T. Kazakov, (2011) Class I microcins: Their structures activities, and mechanisms of resistance. In: Prokaryotic Antimicrobial Peptides: from Genes to Applications. New York: Springer, pp. 289-308.

Stock, A. M., V. L. Robinson & P. N. Goudreau, (2000) Two-component signal transduction. *Annu Rev Biochem* 69: 183-215.

Thomas, X., D. Destoumieux-Garzon, J. Peduzzi, C. Afonso, A. Blond, N. Birlirakis, C. Goulard, L. Dubost, R. Thai, J. C. Tabet & S. Rebuffat, (2004) Siderophore peptide, a new type of post-translationally modified antibacterial peptide with potent activity. *J Biol Chem* 279: 28233-28242.

Trujillo. M., E. Rodriguez & M. Lavina, (2001) ATP synthase is necessary for microcin H47 antibiotic action. *Antimicrob Agents Chemother* 45: 3128-3131.

Uguen, P., J. Hamelin, J. P. Le Pennec & C. Blanco, (1999) Influence of osmolarity and the presence of an osmoprotectant on *lactococcus lactis* growth and bacteriocin production. *Appl Environ Microbiol* 65: 291-293.

Valdivia, R. H. & S. Falkow, (1996) Bacterial genetics by flow cytometry: rapid isolation of *Salmonella typhimurium* acid-inducible promoters by differential fluorescence induction. *Mol Microbiol* 22: 367-378.

Vassiliadis, G., D. Destoumieux-Garzon & J. Peduzzi, (2011) Class II Microcins. In: Prokaryotic Antimicrobial Peptides: from Genes to Applications. New York: Springer, pp. 309-330.

Walker, G. C., (1995) SOS-regulated proteins in translesion DNA synthesis and mutagenesis. *Trends Biochem Sci* 20: 416-420.

Wilson. K. A., M. Kalkum, J. Ottesen, J. Yuzenkova, B. T. Chait. R. Landick, T. Muir, K. Severinov & S. A. Darst, (2003) Structure of microcin J25, a peptide inhibitor of bacterial RNA polymerase, is a lassoed tail. *J Am Chem Soc* 125: 12475-12483.

Yang, C. C. & J. Konisky, (1984) Colicin V-treated *Escherichia coli* does not generate membrane potential. *J Bacteriol* 158: 757-759.

Yoshida, T., S. Cai & M. Inouye, (2002) Interaction of EnvZ, a sensory histidine kinase, with phosphorylated OmpR, the cognate response regulator. *Mol Microbiol* 46: 1283-1294.

Zhang. L. H., M. J. Fath. H. K. Mahanty, P. C. Tai & R. Kolter, (1995) Genetic analysis of the colicin V secretion pathway. *Genetics* 141: 25-32.

Zhao, Z., L. J. Eberhart, L. H. Orfe, S. Y. Lu, T. E. Besser & D. R. Call, (2015) Genome-Wide Screening Identifies Six Genes That Are Associated with Susceptibility to *Escherichia coli* Microcin PDI. *Appl Environ Microbiol* 81: 6953-6963.

Zhong, X., R. Kolter & P. C. Tai, (1996) Processing of colicin V-1, a secretable marker protein of a bacterial ATP binding cassette export system, requires membrane integrity, energy, and cytosolic factors. *J Biol Chem* 271: 28057-28063.

Zink. D., N. Sadoni & E. Stelzer, (2003) Visualizing chromatin and chromosomes in living cells. *Methods* 29: 42-50.

Example 14. McpM Functions as an Independent Protein

Figures 20A, 20B:
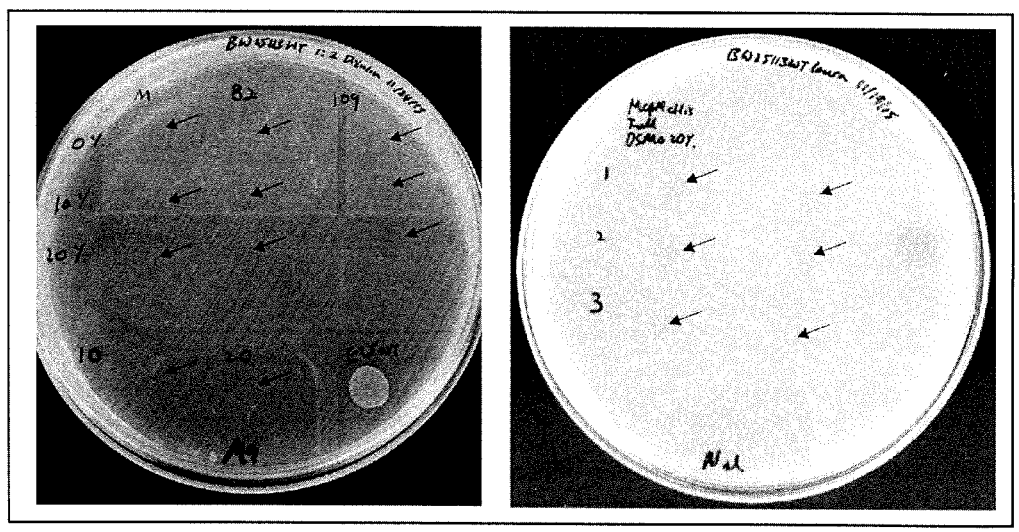
FIGS. 20A and B. Recombinant McpM inhibits growth of susceptible *E. coli* independent of a McpM-producing *E. coli* strain. Plates containing (A) M9 agar media and (B) LB agar media are shown.

Based on our prior findings, it is clear that McpM is the "effector" protein for mccPDI. This soluble protein is excreted via a type I secretion system where it interacts with the OmpF protein that is displayed on the surface of susceptible *E. coli*. We generated plasmid constructs that encode mcpM ("M" for full-length McpM and two additional versions "82" and "109" that lack signal peptides) with a histidine "tag" allowing purification of the recombinant protein using conventional chromatography techniques. The recombinant proteins were incubated at room temperature with 0%, 10% or 20% DMSO to enhance the efficiency of potential spontaneous disulfide-bond formation within and between the recombinant protein molecules. These preparations were then "spotted" onto bacterial "lawns" composed of a mccPDI-sensitive strain of *E. coli*. In FIG. 20A, faint zones of clearance are visible regardless of pre-incubation with 0%, 10% and 20% DMSO (see arrows;

DMSO-only controls are at bottom of plate) and regardless of the construct that was used. FIG. 20B shows a similar experiment with six replicate spots of an independent batch of full-length, recombinant McpM that was pre-incubated in 20% DMSO. The variance in zone clearance between the FIGS. 20A and B is attributable to differences in recombinant protein concentration or in the agar media (M9 FIG. 20A. LB FIG. 20B). Regardless, these results demonstrate that the recombinant McpM inhibits growth of susceptible *E. coli* independent of a McpM-producing *E. coli* strain.

We claim:

1. A method of killing or decreasing adverse effects of pathogenic *Escherichia coli* (*E. coli*) and/or *Shigella* bacteria, comprising
   identifying a surface or subject known to or suspected of contamination with said pathogenic *E. coli* and/or *Shigella* bacteria; and
   contacting said pathogenic *E. coli* and/or *Shigella* bacteria with
   microcin MccPDI having one or more of a sequence of SEQ ID NO: 77 or a functional variant thereof and/or SEQ ID NO:24 or a functional variant thereof, or
   an organism that produces microcin MccPDI having one or more of a sequence SEQ ID NO: 77 or a functional variant thereof and/or SEQ ID NO:24 or a functional variant thereof,
   wherein said functional variant has a sequence at least 95% identical to SEQ ID NO: 77 or SEQ ID NO: 24.

2. The method of claim 1, wherein the microcin MccPDI is SEQ ID NO:77 or a functional variant thereof.

3. The method of claim 1, wherein said pathogenic *Escherichia coli* bacteria are Shiga-toxin *E. coli* (STEC) bacteria.

4. The method of claim 1, wherein said STEC bacteria are selected from the group consisting of: enterohaemorrhagic *E. coli* (EHEC), enteropathogenic *E. coli* (EPEC), enterotoxigenic *E. coli* (ETEC), enteroinvasive *E. coli* (EIEC), enteroaggregative *E. coli* (EAEC), diffusively adherent *E. coli* (DAEC), uropathogenic *E. coli* (UPEC) and neonatal meningitis *E. coli* (NMEC).

5. The method of claim 3, wherein said STEC bacteria are of a serotype selected from the group consisting of O111, O145, O103, O26, O45, O121 and O157.

6. The method of claim 1, wherein said pathogenic *Shigella* bacteria are *Shigella flexneri*, *Shigella sonnei* or *Shigella dysenteriae*.

7. The method of claim 1, wherein said organism that produces microcin MccPDI is a naturally occurring bacteria.

8. The method of claim 7, wherein said naturally occurring bacteria are E-25 or E-264.

9. The method of claim 1, wherein said organism that produces microcin MccPDI is a genetically modified organism harboring a heterologous nucleic acid which is expressed to produce said microcin MccPDI having one or more of a sequence of SEQ ID NO: 77 or said functional variant thereof.

* * * * *

```
                          SEQUENCE LISTING

<160> NUMBER OF SEQ ID NOS: 77

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
tagttgcagg ggcataagaa                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
aggaaacgca aacagcaact                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 3
caggttcaat gctccgttgc                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 4
gcgacctttc gctttgatgg                                                   20

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 5
ccgtaatgac cgttccagt                                                    19

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 6
```
ccatttccac taccatgatc t                                          21

<210> SEQ ID NO 7
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 7
ataacccgta tctttacgtt gccttacgtt ca                              32

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 8
ctagaatccg caataatttt acagtttgat                                 30

<210> SEQ ID NO 9
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 9
aataacgtga ttgcatatta cttatctcag gagttc                          36

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 10
atccctggaa ggactacaac ctatgaccga aaatac                          36

<210> SEQ ID NO 11
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 11
gtaatttaat aaacatagta gcgccctcca ttatatctat                      40

<210> SEQ ID NO 12
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 12
aacgcacaaa ataacaaaca accgataggg gaaatatgat                      40

<210> SEQ ID NO 13
<211> LENGTH: 40
<212> TYPE: DNA
<213> ORGANISM: Artificial Sequence

```
<220> FEATURE:
<223> OTHER INFORMATION: Synthetic oligonucleotide primer

<400> SEQUENCE: 13
attatcttta ctatatttat atatgttatc attcataatg                              40

<210> SEQ ID NO 14
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 14
aacgcacaaa ataacaaaca accgataggg gaaatatgat                              40

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 15
tggtgatgaa ttcctgtcaa a                                                  21

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 16
taccagtttc acccgtcaca                                                    20

<210> SEQ ID NO 17
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 17
tcagccattc ccataaatga cgagtatcaa ggttgacg                                38

<210> SEQ ID NO 18
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 18
ttgacggaaa ggttacttat tgtattaaaa ataatg                                  36

<210> SEQ ID NO 19
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 19
gatatacatc tgacctgtgt gatgttaaag ttttatacta                              40
```

<210> SEQ ID NO 20
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 20
atagaaaaaa taagaacaat ctccgcgaaa tagcattatg                40

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide primer site

<400> SEQUENCE: 21
tgtgtaggct ggagctgctt cg                                  22

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide primer site

<400> SEQUENCE: 22
catatgaata tcctcctta                                      19

<210> SEQ ID NO 23
<211> LENGTH: 356
<212> TYPE: DNA
<213> ORGANISM: Escherichia coli

<400> SEQUENCE: 23
atggcaaata taagagaatt aactttagat gagataacgc ttgtcagcgg aggaacagca    60
actttgaagg tggcccccgt aatgaccgtt ccagtggggc tcgtaactca ctgggtcgaa   120
acgcaccaac tcatatttat agtgatccaa gcactgtaaa atgcgctaac gctgtattta   180
gtggaatgat tggtggtgcg atcaaaggag gtcccatagg aatggcaaga ggtaccattg   240
gtggagccgt tgttggtcaa tgtctctcag atcatggtag tggaaatgga agtggtaaca   300
gaggaagttc cagtagttgt tcaggtaata atgttggcgg aacatgtaac cgataa       356

<210> SEQ ID NO 24
<211> LENGTH: 120
<212> TYPE: PRT
<213> ORGANISM: Escherichia coli

<400> SEQUENCE: 24

Met Ala Asn Ile Arg Glu Leu Thr Leu Asp Glu Ile Thr Leu Val Ser
1               5                   10                  15

Gly Gly Asn Ala Asn Ser Asn Phe Glu Gly Gly Pro Arg Asn Asp Arg
            20                  25                  30

Ser Ser Gly Ala Arg Asn Ser Leu Gly Arg Asn Ala Pro Thr His Ile
        35                  40                  45

Tyr Ser Asp Pro Ser Thr Val Lys Cys Ala Asn Ala Val Phe Ser Gly
    50                  55                  60

Met Ile Gly Gly Ala Ile Lys Gly Gly Pro Ile Gly Met Ala Arg Gly
65                  70                  75                  80

Thr Ile Gly Gly Ala Val Val Gly Gln Cys Leu Ser Asp His Gly Ser
                85                  90                  95

Gly Asn Gly Ser Gly Asn Arg Gly Ser Ser Ser Cys Ser Gly Asn
            100                 105                 110

Asn Val Gly Gly Thr Cys Asn Arg
        115                 120

<210> SEQ ID NO 25
<211> LENGTH: 216
<212> TYPE: DNA
<213> ORGANISM: Escherichia coli

<400> SEQUENCE: 25
atggagggcg ctactatgtt tattaaatta ctttccttta tatgtggttt gttactggga      60
tttgcactat tgagtggctc ctctgttatt gatttatact ggttttcact accttccgag    120
ttttcaaaga ttgtagtcat gctgatcact cttttttcca cggcaagatt catggactat    180
atcatagaaa aataagaac aatctccgcg aaatag                                216

<210> SEQ ID NO 26
<211> LENGTH: 71
<212> TYPE: PRT
<213> ORGANISM: Escherichia coli

<400> SEQUENCE: 26

Met Glu Gly Ala Thr Met Phe Ile Lys Leu Leu Ser Phe Ile Cys Gly
1               5                   10                  15

Leu Leu Leu Gly Phe Ala Leu Leu Ser Gly Ser Ser Val Ile Asp Leu
            20                  25                  30

Tyr Trp Phe Ser Leu Pro Ser Glu Phe Ser Lys Ile Val Val Met Leu
        35                  40                  45

Ile Thr Leu Phe Ser Thr Ala Arg Phe Met Asp Tyr Ile Ile Glu Lys
    50                  55                  60

Ile Arg Thr Ile Ser Ala Lys
65                  70

<210> SEQ ID NO 27
<211> LENGTH: 636
<212> TYPE: DNA
<213> ORGANISM: Escherichia coli

<400> SEQUENCE: 27
atgaatgata acatatataa atatagtaaa gataatgcga tagcgtttct tctacttgtt     60
gttatatcaa cagttgtgat attcacaccg gcattcacca taca atatat tggtttggat   120 ctggcatttt cctttgtctt tattactgaa attttaatgt caacttcatt ttatattttt    180
tacttaagaa gaataccagg ttgtaaaatc accataaaga caaatgcgaa acattaaag     240 ctattagtaa tatcatttgc tgtgattgct ctcatgcaac tgcttatttt tgcttataga    300
gacaatttga caatagtga atcaacttca cttaattgga ttgaaatatt tatactggtc    360
ctgacagttc cgtattatga agaaattgtt taccgaacat gtctattcgg tcttctatgt    420
acgacttata aaaagaatt atttacccccc tgcgtgtgta catctttatt tttctgcctg    480
atgcatccgc agtattataa tgtggctgat caaattattc tgtttattat gtcaatgtta    540
ttgttgaata taaggatttg cagtaagggg atttctctatc caatgctgtt acatgcggga    600
ataaacggct tgttatatatt gttaaatata ttatag                              636

<210> SEQ ID NO 28
<211> LENGTH: 211
<212> TYPE: PRT
<213> ORGANISM: Escherichia coli

<400> SEQUENCE: 28

```
Met Asn Asp Asn Ile Tyr Lys Tyr Ser Lys Asp Asn Ala Ile Ala Phe
1               5                   10                  15
Leu Leu Leu Val Val Ile Ser Thr Val Val Ile Phe Thr Pro Ala Phe
                20                  25                  30
Thr Ile Gln Tyr Ile Gly Leu Asp Leu Ala Phe Ser Phe Val Phe Ile
            35                  40                  45
Thr Glu Ile Leu Met Ser Thr Ser Phe Tyr Ile Phe Tyr Leu Arg Arg
50                  55                  60
Ile Pro Gly Cys Lys Ile Thr Ile Lys Thr Asn Ala Lys Thr Leu Lys
65                  70                  75                  80
Leu Leu Val Ile Ser Phe Ala Val Ile Ala Leu Met Gln Leu Leu Ile
                85                  90                  95
Phe Ala Tyr Arg Asp Asn Leu Asn Asn Ser Glu Ser Thr Ser Leu Asn
                100                 105                 110
Trp Ile Glu Ile Phe Ile Leu Val Leu Thr Val Pro Tyr Tyr Glu Glu
            115                 120                 125
Ile Val Tyr Arg Thr Cys Leu Phe Gly Leu Leu Cys Thr Thr Tyr Lys
130                 135                 140
Lys Glu Leu Phe Thr Pro Cys Val Cys Thr Ser Leu Phe Phe Cys Leu
145                 150                 155                 160
Met His Pro Gln Tyr Tyr Asn Val Ala Asp Gln Ile Ile Leu Phe Ile
                165                 170                 175
Met Ser Met Leu Leu Leu Asn Ile Arg Ile Cys Ser Lys Gly Ile Phe
                180                 185                 190
Tyr Pro Met Leu Leu His Ala Gly Ile Asn Gly Phe Val Ile Leu Leu
            195                 200                 205
Asn Ile Leu
    210
```

<210> SEQ ID NO 29
<211> LENGTH: 1254
<212> TYPE: DNA
<213> ORGANISM: Escherichia coli

<400> SEQUENCE: 29

```
atgaatatat tcagaagtga agcaatagaa catcataatg acactgaata tggtgacatt      60
atttaccaa catcatttag cctatccgta tgtgcaacag ttacattatt cattatgtta     120
agtctgactg tattcatata ttacggtagc tatacaagga aagcgcatct acaggtatc     180
gtcatgccct catcaggact ggtaaaaata attcctcaat atgcaggata tgtaacacaa     240
ctgactgtat ccgaaggaga acacgtaact gcagggacac aactctatca tataagtgga     300
gaacattata acggtaacgg aactggcaca ttagcaacga tgagtatttc cctgaagact     360
cagtatatta tgttggcctc ccagcaatcc tttgagtcgc gagataatag tcaacaacag     420
gaagccatac ggcaaaggat gatatcactt gagccgcaaa taagagtgc agaacaaga     480
cttcagcttg ctgaacgtca ggcagaactg gctatatccg tcatggaacg ctataaaaaa     540
ttggctggta cgcattatgt gtcagatatc gaattccaac agaaacaaat tgatgtttct     600
gccgctcaac aaaacgttga agatcagcgt caggggcttc tccagttaca tactgcaatg     660
```

```
gacacagcca aagatgaact aaatcatctt attgttcagg ggaaaagccg taaagcagaa      720
ctcgacagac aattgcaggt gctaaaacaa caacaggatg aactcgccgg acaagaaaaa      780
tttacactga gggctccagt atccgggact attgctgctg tactgatcaa acaggggcag      840
tctgtgaaag catctgaacc ggtcatgact ctcattcccg ataatgctca tttacaaatt      900
gagctttatg ctaccagcca gaaagccggt tttatccgac caggtcaacg ggtatctctg      960
aagttttcgg ccttcccctta tcagaaattt ggtatccagt acggcacaat tcgtaaaatc     1020
agtcatacga ctctggctcc ttccgactta ttaccagttt cacccgtcac atggaaagaa     1080
aacgaagggc attatcgcgt tattgttgaa cctgaaaata catttatatt tgcatacgga     1140
aaaaaagaac cgctaagacc aggcatgact ctggaaggag acgtcaacct tgatactcgt     1200
catttatggg aatggctgac agagccccta tggagcatga aaggaaatct gtaa           1254
```

<210> SEQ ID NO 30
<211> LENGTH: 417
<212> TYPE: PRT
<213> ORGANISM: Escherichia coli

<400> SEQUENCE: 30

```
Met Asn Ile Phe Arg Ser Glu Ala Ile Glu His His Asn Asp Thr Glu
1               5                   10                  15

Tyr Gly Asp Ile Ile Leu Pro Thr Ser Phe Ser Leu Ser Val Cys Ala
            20                  25                  30

Thr Val Thr Leu Phe Ile Met Leu Ser Leu Thr Val Phe Ile Tyr Tyr
        35                  40                  45

Gly Ser Tyr Thr Arg Lys Ala His Leu Thr Gly Ile Val Met Pro Ser
    50                  55                  60

Ser Gly Leu Val Lys Ile Ile Pro Gln Tyr Ala Gly Tyr Val Thr Gln
65                  70                  75                  80

Leu Thr Val Ser Glu Gly Glu His Val Thr Ala Gly Thr Gln Leu Tyr
                85                  90                  95

His Ile Ser Gly Glu His Tyr Asn Gly Asn Gly Thr Gly Thr Leu Ala
            100                 105                 110

Thr Met Ser Ile Ser Leu Lys Thr Gln Tyr Ile Met Leu Ala Ser Gln
        115                 120                 125

Gln Ser Phe Glu Ser Arg Asp Asn Ser Gln Gln Gln Glu Ala Ile Arg
    130                 135                 140

Gln Arg Met Ile Ser Leu Glu Pro Gln Ile Arg Ser Ala Glu Gln Arg
145                 150                 155                 160

Leu Gln Leu Ala Glu Arg Gln Ala Glu Leu Ala Ile Ser Val Met Glu
                165                 170                 175

Arg Tyr Lys Lys Leu Ala Gly Thr His Tyr Val Ser Asp Ile Glu Phe
            180                 185                 190

Gln Gln Lys Gln Ile Asp Val Ser Ala Ala Gln Gln Asn Val Glu Asp
        195                 200                 205

Gln Arg Gln Gly Leu Leu Gln Leu His Thr Ala Met Asp Thr Ala Lys
    210                 215                 220

Asp Glu Leu Asn His Leu Ile Val Gln Gly Lys Ser Arg Lys Ala Glu
225                 230                 235                 240

Leu Asp Arg Gln Leu Gln Val Leu Lys Gln Gln Asp Glu Leu Ala
                245                 250                 255

Gly Gln Glu Lys Phe Thr Leu Arg Ala Pro Val Ser Gly Thr Ile Ala
            260                 265                 270
```

```
Ala Val Leu Ile Lys Gln Gly Gln Ser Val Lys Ala Ser Glu Pro Val
            275                 280                 285

Met Thr Leu Ile Pro Asp Asn Ala His Leu Gln Ile Glu Leu Tyr Ala
        290                 295                 300

Thr Ser Gln Lys Ala Gly Phe Ile Arg Pro Gly Gln Arg Val Ser Leu
305                 310                 315                 320

Lys Phe Ser Ala Phe Pro Tyr Gln Lys Phe Gly Ile Gln Tyr Gly Thr
                325                 330                 335

Ile Arg Lys Ile Ser His Thr Thr Leu Ala Pro Ser Asp Leu Leu Pro
                340                 345                 350

Val Ser Pro Val Thr Trp Lys Glu Asn Glu Gly His Tyr Arg Val Ile
            355                 360                 365

Val Glu Pro Glu Asn Thr Phe Ile Phe Ala Tyr Gly Lys Lys Glu Pro
    370                 375                 380

Leu Arg Pro Gly Met Thr Leu Glu Gly Asp Val Asn Leu Asp Thr Arg
385                 390                 395                 400

His Leu Trp Glu Trp Leu Thr Glu Pro Leu Trp Ser Met Lys Gly Asn
                405                 410                 415

Leu

<210> SEQ ID NO 31
<211> LENGTH: 2185
<212> TYPE: DNA
<213> ORGANISM: Escherichia coli

<400> SEQUENCE: 31
atggaatcaa taaactggaa agtaaggaaa caactacccg ttatccgtca aaccgaatca      60
gctgaatgcg gtctggcgtg tctggctatg attgcctgct ggcatggact gaaaacagat     120
ttatcgacat tacgggaacg tttcaatata ggtattcagg aatgacgct acaaaggttg      180 atcgaatgtg cagcgtccat ccatttatca tcacgtgcag ttcgtctgga acccgaagat     240
ctgaggtgtc ttaatcttcc atctattctg cactgggata tgaaccattt cgtcgttctc     300
cataaagttc ggggaaaccg gttatacatc catgatccgg acagaggaaa aattacaata     360
agtctgttgg acgcaggtaa gcattttaca ggagtggcac tggaattaac tccagccagt     420
gatttcaccc ccggaacgga gaaaaaaaa tccacctgcg tcaactgaca gggaaaaccc      480
cggggctttt agcatcaatg acaaaaatta ttatttttgc tctggccctt gagattctgg     540
ctttaggtgg tccacttctt aatcaactgg taattgatga agttctggtc gcagcagaca     600
gaagtctatt gtatgtcatt atagtggcac tactgttgtt atcactcata caattattac     660
tctccctagc acgacaatgg gcaacgatca gtttatccgt caattttaac atgcaatgga     720
ctgccagagt tttccatcat cttgtaagac tccctcttgc atggttcgat gcccgaagta     780
aaggaagtat taatgcccgt tttgaagcag tagatataat ccagcaggcg ctgacaacgc     840
aggttcttga aggcattctg gatatgctac ttattgtgac tgctctttgc atgatgctgt     900
tgtatagccc aggaatgaca ttaatcgcag taattgcagc tattatatat ggcgcactga     960
gagcattgtg gtatccggct ttacggcaat ctgttgaaga tgtctgggat gcaggaacta    1020
aggagtcggg gcattttctc gaaacccta acggcattca gagtctgaga atcaacggtg    1080
taactattca cagagaagcg gcctggctga acctcaacgt tacccgcaga aacacacagc    1140
tacgccagaa tcgtttacaa atgagctatg aactgacgca tacactgacg aaagtgtag    1200 tttcagccat tattttgtgg cagggagcag tagaagtgct ggatgggaca tttaccgtgg    1260
```

```
gtatgttggt tgcttactta tcctatcaga tgcgttttc atccagtata agcaatctga    1320
ctgataactt tttttcctgg cgcatgcttg atgtttataa cgagagactt gccgatattg    1380
tgctaacacc acaggaaggt caccagaatc agcaccattg gcaaaccat aatgaaacaa     1440 tatctgcaag ccagtacaga gaacataaat atgataatac ccatccacca ttacttatcg    1500
aaaaaataac atttagccat aagggcgcag ataaacccat attggataac gcgtcactaa    1560
tgctctttcc tggagaaata ttagcaataa caggtaaatc aggatgtggc aaatcaacat    1620
tggtaaagct tattcttgga attcatacac caagtgaagg aagaattaat gcatttggca    1680
taccacatac acattctgat tattttcagg ttcgtcaacg aattggcact gtattgcaag    1740
atgactatct tttcaaaggt tctatagctg ataatataat gttttttagc gaaattagag    1800
atcatgaaca catgcgtaaa tgcgcaagtc tggcacttat agacagtgat attatggcaa    1860
tgccaatggg ctatcaacat tacttggaga accggagggg ggactttcag gtggtcagaa    1920
gcaacgtatt ctactggcaa gagcactgta taaaaaaccc ggtctattat tactggacga    1980
agcaaccagt catcttgatg tggaaagtga atagaaata agccagacat tacgccaact     2040
cggattcctg ttctgttaat agctcatcga ccagaaacaa tagcatccgc agacagagtt    2100
ctatctgaga gatggtcact tttcggaaat aacatatcga cctgccagaa ctcataatat    2160
aaataatcac cccaacagga ggtga                                         2185

<210> SEQ ID NO 32
<211> LENGTH: 729
<212> TYPE: PRT
<213> ORGANISM: Escherichia coli

<400> SEQUENCE: 32

Met Glu Ser Ile Asn Trp Lys Val Arg Lys Gln Leu Pro Val Ile Arg
1               5                   10                  15

Gln Thr Glu Ser Ala Glu Cys Gly Leu Ala Cys Leu Ala Met Ile Ala
            20                  25                  30

Cys Trp His Gly Leu Lys Thr Asp Leu Ser Thr Leu Arg Glu Arg Phe
        35                  40                  45

Asn Ile Gly Ile Gln Gly Met Thr Leu Gln Arg Leu Ile Glu Cys Ala
    50                  55                  60

Ala Ser Ile His Leu Ser Ser Arg Ala Val Arg Leu Glu Pro Glu Asp
65                  70                  75                  80

Leu Arg Cys Leu Asn Leu Pro Ser Ile Leu His Trp Asp Met Asn His
                85                  90                  95

Phe Val Val Leu His Lys Val Arg Gly Asn Arg Leu Tyr Ile His Asp
            100                 105                 110

Pro Asp Arg Gly Lys Ile Thr Ile Ser Leu Leu Asp Ala Gly Lys His
        115                 120                 125

Phe Thr Gly Val Ala Leu Glu Leu Thr Pro Ala Ser Asp Phe Thr Pro
    130                 135                 140

Arg Asn Glu Arg Lys Lys Ile His Leu Arg Gln Leu Thr Gly Lys Thr
145                 150                 155                 160

Pro Gly Leu Leu Ala Ser Met Thr Lys Ile Ile Ile Phe Ala Leu Ala
                165                 170                 175

Leu Glu Ile Leu Ala Leu Gly Gly Pro Leu Leu Asn Gln Leu Val Ile
            180                 185                 190

Asp Glu Val Leu Val Ala Ala Asp Arg Ser Leu Leu Tyr Val Ile Ile
        195                 200                 205
```

```
Val Ala Leu Leu Leu Leu Ser Leu Ile Gln Leu Leu Leu Ser Leu Ala
    210                 215                 220

Arg Gln Trp Ala Thr Ile Ser Leu Ser Val Asn Phe Asn Met Gln Trp
225                 230                 235                 240

Thr Ala Arg Val Phe His His Leu Val Arg Leu Pro Leu Ala Trp Phe
                245                 250                 255

Asp Ala Arg Ser Lys Gly Ser Ile Asn Ala Arg Phe Glu Ala Val Asp
            260                 265                 270

Ile Ile Gln Gln Ala Leu Thr Thr Gln Val Leu Glu Gly Ile Leu Asp
        275                 280                 285

Met Leu Leu Ile Val Thr Ala Leu Cys Met Met Leu Leu Tyr Ser Pro
    290                 295                 300

Gly Met Thr Leu Ile Ala Val Ile Ala Ala Ile Ile Tyr Gly Ala Leu
305                 310                 315                 320

Arg Ala Leu Trp Tyr Pro Ala Leu Arg Gln Ser Val Glu Asp Val Trp
                325                 330                 335

Asp Ala Gly Thr Lys Glu Ser Gly His Phe Leu Glu Thr Leu Asn Gly
            340                 345                 350

Ile Gln Ser Leu Arg Ile Asn Gly Val Thr Ile His Arg Glu Ala Ala
        355                 360                 365

Trp Leu Asn Leu Asn Val Thr Arg Arg Asn Thr Gln Leu Arg Gln Asn
    370                 375                 380

Arg Leu Gln Met Ser Tyr Glu Leu Thr His Thr Leu Thr Glu Ser Val
385                 390                 395                 400

Val Ser Ala Ile Ile Leu Trp Gln Gly Ala Val Glu Val Leu Asp Gly
                405                 410                 415

Thr Phe Thr Val Gly Met Leu Val Ala Tyr Leu Ser Tyr Gln Met Arg
            420                 425                 430

Phe Ser Ser Ser Ile Ser Asn Leu Thr Asp Asn Phe Phe Ser Trp Arg
        435                 440                 445

Met Leu Asp Val Tyr Asn Glu Arg Leu Ala Asp Ile Val Leu Thr Pro
    450                 455                 460

Gln Glu Gly His Gln Asn Gln His His Trp Ala Asn His Asn Glu Thr
465                 470                 475                 480

Ile Ser Ala Ser Gln Tyr Arg Glu His Lys Tyr Asp Asn Thr His Pro
                485                 490                 495

Pro Leu Leu Ile Glu Lys Ile Thr Phe Ser His Lys Gly Ala Asp Lys
            500                 505                 510

Pro Ile Leu Asp Asn Ala Ser Leu Met Leu Phe Pro Gly Glu Ile Leu
        515                 520                 525

Ala Ile Thr Gly Lys Ser Gly Cys Gly Lys Ser Thr Leu Val Lys Leu
    530                 535                 540

Ile Leu Gly Ile His Thr Pro Ser Glu Gly Arg Ile Asn Ala Phe Gly
545                 550                 555                 560

Ile Pro His Thr His Ser Asp Tyr Phe Gln Val Arg Gln Arg Ile Gly
                565                 570                 575

Thr Val Leu Gln Asp Asp Tyr Leu Phe Lys Gly Ser Ile Ala Asp Asn
            580                 585                 590

Ile Met Phe Phe Ser Glu Ile Arg Asp His Glu His Met Arg Lys Cys
        595                 600                 605

Ala Ser Leu Ala Leu Ile Asp Ser Asp Ile Met Ala Met Pro Met Gly
    610                 615                 620

Tyr Gln Thr Leu Leu Gly Glu Thr Gly Gly Gly Leu Ser Gly Gly Gln
```

| | | | | |
|---|---|---|---|---|
| | 625 | 630 | 635 | 640 |

Lys Gln Arg Ile Leu Leu Ala Arg Ala Leu Tyr Lys Lys Pro Gly Leu
                645                        650                        655

Leu Leu Leu Asp Glu Ala Thr Ser His Leu Asp Val Glu Ser Glu Ile
          660                        665                        670

Glu Ile Ser Gln Thr Leu Arg Gln Leu Gly Ile Pro Val Leu Leu Ile
              675                        680                      685

Ala His Arg Pro Glu Thr Ile Ala Ser Ala Asp Arg Val Leu Tyr Leu
          690                        695                        700

Arg Asp Gly His Phe Ser Glu Ile Thr Tyr Arg Pro Ala Arg Thr His
705                        710                        715                        720

Asn Ile Asn Asn His Pro Asn Arg Arg
          725

<210> SEQ ID NO 33
<211> LENGTH: 98809
<212> TYPE: DNA
<213> ORGANISM: Escherichia coli

<400> SEQUENCE: 33

```
gatctaaagc agaaaaatct gcttttaaaa atagatttta ttttttttgac gcaggtcaag      60
attaacttat tagaggtatc agtgaggagg cactggaaga gaagagatcg ttgtaatgct     120
tttcaaatta acgtaaagcg ggtatatttc ggctgttatt agctgtgcag agggtggcac     180
tctgtggagc aaagcggcga agccggacg gcagaatgcg ccataaggca ttcaggagag      240
atggcatgta cgggcagtaa gtcagaagac tgaagatgtt ccggaagcca taaaaggaaa     300
acccccacta tctttcttac gaacttggcg gaacgacgaa agatagtggg ggcctcacag     360
aatacgggta aagtataatg aaaccgtacc agagattcaa ccctgtgcag tgtataaata     420
cacggcacaa tcgctccgcc ataagcgaca gcttgtggca ggtctgaaga atactccata     480
taacgcagta cactggagtc agttagcacc cgaagagcag atccgtttct gggaagacta     540
tgaagcggga agggcgacca ctttcctggt tgaaccggaa aggaagcgca cgaagcgtcg     600
tcgtggtgag cactccacca aacccaaatg cgaaaatccg tcctggtatc gtcctgagcg     660
ctataaggcg ctgagcgggc agctcgggca cgcctacaac cgtctggtga aaaaggaccc     720
ggtgaccggc gagcagagcc tgcgcatgca catgtctctg catccttttt acgtgcagaa     780
acgaacgtat gccggtcgca aatatgcttt ccgtccggaa aaacaacgcc tcctcgatgc     840
cgtctggccg gttctggtca gcttcagtga tgcgggcaca cataccgtag catgagtgt      900
ttcccgtctg gccagagaaa tcagcccgaa agacagcaag gggaaggtta ttccggaact     960
ggaagtgacg gtctcccgcc tttcccgttt gctggccgaa caggtacgtt ttggtgtgct    1020
gggtgtttca gaggaaaccc tgtgggaccg tgaaacccgc cagcgtctgc cacgttacgt    1080
ctggataaca ccggcaggct ggcagatgct gggcgtcgac atggtaaaac ttcacgaaca    1140
gcagcagaaa cgactgcgtg aaagtgaaat ccgccagcag ctcattcggg aaggtgttct    1200
gcgtgaggat gaagatatct ccgtacatgc ggccagaaaa cgctggtatc tgcagcgcag    1260
tcaggatgcg ctgaaacacc gtcgtgcgaa agcagcagcc agtaagcgcg ccagacgcct    1320
gaagaaactg cctgccgacc agcagattca tgagatggca gagtatctca ggaagcgtct    1380
gcctccggat gaagcctatt tttgttccga tgaccatctg aagcgaatgg ccatcaggga    1440
gttgcgtcag cttgaactga cgctggctgc cccgccaccg cactgacag caccattccc     1500
tcagcactga atcatcacca gccccctccgg ggctttcggc gctggttccg ctcagcccaa    1560
```

| | |
|---|---|
| aatccgcagt aatcacctta aatcccctca gaggggcata tctgcccata aaaccacgca | 1620 |
| tcagtcatca gaacatggcc acgttgtttc agttatccac ataaatccgc aaataaagaa | 1680 |
| ctttaagaag ctgcaaacct gaaacagcaa acctgcaata tagtcttaac cccattattt | 1740 |
| aatcccctgc gttgcttcgc cgcagggaaa gtctttatct ctgaaaccac tgtgaacaaa | 1800 |
| tacaaagagg ccttcgcttg cagcggccag ggccacgccg ctcagaatct aaaagcacct | 1860 |
| cccacgctaa cgcgcgggcc ccgacccctca ccattcagaa accacagcaa aaaaacatca | 1920 |
| ggaataaaaa cgccacacaa acgcagcacc gtgcctaccc ctcataactg aaaagcgagg | 1980 |
| ccgcccccgc ccgaagggcg ggaacaacat cgcttttaat tatgaatgtt gtaactaagc | 2040 |
| attcccatcg ctgtcagtct tctggctgga agtatcgagt acacgctcgt aagcggccct | 2100 |
| cacgcccgc taacgcggag atacgccccg acttcgggta aaccctcgtc gggaccactc | 2160 |
| cgaccgcgca cagaagctct ctcatggctg aaagcgggta tggcttagca gggtgggaat | 2220 |
| gggataggcg aaatctatca atcagtaccg gcttacgccg gcttcggcg gttttactcc | 2280 |
| ggtatcatat gaaacaatgg agtaccgcct tccatgccgc tggcgcggca tctgttaaca | 2340 |
| atcaatactt ttatcattat tatcaggaaa aaattgatcg tctgaataaa aatatatgaa | 2400 |
| tgataaaaaa gagagataca tatcttccga gctgtcagat aaaactcaac tttctgtttt | 2460 |
| gcgcagtata gttggatggg gctatgaaaa aataagacat tctctggggc gaccagggca | 2520 |
| acttgaaaga gcgattgcat ccggggagtt aatcccgtgt cctttaaaaa ctcctgtcga | 2580 |
| tacactatgg acgcgatcgg tgatttactg gcaggactgg atatccccat catggatacc | 2640 |
| atctgattct cgccaatgta cgatagattt ctataagcca ggctactatc gtggtttaga | 2700 |
| acgatgtcat atggttgttc ccgaagttca gaatctgatt agcaaagaag atattcctca | 2760 |
| tttttcgtgt gatatcaccg atattcaggg tatctccgca tcgaaatctg agatgtatga | 2820 |
| tattggtgac atttatgaat ttcctctact gagatgccct gggctggtta ccccggtaaa | 2880 |
| tgaagaacat ctcagagaaa atatgcagta ctgggagtta aggctccatc gaatgcgctt | 2940 |
| tgctgaatat ccgtggactg agcgtaagct gtattgctg aatgaaggtg gctcacatca | 3000 |
| ttttgcagct gcccgttatc aggcatgccg tctgggaatt tctgttccgc ttacgggcag | 3060 |
| attgagtcgc ttccatgtaa acatgcagat ggtttcagct ttatgtcagc aatggcacct | 3120 |
| gtttgctatt cctgcagatg aacggttagc ctgctttttc agggcgatga ttgcctttga | 3180 |
| atgcccattt ggtaattcag aattacctcg gaatatgcac aatactataa agtcaggagt | 3240 |
| caaactcaaa ctcgtttggc ttgaacgtgg tcataccaaa gcagacattg ttgcagatgt | 3300 |
| acttgccaca gcaggtttcc ctgattttgg ggatcaattg aagctgctgg ctaccagcag | 3360 |
| cctgcaaaaa acacataagc tggcctgaaa ggaatacttc acaatgaata tcattgtgtt | 3420 |
| ggtaacctgc tgttatcgtg atgaaattac cgctcaattt tttcggttga cgcggtctgt | 3480 |
| tcctgcatgt ttttcatctt tagcttctgt ttttcccta ctgccagcca gcgtctggca | 3540 |
| ttctgcgcat cgcattctga tacctgacct gctggtagtc catccagtcc ataacgaggg | 3600 |
| atacctgcga cagcagtacg cagcagatat acctgtcggg tggtgatgca ggatattgca | 3660 |
| caggaccatt catccagtgt cagttctgtc tcagggtgtt ctgtcaggaa tgcggcaaaa | 3720 |
| tcattggtta tgccaatttt cagtggaaga aatccccgc tttctgcgcg aagatgggga | 3780 |
| aacagagact taactttttc cacgcaattg tgagtaaatt catgagtcca atgaggctgg | 3840 |
| cgtggaaaac ggcgtctttt tctttttttc ttactggcag aagcttcagg gggatgagta | 3900 |

```
tcgacggcag gagaactgct tcccacagat actggatctt ccatctttac cgtctctgaa    3960
cgtgcgataa cacctgtttt ttcagataag gaaggggggta aaagagtgcg acgttttttc    4020
accataatga tgggtgtttt cttttcttcc tgatatttcc ccataaaaac ctctacgatg    4080
tgttcttata taataatata tatcatattt tcacaattaa cataatatct tcgttaagaa    4140
aataacagaa caaaatttgt tgttttttta tgacaggcat gaaatgagcc agcataatta    4200
tattaatcat tatcccaaat gagcttttgt atttgctcat tcgggatggt tggatatttt    4260
aagttatatc tactgtatca ttctcaggta atcgttccat taaatcagaa actacgggct    4320
gtaaccagtc agtgacttca cttacatact gatgccattc gggatgcctg gaggccagat    4380
ccatcactcg tgttaacccg gacggacgat caatgcccaa tttagttaaa atgttcgaga    4440
tataattatg agcatcaagt tcaactctga tatcccttgc tgcttctatt atttctaaat    4500
attctccacc caatccgtcc agtgggacat ttgtaataag ataatgaatg tattgttcag    4560
gcttaactcc atttgggaga ttaaattgtt ttatttttcc ttccgctgcc gcttttaact    4620
cataagttcg tgattctgtg ccggtgaaaa ctttatcaag agcagctttc ttttcatttt    4680
ctgtggagta tttatcgcca tcaagaatat aaagtttatc agatagatta tctccacgaa    4740
taagtgtact ggcaagtaga gtgaatgcgt ttgaagctgc gccaaatttta aatattttca    4800 catatctgct ggccttaagt gaagaacata ttttatttat tattgcaaca gcaagatcat    4860
cttccacata tatttcaatg ggagttgttg atttacctgt taatctgttt atagcatcag    4920
gttttgtttc ttcaaatgaa taactacggc cttgaatgtt tacgacgtgt cttatattta    4980
tcttgtctga taaagtggtt accatttctc tatgggtagt gaagatgatt tgtttatttt    5040
tatcttcggc atgagttgat atgacgtcta ttaacttttt caatgcttcg tcatgcaaca    5100
gcaaatctaa ttcatcgatt aatattaagg cgttcttgtc cgcttttaat attgtttcca    5160
gaattaaaaa tatctttttgc tctcctgcgc tcatacttaa tgatgagtag gccagtccct    5220
ctgactcaac tccaatcaat attttttccat tgggttgttg atgttgattg aaacttgtat    5280
atggtttatt aagtatatag gaggcgtaat gaagaatgtt tgttattaaa tcattactga    5340
cactgctggt ttcatactga atattattct tttttttctga ttctattata ggaacacatt    5400
tatcaatgcc aagatagtaa acttctctta aaggacgacg agcataaatc tgaatccatc    5460
gtgagcctcg aacatcagct tttccataat tttttaattc attttcaatc attacaccat    5520
ctttacgata agttaaattt acaatgaagt cactgccgtt ccattcagca tgtggactgc    5580
gtggaaaaaa atgcattaac cgatggtctt caccggggaa accttttttca ggcatgtata    5640 tgcttgctat ggcatggagt attgttgatt ttccgcttcc atttggacct aaaattgcgg    5700
ttaacgcatg aggtttaaaa ataatctcgt ttaatccatt tatacatttt agtttgttaa    5760
ttttaatgga gttcaagact tgaccagtaa tagttttttc ttttttttctg ccatttttaa    5820 atcctagcat tatgttgggg gaattcacca tgtaattcag aaacatataa ctgtgaacag    5880
gggatatatc aaatcctttt aatattctat tttgcacagt attctacatc aggcctcttt    5940
tatgctacag acttttttgag atgtctgtaa ttttagactt aatgttatga ctgatcatat    6000
ctcctatcca ctggtggcgc aggaaagtta accggctgcc accatgggat gatgtgtaaa    6060
ccgtgcacag gcgtgttctt acggagcggc actttcattt atctgtacgc gaacctccat    6120
tccggcatca tgacaggcct gcagccactg cgccacttcc agcggatcgc cctcccggcg    6180
taccaccctg ccttctttat tccataactg cagacaggtg ctgccgtcga dacgcaccac    6240
aaaatcccca cggcaggcct gatacgtcat gccgttcagc tccaccgcca gatcagtggc    6300
```

```
agaagtgcct tctgcgggca gacctgcggc cgggaccagc ggtagtacga cgacttctgc    6360
cgcacgctgt tctgcccgga ggcggtcctg ttctgcctgc agcagaggct gtgccacggc    6420
ccggccggcg tccgtcagct cgacagccag ctgcagattc ggggcgcgca gggtacgcag    6480
ccagccggca tcctccagac gacggcagga cgcgcgcagg tttggcccgt agatcggggc    6540
ttccccgctt cgctccagca cccgttccag gtcccgcgtc agcacggggc ccggccgttt    6600
ttcatcaagc gcagccagca caatcagcac tctccgctgc agtggcgacg gtcggcggct    6660
ctgggtcatt acctgtcatc ctccggccag atgaggtttc tgaggcgctg aaagtcggcg    6720
tcaatgagct cctgtctctt tatggcattc attgaggcat agccatttat ggccagttca    6780
tgccagaaga tcagcacggc tccggctttg gctgactcgc agagataaat cgcgccctgg    6840
ctgtccagat tgcattcccg gatgcgtcgt tccgcaaacc gggtcagttg ttcatagctg    6900
agtgaaaacg tcatttcctg atccatcctg cacgctccat ctgataatgt tctgacaggt    6960
aaaaatcata tcatgtatga tttatgtact cttgatttct gataatatca gatattgttt    7020 cattttaat gatgaaaatc atatctgata tgattttatg tgtatttctt aattatcata    7080
tcatttgcgt cttttctgcc gcgcagatcc ggtttccggc taacacggag ataataggtt    7140
aggtggttct gttgttaggg tatggagaac atttctcgag ccgagcaagg gaaattactc    7200
acaccatttg ctatgctaac ggccacacta accagccttt tttcggggta atacatgccg    7260
ttagcacaac tgaagcgtga cactctttcc cttgttaagc taaatggcga caggactgat    7320
gggataaaag gaagtgttca aaagaataag attttcatta gccggagcga tattgctatt    7380
gaaaaggggg atctgcttat acgcagtatg ccgcatggcg gtactgaaga atatattgta    7440
atcgaaccta acttcagaat gggtgtaggc ggtattcctg cgacctatca ggctgaggtg    7500
atactgaagg aaaatacaac taccgaggaa atgacatcat cccttccac agcagtaccg    7560 gaagcagtta ttgccactgt aaatacattc attgctctgt gtgtcaccat tgtaaatgag    7620
ggcgcatcaa gtcctgataa atatgcttcg cagtttatc gcttgcgtca ggaattactt    7680
gaactcgata atattatcac cattccttca tggatcagat tctccatgtc acccgctgac    7740
attaagaata atgttggttt aaacgtcaca ggtggcgatg gagcttgggg gcgaagacga    7800
cagtatttac agagcgaatc tattaaaata cttcaagct ataaaaccgc accaattatt    7860
gagcattctg ttagtgagaa taaaataaaa aatactgagc aagtcagcgg gttgacaacg    7920
atggcaagcg atgcagggtt aaacatgaag aagaaagtat tcattgtcca tgggcacgat    7980
gataaactaa aaaacgaggt ttacattttt ctggcaaatg aaggtttcca gcctgtcata    8040
cttcatcatg aagccaatga aggacagacc ataatcgaga agcttgagaa gcatatcgac    8100
actgtatcct atgcagtggt gctttatact gcctgtgatg aagggaaagc caagaatgaa    8160
actgaactaa aaaaagagc ccggcagaat gttgttttag aacacggctg gctcatgtcc    8220
aagctatcgc gtaaattcgt cgctgcgata gttgaagatg gcgttgaatt tcctggagac    8280
ctgtccggag tggtcagaat atctgcatca gactggaaat atgatctgtc taaagaatta    8340
aaagtgctca ataattaaat tgtattcagt gatgtaagga tactattatg ggatacacca    8400
gaaatcagca catgctctca cagtggtttc tcaggaactt ccgcagtgat gatacggcac    8460
agagtccgaa ggagaagcaa cgggtctggg cccacgttgt ggttcctacg gcagaaggca    8520
aaaatgacat aaaggacatc ccgctaccga tatccagcgt ggccgtctgt aaggactgct    8580
ttcgtcttac cgacggtgac acaggcgagg tttttgatat cgagcatgag ctcagtgatt    8640
```

```
atgaacagga tatggctttg cttgtccggg atctggttca gaaccataat ttcgcgcgtc    8700
tggctaactg tgacactgat gattttccgg tagagaagct tgcaagtttt gctatatttc    8760
agatgttact taacctcaat aacccgcaaa gcagatttcc gggtaaaaat gagttatttc    8820
agtcattcat taacctagta aaaacaacc ttcagcatat catttccgaa acaatttctt    8880
tgtctgacgt tatgccggag ttggcggctt aagtatcta tcagaaactg attcgtatag    8940
ctcgttcttc ttctggggat gacgaaaaag ctaaggccat gtttgtatta ttttcccttc    9000
tcgcacttca gggtaaaata caatgattg acactatggc ctggctacgc ggagaggttt    9060
tttccggaat acatcgtgtg gatatatttc ataccgggca ccacttttac agtacagaac    9120
cacgtccggt atttacagta tcacctaatg tattttgcaa aatgacagaa gaacgcgtcc    9180
tgtaccttcc ccttgctcat aatttggctc ttaagtttta tcagtacccg gaacacgggt    9240
ttttcacccc actggaaatt aatgtattca gcccggaccc tcagaaacta cttacaaaag    9300
acatgtcacg aatcaaagtt tataaatgct cctatgatta tattgatcag gttatgtcaa    9360
caattgatat gtataacgtc ggattttcaa atattattta ttctagctgg cagctcagtg    9420
atgttgaaaa ttatctgagg ctacagaacg aacatcatga tacttattat cttccggaac    9480
atcccgtttg ctggactgta tccagggaga aagggtgatg ccctgaccc cggaacagat    9540 aagttgccga cagcagctcg tggcaatggg tgacttcaat gcccataccc tgctgcccgg    9600
agaggagtgg accaggccag aaaacgctga tgtccggcac gttctgtcgc tgatcccct    9660 gacggacatc cagctggcta accggctgga tgtggacgaa cgcaccatcc gcaaggggaa    9720
atccggcgag accagtatgg tattcaccac ttggtgctgc ctgtgctggc tggccgggct    9780
gggaatgctg ctggaagaac cggcttagcc ggttctgatg cgtttccaga ttcttttgag    9840
tatgaagcgt cgctgatatc gccattgtga acggtagata tgggggagtc gatcatagtt    9900
cttccaaaac aaggtccagc ctttataggc atcaacaagt agggcaatga gagagccagt    9960
ttttaagagg ccaaagaaaa cggccatgag aaatacagtc atacgatgtt ccttatgtaa   10020
aactgtattt aggaaatccg aagcggcctt taaggccggt tgatgaaaat gaactgaaaa   10080
aagtttctct ggcctatttg ttgccatttc aggctagctc tttcgtgaat tttgcctctc   10140
aggcaataat ccactcatca caacaattca ccgttttag tgcttatcct gcaaaaatct   10200 gttttttttcc cttcctgaga tccgaaaact tatttaagag gatcacttgc agccggcaac   10260
aggaaggttt tacattgatt tgaattatgc cgtttctttt cctcctgcct tgaaaaggat   10320
atctgaatgc acttttatgt ggatgaaaca ggccagactg gccgaaacct ttttgacaaa   10380
acccagccaa tcctctccta cggagttctg tcctcagagg ctgacctaga taaggttgct   10440
gaagcggatc ttgccgcatt acgcaaaact ctgggcgtgg agcgcctgca cgctgcggaa   10500
ctgggcgtgc accgcctttc agaagttgtg gatacgctgc tggtcctgca gaaaaatcac   10560
cggatacggt ttgatatctg gcaggtggtt aagcgcgatc acgccattat ttcgttcttc   10620
gaccaggtgt ttgatcaggg actgaatccg gttgtgccct ggagtgccta ctggaccccct   10680 ctgcgctatc ccctgctgct gaatctgtct aatctgtttg atgatgagct ggctgaaaaa   10740
gcgtggcgtg cccgtcttga ggctcatgat gaacgttctt gctcattatt cagtgaggtt   10800
tgtggagtgc tgcttcagcg cgttcactct ctgggtgatg cccgttcagt tgaactcatt   10860
accgatgccc tatcttgggc gatggtcaac tttgatgagc tggggtacaa ctgcaaaacc   10920
aataaggaaa agttgcagat catgcccaat atgattggtt ttcagtccgt tttgcacggg   10980
atctgctctc gtctgggggc accgaaccgg aaagcagata tcattgttga ccagcagtca   11040
```

```
cagttcaaca ccacccagcg ggagttgaac gagtttract accagatccg cgaacagccg   11100
tgggcactgg ggccgggttt gcctgtcatg gatatgaaga acatgccagc aaaaccgctt   11160
gtcttccagt cgggaacgat gagtgccggg ctggaactgg ttgatattta tctctggatc   11220
ttcaaacgat acatggaacg gaaggaactg accaaacccc tctcccgcct cgtctacacc   11280
aatcttaaaa cagcgagaac tgacagtgtt tctctgcagt cagttgcaaa gaggtttaag   11340 gagtttttg aaaaactttc tgaaccaacc gcagaaatga tagaaaaagc aaatgaactc    11400
agggccgtgg aagaaacgcg ccgtcttgcc catcgtgtac aaagtgtgtc gcaatcctga   11460
tcagaaaggt taaccgcata tgaaggcaga aaatgcccgt caggttcagg ggctgataga   11520
actagagaaa tttaaccctg aaacactgtg ctcgggcgag agctggatgg caccttcagc   11580
cagtgaagtc agcgtggtcc gggcgctgat cccgctcaca gatatccagc tggccaaccg   11640
gctagatgtg gacgagcgca ccatccgtaa gtggaaatcc ggcgagacca gaatggtgtt   11700
caccacctgg tgctgtctgt gctggctggc cgggttgggg atgctgctgg aagaaccggc   11760
ttagccggtt ctgatgcgtt tccagattct tttgagaatg aagcgtcgct gatatcgcca   11820
ttgcgaacgg tagatatggg ggagtcgatc atagttcttc cagaacaagg tccagccttt   11880
ataaggctcc gtttcccaaa cggagccctg agtcgctgac gccggaattc tttactacga   11940
attagtattg aggcgagcgg ccaaaacaat atgctgcata tcctggtgcg tcggcttaaa   12000
gcccagacgc tctaggttta tttcagcaac cacttcatct gggccacccc agatagtatc   12060
gccagcctgt tccagtaggt cgagtttgcc acaataagct tcaggcttac cagcggcatt   12120
tagctgatac tccagttttt ccccatgaat tttcatgacg ttaatcagca cgtcattccc   12180
cagagccata tagagccaga tatatatgcc gccagcggtc tgctgcgtat cgcttacaac   12240
gacaccataa tgtgccatga ttagccggta tacgtgctgg gacagttta ctgccctata    12300 ttcatcgccg acaaatgcac tgataacctg cggaatacga tcaggaaaac cctctggagc   12360
ttccagagca aactcaagca tatagtttgc ggaaacttca tttgactcga tatgacgcaa   12420
gtaaagacgt gcttgttcgc cgatgtcttc aagaatgacc tcgtgcttaa agcctgcgtc   12480
gtcagtgatg ttttctaatt tttggtagga ctggcccgct tcattgagat cttcaggcca   12540
gattaatttt ttatcgtgtt cgcgtattat cagtggtgac atgccagatt accgtgctca   12600
ttccattgaa aaaattctat cgcgcggcgg ctgaaatcag ccagattcac cgattttgat   12660
agctcggttt ctttctgttc tatgcattrc ttacggccat cttcttcaaa ctgaacaaca   12720
accagcggca caacacggtc gcgacgggtt gcttgctgcc agttttcatg caccacgatc   12780
agcatcggac gcttctcgcg ggtattattt gaacgtactt cgaatttacc ctgaacgcca   12840
ggtatgcaaa aactacccaa aagagcatag ttatcagcaa tagtgaatgg tgaatgagtg   12900
atcattggca cctccgcaaa ttcaaagtat tcagtaagat ggcggaaacc cttgacgcgc   12960
aagtggttga cgcttacgtc agtataccte atagaaatat tcggacaata atattgttta   13020
cgatttcagc ggcgttcgta taggaaaagc cattcctcag gatggctttt ctcgtttcag   13080
aacgtcagaa aacagaccgt tctgtgggcg gcaggcgcag tgcttgccgt atctggtcga   13140
ccatgtccag aaaatcccct tcctttctgca ggaagaacag ttcttttatgc actctgatta   13200 gcgtcggtaa atcgcggcga gcagcctcaa tgaagagggc aaacgccagt gacgtgccat   13260
gcgggatatg ggtgatgcca ggtagctgtg cggcgcgcag ttcaagcagg gaacgccgt    13320 tacgcataat atgctgcaga tcttcttctt tataaatgcc tagtaaacgg caccaggccc   13380
```

-continued

```
ggttttcagc gagcgtctgg gcgctgtcat accagtaatc ggcgagggct gccttcatca    13440
ttgtggccac gtctttatcc atcagcgcca cgaggccatt ccgcgcata aagttaccga     13500 tcagatcccc gaaggaggct gagaggaatt ctttgacaaa atcactttt gactttcctg    13560 ccgccctcgc ctgttccgtg atttcgttat ccacatcaaa aggcatgttt cgcacggtca    13620
gcgtgcgtgt ggatcctttt tcggcatttt cattctgttc agtcatttct ttctccgaag    13680
gacgtgacac tctcaacatc caccacttgc attgaaataa gatgtttgtt gttaagatat    13740 ttatttgct tcccgatttc aatatgtgaa ttcataatga taaaagtggt gctaagcaag    13800
ataaaattta accaggcgtg aggagaactc ctcatcttca gcactgagat ccgaaaaccc    13860
caagttacgg atccgcggat ccttcgctgc cgcccgctgg tccgctttca caggatgtgg    13920
tgtcccgctc cgctgacatg acactgtatg ttgtgtttct tcccgtgttc ccgagccagt    13980
catcagcggc agaaaagatc gcttcgctta ttcactgatc ctgattcact tccggaaagt    14040
tgtaaatacg cagtaaatcg gatcatctga aaccactgt tcgataattt aatggagtgg    14100
ttatatgcct gattattatt tcaatatgtg aaatccattt ttgtgaaagt cacttctca    14160 acagagtagc actcatctgg cgatgattga ggtgtggtaa aattgcacgg ctaactattc    14220
aactgaggaa atgacatgtt tactgcattc aatgagagaa atgatttcag ttatgctttt    14280
gaaaaaattc gcaatgcgat ttccgcgcca ggagaaaata atgtttatgc tgccacagaa    14340
ttaggtcttg gcattctgct ccgtaaatac gagcagtttc gccggagct ggatgtggcc    14400 ggtgagctgg gaaactggga atacgatctc gatacctaca atcactgtat tgcggtgctg    14460
caacgttact tcactggcaa tccatccgga ctgacagaac gtgacgcccg gatttacagt    14520
cagtacctgc agactgagca caagggtttt gtgaagctgg ctgaagaact ggcggctgac    14580
cgctgaatac atacagtagg cgggattcc ggataaggta ccgaaccggg gctgttaaaa    14640
gattctggag ttgaaatgaa aaagggaaaa acgttagaac cggggctgct ggccagcgac    14700
agcgactggc acaataatgc ctgcctgaat tacatgccgg atcatggtac agcttacacc    14760
gaaggttaca ggcgagctgc tgatattctg attaaccaca ttgatgaatc cgggcgggac    14820
caggattttc tggtttatcc ggtgttgttt ctctaccgac atcacttgga gctccttatc    14880
aaacaaatta tcggactggc ccttgcactg gcagaagacc cggataaaca ccagtacaaa    14940
aaagatgacc ataacctgaa taatctatgg ccgctggcac aaaagctgat cctggaagtt    15000
gatgacagct accggccttc cgattttaaa atcgtcaaag aggtggttaa agctcttcac    15060
caagcggatg aacgggcgac agatttccga tatgccagga gaaatgacgg cacccggagc    15120
cttgaaggaa ttcattacgt caacacccgc cgctttgggg aaaaaatggg agaggcttcc    15180
gatttacttg acgggtcga caatagcctc cggtacctgc tggactgtaa agccgaatgg    15240
aatcaaattc tggacagctt ctgacagcca gaaacggcgc gaaaaatcca tcagacttac    15300
ctgaacaact aatgatactg agataccgat catgactggc ctcataccttt cagctacttc    15360 tcagggccca atggccgccc tgccagtgac catcgactat cccgcagcac tggccttgcg    15420
gcagatggcg ctcgttcagg acgaactacc gaaatacctg ctggcgccgg aagtgagcgc    15480
cctgctccac tatgtgcccg atctgcaccg taagatgctg ctggccaccc tctggaatac    15540
gggcgcccgc attaacgagg cgctggcgct tactcgaggg gattttcgc tggcaccgcc    15600 atatccgttc gtacagctgg ccacgctgaa gcaacgtgcc gagaaggctg ctagaacagc    15660
aggacgtctg cccgccggca gtcaggccca tcgtctggtt ccgctatcag acagccagta    15720
cgtgaaccag ttggaaatga tggtggccac gctgaagatt ccgctcgagc gacgtaataa    15780
```

```
gcgtaccggc agaaccgaaa aggcgcgtat ctgggaggtc actgaccgga cggtacggac   15840
ctggctgaat gaagcagtgg agaatgcggc cgctgacggg gtgtcattct ctgtgccggt   15900
taccccacat actttccgcc attcctacgc gatgcatatg ctgtatgctg gtattccgct   15960
gaaggtgctg cagagcctga tggggcacaa gtcgattagt tcgacagagg tgtacacgaa   16020
ggtgtttgcg ctcgatgtgg cagcaaggca cagggtgcag ttttcgatgc ctgagtccga   16080
tgctgtcaca atgctgaaaa acagacacgc ataagtcaca aatcataatt atgaattgtg   16140
atttattcta taaaagaaga gaccactgca atatgtgatc tcttgtatgc aagggtgctt   16200
aaacagtgtg aattcacaag tgtgatttca taagtaataa cttcttgatt attacgttag   16260
tgtttttaag tattgctcaa gggctactct gacgatggca cttacatttt ttggatcttt   16320
accattgcgt ttattcctca atgccagatc ttctattgtg acaagcatgc tttcaccaag   16380
agagattgtc gtccgacatt gttttctgg ttcgggtttt tccggcgcgc cgtatggttt    16440
atccgcaagg cgctgagcca gagcctctgc ttgttctacc gtaactgcag ctctgtttaa   16500
tgcttgctgg ctgggtttct tcaccatggg ccaaatacct cattcattaa atgttcaatt   16560
tctgctctgg ctgctgtatt gttcgtttct actacaccgg tgccgttgct catgcaatcg   16620
cgatagactt ttctgaaaca ataactgaa tccaggactt gaattgttgg gaattcttca    16680
agatattcaa ggaattcttt tctctcattt cccctcaaaa ccggattggt tgttgccata   16740
ctttgtaaac aataaacctt aagttccggg ttaaggttac gcattgcgtc tatctgttgt   16800
tctagttctg taagagtatc cagatctggt tgagaacact gtagtggcgc aattatttga   16860
tgtgcgacaa ctccactcgt tatgaattcc tttgagtttc ttcctgcgac atccactatt   16920
acatcatcga acttttcatt cagagcctgt agtgtttgtg tcaggttatc aaatttctca   16980
acaagggtta ttgctggtaa cagtcctgca gcttctcgtt ccgcatgatg ttttgcggct   17040
gttcgttgta gatctccgtt taacaggcag acttcctttc ctttatttgc gagagcaata   17100
gccaggtttg atgcaatggt agttttccct gaaccacctt tgttcccacc aactacagta   17160
atcattgcaa cctcataaat gtgatgtgtg aagtatgatg atattttgac acggtaacct   17220
gatgtgtcaa catgcattca tatttatgaa gtatgaaata tgaagtatgt catgtgatgt   17280
aataaatatt acttgtgttt tgtgatttca taactatgat agtgctcaaa ttgagtatta   17340
ccttgcaacc agaaacagtg atttactcag attgagtatt taaggggcta tagatgaacg   17400
tatactgcga tgatggttca acaacaatca agttggcatg gaatgacaat gggaaaatct   17460
gtaagtcgtt gtcgcaaaac tcatttcgtc atggatggaa ggttgacggg ttagggattc   17520
gccagacatt taactatgaa ctggatggta aaaaatacac gtatgatgaa gttagcaacc   17580
aatctattct tacgactcat attgagtatc aatatacgga tgttaacctg ttagctgtgc   17640
atcacgcttt actgaatagt ggattagcgc ctcagcctgt atcattgact gtgactttgc   17700
ctatcagtga gttctacacg aaagagtgtc aaaaaaatga actcaacatt cagcgtaaaa   17760
ttgagaattt aatgaggccg attcgtctta ataaaggcga tgttttcacc attgaacacg   17820
ttgatgtgat gcctgaatca ttgccagctg tgttttctcg tctggtcatg gataaagttg   17880
gtcagtttga aaaatcgctg gtagttgata ttggcggcac tacgcttgat gttggtgtta   17940
tcgttggtca atttgactct gtaagtgcca ttcatggtaa ttctggcatt ggtgtgtctt   18000
cagttacgaa agctgcaatg agtgcattgc gcatggcatc cagtgatacc agtttcctcg   18060
ttgcagatga attgattaaa cgtcgtaatg acccggactt tgttcggcag gttataaatg   18120
```

```
acgaaacaaa aactgatctg gtccttaata ccattgaggg ggctattgcc agtctggggg   18180
agcaagtagt caatgagctc ggtgattttc atcatgtgaa tcgtgtttat gttgtcggtg   18240
gtggggcccc gttgatctat gattcgataa aaacggcatg gcaccatctt gggcaaaaag   18300
tagtgatgat ggagtcgcca cagacagcac tggttgaagc tatcgcggct ttcaaagagg   18360
agtaatattg tggacgatga acggaaaagg aaaaaattca cactttatct gcatccggaa   18420
aaagctgcag actttcaaac tttggaagcg atagagtccg ttccgcgttc tgagcgtggt   18480
gagctgttcc ggaatgcatt tatttctgga atggcgttac accaacttga tcctcgcctg   18540
cctgtattgc tgactgccat tttgagcgag gagttttcag cagatcaggt tgtaacctta   18600
ctcagtcaga cgacaggatg gaagccttct caggccgata tcagagctgt gttgactgaa   18660
ctcggtgctt tgcaatctgc tgaaaaaatg cctccttctg ctactgattc ggtgcaggag   18720
gcaatgaatg atgtgcgcct taaaatgcaa aaattattct gatatatcag aatgaagcaa   18780
tggggatctc agtccattgt gttgtatacg aaggcgagag catttcccgt ttcatttgcc   18840
attcagggc ggttcctcgc cccgcaaacc acactttccc ttttccagac tggttcagtt   18900
catcgagtgt tttcattaac ttttcgctgt ttttacgggg ctggatctca tcaaataatc   18960
ccggctcgcg tatacccgat ggtgtgaaat cagccagcat gactcctgcc ttcatatagc   19020
ggtacccttc acgccagaca tggtttaacg ctctgcatgc tgcggcaata atgtcccggc   19080
tgtcctgtgt gggtaatgga agcttttcca cagcggcatt gctgtaacag agttctttta   19140
ctgcaaaggg ggatgtccgt acaaatgtcg tcacctgccg gcaatactga cgctccccac   19200
gtagtttctc tgcggcccgc tctgcatact gaacaacagc ctggtgcatg gcatctttgt   19260
ctgtgattcg ttcaccaaaa ctgcgactac agacaatctg ctgttttgcc ggtggtgctt   19320
cttccaggga tatgcaggac tcgccgttga gttcgcgtac cgtacgctca agaatgacgc   19380
tgaagttttt ccggatgaat gccgtgttag cctgcgccag ctgcagtgct gtgttaatac   19440
ccagcgcatt cagcttttcc gtcagtctgc gtcctactcc ccagacctca ccaactggct   19500
gcagccccag tagcttcaag atccgattac ggttttctgc cgtcagcgcg accacaccgg   19560
aaaactgtgg ccattgcttt gttgcccact gtgcactttt agccagcgtt tttgtaggcg   19620
caatgcccac ccccatggtg agtcctgtcc agctctttac ctgttccctg agctgatgac   19680
caaaaacctc cggagagatg caatgattta tcccccgcaa atcaatgaac atttcatcaa   19740
ttgagtaggg ctcaactgcg ggagaaagcg actccagaac agccataacc cgttggctca   19800
tgctgtggta cagcgcataa ttgctggaaa atacatgtat tttcttctcc aggcgcatct   19860
gtctcacctg aaaccagggc tgccccattc tgatgccaag ggcttttgcc tccgggctgc   19920
gcgcgatcac acagccatcg ttattgctga gtacgattac cggttcgttg cgaaggtccg   19980
ggcggaaaac ttttcacat gaggcgtaga aactgttgat atcagccagt gcaaacatca   20040
gcgtaactcc cgcgtcctgt gtatcacgtg agtgacaaca ccaaaaatac agatgttttc   20100
cggatacagt gtgcggaact ccgggctgtc tgaaaccggc tccagtgccg ggcgtgggcg   20160
caacagcagt cgtttgacgg tgaactcacc gtcgatctca gcgataacga tgtccccgtg   20220
ttgtggtttt tcggccctgt ccactaccag cagatcacca ttctgcacgc cagcctggtt   20280
catcgattca ccgctggcgc gcagaaagaa ggtggctgca ggtctgctga tgcaatagct   20340
gttcagatcc agttcctgct cagcataatc agtggcaggc gaaggaaaac cggcctggca   20400
acgatcggca aacaacggtc gcacgtaact gtcatcgcct gaagggtcag ccggacggtg   20460
ataaacggta ctcatgctgc aggcagccag ctgtcgtcct gccagatttc ttccagcaga   20520
```

```
gacaggatac gttctttatc cttgtcgttg cgggctcctg tgacagatac agacggggcg   20580
ctgccctggt ctatacgcag ccagatttcc gggtagtgtg gtttcagacg ttgttcgatt   20640
tcattctgta gcgcctgaag tgtgcctgat ttgaggtttt ttgtgctctg gcggtcgaaa   20700
agaatttcaa tgcggatcat gttctcatct ccctttcttt ttgctgtatg catatacagt   20760
atcctaataa ctgaatccac acacagtcaa atgtcattgc tctgactaaa aaatgctcaa   20820
ttctctgaga gtgtggctgt atgcctgctg tggagtgctg tgtccagctt atccacagca   20880
ttttgtgcac ggttctgtgg acaaaatacc tggttaccca ggccgtgccg gcacgttaac   20940
cgggctgcat ccgatgcaag tgtgtcgctg tcgccggcct cctcacccgg tcacgtttcg   21000
tcgttcctcc tccacgcgct gcggcttcgg ggccgcacct gcattcgtat gcggtcgccc   21060
ggttacaggt gcggcacggc ctgatggagg ccgcatgtga gaggagaatt cccatgccaa   21120
actggtgctc aaatcgtatg cattttcctg gtgaaccagc acagattgct gagattaaac   21180
gactggccag cggtgcagtc acccatttt atcgccgcgc cacaaatgaa ggtattcagc    21240
tgtttctggc cggaagtgcc ggacttctgc agaccactga agatgtgcag tttgaaccgt   21300
gccccggact gacggctgcc ggacgtggtg ttgtatcgcc ggagaatatc gcgttcaccc   21360
gctggctgac acacctgcag aacggtgtgc tactggatgt acaaaactgc ctgatgctgc   21420
atgaactctg gctgcagagt ggtactggcc agcgtcgctg ggaaggatta ccggatgagg   21480
tcagggatac catcaccgca cttttcaccg caaaaagagg tgactggtgt ggcttctgga   21540
gtaacgagga tgtatcggtg tggtggaacc gtctgtgtga caacgtactg ccggaaaaaa   21600
ccatgccgtt tgacctgctg acggttctgc cgacccgcct ggatgttgaa gtgaatggct   21660
ttaacggtgg tgttctgaac ggtgttcctt ctgcatatca ctggtatacg gaacggtatg   21720
gcgtgaagtg gcctgtgggg tatgaggtga atatcagtag tcaggaagac aacttcattc   21780
aggttgattt cgacacgccg tggtgtcagc cggaaagcga cgttattgca gaattaagcc   21840
gccgtttcag ctgcacgctg gagcactggt atgccgaaca gggctgtgat ttctgtggct   21900
ggcagttgta tgagcgcgga gagctcgttg atgcgctgtg gggggaactg gaatggtctt   21960
ccccgacaga tgacgatgag ctgccggaag tcaccggacc tgcgtggata gtcgacaatg   22020
tggcgcatta tggcggatga agtatgacgg agacgggcgg gcaaccgccc gtttcttttc   22080
cgacaaagga tgtcgccgtg ctcctctttt tactgcgccg gctgacgcgg cgcggcagga   22140
acgctgcctg tggtcagtgt cccgcgtccg gcgggcacgg gacgggcgct tttaccgctc   22200
ccggctggcg tcgtgacag tgtacgccag cccgtcgccc ttttctgatg aacgcccttc    22260
aagccgcttt cgcggcataa ccttgccgtc agaaagacga cggctgcggt attccacggt   22320
cggcctgacc cgttaccgga cgcggtgaac agcccacagg cagcggggaa cgggcaccac   22380
aggggtgccc tcccggtgcc ctctgtaaga gaaggagttt ggtatgtccc gttttgtcct   22440
cggtaactgc atcgatgtta tggcccgtat ccctgataac gccattgatt tcatcctcac   22500
cgacccgcca tatctcgtcg gtttccgtga ccgttccggg cgcaccatcg ccggcgataa   22560
aaccgatgag tggctgcaac cggcctgtaa tgaaatgttc cgcgtactga aaaagacgc    22620 gttaatggtg agcttctacg gctggaaccg cgtcgatcgc tttatggccg cctggaaaaa   22680
tgcgggattc agcgttgttg gtcacctggt cttcaccaaa aactacacat cgaaggccgc   22740
atatgtgggc tatcgccacg aatgcgccta catcctggca aaaggccgtc cacgtctgcc   22800
acaaaacccg ctgccggacg tgctgggctg gaaatattcg gcaatcgcc atcacccgac     22860
```

-continued

```
ggaaaagccc gttaccagcc tgcaaccgct gattgagaac ttcacacacc cgaacgcaat   22920
tgtgctggac ccgttttgcag gcagcggctc aacctgcgtc gccgccctcc agtccggacg   22980
ccggtatatc ggtatcgagc tgcttgagca gtatcaccgt gccgggcagc aacgccttgc   23040
cgccgtgcaa cgggccatgc agcagggggc cgcgaatgat gactggttta tgccggaggc   23100
tgcgtaaatg aactatgcag gacacgaaaa actgcgcgcc gaagtggcgg aggtggccaa   23160
tgccatgtgc gacctgcgta caaccatgaa tgagatggag cagcggtaca gctttaatgc   23220
cgacaccctg ccggaacgtc tggtgcgtca gacgctgttt cgcgcaaacc gcctcctgat   23280
ggaggcatat accgaaattc tggaactgga agcgtgcttt aaagattgag aaggagacga   23340
gaatgtacgg aacatgcgaa acgctatgcc gggagctggc agtaaagtat ccgggagaca   23400
tgccgctgat gctggttatc tggtccccgg aagagattca ggccctcgct gacgaaatgg   23460
atatttccct gtccgatcat gaaatcagaa ccgtcctggc gcgcctggag gacatcccgg   23520
aagaccagcg gactgaatcc ggtatttctt ccggcgtggc gatggagatc atcaataacg   23580
tgagcgaaaa ccgccaggtg accgtccctg ctgaactgct ggcgtccctg attcagaccg   23640
ctgaacaggc attgtggaaa cgtgaatggg ccgcccggga tcatggcctc gccgtcccgg   23700
aatgcgtcac ccgccgtcag gcggtgatta atcaggcccg caccctgctg aaaaacaaca   23760
gacacgaaaa cgactgatgt tatcgccgcc tccgggcggc gattcaggga aacgattaa   23820 tcatgaacga aaacacaaca ctgaacgcac tgatttgtcg tcacgcccgc aacctgctgc   23880
tggcgcaggg ctggccggaa gagacggatg ttgaccagcg gaacccgaac aatccgggct   23940
ggatcagcat ttatgttctg ctggatgcgc cccggctggc gacgttactt atcaaccgtc   24000
acggcggcgc actgccgccg ctcctggcct ccgccattca caaactgacc ggaaccgggg   24060
cggaacttgt actgtccggc agtcagtggc agtcgctgcc ggtacttccg gcagacggaa   24120
cgcaggtgtc tttcccgtat gccggtgagt ggctggcaga ggacgaaatc agggcagttc   24180
ttgatgcggt acgcgatgca gtacgctgtg tcagttacca ggtggcagaa gatacgcggc   24240
gtatccgggc ggcgctgacc accaccggtc agacgttact gacccgccag acgcgccgct   24300
ttcgcctggt cgtgaaggag agcgatcacc cctgctggct cgatgaggac gacgaaaacc   24360
tgcccgtggt gctcgacgcc atcctgaacc ggggcgcacg ttttcggcg gtggaaatgt   24420 atctggtcag cgattgtatt gaacatatcc tgtccagttg gctggcctgg gatgtgctgc   24480
gtataccgga tgaaccgccc cgccgctggt ttgaccgtgg tgttctgcgg gaggtggtcc   24540
gggaagcccg gaacgaaatc cgcagcatgg cggatgccct ggcaaaaatc cggaaatgat   24600
gacactggcg gggtaaatcc ccgccttttt cctgccggtc cccggacaga gcacaaagga   24660
cgtcgccgcc ggctccgctt tacccggcca tgcagggcat ggccttgtgg ttttcagtt   24720 atgtggccgc cgtgtcgtgt gcgggctgtg ccgtgcctcc atcttagccg ggctggcagg   24780
gatgcaaggg tacgcttcgc cgctgcggtc accggtcccc tccttcccgt ctgccgtgat   24840
tttccggtcg ttcacccgct cagatttcgc ggtctcaccc tccaactccc gccagccgtg   24900
tgcgtcaggc tgcggcttcc cttgcgccct gtgcatcccc accttatcgc ccggcttta   24960 tggaggcacg gcaccgcccg tgtcgcggaa tatgtgaac aacggaggaa acatcatgc   25020 aatatgcgaa acctgtcact ctgaacgttg aagagtgcga ccgtctgtct tttctgcctt   25080
acctgtttgg ccaggatttt ctgtatgccg aagcgtctgt atacgcgctg gcgaaacaaa   25140
tgatgccgga atatgaaggc ggattctggc acttcatccg cctgccggac ggtggcggtt   25200
acatgatgcc ggatggcgac cgttttcaca tggtgaacgg tgcaaactgg tttgaccgta   25260
```

```
ccgtgagtgc tgatgccgca ggcatcatcc ttacctccct tgtgattaac cgccagttgt    25320
ggctgtacca cgacagcggg gatgcaggac tgacccagct ttaccggatg cgcgatgcgc    25380
agttgtggcg tcacatcgaa tttcaccctg aatgcaacgc gatttacgca gcactggact    25440
gattaacgga cggggcggca atgccgcccc tgtaaaggag acgagaacat gtactgtact    25500
gttaaagaaa ttatccgcga tgtactggat acagacgtgc cggacagtga atgcgttttt    25560
gccgtggtgc tgacccgtgg ggatgtgcgc cacatagccc aggactggag tctgacagac    25620
gatgagctgg aaaccgtcat gcagcggctg gacgatgcct ttgaatatgg tgcggatgtc    25680
agcgttgttc acgcgttgt tcgtgaactg atggaagaaa gcgcgccag ccgtcaggtg       25740 acagtcccgg cggtgatgct ggaaaaagtg ttggcgctgg caggcagtga atgaagcgc      25800 ctgtatgccg tcgggagtga aacgggggc gacggtgatg cgttcgtcag ggaagaacgc     25860
gaagcaatgg acgttgtgtt acaggcgctg gacggggagc acatgtcatg aatatcagca    25920
cagaaacccg cgaaattctg cgcaattaca aagccgtgat taatgcgcgg cgtcgtgaaa    25980
tggggcagaa accgctcacc actgcgcaga ttgttgatga aatctgcgat tttgtggcga    26040
atcagcaggc ggtttttcctc ggtggtcact atatccttca gggcagcaga aacaggtgat   26100
acagggcagg cggtggaggc cgcctgtcag cccgcgcgaa aacccctggc aggctgacgc    26160
ctgccggaaa tgcggggtgc agcgcctgcg gcgctgccgg cccggctttc cggtcagaag   26220
gtagtgtatg gctgtatgca gggaacaggt gtgatattcc gtgacactgt caccgttctt    26280
ggctgtcttt tattgcgccc acttcggctc ccggctgcct ggcggcatcc ggtcgtcagg    26340
cccgactccg acaggcagct gctggcgcac ccgccagtct ccgccgaacc cgctggcgcg    26400
gtttcgggct gccgctacgg tccgatgcgt gaaaacccgg cttgcagcga ccgttccggt    26460
cgcgccgccc ctgtcgcgcc gtgacctgcg ctccctgcac acctgacggt gtgtgaggaa    26520
actgcgcctg atggcgcagc agtcttccct cctgccgcca cccctgcggc ctgtttcccg    26580
ctgtggactt tccgggggc agacgtaacc ccctcccgtt ccatctgtcc agggtgagat     26640
gcaccggcca caaaatttt agccatgaac ccggctaaaa atttttgcgtc cgccccgga     26700 cagctgtccc gtgaggcgt aaacgggccc ccatcggaaa ggtccactgc ggggagaaac     26760
ccctgtgaag tggacggcag gaggagcttt cgctcctctg aagggcaca tgaacgtccc    26820 gtcgccggta tccggtttat ctcacatctt tcagtcagga ggttcttatg agtgcacgtg    26880
gtatcaacaa ggtcatcctc gtcgggcgtc tgggcaatga tccggaagtc cgttacatcc    26940
ccaacggggg cgcagtggca aacctgcagg tggccacatc agaaagctgg cgtgacaaac    27000
agacggggga gatgcgggag cagacggaat ggcaccgcgt ggtgctgttc ggcaagctcg    27060
cggaagtggc aggtgaatat ctgcgcaagg gtgcgcaggt ctacatcgaa ggtcagcttc    27120
gcacccgtag ctgggaagat aacggtatca cccgttacgt cactgaaatt cttgttaaga    27180
ccacgggcac cgtgcagatg ctgggacgtg caccacagca gaacgctcag gcgcaaccga    27240
agcctcagca gaatgggcag ccacagagtg ctgacgcgac gaaaaaaggt ggcgcgaaaa    27300
cgaaaggccg tggacgtaag gccgcgcagc cagagcctca gccgcaaccg ccggaggggg    27360
aggattacgg gttttcagac gacatcccgt tctgatcggg ctgactgtga caaccgcccc    27420
gccctgtgcg gggcatcacc ggagatatga ggatgagcga atatttcaga atacttcagg    27480
gactgccgga cggctccttt acccgcgaac aggcggaagc cgttccgca cagtaccgga    27540 acgtctttat cgaggatgat cagggaacgc attttcgcct ggttgtccgt caggatggca    27600
```

```
cgttgatctg gcgctcctgg aattttgagg acggtgccgg gtactggatg aaccagtaca    27660
tcagggattt cgggattctt aagtaagaga ggtgccggac gcgcgaacgt ccggcaggac    27720
ataagcaatt ataagtggat gattatgcct gtaacgaagt gtgaaccaga aaccacccgc    27780
aaagcaagcc gtaaatctgt aaaaacgcag gaaactgtcc tgtctgccct gctggcgcag    27840
acggaggaag tgagcgtgcc gctggcctcg ctgattaaat caccgctgaa tgtgcgcacg    27900
gtgccgtatt ctgcggagtc cgtcagcgaa ctggcggagt ccattaaggg cgtcggactg    27960
ctgcagaatc tggtcgtgca taccctgcct ggtgaccgtt acggtgtcgc cgcaggtggt    28020
cgccgactgg ctgcactcaa catgctggca gagcgtggca tcattccggc tgactggcct    28080
gtacgcgtga aggttattcc gcaggagctg gcgactgccg catcaatgac tgaaaacggt    28140
catcgtcggg atatgcaccc tgccgaacag attgccggat ccgtgcgat ggcgcaggaa    28200 ggcaaaacgc ctgcacaaat cggtgatttg ctgggctatt cgccccgcca cgttcagcga    28260
atgctgaaac tggcagacct tgcgcctgtc atcctcgatg cgctggcaga agaccgcatc    28320
accacagagc actgtcaggc gctggcgctg agaacgaca ccgcgcgtca ggtgcaggtg    28380
tttgaagccg cctgccagtc gggatggggc ggaaaaccgg atgtacagac cattcgtcgt    28440
ctggtgaccg aaagtgaagt ggcggtggcg gggaacacta aattccgctt tgtgggggct    28500
gatgccttct cgccagatga actgcgcacc gatttgttca gcgacgacga gggtggctat    28560
gtggactgtg ttgcgctcga tgctgccctg ctggaaaaac tccaggctgt cgctgaacac    28620
cttcgggaag ccgaaggctg ggaatggtgc gccggacgca tggagcctgt cggtgagtgc    28680
cgtgaggatg ccggaacata ccgcagtctg ccggagccgg aagcggtgct gacggaggcg    28740
gaagaagaac gcctgaacga actgatgacg cgttacgacg cgctggaaaa tcagtgtgag    28800
gaatccgacc tgctggaagc agaaatgaag ctgatgcgct gcatggcgaa ggtcagagcg    28860
tggacgccgg agatgcgttc cggaagcggt gtggtggtgt cctggtgtta tggcaacgta    28920
tgtgtccagc gtggtgtgca gttgcgcagt gaggatgacg tggctgacga cgctgaccgc    28980
acggaacagg tgcaggagaa agcatcagtg gaggaaatca gtctgccgtt gctgacgaaa    29040
atgtcctcag agcgcacgct ggcagtccag gcggcactca tgcagcagcc ggacaaatct    29100
ctggcactgc tggcatggac gctctgcctg aatgtgtttg gcagcggggc gtacagtaaa    29160
ccagcacaaa tcagcctgga atgtgaacat tattcgctga ccagcgatgc gccatcgggg    29220
aaggaaggtg ccgcattcat ggcgctgatg gcagaaaaag cccgtcttgc tgccctgtta    29280
ccggagggat ggtcacggga catgacgaca ttcctgtcac tcagtcagga ggtgctgtta    29340
tccctgctca gtttctgcac cgcatgcagc cttaacggtg tccagacccg tgagtgtggt    29400
cacacgtcac gcagtccgct ggattcgctg gaaagcgcca tcggctttca catgcgcgac    29460
tggtggcagc cgacaaaagc aaacttcttc ggacacctga aaaagccgca gattatcgca    29520
gccctgaatg aggcaggact gtccggtgcc gcacgggacg cggagaagat gaagaaaggt    29580
gatgcggctg aacatgcaga gcaccatatg aaagacaacc gctgggtgcc tggctggatg    29640
tgtgcaccac atccacagac agatgccact gaacgcaccg ataacctggc tgatgccgcc    29700
tgatgaacaa ccacaccgcc ccgcggaga cgggcggca gcaagggaga taccgtgatg    29760
aaaactgaac tgaccctgaa tgccctgcag tccatgaacg cacaggaata tgaagatatc    29820
cgtgctgcgg gaagcgatat cgccgtaat ctcactcacg aggtgatgcg tgaagtggac    29880
gcaccggcta actggatgat gaatggcgag tatggcagtg agttcggggg cttttttcccc    29940 gtccaggtcc gtttcacgcc agcccacgaa cgtttccacc tggcattatg ttcgccggga    30000
```

```
gacgtctctc agctctggat gctggttctg gtgaattgtg gtggacagcc tttcgccgtc    30060
gttcaggtgc aacatatctt cacgcctgtc gctatcagtc acacgctggc gcttgccgcg    30120
acacttgatg cgcaggggta cagtgttaac gatatcatcc atatcctgat ggcagaagga    30180
ggtcaggcat gagcgcacgt tcacgggcac tgatccccct cagcgcagag caacaggccg    30240
ccatgcaggc tgtggctgtc accgaacaac gtcgtcgtca gggacgcaca ctttcagcat    30300
ggccttatgc cagcgctttc tttcgctgcc tgaatggcag tcgccggatt tcgctgaccg    30360
atctccgctt ttttgctcct gcgctgacga aggaggaatt tcatggcaac cgtctcctgt    30420
ggctggctgc cgtggataaa ctgattgaaa gttttggtga agtctgtgtt cttccctgc    30480 catccgatgc ggggcatcgt ctgttcccgt ccgttccttt tcgtgaaggt gagcggcgtc    30540
gtcagaaaac cacgctgaca gagcagaaat acagccgcca gcgggaacgt gaggcagaac    30600
gacgggaact ggaataccag acatgttttg ctcaggcgca gattgacctt gcgtttcata    30660
ctccctccac ggtcggaagc tggttgtccc gctggtctgg tgttgttgag gagcatgatc    30720
tggaaacgat ttctgggggg tggtgcgggc gttttccatc actgtcatca tttgaccggt    30780
ttttctggca ggaggaacca ctctggcggc tgattttga agctggtgag gccggtcgtg    30840
gtgcaccggt acaggtacgt gcacttgagc agtggatgat cccgaacaag ctggagaacg    30900
caatatgatg aaatcagacg aacaatatca ggttcccgtg tggatgcgac ctctgttgcc    30960
gttgctctgc aataccggtg gtaatgatcc ggaggaactg ctgaatgata cagaaaccac    31020
cgccagtgcg aatattgtcc gttatgtact gatagttgca gtgcggtcgc agattgatct    31080
gctgcagcta ctgtacagga aaggactgtt gcgcacagag ataccaggtg gctttcacc    31140 ggaagaagcg caggaactcc tggataatct ggtgcgcagc catatcagca aggcgctgtc    31200
gggtgagcga atggcagccc gtgacagaaa tgccgatctg acctggattc gccagcaact    31260
ggtcgatgcc gcctggtttg tccgtgccac actggaagcg catgggatgg gcgtcggaaa    31320
tgagagtccc tctgctccgc cggagacaat gccggacata cagacacggg aactggttat    31380
gttgatcaag cgactggcat catcgctgaa agcggtgaaa cccgacagta gcgtggtgcg    31440
tgaagcgcag gactggctgt gcgacagaaa acttgtggat atcacagata ttctccggtg    31500
aaccagacat gtatatttta cgcagggaca cgccgatcat gatcgtttca tatcaggggt    31560
ggtctggagg tcatgcggcg tgtcctctgc actcgccgga ataaggaagt cgccggcggc    31620
tccgctttta cccggccatg cggggcatgg ccttgtgggt tttcagctct gtggcctcag    31680
cgtcgtgtgc gggctgtgcc gtgcctccat cttagccggg ctggcaggga tgcaaggta    31740 cgcttcgccg ctgcggtcac ccggtccctc cttcccgtct gccgtgattt tccggtcgtt    31800
cacccgctca gatttcgcgg tctcacccct caactcccgc cagccgtgtg cgtcaggctg    31860
cggcttccct tgcgccctgt gcatccccgc cttatcgccc ggcttttatg gaggcacggc    31920
accgcccggt gccgcagaac atgtgactat ggaggattcg ggaatgtctg ttgttgcacc    31980
tgctgtatac gttggaacct ggcacaaata caactgtgga agcatcgccg gacgctggtt    32040
tgacctgacc acgtttgatg atgagcgcga cttttcgcc gcctgccgtg ctcttcacca    32100
ggatgaagcc gatcctgaac tgatgtttca ggattatgag ggattcccgg ggaatatggc    32160
ctctgaatgc catatcaact gggcctgggt tgaaggcttc cgccaggcac gggatgaagg    32220
ctgcgaagag gcttatcgtc tatgggtgga ggataccggt gagacggatt ttgacacctt    32280
ccgcgatgcc tggtggggcg aggctgacag tgaggaggct tttgcggttg agttcgccag    32340
```

```
tgataccggc ctgctggctg acgtgccgga gacggtggcg ctctattttg actatgaggc    32400
gtatgcgcgg gatttattcc tggactcctt cacctttatt gacggtcatg tgttccgtcg    32460
gtgatttact cccccgctcc ggcggggta tggcctgcca ggccgccgga aaaccctggc     32520
aggcttacgc ctgcctgaaa tgcaggaggg ccgcgcctgc ggcgctgccc ttcctgcccg    32580
tcatggtgtg aggcattttt ctgttatgtc gtttctgttg ttctgatttc cggaggcggg    32640
gacaccttcg gctcccggct gcctggcggc atccggtcgt caggcccgac tccgacaggc    32700
agctgctggc gcacccgcca gtctccgccg aacccgctgg cgcggtttcg ggctgccgct    32760
acggtccgat gtctgaaaaa ccaggcttgc agcgaccgtt ccggtcgcgc cgcccctgtc    32820
gcgccggaaa cggcgctccc tgcacacctg acggtgtgta aggccactgc gcctgatggc    32880
gcagtcaacc cttccgccgc cacccctgcg gcctgtttcc cgctgtggac tttccggggg    32940
ctggagtaac cacatcccgt ttcagcagtc caggggaaga tataccgtcc acaaaatttt    33000
tagccataaa cccggcaaaa aattttgcgt ccgccccgg acagctgccc cgtgacgtgg     33060
tgacggacgc cccatcggaa aggtccactg cggggagaaa ccccgaagaa gtggacggca    33120 gaagggctt tcgcccctcc ggggagcaac cggtcggccc ggcgacctga ttcagcagaa     33180
ggagacgttt tcatgactgt cagcagcacg atttccgttt tttgccgcga cggggtgttc    33240
cgtaccgttt actgccacct gcacggtgag ccgacctgga acgtcgcat cctgcatacc     33300 cactatgcca ccgtcagca ggccgaagcc ctggttgaac acggtgatat ccgttgcctc     33360
ggtccccgtt gcgacaaacc cgccgggcat acgcttcaga acccggtgga cggtgtgacg    33420
gcttattacg gacgtgacag tggtttccgg atggacagtg aggcgcgtga gtaccgttct    33480
ttcagggagg ctattgccac tgaaagcact gaagaggtgc gcttccatta tgtgttcatc    33540
gacggctact ggaaggtgat gtaccgcacg ccggaaggct ggaagatgaa agcgctcgcg    33600
ctggcactgc gtcgctgtcc gaaatgaaaa aaaggcaggg cgataaaccc tgcctctctc    33660
cgccggcgct tccccgccag gaagtccggc atctcaatca ctatctatgg agattatgcc    33720
atgagaccat caattatctt cgcaaccgcc gagtatgtaa agcgtctgcg tgaagagtgc    33780
ctgcgggaga ataaacccct gcaccgccat acccgcttca gacgtcagga gctggcacag    33840
gatgagatta acccggacgt cctggcgatg agcggccata tcgccagacg ctgcagtgag    33900
cagaagcggg tgcgtatccc cgctatgaaa gtcagcgaat ggggccacct gctccgcgcg    33960
cttgaaattg agcgggtctg ccactgatta accttgccg tctgcctgtg caggcggcag     34020
gatacgttca gacatctcac caggaggaac cgtgagtaag aagaaaacca ccacgacgcc    34080
cacgccgcat gatgccgcgt tccggtcgtt cctggcgaat cccgacgtcg ccagagattt    34140
tctggaactg catcttccgg cggagtaccg gcagttgtgc gacctgtcca cgctgaagct    34200
ggaacccgcc acctttgttg agccggacct gcatcagtac gccagcgata tcctctggag    34260
tgtgaaaacc accggggtg aagatggcta tgtttatacg ctcatcgagc accagagcac     34320
cgaaaatctg tacatgcctt tccgcatgtt acgttacagt gtggcggcga tgcagagaca    34380
tctggagcag cacaaaacgt tgccactggt cattccggtg ctgttctatc acggtgagcg    34440
cagcccgtac ccgtacagca tgaactggct ggactgtttt gagaatccgg cgcttgcggc    34500
taaaatatac acaaagccgt ttccgctggt tgatatcact gtcgttgatg acaatgaaat    34560
catgaaccat cgccggatgg ccgcactgac gctgctgatg aagcatatcc gccatcgtga    34620
catgatggag ctgctggaca aactcccgca ggtcatggtg gaaatttcag acgagcaggt    34680
gcgtgttctg attcattaca tcgttaacgc agggggactct gtatcaccgg aatttatgcg    34740
```

```
ggcgctggct gagcgtctgc cgcagcatga ggataaactg atgactatcg cagaacgtct    34800
tgagcaaaaa ggtcgccagg aaggcaggat ggaaggacgc atggaaggac gcatggaagg    34860
agcgcttgaa aaagccctgg ctattgcgtg ccagcttcag aaaatgggga tgacgccgga    34920
gcagattaag caggctaccg gacttttcga tgacgaactg aagaaaatct ctcactgagt    34980
aaacatcaca gcccggcaaa atgccgggct tttttgtcag caggagcaga gcaaacagca    35040
tgacgattgc agaacgtctt attcaaaaag gcgcacttga agtggcgcgg gaaatagcct    35100
gccggctgcg ggatatgggc tggacgccgg aacggattca ggaggcaacc ggactttccg    35160
gtgaagaact gaaaaagctg tttcctgatg agcagtagcc tggcattcag ccaggctgtg    35220
aatcacgctc acacatcctc tgccgtttcc cccagttcat tttccagtcg cctgatgata    35280
tctgccttac gcatcccctg catgtgaggc agcaggtcac ggactgaaag tgcctgggtg    35340
gtcctccaga cggtgacgtc cacctgttcc gcattttccc aggcgtgcca tgttctctgc    35400
gtcacgccaa attctctggc cgcttttcg cgtgaccaga gcatgctttt tgccagatt    35460 cgcagttccc agccggtcat aaaacacctt tgaaaaagtg aaaaaacttc actttatttt    35520
atcatcacaa ttgccaaatc agcgcgataa ataagtgtaa aaaagtgaag aaatttcact    35580
ttttttgctt gtaaatgtcg tgcggttttc tctgttttca cctgtgcggg agtggtgtgc    35640
cagtgaccac cacatgccat tgttgtgccg tcgttttct tcagtcgcgc cgtatgcggc    35700
gctccctgca caccttacgg tgtgtaaggc cactgcgcct gatggcgcag ctgtctctgc    35760
ctgtctgccg ccgcactgcg gcctgttctc cgcagacgga cttccgggg gtacatacat    35820 gaccacatcc cgtttcagtc gtccagggga gagatgtacc agccacaaaa cttttgccg    35880 caggcgtcaa aaacttttgc gtctgccccc ggacaactgc cccgtgacgt ggtgagcgtc    35940
ccccgtcgga aaggtccact gcggggaaat tcccgaagac ccggacggca aaggagctt    36000 cgctcctccg ggaaatgacc tggctgaccg ggcagtcgtg acgatgagga gacaatgtga    36060
tgaatcagac tttacccact gctgacctga atactgccgg tacgacagat gttattccgt    36120
ctgtggctat cgaccgcatc atcgcgcagc gtaacgaagg tattgcactg ttcatgcagg    36180
cgatggaatg cctggcgaca gcgcgcaaga ttctgctcga tgcgtcaggt gatattttc    36240 tttacgggtt tgaagactgc gtgactgatt ccgttcgtcg catagataaa ccggaagaag    36300 cgaaaggaa tatcacccgt cttgccgacc ggaaaatctg ggaccgcctg atgacagata    36360
cgggcatgta caccttcatg agttcatgcc agcgtgatga gtggaacagc cagctgatga    36420
gcgacacctg tcctgaaatc accctggaca atgtactggc aacattccgc catctgaatg    36480
cctgcaagat gcagacattt gaacagggac tgattgatgt ctaccggaaa ttgtcatggg    36540
attacagaac caataatccc tgccgtctgg gtaagaaaat cattattgaa aacctgctgt    36600
accgctggag taacgggcgt gtgacgctgg actgcagcgg acgggaggca ctggatgacc    36660
tggtacgtcc gttttatctg ctggaggggc gcaacgttcc tgacttcagg aacagtatcg    36720
gggcgcagta tggtgaattt ctcgggaacg gcgacaatgt cggtaagctg ttagaagggg    36780
aatattttac ggtgcgtggc taccagaaag ggaccgtaca cattgtcttt aagcgttctg    36840
accttgttga aaaactgaat gatattattg cacggcatta tccaggtgca ttgccgccac    36900
gagtctgatt aaacagaaaa gccctggtat ttatgccggg gcttttttt ctgtaatcat    36960 cataatctca gaacacgatg tgacattgtc acatcaatta ttgttcatat cgatgccatc    37020
tttcctgcct gaatctgtct ttttaggtgc tgttttagag gaagaacggc gggatggttt    37080
```

```
tttcgattct gcttcccgaa taatgtcacg aagtgccttc tctcctactt catacccctgc    37140 attttttgagc gtgtcacgaa catctgccag tgtataaccc tttgtcctta ccaggacaat    37200
aatgtcatca cgaatggcat caagaaaatc acgcaatgtt ttccgttgag cggtgagatc    37260
tggcaattcc gataaagcag cttttgccag ctggatgtca tcatctgagt aaaatttttt    37320
agaagccatt ggcactttct ctccgtttca tgttgaagtc tgattttatc atcaaaaact    37380
gactcctggc agggctgcgc cctgcctctg ccgtctgcat aagactatga tgcacaaaaa    37440
taacaggcta taatggcctg aaaaacggga caggatgtgc aattgtaata ccgtcacacg    37500
cgacgctatt acaattgcca tctggtcagg gcttcgcccc gacacccgt aaggagcctg     37560 aagtgagtga tagtgtggta agaaaaaaaa gtgaggtacg gcaaaagaca gttgtcagga    37620
cactcagatt ctctcctgtt gaggatgaaa ccatcaggaa aaaagctgaa gattccggac    37680
ttactgtatc tgcttacatc cgaaatgcag cactgaataa gcgaattaac tcccggacag    37740
atgatgcttt tctgaaggag ttaatgagac tgggaaggat gcagaagcat ctgtttgttc    37800
agggaaaaag aaccggtgac aaggaatacg cagaagtgct tgttgccata accgaactta    37860
caaatacatt gcgtaaacag ttaatggaag gttgaggatt ctccggtgaa tgcagtcatt    37920
ccgaaaaaga gaagggacgg aaagtcttcg ttcgaagacc tggtatccta cgtctctgtc    37980
cgggatgaca tgaccgatga ggaactggat ttatctcctt cttcgcaggc tgaacaacca    38040
taccgaagcc gcttcagtcg ccttgttgat tatgcgacac gtattcgaaa tgagttattt    38100
gtggcgctgg ttgatgtcat gaaggacggc tgcgaatggg tcaacttta tggtgtcacc     38160 tgctttcaca actgtacttc tcttgaaact gccgctgcag atatggagta cattgcccgg    38220
caggcacact atgcaaaaga tgacactgat cctgtttttc actacatcct ttcctggcag    38280
tcacatgaaa gcccgcgtcc ggaacagatt tatgacagtg tacgtcatac gctaaaatca    38340
ctcggccttg ccgaccatca gtatgtctct gccgtgcata ccgatacaga taatctgcac    38400
gtccatgtgc ctgttaaccg ggtacatcct gaaacgggtt atctgaatcg gttatcctgg    38460
agtcaggaaa aactcagtcg tgcctgccgt gagcttgaac tgaagcatgg ttttgctccg    38520
gataacggtt gctgggtcca tgcaccgggt aatcgtatcg ttcgcaaaac tgccgttgaa    38580
cgtgatcgcc agaacgcatg gacacgtgga aaaaaacaaa cttttcgcga gtatgttgcg    38640
cagacagcgg tcgctggttt acgcagtgaa cctgtacatg actggttatc cctgcatcgt    38700
cgtcttgcgg aagatggtct gtacctgtct cagatggacg gaaaatttct ggtgatggat    38760
ggctgggatc gcaacaggga aggtgtacag cttgattcgt ttggtccctc ctggtgtgca    38820
gaaaaactca tgaaaaaaat gggtgactac acgccagtac caaaagacat tttcagccag    38880
gtggaagcac caggacgcta taacccggac tttattgcag ctgatgttcg cccgggaaaa    38940
atcgctgaaa cagaaagtct gcagcagtat gcctgtcgtc atcttggaga acgtctgccg    39000 gaaatgcac gggaaggtcg gctggaaaac tgccaggcta ttcaccgcac actggctgaa    39060
gtgggattat ggatgcgtgt tcagcatggt cacctggtta tctgtgatgg ttatgatcat    39120
acccagactc ccgttcgtgc tgacagcgta tggtcactgc tgacgctcga caatgtgaat    39180
caactcgatg gtggctggca gcctgtacca acagatattt ccgccaggt tacgccaaca     39240 gaacgcttca gtggtcgtcg tatggagagc tgtcctgcga ccgataaaga atggcaccgt    39300
atgcgtacag gcacggggcc gcaggggct atcaaacgcg aactgttttc tgacaaagaa     39360
agtctgtggg gatacagcat cagccattgt agccctcaga ttgaagaaat gatcacacag    39420
ggtgagttta cctggcagcg ttgtcatgag ctgtttgcac aacagggact gatgctacag    39480
```

```
aaacaacatc acgggcttgt tgtcgttgat gcctttaatc atgagcaaac gccggtgaaa    39540
gccagcagca ttcatcctga tctgacactg aggcgtgcgg agccacaggc cggacctttt    39600
gtgagtgccc cagcagattt gtttgacagg gtgcaacctg aaagtcgcta acccggag      39660 ctggctgtca gtgacaggta cggggtcagc agtaaacgtg acccaatgct cgccggcag     39720 cgacgtgaag ccagggctga ggcccgtgct gacctgcgtg cccgctatct agcatggcgt    39780
gaacaatggc gtaaaccaga tctgcgttat ggggaacgtt gtcgggaaat tcatcaggca    39840
tgccgtctgc ggaagtcaca cattcgtgcg cagtacaatg atccggcatt acgtaagctg    39900
cattatcaca ttgcagaagt tcagcgaatg caggcattga tcaggctgaa agaagacatc    39960
agggatgagc gacagaaact tattgctgac gggaagtggt atccaccttc ttaccgtcag    40020
tgggtcgaaa ttcaggctgc tcaggagac agggctgctg tatcgcagtt gagaggctgg    40080
gattatcgcg atcgccgtaa agacaagtca cgcacaacga cgacagaccg ctgtgtcgtg    40140
ctttgtgaac cggcggaac gccggtatac ggtaataccg gtgatcttga ggctcgtctg     40200
cagaagaacg ggagtgttcg tttccgtgac cgtcggacgg gagagttggt ctgtacggat    40260
tatggtgaca ggttgtttt ccgtaatcac catgaccgca atgcgctggc agataaactg     40320
tatttgattg cacctgtatt gtttgagcgt gatcccagaa tgggctttga accagaagga    40380
aacgatggac agtttaatca ggtctttgct gaaatggtgg catggcacaa tgtgacggga    40440
ttctctgaac atgaaattaa cgttattact cgaccggacg tagatcagca cagggaagtg    40500
agtgagcggg gctatcgcaa ttacatggat agtaacactt acagagatgg aactcagcca    40560
gttcaggata gtgagaatcg ctgggaacct ccaacaccgg tgtaaagaat gttataaacg    40620
ggagattgtt atggcttatg tcgatgattt aaagaagca atcatcagga ctcggcggtt     40680
acaacttgca caacccgttg atttatgtga gacgcatact cgcataatga acgataaacg    40740
aatccgccat ttgggaggaa ttatacgtcc tgtactggat ctgaattctg ggtatgaaca    40800
actggttgcg cgatgtatgc ctgttcatct tcaagccaga cctttggttg aagaatggct    40860
gggatgtcct gtttatttta cgttgggatg gattgatgat gggacccaa aaggtatgtt     40920 caggtttgat gaggacttta ttactgatac attgaaaaat ggttatacag agatactgt     40980 caatcttcat gcatggctaa ctttacccag tatggaaatt atagatatca cattatcaac    41040
aacaatttct atgttgcagg ggcataagaa tcagttaggc ggtgttatta tcaagagagc    41100
tgatgatatt aaaggattct catataagcc aatgcttatt ggtgatgaat tcctgtcaaa    41160
atctggtata ttgcataagt ttacatatct agaattgaac tagtgatttt taaataaact    41220 ggtttttga cgttcttatc tctgttcaga aatcacctcc tgttggggtg attatttata    41280
ttatgagttc tggcaggtcg atatgttatt tccgaaaagt gaccatctct cagatacaga    41340
actctgtctg cggatgctat tgtttctggt cgatgagcta ttaacagaac aggaattccg    41400
agttggcgta atgtctggct tatttctatt tcactttcca catcaagatg actggttgct    41460
tcgtccagta ataatagacc gggttttta tacagtgctc ttgccagtag aatacgttgc    41520
ttctgaccac ctgaaagtcc ccctccggtt tctccaagta atgtttgata gcccattggc    41580
attgccataa tatcactgtc tataagtgcc agacttgcgc atttacgcat gtgttcatga    41640 tctctaatt cgctaaaaaa cattatatta tcagctatag aacctttgaa aagatagtca     41700
tcttgcaata cagtgccaat tcgttgacga acctgaaaat aatcagaatg tgtatgtggt    41760
atgccaaatg cattaattct tccttcactt ggtgtatgaa ttccaagaat aagctttacc    41820
```

```
aatgttgatt tgccacatcc tgatttacct gttattgcta atatttctcc aggaaagagc   41880
attagtgacg cgttatccaa tatgggttta tctgcgccct tatggctaaa tgttattttt   41940
tcgataagta atggtggatg ggtattatca tatttatgtt ctctgtactg gcttgcagat   42000
attgtttcat tatggtttgc ccaatggtgc tgattctggt gaccttcctg tggtgttagc   42060
acaatatcgg caagtctctc gttataaaca tcaagcatgc gccaggaaaa aaagttatca   42120
gtcagattgc ttatactgga tgaaaaacgc atctgatagg ataagtaagc aaccaacata   42180
cccacggtaa atgtcccatc cagcacttct actgctccct gccacaaaat aatggctgaa   42240
actacacttt ccgtcagtgt atgcgtcagt tcatagctca tttgtaaacg attctggcgt   42300
agctgtgtgt ttctgcgggt aacgttgagg ttcagccagg ccgcttctct gtgaatagtt   42360
acaccgttga ttctcagact ctgaatgccg ttaagggttt cgagaaaatg ccccgactcc   42420
ttagttcctg catcccagac atcttcaaca gattgccgta aagccggata ccacaatgct   42480
ctcagtgcgc catatataat agctgcaatt actgcgatta atgtcattcc tgggctatac   42540
aacagcatca tgcaaagagc agtcacaata agtagcatat ccagaatgcc ttcaagaacc   42600
tgcgttgtca gcgcctgctg gattatatct actgcttcaa aacgggcatt aatacttcct   42660
ttacttcggg catcgaacca tgcaagaggg agtcttacaa gatgatggaa aactctggca   42720
gtccattgca tgttaaaatt gacggataaa ctgatcgttg cccattgtcg tgctagggag   42780
agtaataatt gtatgagtga taacaacagt agtgccacta taatgacata caatagactt   42840
ctgtctgctg cgaccagaac ttcatcaatt accagttgat taagaagtgg accacctaaa   42900
gccagaatct caagggccag agcaaaaata ataattttg tcattgatgc taaaagcccc   42960
ggggttttcc ctgtcagttg acgcaggtgg attttttttc tctcgttccg gggggtgaaa   43020
tcactggctg gagttaattc cagtgccact cctgtaaaat gcttacctgc gtccaacaga   43080
cttattgtaa ttttcctct gtccggatca tggatgtata accggtttcc ccgaacttta   43140
tggagaacga cgaaatggtt catatcccag tgcagaatag atggaagatt aagacacctc   43200
agatcttcgg gttccagacg aactgcacgt gatgataaat ggatggacgc tgcacattcg   43260
atcaaccttt gtagcgtcat tccctgaata cctatattga aacgttcccg taatgtcgat   43320
aaatctgttt tcagtccatg ccagcaggca atcatagcca gacacgccag accgcattca   43380
gctgattcgg tttgacggat aacgggtagt tgtttcctta cttcccagtt tattgattcc   43440
attacagatt tcctttcatg ctccataggg gctctgtcag ccattcccat aaatgacgag   43500
tatcaaggtt gacgtctcct tccagagtca tgcctggtct tagcggttct ttttttccgt   43560
atgcaaatat aaatgtattt tcaggttcaa caataacgcg ataatgccct tcgttttctt   43620
tccatgtgac gggtgaaact ggtaataagt cggaaggagc cagagtcgta tgactgattt   43680
tacgaattgt gccgtactgg ataccaaatt tctgataagg gaaggccgaa aacttcagag   43740
atacccgttg acctggtcgg ataaaaccgg ctttctggct ggtagcataa agctcaattt   43800
gtaaatgagc attatcggga atgagagtca tgaccggttc agatgctttc acagactgcc   43860
cctgtttgat cagtacagca gcaatagtcc cggatactgg agccctcagt gtaaattttt   43920
cttgtccggc gagttcatcc tgttgttgtt ttagcacctg caattgtctg tcgagttctg   43980
ctttacggct tttcccctga acaataagat gatttagttc atctttggct gtgtccattg   44040
cagtatgtaa ctggagaagc ccctgacgct gatcttcaac gttttgttga gcggcagaaa   44100
catcaatttg tttctgttgg aattcgatat ctgacacata atgcgtacca gccaattttt   44160
tatagcgttc catgacggat atagccagtt ctgcctgacg ttcagcaagc tgaagtcttt   44220
```

```
gttctgcact tcttatttgc ggctcaagtg atatcatcct ttgccgtatg gcttcctgtt    44280
gttgactatt atctcgcgac tcaaaggatt gctgggaggc caacataata tactgagtct    44340
tcagggaaat actcatcgtt gctaatgtgc cagttccgtt accgttataa tgttctccac    44400
ttatatgata gagttgtgtc cctgcagtta cgtgttctcc ttcggataca gtcagttgtg    44460
ttacatatcc tgcatattga ggaattattt ttaccagtcc tgatgagggc atgacgatac    44520
ctgtaagatg cgctttcctt gtatagctac cgtaatatat gaatacagtc agacttaaca    44580
taatgaataa tgtaactgtt gcacatacgg ataggctaaa tgatgttggt aaaataatgt    44640
caccatattc agtgtcatta tgatgttcta ttgcttcact tctgaatata ttcattattt    44700
ttaatacaat aagtaacctt tccgtcaaca agagggtttg gttgaataat attgatattt    44760
gatatacatc tgacctgtgt gatgttaaag ttttatacta taatatattt aacaatataa    44820
caaagccgtt tattcccgca tgtaacagca ttggatagaa atcccctta ctgcaaatcc     44880 ttatattcaa caataacatt gacataataa acagaataat ttgatcagcc acattataat    44940
actgcggatg catcaggcag aaaaataaag atgtacacac gcaggggggta ataattctt    45000 ttttataagt cgtacataga agaccgaata gacatgttcg gtaaacaatt tcttcataat    45060
acggaactgt caggaccagt ataaatattt caatccaatt aagtgaagtt gattcactat    45120
tgttcaaatt gtctctataa gcaaaaataa gcagttgcat gagagcaatc acagcaaatg    45180
atattactaa tagctttaat gttttcgcat ttgtctttat ggtgatttta caacctggta    45240
ttcttcttaa gtaaaaaata taaaatgaag ttgacattaa aatttcagta ataaagacaa    45300
aggaaaatgc cagatccaaa ccaatatatt gtatggtgaa tgccggtgtg aatatcacaa    45360
ctgttgatat aacaacaagt agaagaaacg ctatcgcatt atctttacta tatttatata    45420
tgttatcatt cataatgcta tttcgcggag attgttctta ttttttctat gatatagtcc    45480
atgaatcttg ccgtggaaaa aagagtgatc agcatgacta caatctttga aaactcggaa    45540
ggtagtgaaa accagtataa atcaataaca gaggagccac tcaatagtgc aaatcccagt    45600
aacaaaccac atataaagga aagtaattta ataaacatag tagcgccctc cattatatct    45660
atttatcggt tacatgttcc gccaacatta ttacctgaac aactactgga acttcctctg    45720
ttaccacttc catttccact accatgatct gagagacatt gaccaacaac ggctccacca    45780
atggtacctc ttgccattcc tatgggacct cctttgatcg caccaccaat cattccacta    45840
aatacagcgt tagcgcattt tacagtgctt ggatcactat aaatatgagt tggtgcgttt    45900
cgacccagtg agttacgagc cccactggaa cggtcattac gggggccacc ttcaaagttg    45960
ctgtttgcgt ttcctccgct gacaagcgtt atctcatcta aagttaattc tcttatattt    46020
gccatatcat atttcccccta tcggttgttt gttattttgt gcgttcaaga tagccaataa    46080
caaaaatgta atgaaagtga aattgtgtga ttaaatgtaa atatgtgaaa aaatttgtat    46140
gttttcgagg ttgtgtaatt acaaaaatat catcgtgtga agatataaaa ccgttccagg    46200
gctggcacgg cctctgttca gtacatctcg ttccagtccg aacggttgtt ttttctgat    46260 gaaaccagtt tacaggacgc cctgtcgggt ggttattgtc ctgtgggagc gttaacaggt    46320
ttatattggc ttttttctgct ctcactgata tctgattttc ctcttttgtt tcaggtggtt    46380
ctggtctgtt cagcgtgata tagcgaattc gtcgctcttc cagtgtggtc gttttaagcg    46440
tattcaccgc tgtttcccac aaggcacttt cacgtgcgtt gatatccgtg tcgtactctt    46500
ccagcattgc catagctgcc tgacgtcctg caatgcgttg ctggaatgta tccacgatcg    46560
```

-continued

```
tgtgcggctc tgtgcgaatt tttcgtcttt ttctggaggg ttttgcagtc aggacgccaa      46620
tgatggcact gacatttttcc ggtgacggga ttcgacgttg agctgtacgg ggaacaagac     46680
ggcggagacg gtccaggcgt ggcgcatcca cgctgatata cctgtttata acaacgggat      46740
cgctgctgca gcttttctca tcgtcaggga tgaagaatga tgctgatggt acggtttctc     46800
cccggaatat agaaaagaac tcgccaggat gaagttcaat caactcctga acatctatct     46860
tactttccat caggatgctg atttgtgggc tgtcaatcca tgattcacca aatatgccgt     46920
cctgacgctg caggttgttc atcctcgccc tggcttcttc accggcggcg cttttcagcg     46980
ttctggccgt actgccctcg ctgacaatcc tgccggcaaa ttttgtcccc gtgttctgca     47040
tcagtgttgc agtattcgtg gctgttgtct gtccttctat acgttcctgg tcctgtgcca     47100
tcaaaatcag agcaaaatcc agtgaacgca cctgagtggc ttccacagca atacggtccg     47160
tatagtatgc ccccacttca tcaaggaaac acagataagg gaaacgcccc ttatattttt    47220
tgacttccag tgcatcggaa tcagttcctt cgaggcggta gcccaaatca cgggcgagaa     47280
tcatactttt ctgggtgata acattcgtc ccagagcaga cgttgtatgc gctgatgtat     47340
ccagagcggg gatcattacc atcagaatcc tgtcgctgtg aatgctgtca cggatatcga    47400
tatcaccgga atcttcagca aaaatatccc cgaatgcttc cgtgaatgtg ctgaaagttt    47460
cagaaaactg cccggagaga taagcatgtt gttttctggg ttcttccgtc aggctgatg     47520 gtgtcctgac cagcgacagg tcgaaaccgg gaacgtcctg aaggtagtta cgtaatggtg    47580
cgatagcttc ttccggccac tgatcatcga ggccatgaca gtaaagtttg gccattcctt    47640
cgagagtcat atgttcacgg agcatctgca gcgacattgt tttgccttcg cgcacacacc     47700
agaatttagt accaaatacc agtgccttgt tcatggcaat ggcccgggac tgccactcgc    47760 cccctggac gttctgggc agcattgact gcattgtctc cgctgtgaat gcctcagtgc      47820
tgtaacagaa gggattccag gtatttgact gaggacgcgt ttttcacca ctcagaatga     47880 tttcactgcg ggatttttcct ccgttcatga agttgatgac ttccacatcg tcttcacgac    47940
caaagcgtct ggccagatac cagatcgttc ttgccgtatc attctgtgcc ttgccatcga    48000
caagggtgaa tcctcttgcc cagcaaagcg ggttaatcgc ccaggcaaag atggtttccg    48060 ttttacccc accggtggtg gcgaaaaaca ttatatggcg ggtcagatcg tccatactca    48120
gccacaactc ccgacctata tccctgacgc gttgataacc aacataaaat atgccgctgg    48180
ccggtgactc caggatgacc tcatactgaa acagagttgg ccagaagctg aaaaggcttc    48240
ttttaatcat tctgtcctgt gacgggtcag cacattccag cgtcatgggc atacgaagag    48300
ggcagcgcca tcgctgcaga ctaaatacca gcatcgttat cagtgtgaac aacagacatg    48360
ccggtaatgc aagtggccag ataaaactgg ccacaagact tgccaccagg caaaagccat    48420
agatattgag actctggagt gcattccaga caggatttcc ccaggctgta cggtgtaaaa    48480
gctcggggtt aacgcgatgt tcactcatgg ccagactcgc tgtcggttgt tttcaggaat    48540
aaattaagcg tgccagtttc ctgcagaatt ccagtaggca gatgccagcc cgtgtcggac    48600
agtacccatg gggtaccggc aaatccgaac ttacggaagg cgacattgtt aacatcaatc    48660
gcagctctgg ccgctttcag gcatgtttca tctgcaggcg ttgtttcttc tgatggcgtc    48720
atcattccgt tatctgcgga atacagtcgg tgccagccgg cagcacgttt ctgagcatct    48780
ttttcacaca gcagtggtgc cacacggtcg gtggattcct ctccaccaat aactgaaacc    48840
gggtagataa cgacattgaa ggcgctgcc aggcgtttta aggctggctc cagaagtctg    48900
cagttaggac aggcaggatc gagaaatgcg taaagggttc gttcatgacc ggatgacagg    48960
```

```
ttgacggtaa acattccccg atcggcgttc cgcttcagaa cagcagccag attatgtcgg  49020
gcagctgcgg cttccggatt tttgcttgtg agtgttttat ccggtacctg dacgtctttt  49080
ttcggggtaa ccgggagttg aatgccttca tttaatggca cggtgtgatt caggtgaggg  49140
gggagcagtc gtggctcacc tgccgtctgt actgcttcag gcgttgtatc atcccagaat  49200
acacgatcaa catagcggaa cagagagacg gcaatcgttg ccattacgaa cagtacaacg  49260
ctggcgatta ttgcacggaa caaaggcgtt ctgctgaagc ggcgttccat caggtattca  49320
aggcgcagac aggaatcaat agctgtaagt atctggtcag cgttatgctc ctgcttgtca  49380
atcaggacgg tttctctgtt acgagtgccc atggcgtcaa aggctatatg aatcagttga  49440
ttgtttcgtg ttaccagccc tgacagggca tcccgtggaa ggacggcaat aatttctgtc  49500
ctgctatccg gccagattgc ctgcacggaa atatgttttg caatgcgtgt tgcaaagtac  49560
tcgattgtca ttttcagttc tccggataat cagaattcgt tgtctgtagc aggtgtgcgg  49620
ggcaggatgt cgtcggtgag ggaccagttg gtcagaatgc ggcgtttccg gtcgcgatct  49680
ggttgtggtt catcccagat aagaccgaga ctgagcatat cccgccgtaa gccttccacc  49740
gcttcatcaa cacaggggtc agggcaggga aggccaaaac gcatggcttc ggcctctgca  49800
cgtgcaacgg ccaccacgcc agcgccttca ataaatcctt tcgtggtatt ggcgcggtgt  49860
aatgcataaa acagcgttct gtccacgcct ttcagccaaa tccagttggg tggcgtaagc  49920
cgcaggtcat gtgcatacag ccagaccagc ccactgcgga cgtagcgatg ttgcttcagc  49980
cattgctgtg ctccatcgct tttaatcact cttttgaatg cagatttggc cagtgaataa  50040
actggggtac agaatttccc actgtcccgt tgcttttaa ttctgcatga gaggttcagt  50100
gtatccatga gctttaatgc tgccttacga tcatccagga aatactgaag gccaaatatg  50160
gcaaagagcg cttttcatg tggtgccatg tcttccagg acgttaaagg tttacccaac  50220
tgggccatga acatcgtct tgcagctgca acatcgagct gcatattggt gatgagagta  50280
tgctgctcga caaatgcttc cggggtgaga gcaacccgcc gttcaggtcg tttgccacca  50340
tgaaagagtt tttccggatc accatctgcc agtacagggg cgatagcagg ggacaacgaa  50400
gcaaagatgt gtggcagtcg ggtaatatct actggtctgc gggtgaaacg actttgtccc  50460
ggatgttgat accactccca caaacaccag agtgtcacag gtaagaggta catccacaga  50520
ataccatatgg tctgctccat gacgttaacc cactggctat agcttatgtt ggcggcgttg  50580
ttaccggtca tggcaagcag gttgtatcgt ggtgctgcat agttatgaaa tggtccccag  50640
tcaaccagtc cccataaggt atgaagaatc aggcagctgg cgtaaaccac ttccggcaag  50700
aataaccata taacgaatag cagcaggata agaaggacac caacagcgcc ccatatctgc  50760
ataggatctt ctgcgacagg ctgtcgattg taagacatga caaagtctcc atttctggaa  50820
tttaaatcaa acggaaaggt taaaaattta tttgcaggcg ataagagcta accagaggaa  50880
ttagccgtgc gataaaagga ttgttgcaga tacgaaagtc gttagaatag ctgcgggcgc  50940
ttgaggctgt atgccgaaag cgttttgtgg acggtataca gcagaaagcc cctggagatt  51000
tttttatcaa tcaaccaagg gctctactgt aatgcttcga caacattata gtagcccgat  51060
aaccgccgta aggcaatgga ggggctatga tgccacagcg aacatttta atgatgttga  51120
tcgtcgtctg tgtgacgatt ctgtgttttg tctggatggt gagggattcg ctttgcggat  51180
tccggctcca gcagggaaac acagtgcttg tggcaacgtt agcctacgaa gttaaacgtt  51240
aacgggcaac acggcggcag gttttctgcc gccgctttgt tgcgaaggct gacctcattg  51300
```

```
cgcccttcct tcttcaatga agcgtatccg gtattgtttc atttcccctg aagccgatta    51360
gctccagccg aatgcctttg ccatcggggg ccacgttctg catttcgcag ataccacgtc    51420
gggtcatgag tgtgaaggct gtcattgcca gcatggctaa cgcatttcc tcgcttccgc     51480 tgcgtttctc gagagcatcg gcaatttctt ctatgctccc cacctgaaag caagagtcga    51540
attctttact ccacttttct gacatcggat tttctctctg tatttatggg tagttatcga    51600
actgaatgtg ccagttttt caggagacga caaagttgag atggctgatt caggttcaga     51660
gcatgagttt ccccggtgtg acgggcatgg cggggcggat tttgcagata caaagacgt     51720 aaaaaaccg actggtgagg ccggcttttt tactgttacg ctacaaagtt gatgactctg     51780
accagaaaag agctgtctat aactgacgct aaaaatgata atttgttcta cctgattaat    51840
gcaacatgcc ataagtttac gggaaaggct gaccacctga tattgttgca aaatacgaaa    51900
gtcgtcaaaa tcgcggtggg gagcttgagg ctgtaagctg aaagttgaaa gcgtttgtga    51960 aagcccccagg agattgttct atcaatcaac caagggctct actgtaatgc ctagacaaca   52020
ttatagtagc ccgctgacgt cctccacgcc agagggagct tgctacgtac agcttgtcgt    52080
tactcagaag taataaatgt aaaaaaaccg actgatgagg tcggttttct tactgttccg    52140
ttacaaagtt ggtggccctg actggaggaa atctcttttc aactaacgtt cttataatag    52200
tgttctgttc atttgataac aaccaccctt ataatccgca ggttaacact gtcgcgcgac    52260
acttctgtcg tgatgaaggt aaccagaaca tgagtcttcc cggtgtaaca ggcatggtgg    52320
ggcggatttg cagaaacaac agatgtaaaa aaaccgactg gtgaggtcgg ctttttact    52380 gttccgctac agagttggtt gctctggacg ggaaaagaca gtctgtatct aacataatca    52440
attctatgct ttgtcccaca ctatgtcaaa atcctgcta atcaagtagt atacaaaatg     52500
ttagctctac tgattgtctg agttcgacaa ctgacggatt tgttaagtcc tggtcgggat    52560
aacaggtggt gctgcttccg gtgctctggt cggagtgagg cagtctgtat ctaacaatag    52620
aggcaaccgt agtgacaggc agcccatgag taagctgcgg tgtttcgctc ccttatcaag    52680
ggaaaacgga tgattaatct gttaatcatc gttctcaggg cagtggttgc cgttgcaaac    52740
gcgctgattg ctgttctgga actgatccgg gaacttgtcg accgataagc ccggaaacgt    52800
aactaagggc agggagttac cgcttcctgc cctttaacaa aaagagatct cacgttaaaa    52860
atttgtaccc ttccttaact tccagtgcct gctcctttga gtcaaacatc agtcttgttt    52920
ttccgggaac accccatgaa atgtattcga catctatcca ccatttccca tattcttcat   52980
atggcccgga tattactttt ttgacaaagg cgtctaccag attcattgtt ttttcctttt    53040
tattttgaaa ataattaatg ccagagcaca gcgaaaataa tgaatgcact ggctgtgata    53100
attgcgattt tctcccatat gatattttc tcatgggagt ttctgcggag attatttctt     53160
cgcattggaa tatattggat atgtttattc atgaataaga gcaggtgtgg gatttcctgc    53220 tcttttttgtt ggcgttattt tacatgcttc cagacagaag ccggtacttt gtcgtacaat   53280
ttgttcattg tcagttccgc aaggcgatga tcaactgcag agttgaatgc ttctatttta    53340
tccgagacca agtgccttg gttttagca ataatttct caagtgtctt taagctggaa       53400
cagcgacgta attgatataa ccattcctgt tttgttttg ccataaatag gtccttgggt     53460
ttatttaata cggcataagc tatgtgttgt tgcaaacaaa agccggctca tctgaaccgg    53520
cagttatgga ggctgcttat cttaaaatac ttcagctaca ggcatacctg caatctgctc    53580
ccactcctta cgcttttcct gaatcaggcg aggaaagtcg acagggtaat cgtatcctct    53640
ttctgccatt gcgtgtaatg tgtttgcaat agaacgagca gagttaacac caatagacaa    53700
```

```
ttctaacatt ggcatattga catactttgt gtgtatttcc atacagtttt ctcttactac    53760
tgtccgtgtg aaattatcaa tatcaatgcc aatgacatct aatgttttat tggggtaaag    53820
ccgaatatat aacgcagtac cttttttgat atcaattccg aaatataatg atgatattga    53880
tttgtgttcg taagatgggt ctggatcgaa tgcatcatga cattcggtct ttatctgttc    53940
taagatatta tttatgattg ctcttttctt tcttccttct ttatatccgg agtatagtag    54000
taatccagtt gggattactg ctagtcccca actggtaggt gtattccaaa tgattagtaa    54060
tgggacggcg aaaataatgt agaaagtgc gaatgcgatc acgcatattt cttttttaga     54120
atgggtgccg ccacggtttg catatgctcc aatcattata tatgacctcc ataaacactt    54180
tttgatattt taatctctcc aagtgtatat ggcaagtcat atattaagtt attatcccctt   54240 tattccatcc ttattgttgt cgttattcat tcttttaatt tgctcctctc ttatattagg    54300
tgcgtgtctt atgtttctat tgctgccagc aaaaatctct tttattgaac cagccatatt    54360
gccaagcgtg tttacaccat cacgtcctcc taggaaatta attacatggt ctgggaggta    54420
tgcttgtaag gcaaatgctg cggctacaat ggttgtgcaa cttctagcat aaagaagtaa    54480
gaaacctgcg aggctaaata tacctgtaaa tgaacttatt tgtacattgg tcagtgcagc    54540
accgaataaa aagtttaata tagtacctat tgctataatg gctacagagg caaaaaagaa    54600
tccgaaaacc atgataggag gtcttatcat gctgtctatt aaatatatat aaccgtaggc    54660
agcacgactc cctctgtcct gtgaggtgcc tagatgagtt gccccccaca gaggtccagc    54720
tgtacatccg attaatacac taatgaccca gttaccaatc ccagtcatcc agaaaataaa    54780
cggaataaat ggtaaataaa tagataaaga gaatcctgca caaacagca gtagtaacag     54840 aaagtatacg gggggcgcta aggcctcaag taaggcattt agtgttgaaa tagcacttgt    54900
cgtcaaatct atgaatttac caaatataga actcccagtt cctgaagtaa taactctagc    54960
agatgtataa gtaatccaaa taccctctgc agcgaccata gttttatcac caatattttt    55020 cattttatc agtggattaa cttgattgct acttgtaccc gaatcagtcc actcggtggc     55080
aatattgttc gtaagccatt gcccaaactt ctctgtgggc ttgattaaag catcttgtgg    55140
cgtgcttgtt tttgaaagta gttgttcgtc tgctgaagtt atagtaccta aaggtggggt    55200
ataagttgaa ttctgcaatt gggtcttgta tgcccccata acagcactaa ataaatcagt    55260
gtcgccaact tccccaagtg atgacattga agttacagct ggagctctgt cagccagctc    55320
tgccagacgc tggttagcag tggcaaaggt ctgataccac gcgccaagcg ttacccatcc    55380
ataggttgtg agataagact tgagagcttc tttcctggat tgttctccgt tatcaatagg    55440
tagcgatttt tgtacagcac gctcatactc gtcggctgct ctctgaatcc gtgtctcgat    55500
atccggcaat gttccgttgc cagaatttct ttttccaga aatgttgtca caaactcact     55560
ggcagcgttg tccatgtcgc taatcatatt atccatggct gcacgttgtg ctgagataac    55620
accgctgtat tcgtttttac tgaagggatt aaagaatttt ccaatcgtcg attgatctgt    55680
tgttccgttt ccttctactg acaggctggc tgaaccacag ataccgctgc cattggatac    55740
cgtgacagtg taattaccac tggcggtttt agctgattct gtcatcagtg aagtcgagga    55800
tttggccgtc tgattaaaat catttagtcc tgcgttaacc gcatacttac acagttccat    55860
ttcaaaaatg ccacgcgctg ctgttcgtgt ggatgcctga actggctgta cagtcattga    55920
ataaccattt gcgatattat cagcggcaag ttgcaccatc acattggcgg acccaacccc    55980
cattatcgat gcgccccata acataatgag ctgagcgata ctccagccat ttccggttgg    56040
```

```
aacgatcatc agaaaacctg caacgacact cagtgtgccg acgatatcgc gtccggtgct   56100
gaatacctgt ccctgatgcc ccgaacgcac aacatgacgg ataccaatga acataaacca   56160
gacaacggca agtacggcga tgatactgtt gaacgccccg aacatgcttc cgatcagagt   56220
gggggcgctg gttgacagtg gattggtgac tacatcaccg aatatcgtga ccagcgcctg   56280
gcgggacaga tcgtcaggat tggtggcagc agacacaata tcctgatagg tcactgaagc   56340
cattgccggc agtgaggata tagcaaggcc tgcacagagt gcgcgaagta aaattttcac   56400
agtaactccg gaatagaatt gcgtatgggc aaaggccaca caggatttaa ttaaggggga   56460
tggcgacatg ccagtggtac tggcatctgg acgtgatcag tattgtttac tggttacggc   56520
aattaatgtg gcattgcgcc agccattgcg gtcgttcaga aaatcacgga aagtcccctg   56580
ctcgggttcg ctgacttttc gttcatgcaa ctgccagagg cggtatgtaa caatcagtgc   56640 tctgaagca caaagagcga cgcctgacag tatcaacaca agagtgctga tggcgcgtac   56700
cagagtcgta agaggtaatg aagaggcggc aaagagcata ccactgagaa acaaagcgat   56760
ggccagcaga ctccagcaac agaatcgcca tactgttctg cgccggcgga aacgacgatc   56820
cagatcgtct actgacatat ggctggcctg cagagcttct tcccacgtga ggtggagttg   56880 cgcctttta ttatttacct gacgaaatct gtccagcctg cgttttgtt gttccagcat   56940 atgctgtaca gaattcgtta tcaggcgagt ctccatcaga ggaacaaaaa tgttaataat   57000
cccccgggtg gctatgcggg ttatggatgg tgattttttg acgttttcg tctggtctga   57060 attttccggt aacttattca ttttttcagt cctgttctga cgtcagcttt caacgtgcgt   57120
ttgcctgatt gattgttttc tcaaggctac cgagttgttt ttcataatac tggcgggcag   57180
tcagagccag ttgctggcca gagataacat taccctggcg gatctgttct ttcagatcgt   57240
tcagctgcca gttcatttgc gcagtgattc ttaccagttc acggagcagg ttatcccct   57300 gcatttcctg taaatccacc aggtatgctg tgttggcgta gcgccggcca gcctcaaaag   57360
cttcaaactc acgggtactc atatatcccc gtgcttttgc ttctggtgaa gccacctggt   57420
cgaagtaagc ggccgctgag tctgactgca gtgtttcagc cagtgcttta cgtgtgcttt   57480
cattaggcgt gctgtcagca atcaacgtca gttggggatt cgacgcagaa tcaatgatgc   57540
cgttgtattc gttctggagt ccgacgtagg ttcgcccact ctgggtattc acttctcctt   57600
tacccagagc acgaccggca gaggggcggg aagtgttttt catgtaagca gtcgctgcat   57660
ctatttgctt ctgatcccat gtcagtgccg caggtgtgtc cgctgtacct cgccgtggt   57720 aaatcgagcg tacctgactg tctccacctg gtatttcgcc cacagaagga caaacggcgg   57780
ttcctccaaa acgtgcatat tctgcttctg tacagtaact ggcgtgtatg gccgcgccat   57840
cataagcttc ccgcacggga gagtttgctg cgctggccag acggtcgcgg atgctacggt   57900
tgctcacacc gccacctta ctgagttttg aggctgcgga tgctgaggca cttttgcttt   57960
ctgttgcaat ccctgatgcg gattcactgc agatggagtc tggcacggtg aagcttttcc   58020
gtgcctcctc gaggcgctga gtttcattac tgaaaatcat ctgctgacgt gtcgcctgtc   58080
cgttctgggc aatgacactt gccagctttt cagagttctg attgatagcg gtacccgtgg   58140
ctgtctgggt actcagtatg tcactcagca caccttgat ggcctccatt ctggggacga   58200
cctgctgttc aacgggacgg ctggcgacga cggtgactga ataagcatga gcctggtatg   58260
ccgttccatt caggatagct ataagggctg cgagtaatgt ttttctttgc attttattgt   58320
ctcctgctcg gggtggagca caaggtcagg aaggctgtcg tattttctgt cttcaggtag   58380
tggggccagt gggaaacact gatatcgcct ggtgatataa cctttcctgt tccggttatc   58440
```

```
gatgatgctg aaagaacgac gtctgacgcg ccgtaaggtg aaggggtcag tatccataac   58500
aggccagtca ccggcactca gtgccggcgt tccgggaacg gatggccata accaggtatc   58560
atcggacatc agcgaagtca gcggtgaagg gagtatccac tggatgacat gctgaacgtc   58620
gaatggtgct tcatccggga cagaaacctg ccatattgcc gttgttatca gctcatctgt   58680
gctggacggc aacaacagcc gcatgcctgt aacctttccc tgtgttctgg catccgaggc   58740
gtatatcact ctgggattgg gggccggatg taacctgaag acacgtgacg gcagagtgaa   58800
tgagaaactg tcacctttta cctcaagttt tttaagaaat acctgccctc tggcaggtct   58860
ccggcagcgt ggggtgatat gaattgtaca catcagagat tgtatccctg ttttcggatg   58920
agctccgagg ccagttcttc aataacattg tcactgttat gttggcccgc ccggtgctca   58980
attaatgacg ttgcagaacc tctggggaag ttttcggcca gaatcttacg tgcccgaact   59040
gaacctaact tatttgtcag tgttttacgc agggcactgt cttttggcga tgagttcagc   59100
gcccatagct ccagtggacc gacggtaaat ttgagtattc tcgcaagcgt gccactttt   59160 accctgaata ctcccagaac aggaacacca ctaccatctg gtgccgggcc ttccggcatt   59220
ttcaggaagc gtttcagcat aaattcagga acgttgaagt tatccctcag tacggggata   59280
tcttcgggtt tgtagcgcag taaccagaga gtatttgctg acttaagaac gctttccggg   59340
tagtccctca gatactgcgt actcagaacc gtgcggatag caaacttgcg ttgctcacgc   59400
tcctgggtat ccagattttc ccagatgaag tcaatgcccc gggcgttatg cagttcatca   59460
taaacttttg tcttaacctc ctgatcaagt tggttaatac gtttaagagc gatttcatgg   59520
tattcccgtg gaagctgctt taacacttca tccctgtatt gtggcagggt gaagtcacca   59580
ccggcgatct gacctgcaag caggtacatg atgccggttt taagcctgcc tgcaggcgtt   59640
ttgtcaccgg caacattatt cagatcgaca gcgatgaccc gggtttccgg gttgatcata   59700
aaccgggtat acccggatat catgggggtag tcgttatgtc cctgctcgag cgcgcggcgg   59760
atgtagtcca gcagaagttc gtttgaacca tcacgctgaa cagtaccgaa aacatccctg   59820
agactggtat ggcccagcat cgaggacact tcgggaagct ggggcattgc ctgataatgt   59880
gcccgctgag ccgccatgat ataccccggca ttgtggagca tatcccggac ttcgaaccag   59940
gttgatctgg cccaccaggt tgcatcatgt ttttcataca gtcccgagtc ctgcagtgct   60000
gaatccacca gttcttccgt tgaggcgcga taaagtcgcg gattatttc accgtactct   60060 ttaaaagcca gctcgataag ctggttgata atttgtcggg tgtctccggg gttacagggt   60120
tgaccggtac cggtatcgac acagagagca cacagcaccg atgacatgaa attctttcc   60180 ggcgtaatag gcttttttagc gccgtacatc acgtcaaaaa ggttacgggt gtattccgga   60240
tcattgctca gaataatacc gacagcttcg tcttttcttt ccggaggaag actgtcgcga   60300
ataagctgaa ccagtccctg agcactgtat cccttatcga tataggcaat gaagggcagg   60360
tttttctgag cagatgatat ctgtatttcc gacaatgtat taatcagaac tgatttaccc   60420
agtcccggat cgcctggtgc gagttctgta tgtttatttt gttgggatga cgccagacca   60480
acctcaattg cggaaccgtc ttctgtatgt aacataagat tccctttacc tcgccagaca   60540
gagcctgccc tgttaagcgg gaaaagcgag atggcatgtg acaacggggg atacagggga   60600
accgggccgg agcctccgga tgccgcgaga atggtattca cccaggcgcg tcggggatcg   60660
ccaaatgttg tcgtggtgcc acatacgccc cagccttcaa tggctgattt cagaatggcc   60720
tggtttcgtg tgcatatttc acgtgttttt ccccacgtgg aggccatgat ggtcattatg   60780
```

```
cagacaggtt cttttccatc cgttgccgcc agggccataa cggattcata cattggacga    60840
acggcagaaa tgaagctgct gtaagtcaga agcgttttct tcagattaag agccttcatc    60900
ccgccgggca tcagatccat tctgatgcgc caggggactg cgcggggac ggcacggacc     60960
agttcgttaa acgtctgcag attttgcgga ggtaaagtaa tcgataccat tccgtgccag    61020
agtccgcccg cctgaaccag gttgccctgt gtggtcacct gagtgttgaa taactgcaaa    61080
tgcaatgaag gagcatgtag tacggattca tcgtcagtcc agcgatatcc cgctggctgg    61140
gcatcttcag gcaggtgggg ttgccagtta cgcggtgtgc tgtgccgttc tgtctgacga    61200
cgtatttcac gcccgacctc gtgtatatcc agtagccgga gaatcaggcc atcagatgaa    61260
tgtctcagtg cctgttccac attatcaaga aaagcttcgt ggcggatttt cagtgcagat    61320
aaggtccact gccaggggga ctgggcaaag cgtgctttcg gtacccgttc agccagtctt    61380
ctgacaagct catcatgggc ggtgcgatcg ctgttgctga taaggtcggg tccactccag    61440
atcgccagcc agcaacgctc ccggaccagc catgggaca gtgttgtgac tttctcatcg     61500
accacatcct gtaactggat acctgtatta gccagtgagc gcttttgtgg ggcgaccatg    61560
tcttcgattt cttctttccc catgtcagga tcacgctcaa aaacgaagct gattttatga    61620
ccgctgtttt tatatgccgt attcaggctg tcactcatgc tggtgatcag cgattccagt    61680
gaacctgggc cagtctggtc ggatgcttca tccatttccc tgaaagcacc gctgacttca    61740
aagacagaga gatattctcc acgctttgtg gctgcaatat agggcgaatt cagccatggg    61800
cgacgttcac gatcctgtct gtccagacca attacagtac gtaaatcgca atactcaaca    61860
aaactgcttg cgacagagaa acgggatagc gtgttcagac agtcttcgat agtgaagatt    61920
aaacggttta tgttcatagg tgagggaact ccggacttac aggagggagg tttgtgcagt    61980
ttgatttttt taatgccacc ccgcgctgga gtggcatgaa gaaaaatcaa tcaacgtatt    62040
cttttttgat gaatgaatct ggtgtcagaa tcagggcaat cccgttcatt ttttcacgca    62100
ggggcgaacg accggaaggt ggatagcgac gaaaaacgtc agcgaaatcg ccgggcgga    62160
aactgcggaa tttatcctca accgccagtc tgttttgcat cagtgcagag agcgcttccc    62220
gtccccgccg gacccggaac ttatcattac tgaaaacttc ctgtaatgaa cgacggttaa    62280
gggccacgac cgtggatgga tgaaggtcgg gtagccacac cataacgccc tgtgctgcgg    62340
cataaccatt cagtgaatgc caggcgtggc agaaagcaca taagctgtaa ggcgggccgt    62400
cttcatgaaa cagttcctgc tctttctctg acaacgactc tgtactggtg atttcagctt    62460
tctgtacatg gcggagtgaa agacgtctgg cagacagacg ggcctgctca agcgcccgtt    62520
cagcggcttt tactgccgtg ttgtactttt ccttttcgcc ggttgcgact ggttcaccac    62580
gcttttttaa cttatccaga tgttctgtgg ccttattaag acgaactcgt gtgtcactga    62640
ttgtgtcggt aagctgtctg agtggccatg agtcatccag tctgaaacgg tgcctgacgt    62700
tttgccggca gcagatacat cgaccggcg ttgttaattc cggttccggt aacagtggct     62760
cctgtgtatg aaccacatca atttctggaa agggatacaa ccacaagtct ttaatgctgt    62820
gttgcatgag caggctccgt actggtgtaa cgtttcacgg cttccagaat gatgtttgcg    62880
atttcatcgg aacagcattc tgcaaaaatg aattcctgat cgtcccgact gtcgtgggca    62940
atcacattgc cgttttctgt tcgtcgtaac gttatgtgct ccgggctcca ggcagacata    63000
tgtgcctcct tgtattgccg aacaggaagg gcaccggata aatgccagtg ccctggacaa    63060
gattagccaa tggaaattgt ggaaatcccc agctgttttct ggctgcgact catcatttca    63120
ggtccggcga caagtagcgc cccaatgacg atagatacaa tgcaaccagc cagtcccatc    63180
```

```
ccccttgtt tcccaacttt tttcaggcca atcaggcccc cgagaaacag aattacgccg  63240
atgaactgcg caatagtcag tgatgatgac tgtgctgttt tggcaccttg ttcgacattg  63300
cgaaccatat cggcaagatc tccatcggca agaacggctt tgggcagcaa catcatggga  63360
atgagcagca ggaacttagt cagtttgctc cggcatgaca ttacaaacag ttgtgcgtgg  63420
ataaatgcgg cgtacagacg ggccgctacg acacgaatac gtgacatagt ttctccttaa  63480
atggatatat cagtggttta tatgaaggtg aaaaaaatca gaagacgatt ccaatgcttg  63540
ccagcagggc attgaggaca cgatcgataa agaccagcag gacgccggca ataaatttga  63600 cgtttcccctt actgacggat tcactggcac tcagtgcggt atgtccatcg agtccggcct  63660
tgcgccagat ggatatcccg ttcattacaa atccaacacc ggccagcttg ccagcgaca  63720 gaactgcatt tgctgcgcca gcagcagcgc caaacgtctg aggttgtaca tatgcaatcg  63780
ggccaaatga gtcagccctg aatcccattt gtacgcctcc ggcgttaatc attgccggga  63840
gtgatacgag catgcagctg gttaacatcc ccgcaataaa ttttccggga gacattttta  63900
ccggaccggc tgaacgggcg cgggcaaaca gggtaatcat gctgatcacc ccgatgaatt  63960
ctccccaggt aaacaggaaa tccattccgg cactgaaaat actgctggca aagttctcaa  64020
tggcggtcag ggcatccatg ttcatcagcg taacgtccct gcactggtga tgatggtccg  64080
ggtcgtcgga tcaatccgct ggatcaccac attgcccaga gtctgacctt ctctgacagc  64140
ccaggtacta ccctgccagc gaatccaggc catgccagtt tccatcgaca tgattttcat  64200
tccgttaagt acagacgacg ttttttcctt tgctggatgc ggtgtggaag aggattcggt  64260
gacgcttttc tgtgtcatca ttccgttcag gtggctccgg atatcatcca gctgacggcg  64320
cgtttcctgt gcgtattctt catccttttt tatagcttcg cccagcttgt taatgctgtc  64380
gtgaagcata ttcagtgttg cctgaatttt ttcatcgcgg ttatccagct ctgtttttac  64440
atcccgggca agctggctca tatcttctcc tgtccggaca gtcatggtct cagtggactg  64500
aacggaaggt gatgattctt gtgtggtttg ccaggtctgt acgccagcat ccgcatcatt  64560
aaacggaggc atgcctgttt ccgatggtgc tctcaggaac agataccata tggctgcgag  64620
caatacgact gcacatagcc cccatgttgc tacagatatc ccccagacgg aacgtttcca  64680
gaaaggggcg ggtttctctt cgggttcacc gaagctgccg gtttcatcta tttctgtttc  64740
aggtttcatt atggtgtctc cggttgttca tcataccgac gttgcatcac agcttttctt  64800
tgctccatgg ctgtctgcat tcgtgcctgc gagcgttgtg ccgtctgtga tgtacgatta  64860
actgaagggg aaatgccact ggaaagggaa gatgacctgg cgtcgtttgt cattaccggg  64920
tcaacaaaca gaattgatac gacttcatgc tgatacactt ctacctgttt atagggctca  64980
ctttctgcct ggcgggttaa tatctgactt cctctttccg ccataccacc ggcaataacg  65040
cccgcaacag cttcaccact gggcattccc acgcgtccgg taaccgtgcc atagttaccc  65100
tgaataacct cgcgtgttgg catctttataa agtgtgccaa tactgcccac acctcctaac  65160
actgacggca gaatgatatg tttaaaccag cgtgtattca cattgctggc cacggatgac  65220
atcaggttgt cttcccgttg agcatatgca ttgaccttaa ggtccatgcc gttccagctc  65280
atccggtcga aatggatctc cacgccgtta cccaccagtt tgactcccgg actgaacagc  65340
gttgcccctg cccaggggcc agcgggaatg gttgcgataa ccttggatga cgggttatca  65400
gaatccactg cagtatcaat atatgccggt atacgggtca gagcaggtat cagttgtatc  65460 ccttttctg ctacaggcgt ggacaggctg gcattctgta atgcgaattg ctgcgtacca  65520
```

```
ttctgccctg ttgtttctgc cggagattta ttccacatag tcgttgctat ggttggtgta   65580
ctaccggcag gatgctgatc ttttattctt acaatcagct tttgcagccg ctccatacgt   65640
ttttcactgg ctgctcgatc ctcctgtggt gtgccggaag cctggcgatg agcatagttt   65700
tccggttttg ctgcaggctg ttgttgcttt tccggagtgt ccggaatatc aagcccctgt   65760
ggaagactgg caatgaacgt ctgattattg cgggctgcag ctgcggcccc tcgttcatta   65820
tccgctctta acagttcacg atagtgaggc gtttcggtaa cgctgcgcgt tccgccgctt   65880
gctgcactgt taatgttcac ggctgactgc atatcgctgt tactccctga tagtttggaa   65940
aacgcgatat agccgccgcc aaataagatg atgctgccca gtccaagcag ggcagccagt   66000
ttctttccgg atttaccggc atcctgttca gcactcatga ttactccagt tctggtgtca   66060
cgtgaacgga ctggccattc acagagaaag tcagtagtgg ggtgacggga agtttccaga   66120
gatgagttcc gtcggcagag gacaaggtct gttcaaattc atcgcgcaac atcgcccggg   66180
aacgaaccag aaggtcatcg ccgtgttgcc agatcgttgt atccgggaca ttacctgtga   66240
atttcagcct cttaactgaa gggtcccggg gaggaatacc atccagaaat gcctgtaatg   66300
ttgcatcatg cagggcgatc ttatccgtcg ggatggagac aactgggctg ttggtccct    66360
gccgtggtat tcgcagatcc agacgactgt ccatttcctg actggatgac ggcgtatctg   66420
tttcgccact ggttacgttc aggatgaccg gtaccgacag acctttcagg tagacagaaa   66480
tatttccgga tgcccatggc cgcaatggtg tgattgtcac catgttctcg ttgtactgca   66540
catcaaagag ttttggtgcc gcgttataag gaggatcgga ttgtggccat ggtgaaccgt   66600
tgatatcggt aaatgtcacc acgctcaggt tgttcatggc tgtgcgaaca agaggaaggc   66660
tggcaccggg ggacagatta actgtcagag agctgatacg gggtacaaca ctggtgatgg   66720
gcgcattgat ggcccgctcg ttatccgcca tgagactgcg tagtgagcga atctcatcgg   66780
cggagagctc agaatcaagc cttgccgcat cctgtaccag cgggctggcc tgcccggggg   66840
caggcagctc acctttttacc agtgttgccg gaacacctcc ggtgttttgg gaggcgttct   66900
gaacgtgatc gctggcagaa tttgtcgttt gtggtgtgcg tgcgttctgc catcctgcgt   66960
tatctgcaga cgtggcggcg ctgcacacca ggagcagtgt gctcagtaaa taacgtgatt   67020
gcatattact tatctcagga gttcggtccg gcgttacggg agatcatctg ccggatttcc   67080
ataccggatg gtttcagtct gggtcaaca cgctggatgg tgatttcgaa acaaaaagac   67140
tgttctggct tgctggttgt ctggccgacc agacgcatac ggacaggata ctggaatgtc   67200
cagaaccata cgccgtcgga catttgtccc tgtcgtacca gaacgccagc acctgtcgtg   67260
gcggtcagat tcatcttctc tttcttgatc gtctccagaa tgttagatgc ctgtaatgca   67320
ttcacatatc cgacaaaacc ttcgtcagaa aaacgcggag acagggagga gatctgtgaa   67380
cgatagtgca caaaatccag gttgaatgcg gtcgccagtg cctggctgcc aaaggccatt   67440
gcatcattct gactccatgc tggctgactt gttggtgcca gcctgaccag acgaccattg   67500
tctgtagcga aatattcgcg ctccacattc gttgagtgcc agtactgaat ggcgttacca   67560
gtaatactga taagaagaca tgtgcccgta cataaaagcg cttttatcag cgcagggaca   67620
ttatttgccc gctgttctga ctgcttcata gccctgattg tgctcttcag tatttccggg   67680
tcaggtgccg gatgtgatgg cgaggatggc tcggtatttt cggtcatagg ttgtagtcct   67740
tccagggatc aatattcccc ggcagctttt cattcacctt gtccacgacc gcgtcgcaga   67800
cctggttttc cagctgcgac agaatgtcgt caaggctggg gaactggggg aggtttatgc   67860
tgatttttt gattcgtgac agacaggact gcagggatga ggaaacatcg ttttcacgtt   67920
```

```
gtgaccatgc atccgcagct gcacgtgctc gctcatatcc tgtattacta ccggcctgtg   67980
ccgcgctacc cgcacgacag gttgcagcac ttgccgtgga tgaaatcagg ataaggccga   68040
gcacggcaac cagagactta tgcatgttca tatggcttcc ttaccggctc atcggccggg   68100
gctgtgggag agatcctgat gcagagtttt ttcctgcctg tcctccggct tttggctgtt   68160
ggaccactgc tgccatgact gctcgaagcc caggttccgg tacaacgcat caggttgttt   68220
ttccggcgtg tagacagcag caaaaagcgg ttcttcccgg gttttcagat gaaactgcat   68280
aagctccggt gcagggcgat tcgtgctgtc agcatcgtgg tttaccgctt caccataacc   68340
tgcaaagcgt aaacctttgt cggtcagcgc attgataacc agctgactgt tgtcggctga   68400
tggggtggcc agtgccggat acaatgtgcc gttcagccgg accacaccct gcagatgttc   68460
atcggcactc tggacaagta gcaggttgag ttcacgcgta tccttatcca ctgatcccag   68520
aacaggtgtc agcttgtcag gggctgcgct ggttatttct gttacctgat ttgcgttctg   68580
tggcgcggag accggatgtc ggtcttcacc gataaacaga tgtgagccga cgttttctgg   68640
catacgtaac gctttcatct cttcgggcca ccctggctg atttgcgcag ccactttcat   68700
aaaggtttcg accggaatcg cctgaatacg ctgaccttta tccggattat catgtgatac   68760
cgagatcccg ttggtaactg actccatgga ccacttattc cggaaacgtg cttttgctc    68820 tcctgggagg atgaattgtt cgcggttctg aagtgtcagt gtcaccacgt caccttctg   68880 atggttttg accagacttt ccagttgttc cccccagtag agtttgctgc cactgcggtt    68940
tttaagctca acaaagaaac tctctccttt gccgggtgca tattcagcac gaccaaaatt   69000
gtgcagtacg gcagtcacgc tctctcccgg gcgaagtttt cctggtggtt cttcaccttg   69060
tgccgcatct gccgttttgc caggttcagc cggtgatgat gcaggacgg tgctgacggt    69120 tgatgcttca ggggctactg gggacgccgg ggattgtgtg gcttcttttt cctgaacagg   69180
gtctgggact gctggttgtt caggggtatt ccggttaagt tccggtgttg gcttatgggt   69240
gacaacagta tctttaccga cagccatttc cttgcgtaat ttttcgagcg ccgctcgctg   69300
atccgggaat ttcatgcgca ctttgatgtt gtgctcgatg atcaactgca tcgcttttg    69360 cttaaaggca tcactgcccg tcagctcaat gacaccacca taaaaatcag tggccacagc   69420
aagtgcagcc agaacactgc gatcgtcatt gctggcaccg ttgaccattt ccagccggtt   69480
tacccggtca atgaaggcag gtttgccatc cagtttgtac aggacggttc tgtctgctcg   69540
ttcttcacct tccagcgatt taatgatttc gtccagattg agcgatatcg gtgcatcagg   69600
gcgttccggg gcgtagacaa tactgtcagg tgccggtgtg gtcgtcgtgg tttccggtga   69660
gggtgtggga tcactgttct catgcgcctg tgaatccgtt tttttacgcg taaaaaagcc   69720
acgcgctttg tcgagaaacg atgaagtatt atcagaagat gatgtgctct gaacaggttg   69780
ctgtggagtg ggggcatccc ggacagccgg ttctactgta tctgttgtgg cctgaagttc    69840
tgactcatca gcctgaacgt ggcctgtgtc cggttgcgac ggcatatcac tgttttcctg   69900
cagatgctca ggattttcat tgttcatcag ctcctgatat gcgctgtagt tttcgtattc   69960
ttcggggcca tctgactcag gaaggaacgg ctctggctga aggggaatgt cttcagttac   70020
atggttgacc gcctcttccc ggggagtatc cggggatatt ccggtgcttt gtttgtcatc   70080
aggctccgtc atcacggtca tttcctcttt gactgcatca ggggaaggtg atggctcggc   70140
tgattcattc atggtttcag atgagggact gtcttcaggg gatgcggtgg tggcagcagg   70200
ggccggtatt tcaggtgaag tgccggattc ctgttgtgac tcgttttttt ccggttgtga   70260
```

```
cagttcggct tcaaattcac gccagtcttt atctgtggcc accgagacaa cttttttccgg   70320
aggttccgcc ggatgagcgg gttcatcagg ggcagacgcc gttgtactt  ccggggacgc    70380
cggtgattct gcagggagt  cctgaactac agagctttcc gtttgcgcct gaacgttatc    70440
agcgtgccgc tcatctttgc cgttattttc agtggcgtga ctggtaaatg actgtgtttc    70500
atcagcaatg ttactgctgg aagcagctgg ttgttcctgc tgcgtggcgg acggcagaga    70560
aggtccctgg tcatggctgt gccctgtatc gggtgatgtt tcaggatatt ctgtcggagt    70620
catggttttt tcctcagtgt ggaccggtgt aaaaacgagg ttgcctatca ccagtgcctc    70680
gcgcatttcc ggggtgttac tgttgggggt ggaaacccg  atgtgttcta actgggcgtt    70740
gatgacatgc tgaaaagcgg cccgtccccg gcttgcgtcc aggtcattga atcggtcag     70800
cccctgcgct ttttcggcat cggtgaacgc aggaaagatg accgatcctc ctgtcagttc    70860
tgcggctttt gttgcactga cgataccttt gttaacccgg attgcatgat cgttgtcggc    70920
acagaagata aaggggcttt gcgtccactt tgccgggca  ttttcggcaa cggcaatcat    70980
gttgcctcca tccaccgtca tcagtaccgg aaggcccgtg gcttcgtgca gggaggccgc    71040
agtggcatag ccctcggcaa acagtaccgg ctgaccgttg cgcggtgtgc ccagcgcaaa    71100
ccagttaccg gttttctccg aatctatcag gatgcgggca tctttccccc cggtgaccgg    71160
aatacgctgg taagagcgta tcgcgccgtt acggttactg aagggaataa ccagttcatt    71220
tttgttgttt acccgcaccc ccggtgcagc ctgaatgcct ttccgggtca ggtattcatg    71280
tgctgtggcc tgcggccatt tgttgatata gcggcgggca tacgcggcct gtcggttgta    71340
ctgtgctttc agttcccgct ccgcgtcctc cctgcgttgc attgaatgcg ctttcaggtg    71400
gagtcttgcg cggggatctg tctgttctcc gccggagaag gtccaggtga tcggcgaatt    71460
atccgcgctg cgataatccc tgtaccagcc ggcaggtctg ccgtccagga agccgcgata    71520
tgcgccactt ttttgtcctt ttttgtcatc ggcggtcggg acacggtgga ttttcccgtc    71580
catgaccgga agttctttca gaaccagtcc ggcattctcc agaacctggg caaactcggt    71640
gaccggatca ctgccgttca tggagacgtc ctgtggccgg ggcagccagc ggtccagcct    71700
ggacaggtcc gccccggc  gggcgaacca gagtttgtgc tccttgtccc agatgacggg    71760
cgtgtgcccg ttcatcgggg gatgtgcttt tttgagatct tctatttcat ctgcaggcac    71820
ggcaagccag gtgcggtagc gggatacaga cggcatgagt gcttctcctg aaaaaagacg    71880
gaaaaaaacc accgccggaa gccgagggtg gctgggggga tagaaaatcg ggggagaaat    71940
gtttgtcagg gtctccagtc tgtaccctta ttccagcgat cctgccagtg ttcaagatat    72000
tgtgcggcta catccggcat attcttgagc acaacgacat tctctgaatt cttgcgtgca    72060
gcagcacgag agaagttata ggagccagtt tcaaccgtgt ttccgtcaac aatgatgact    72120
ttgtcgtgat ggatggggaa ggcatctaca gtccggagag gaatgtccag caggttgata    72180
ttgtcaacga cggatgaaaa gtgatccact tatatctcca ccaacggccc aatattgatc    72240
caccgttta  ctcaggatta gcttctgcta taaccccggc ctttcgtttc tgtctgagtc    72300
gatagctttc tcctttgatt tgaacgacat gtgagtggtg taagatacgg tccagcatcg    72360
ctgaggtcag tgctgcatca ccggcgaacg tttgatccca ctgcccgaac ggcagattgg    72420
atgtcaggat cattgcgctc ttttcgtaac gtttagcgat gacctggaag aacagctttg    72480
cttcttcctg actgaacggc agatagccta tttcatcaat gatgagcagg cgggggggcca   72540
ttactccacg ctgaagcgtc gttttataac ggccctgacg ttgtgccgta gataactgaa    72600
gtaacagatc tgctgctgtt gtgaagcgaa ctttgatacc tgcacggact gcttcatagc    72660
```

```
ccatcgctat tgccagatgg gttttcccca cacctgatgg ccccagtaat acgatatttt   72720
cattacgttc tatgaagctg agtgagcgta acgactggag ttgcttctgc ggtgctccgg   72780
tggcgaatgt gaagtcatac tcttcgaacg ttttcaccgc cgggaaggct gccattcggg   72840
tatacatcgc ctgtttacgt tgatgacgtg ccagttttc  ttcatgaagc agatgctcca   72900
ggaagtccat ataactccat tcctggtcta ctgcctgttg tgacagcgca ggcgctgcgc   72960
ttataaggct ttccagttgc aactgcccgg cgagcaccat cagtcgttga tgttgcagtt   73020
ccatcatcac gccactcctc tgcagaatga gtcgtagatg gagagtggat gatgcagggg   73080
gtgtttgtcg aagttcacca gattttcatc aagatgcacg tcatactctt ttttctccgg   73140
aggcagtgcc agcatggact gctgctcttc gagccagcga tcgcagggac gtgcctggat   73200
tgtttcatgc tttcgttggt tagcgacatc gtgcagccag cgcagaccgt ggcggttggc   73260
tgtttcaaca tcgacagtga tccccatcgg gcgcaggcga gtcattagtg ggatgtaaaa   73320
actgttacgg gtgtactgca ccatccgttc caccttacct ttagtctgtg ccctgaaggg   73380
gcgacacagt cggggagaga agcccatctc cttgccgaac tgccacagcg aaggatggaa   73440
ccggtgctga ccggtctgat atgcgtcacg ttgcagaacc acagttttca tattgtcata   73500
caacacttcg cgcggcacac caccaaagaa gcggaacgca ttacgatggc aggtctccag   73560
cgtgtcataa cgcatattgt cagtgaattc gatgtacagc attcggctgt atccgagaac   73620
agcaacgaac acgtgaagcg gtgagcgacc attacgcata gtgccccagt caacctgcat   73680
ctgtcgtccg ggttcagttt cgaaccgaac ggcaggctcc tgctcctgag gaaccgagag   73740
agaacgaatg aatgccctga gaatggtcat tccgccacga tatccctggt ctctgatctc   73800
gcgagcgatt accgttgccg ggattttgta aggatgagca tcggcgatgc gttgacgaat   73860
ataatcccgg tattcatcca ggagtgaagc aacagcaggt cgcggcgtat attttggcgg   73920
ctcagatttt gcctgcaaat aacgtttaac ggtattgcgg gagatcccca gttctctggc   73980
aatcgcccgg ctactcattc cctgcttgtg caggatttta atttccataa ctgtctcaaa   74040
agtgaccata agctctcctg aatcaggaga gcagattacc ccctggatct gatttcaggc   74100
gttgggtgtg gatcactatt gcaccgttcg tgacagatat atttcatcgc ttcctgactt   74160
gcccggttcg tattccccctt gtcatcaaca acaatacgga cgtccactcc gcgttttttc   74220
gcttttgcca gcgcatgcat tacatccggg tcggtgaagg aatatgccat catcctgatg   74280
gagctttccg cactgttgat tgtgtcaagc accagagcgg atgcgcttcc ttcaggagaa   74340
aagccgacct tcacgatgg cgtgtcgatc attgcaaacg atggtgtcgt gaacagtaac    74400
gggcatgcca gtagcgatac ccggagcaga gtaacgatag ttttttttacc tgacataaag   74460 actccagaat ttaatcgagg ccagtccagt ctcgtggtga ttccgtatgg tggcgatacc   74520
accatggacg accggaggcg atggcccctc tcagaatgct gaaaatgcga gtacagatcg   74580
tcctgacagt ccagcctgaa cggtcgagaa taacgaaaaa taaatgatg  ccggtgcaaa   74640 tccagaaggt tgttttggag ggaaagggc  atataaacag ataaatcatg gtgaacggca   74700
gaggtacgcc ctggatgttg actggcggtg ttgcatatcg ccagaaacct tctcttttca   74760
tgaccgtaac tcccctggcg ggataaaaag aatcgcttct cttcggtcaa cttcattccg   74820
gatatacatt tccagaatct ggtcccggat acggcgcttc tcctgccgga ttatggcatc   74880
aatgtgatgc ccccactctg catgtggcat tccggaaaga ttgtcgcgaa gctcatcgtt   74940
aatgacgata tattcccgga cggctttacg accaccgtca tttgttctga ccagaacctg   75000
```

```
aaccagaatg aactgcaaca gtgacaggac agcccaggcc atcgaatccc tgatgacagg    75060
gggaaacagc ccaagaagac gtgccagcgt ttcaccagga gatttcgtat gcatggtgct    75120
caggcagtaa tgcccggtgt tgcctgcctg taccgctgcg tcggcggttt cgttatccct    75180
gatctcacca acaccgataa tttcgggatt acgtcgtaca gcagaacgca gtccggcagc    75240
aaaactgacc acatcacgcc cgatttctgc ctgatgcggt gggagcagat cgttttcatt    75300
tcccaggata tattccaccg ggtcttcata tgtcacgatt ttggcgtcgg ggaaattgtc    75360
cataatgtaa cggtacagtg ctgaacacag cgttgatttt cctgacccgg tttcaccaca    75420
tacaaatccc agaccgcttt tgcagaccat tgcttcaagc agatctggtt caatgttcat    75480
ggagagaatg tccggtattt ctgtcgggat gacacgcatg gttattgaga ctgctttctc    75540
ctccgcacca gatgtgccct gaatgaggtg agagcgtaac cggatgcgtt ctccgcgttt    75600
aagaccatag cgaccggatg catccccgtt aatctgtatc gtcctgtcaa ccggattgcc    75660
tgccagaacg cggggaatga cttcccgacc gaacagttca tcaatcaggg aggacatgag    75720
tgtggttggt aacgttgcac tggaacaacg cacccgtcgg ccaaagcgac tgacagatac    75780
aggtgaccca ccggtcagat ccacatcact gactttatgt gcggcacacc agacaaagaa    75840
atgccgtagt tcatctgcag tgaaacgctg aaacggaaaa agaccaaaact catcaggaat    75900 attcatcggg agcctccttc agtgcctata agcggacgcc agtgagattt ctgaagattg    75960
aattccgcat gatttttaag gcgacgaaca cgatctccag tgaccagttt tttcccgtca    76020
cctgtaacgg tttgcatttg atcagaaaca tccggacggg tgatcatgcc ctgacgccag    76080
agaagtgagt acagcatcat gccccggtaa tcacgggtga gggttttctg gttggcttca    76140
agcgtcaggt cggcgttttg tcttccttcc tgccatccct gccgtaatgc ggtttcccac    76200
acttttcgtt gcacgctgtc ttctggaacg acgctgcctt ctgtacccgg agtggctgtc    76260
gttgaaagcc cccggagaag ccagtcacgc cagcccggtg gattgctgac aaagcgttca    76320
gggcgaatga tggtccagac ccgggaagag gtccggattt gatctggcgt gatatgagct    76380
acgtcctgtg cttcatcaat aaccggtggt agccagcctt ccgggctaat cagtggccgg    76440
aaatcgtata aggcattaag tgtgcttttcc cgggcgttga gtgcctgaat cagctcccat    76500
gaacgctgag ccttgccacc acgaaatcca agcgttttac ctgcgtcggt cagcatttct    76560
cagcgtgttt ctgacagact atccggcttt tcacttcgtg gtttaagcca tgcattaatg    76620
tcaggtggtg gcgtattgac cccacctggc gagatggtag gggaagaaga caaccagta    76680 agcagtatta ctggcaaaat gagagaggtg agtgcttttca ttttttccgg ttctccggct    76740
gcatgaagct gacctgtaac aagcccggat attgatggat tgttgctctc caggctgtct    76800
gggcttcaat aagtctcaac gtattggaaa acgtcatatc ccggacgtga aggttgactg    76860
gtaacggcag gcggacacca ttgtagttaa actgcatccc cctgactctg gccagttcgt    76920
tcagtaattc aattgcatca ccttcccagt caaaggaaag gcgatcgctg ttagctgtca    76980
gaagatgaga ccccgttgaa accggaagtt ggccggaaaa cacacctttg tcccataatg    77040
tgtactgagt gtgccgggta accgccacat cagaggcagc accgtagtta cgcggaacag    77100
gagtatgctg agaagggaag ttgcagccag ccagaaaaag ggcggcaaga caccccgcag    77160
gtataatacg gttcataata attcctgagt agttaaatca gaatgggata taccggtgct    77220
ccggtacaga caggatgatg tttgtttccg gctatacttg cgttaccgga aataaatgcc    77280
agtgtggcca ggtaaatagc ctcatagttt actgaaggtg attattcctg atactggctg    77340
gttgatgtgt cgtcagacat aaaacgaata tgagcgtaat cttaacgct ccgcgccgaa    77400
```

```
tcgatccatg atggatgact cgacgattta tgaatcgaac gtaccggcgc ttgtccctga   77460
aacagttccc ggccctcgtc cggataacct gcaattcaga caggcacatg tgcccgtaca   77520
ctcttgtatc ttactgagta tatcagaatt tatgtaaatt caaatatcct ctatgactct   77580
ttgttgtatt ttccgtcaag tatgagccgg gtaccatcgt aatgcatgat cagggcatca   77640
aggtacgccg gtttgaattt cttgccgagc ctatctctgg ccagaaatga taaacaatga   77700
ttatgtgtca ttattactat gttccttttca tgagattctc ttgcgattga ttcaagcgtc   77760
ttataaagat cattattgca gtctgataaa ctgtccataa cgacgggttc tttaccggag   77820
aagaattttg cagtttgtat ggttcttacc gcattgctgg agtaaatatc atattcactg   77880
aagattgttg cgaacttaat accttcctgc tgtgctttct ctgtaccggt aatagtgatt   77940
ccgcttttat ccgaatagca tggcatatct gaacggtcgc aacgttctcc atggcggaaa   78000
aggaaaataa cggtgttatc agcattaatt tcttttgcct gttccagggt gatatcggga   78060
agcgagcttt ttgcttttgt cactgccgct accaggaaaa cagaaaataa aagaatgaat   78120 gctgttttg aataagaaga acgtggtttc atcatgttat ttaaactgaa tataaaaata   78180
cccccgggtt tagtgccggg ggcggggact gtaatcagaa agtgaactga agttgtgcca   78240
ttgcaccgta atcgtggtca gttcctacca ggccggaaac atcgatatgt acgacgtcaa   78300
atggagagat accaacgcca gcggtgaagg cgcttccgga gtttgatgcc atgttctgac   78360
gataaccggc acgcaattgc gcccatttcc atgcgttaaa ttcagcacca acacttgcaa   78420
actgacgttt gctgtcagaa gtgaagccac tggcaggagt cagatcaacg tcaagagcag   78480
tggtaaacag gtcattatgc caggatacac cggcggttgc ctgtggacga actttgaagg   78540 tttcttaaa gccattgacg actttagtat caatactgcg tggaatgatg ttctgggcaa   78600
caagaccgac agtccagttg tcattcaggt ctgtataagc accaatatcg gcgttgaatc   78660
cgttttccgt gttgtggtac ttgtcaccgt caaaatcgtc tttgtcgtaa tcacgaaccg   78720
ttacgttgta gttaaacagg tccacacgct gatattttgg tgtgacgcca agagaccatt   78780
tttgtccggc cgtttccagt tctttggcaa atgaaattcc gacgtcggta attacagctg   78840
cacgcccgaa tgcgcgtgag gtcagggcat tcttatcgac gtcggtaatt gttccattgg   78900
caactttgtc cagataatcc aggtctgcat cgtttacttt tccgtttacg ctgacagttc   78960
cgtaagactt gaccataagg gcaaacggca gagtgtcatt tgccatggct gctacagctg   79020
atacacctac ctgagcatct gcattgatat tgcggaattc ctgcagacga tgtttaagat   79080
ttgccgctgc ctgttgtacg ccatgctggt tatctacagc actgtcaaac aaatcccagt   79140
catctttaac atcatcagct ttatttgata catcatcagg atcagcaact tgtgccccaa   79200
cagacggcag aagaaggctg aaatcatcat tgctgttgtg ctttgtcagt aaagctgggt   79260
ttgccagagg tgccacacca taatgggaag atgctacccc ggtgccaccc attgcatcgt   79320
tacgcgcttc aaaatatgac gtcgctgctg cagcgttaaa ggaaaataat acagcagatg   79380
caatgatggt gcgggtaata tgattttttct tcatcattta atttcctgtt tatcagaatt   79440
tagacaaaac aacgctatga cacggatgtg ccgtaatttt tactttggta ctatctggta   79500
tttaccaggg taataaagac gtattaaata agctaacagg tagtatttgc cctgtaataa   79560
ggttcccggc aaggccaggt ctcaacgtga cgcgtcgcaa agacattgtt gtattctgcc   79620
tggttgtata ttcagttaac cattttcttt tttcatcgtt cagaagtgtt ggtgataatg   79680
atagtgccgg atatattaca gagccattta tttctttttt ctgtctcaat attaccccgt   79740
```

```
aatattctct tttcgtgttt cctgcgaagg ggaaactatg ccagaaaata acttcagtgt    79800
tgctgctatc attaataagc attctgaaat tatcagcagt atctggccat tcaccggaca    79860
acgctatcgg atagttttca tggccattca gccagtccgg attgagatta aaacattcag    79920
caagatgttc gagagcgtca gctgaaagat agtctgcaag tctggccggg tcctgtataa    79980
ccgtggagcg atattccat ggcgacagca atgttgccag taatggcgca tttatatcat    80040
gcgacagcat gatgtattca attctgctta ttatgtttcc tgtggtgtta ccgcaggca    80100 taaacatatt atgaagagca tcctcaagca ggattcgggt aaatcagcg gtggatatgg    80160 ctaattgttc gctcattatc cccagaactt ctcttacccc ttgtgggtaa cggacctgca    80220
gtggtgtcgg gtttatctga cgaccgttga tgagttttc gccgattgct ttttgtcca    80280 gcgagagcat cattcgggcc gcaataccgg tcgtattcag tctcattgtt cctccgactg    80340
aaaaagtctt ttcagctcat gtggttattg tatcttcggt gttttttctg gtgaaacgaa    80400
taatttcgat catgcagatc gaatgtgttt ggcgagttgt tgcaactcgc ctttctgtat    80460
gtgttttgaa tgatgtttac agcggggtgc tgcccgggtt cagagggcaa atcataatgt    80520
agtcagggtc gttaacaggt aacgctccgg gagatgggac acgttcgcct ttctgtgctg    80580
caatggccag tgtacgcaac aaaacctcac tggcgcggtg aactgcttcc tctttcgttg    80640
tggcagtgac gtgaaggtta tcaaaatcac cgatctcaat acgatgcgct ttctgcccat    80700
tttcttcatc gatggtcgtg atatgggcag gatacgcac aaaccatgct gccactttt    80760 gtgtctgccg ccggcgggca tcaagtttac tgaccagttg ccatgcacga agatgagtat    80820
accgtttcag catattcatg gaacgatgtc ctgatattgc agcaatctcc attacattca    80880
ggctacccag ttcgaagaag cggcttattg cttcatgccg tagatcgtga aaatgcaggt    80940
cctcgatgcg aagtcgttgt gtggctattc tccaggcatt tttaaagccg gatgcggtgt    81000
aatcaaaaac attgccgtgg agattaacgg gcatcatctg aagaaagtta cgggcacgtc    81060
tggacagagg aacatcccgt gagtgaccgt ttttggtttc aggtaaatga ccacaccgt    81120 ggcgcaaatc aatgtgctcc caacgtaagg ccagtatttc gccctgccgc atggctgtct    81180
caagggcaag atggaaaatg acatacaaca tcagattttt ttcgcggaaa tagcgagaaa    81240
ggcgacgttc ttctgaagac gttagccggc gatctcgtcc ggaggatact ttcggcttgc    81300
gaaccagttc aaccgggtta gtacgacagg ttccccattc aacacgagca atattgaaca    81360
gagatgacag aagggcgagt tcaagacgta cagtattacc tgtaatgggt ttacccgttc    81420
gggggttgat ttctgctaaa cgaacgtctc tgtatgtagc aatatcaacg gttgttattt    81480
cgtccatatt ccgaagggca atgggatatc gcttgataac attgctccgg taaaactcct    81540
gttgatgccc tttcttgtgt acagaaactg ttttcaggta cttatccagt gcgcgtgaca    81600
gggacatttt acggatgcgt ggagacggca tgctaacctc aaaagaggca aaaaataatg    81660
ccaacaatca ttctctgcaa gcgtgccaat ccggtacctg gcgtaaaagc aattctggta    81720
gtacggtgat aactggtcgt atagcaaatg gtcagcaaat accgctgcca acaggatttt    81780
ctgccagtca gtgctcatgg agtgtgagca atgcagaaaa ccctcaaggt tggaagccga    81840
attactttgc gggatcagtt gcaacttatg atgcaaatcg aattgttaaa tgtggttttt    81900
atgatgaata caatttccat aaagggacat ttagagctga tttaaccgga aaatgtagtt    81960
atgtcgtcgc gtgtcagaac tgagattaaa ttgctggcgc tgctggccta cgtgccaatc    82020
cggtacctgg ggcgctccta aaattcaatt cacaacgcag acctacaaca tagctaaaaa    82080
cactcgtaat ttaaggctcg gggtccatgc atattgctca tggacttacc tgaatggctc    82140
```

```
acccttttggt ggttttcaac aggtatattc cgaccaaaac aacgtttggt atgagagtaa   82200
ttatgcttgg ggaaattatg agtctggtgg gaccatatca gtcacatgcc tcaatcttcc   82260
tggtgctgga gtttaattaa aggggcaaca gtaggcatcg acatgttcct catcaacacc   82320
atcaccaata ccgtacatgc gtgttccagt cataatgtat ccagtcggac attgaatcgg   82380
cttgtaatag atcgaaccac cactcttacc gccgataaag tgattcattg ctacggatga   82440
tttgtaccaa ttacatgctg agtaattaat tttattaccc cctgaccacc gaccggattg   82500
gcacgtaggc cagtgccaat cccggtacgt gggggacaat aggtggaaaa ctcaaagtta   82560
ctcagctttc caccacaggt tatctggggc aattcgactt ctgtgccatt gccagaatgg   82620
gcaacgcaga ggatgcccac tactgccagg tagttgagag cccagcaggt tcacgtaaat   82680
ggtacaaata cgagcataag acaggttgta ttgcgtcgtg tgtaacgctc aattaagttt   82740
gatatccaaa tactgaaaat accccggcac cacatgatgt atttctgtt ggataggatg   82800 ttatctgata ggaagtacct gcaggtacag caaagctgat aaaggctgtt tttccatatg   82860
cagggttatt gctggcattc acgctaatta gcgtcccacc aacatatccc tgcagtcggg   82920
atgtatttgc acatgcacct ccggcagatc ctccattacc tccagatgca taaataaaca   82980
atgtactgcc ccctgaattc cgccctgaga atgaacctct atgtgaacct aagtttgtgt   83040
aagaaccatt gagcgaacca gaagtcttcc aggtaccgga ttggcacgaa agtattgccc   83100
ctgtattatc gcggcctaca aggccgttag gcgaacatga tgcgccagca acggcagttc   83160
tttccagttg taagtattca ccagtataaa ggcgaccatc agcccgaaca gaaccgcctt   83220
tcacctgacc gccggtatag atgcccttgt tgtttacact tcgaacccat gatccatcgg   83280
acatataaaa tccgccaccg tgagtttcat tgagccagcc tttgctgtta cgagtaatta   83340
accaaccatt attacttctg atatcaccgc cagcggtgac atttacgtca aagtttccgc   83400
tattgccttt tacctgaccg ctgaaagtgc catttacacc attcacattg ccgctgaaat   83460
taccagtctg ggcatttact gccccaacgt tattcaggtt atttgatccc atatcaatgg   83520
ctgtgtgcat tttgtttaag tcagggcgac cattgacctg gaatctgtaa agacgatcag   83580
tgtcctcagc tgcaccacta agttcatctg tcgataacaa tacggcaata tgcccgttac   83640
cgcttttggc accataatta cttaaagcta ctgaccagga acgtaatgca cctgtggctg   83700
ttttgccgtc ctggatatat ccaccaagac cagtggtaat atccttagcc atctggataa   83760
gtgctttcac tggataaggc gtgccaccac tggatacaac cattgcctgt agtaattccg   83820
ggttttgggc gtttcgaacc acatatgcct gtaaccgctg cccctcgctg tttgtctcag   83880
taaacccgct ggacaaaaag ccggtatttt tcagcatggt tgtcgtgatg acggcaggag   83940
ttgttgtggt actactgccc tggagagtcg tatagttttt ccctatgtaa gagcgggccg   84000
cactggtcca gttgctgaca agacgtgctt cagtttgcca ccctttgtt tgaatatagt   84060 cctgccatat gcccgctccc caggcaatca ggagcataac aatcaataaa gccgcgccag   84120
tttccagcga tgcccagcct cggtcatatt ttttcatcag attacccata gtggttgata   84180
aagattatcc agcagcaaaa ggacatggcc aaaacatagc catggaccca gagggccttc   84240
tttatgccct tttatgcacc atgttgaatg ccataagaca aatcctcctg tgcccagcaa   84300
cacacaccat atggcgttat ataaccctga ccatgcggta atacccgcaa taagccacag   84360
gtctccagtg ccaatattaa gacgatggcg gttaactaat ttatgaagac agaataagac   84420
aattgcagca gtggcaaatt ctgttgtacg gaaccaccat atatcagtcg tgatttgcga   84480
```

```
tagcattcct gcaattaaaa aacgctgtgt gaatgttcct ggtaataaac ctgtcagtgc    84540
atccgttacc gccatttgca gtatgaacga agaataagg acagcatgaa tacggtagag    84600
cagtggtgat gatgataaaa taattaacgc cacagctata ctgtatagcc atattcctga    84660
cagaacagca gggtgtgtct tataccagag atgtcccgta tcagataaaa aatgacgaac    84720
tctgaatagc agagttcgtc caataatgga aaatgtgaac atcaatggca gtatataaac    84780
aggggataga cttatgccta cgattgtctg cattgcctgc ctccctgtcc gggaagacat    84840 atcccttca tgtcacgata aattctccat attttattgg catattgctc tcttgtttca    84900
tgtctgtcct tacggaatcc ggcattgtat gacccaaggc aattccagct gacgccacat    84960
atctgaaaat gtcttgccag tatccagctt cctatatgga tattaaggca tggtttggta    85020
attaaatcct cagactttt tattacgccc atatttacca gctttggaat atgggttgag    85080
tttatttgca tcaacccata atccgtgcta ctggctttac ctgtttttt gtccttattt    85140 atattaattg cgcccggcct caacgaagat tccccggcag aaatagcctt caataataat    85200
ggttcaattt gatagcgcgc gccggcagcg gcaaagcaat tgtcccactt gttggtccag    85260
atctgtttgg gagctacgta tgaagctcgg gcgggtggaa taagagaaaa agcaggatt    85320 aatgaaataa gtctgagggg tactgtaccc cctgacatta aaactcctta accattgatg    85380
gtgaagataa gtttgtttgt accagtgctg ccattatctg ccttgcattg cgtactggct    85440
tcttcagtag tgactttcc atcactgtga gcagtactgt tcagggtaat gccgttagtt    85500
aaaccagttt tactgattcg tgtggcaatc tggatacagg catcctgtgg gactttatca    85560
taggtaacgg taaaaccgtt gttgaaccct gatgttgaag ccggggcaac agttacagca    85620
ccgccccatg cgttatagag cgttgctgta ccagatgttt tgtcgccctg tacggtcatc    85680
ccagagggaa tgacacccat ctgaatgagg gcacctgtca ttttggcact gctggtaaat    85740
gtatatccat cgctaccttt tagcaggctc tgggcacttg tgataattgt ttgtatattt    85800
gcggtttcag ttgccacatt ggctcttgta cgcaacgcat acaaactacc cagaacaacg    85860
actataacaa aagaacaac gagcgctatt gttccctgct ccaaaattgc ccatccttta    85920
tcatgaggct cattcttctt attatttcca gttaaagtgg tattaatatt ttctactaac    85980
ataaatatcc tcgttttgtt taaaagttac ccatgctgtt gtcactaata gactgaatat    86040
ccataatggc aaaaaccagt aacatgagag acatgacaag aaatatcagc ataattaaac    86100
gaatcacgtt tgcccgtttc tttacacgtt gaagtgtttg actaagccat cgttgaccat    86160
aattgctgat tagctctgtt gcgccatctc cctgtaataa agacaggaag ttggctgctt    86220
ccctggatgg gaactgataa ccgcactgac gcaaagccag tccaagatga tccccctggc    86280
ggacgcggta ataatgctg tcaagacgtg tgcttaacca tggtgatgca aactcctgaa    86340
gaatgtttag cgagttgagc gtcgtcattt tggctttcag aagtgcagcc atattcagga    86400
gaaatgttgc tccctgtata tcctgataaa tactccatgg cattatcttg tcggcaaaag    86460
tacgaacact gtcagggctt ttccagtttg gcagagacca tgatattaaa cctgtgatca    86520
ctgcaaaaag aacggcacat atagcgccgt aattatcgac aaaaacagat aatccataaa    86580 gaaaccaag agcaccactc catgaatcgg gggagcttat tttgctcagt tcaggtatta    86640
gctctgtatt cagaacatat aatgtccccg tcatcatgat aacaatccc accggataaa    86700 tagccatttg ccatatagcc tgatggattt gttcttttgc atctgtaaga gtggtggcga    86760
attgcagtgc atccacaatt gaaccacttc ttatcccggc gctgattact gcggcctctt    86820
cctgaggaac ccataaacta agagtatatt ccagagagtt ttcgccactg ttttcacgaa    86880
```

```
gagactcaat gcagtctgtg gccagttcag caaagggatg ccatttcgt ccaaagtctg   86940 tccaggcatc ccgcatctgt tccagtgcgg tctttaatgg ctgtttattt tccagcagaa   87000
aacgcagggc ttcgtaaaac tgcaccctgt aggggcgct gaacgtttt ctgacaatga    87060 aacgcctcag ccgttgactg aaattcattt cacgcatgtt gttctcctgt tagacatcat   87120
cgatgctgag gcgctcgtct tcgtccagag ggatgattct gtcggcttca agagggtcta   87180
ccagaccttc attgatacgg cgaagaagat gctctacacg actgatgcct ttcatgtttt   87240
ccagccagta tttacgtgct gcaactttgc cgcgtgtttt cagaatctga ataagcggt    87300 tatcaggttc tatcacctca gcaattacag tcctgccggt gaggccttta cctatttcac   87360
cgcgctttct gccgttaatg attacgtcgt gattacattc agagcatccg tgatgatttc   87420
ggaaccagat attatctgta ctgcagagtg aatctttatt gcagtgccgc tcaaggtaat   87480
cacgctcgtc gtcgctaagt tcaggtgctc gcttttccca tggaatacgg caggagggac   87540
acagagttgg tacaaggcgc tggctgatca tcccaatcag taattgcgca tcgcaaataa   87600
gatcggcatt catacccatc gtaatcattc gctccggtat acccagagct gagtttgtat   87660
gtaatgtcgt cagaactatg tgcccggtct gtgccgcgta ggtggttgac atcatcgaga   87720
taagatcgcg catttcccct tccatgatgg catcagggtc aagtcgcatt gccgatgaaa   87780
tagcccgact ccatgccagt ttgacggcat cttcgtcgga tttgtcgcag ataatcggag   87840
tctgtgttgc tcccagtatc tgtccttcca gcggatcttc gattgttagc aggtgtcgcc   87900
cctgattatc gtcaagatat acacggcagg cgctgcgtaa cgttgtcgat ttaccggaac   87960
cggttggacc tgacaggact atttttcctt ccgggcggcg cagcattatg ttcagcaacc   88020
ggatttgttc cgggataaag cccagttgtt taaacgtggg aactttatct ccgtcatcgg   88080
gtatcaggcg cataactgca atcagaccgt ctcccgtagg tctgtgactg tagcgtgcac   88140
caaatattcc tattttcgc attaattgtg gggacaggcg cgcatcctgc tcccttgag    88200 ggaagaaact ggtttcagtg acatcagcca ttgacagaat ggctgttgcg caaagtgaat   88260
agcccagtgc tggttgatct tcatctacag tctgcagttc accgaatatt ctcatgcgaa   88320 cttgaaat agactctgaa attaagaaat gaatatctga agcaccaagt tttctggcag    88380
tttcaaaata agatagaact ttcttctcac ttcactgac atcagcaagg tctttcagat    88440
gaataattcg ttcttcggg cctctgtttt tctcatcctg acctgcctcc tgtaactccg    88500
acaacgagac tacttttggg ttgatatccg gatataattt tagcagctcc tggagattac   88560
tttgtacgtc aggccttgtc cgctggtttg tttctataag aatttcatgg gtgtctcccc   88620
tggatataaa aaggagagca tccttcagat tatatttatc catatcacgt tactcagaaa   88680
gtaagggtgg tgccatcact taacgtgacg ccagacaatg agatcgactt cactgtgacg   88740
gatgtgcctg gaagctggct gccagtggtg acgcttgtct gacgtccatc agccatgcga   88800
agaacggcat taagacgttt atctttgccg tttatttcca taatgatggg caattccttt   88860 ctgttttag atgtcggctg ctctgaaact gatggcaaag aggcagtcac accagagaaa   88920
cctgaaacag tttcagatga tgaagtaaca tctgattctt cgagttgttt ctgtagctgt   88980
gcgccctgaa cttttgcctg taaaagaata ttccggtttt gttgtgcttc aagttctcct   89040
attgtgacaa gaggttgtgt tgttgcaaat gaaaaaccgg agaagaaaaa tatggatgga   89100
ataatgagta atttacctgg acgcataaat atgaccttct gaggaataac tgaaagtacc   89160
gccgtttaat tcaaaatgga tattgctcag acgaacgccg gtatcctgaa ataaagggaa   89220
```

```
caactcatca ggatttacag gcgttgataa actgaactga tattctttcc atttctgaac    89280
aggggctggt tcaccatcgt tacctggtaa tggttccggt atggctattt cattaatggc    89340
cggcgttaac tgttttttct gaaaccacgt gaacacccgc atcagttgtt ctgaggggt     89400 agggactgcc tcatccctgc ggggcaggga aggcagtggc cgggttacag aagccaggcg    89460
tgcaccatct ttaaggttaa agtcaggaat aacattaaag atttctttgc ttcttgccag    89520
aaagccttca atagttcctc ctggctgtcg ttcgtaaatc agtgtgaatg tctcgggagt    89580
acatgttcca ccggtaagtt tccagccttc tagcgcgacc ggtgatggtt ttcgaaggtc    89640
cgcgcaggct ttcagaaaat cactgattac aggttgtgat gcccatggat gcggagttc     89700 tggcggtgga tcgggctttt taaactgcaa tcttgcccgt gcagctatct cctcgggcgt    89760
cggtacgaca tccggctctg ctgagtcat ccagaataca gtgcctgcgc cggctgctac     89820
taaaaacagt acggcaggca gtgtgaattt gctgcgattg ccgacagtaa gtttgcaacg    89880
gcggagatct gctgatgata accgggtaat aatactttcc cagttatcag gatgttccag    89940
aggagatacg acctgccatt tttcgggggg ctcttcgttc atcgtcagaa aaagactgac    90000
cttttgagca acatcagcat catttcctga cagatcagcc ataacggcag gctggccatt    90060
aatggaggca aggaataaaa gctccttatc gctgtaccgg aagacgccgt atccatttct    90120
cacccatgag cagaaagcca gagcaaggga aaaataatga ttgcgctccg gcctggccag    90180
tattcctgtg ccggtaatgc ggctgatctt cccacgggaa cttctgctgc ctacagtcac    90240
tttcagagag gtaagccgtc tggattttac atggggcttg tgtttctgat gagaagggac    90300
tcgctgtttt tttacgacag gactccattt aagacaggct gcccacacgc gatgatttac    90360
tttaggatct gcgagaagca caaccggtt gatatcttca tcagccattg ttgcctcctg     90420 acggaaagt cggggtaatg atgattacaa gcgtgctgcg ttcatttttc ccggtttgtg     90480
aaccaccaaa taatggattt gctggcgtaa acgtaccggc tttacttgtc gtcgtattgt    90540
tctgatcgaa accagtaacg acaagtgatt gcccttcttt cagattgacc ttctggctca    90600
gtgaacgcag tttggtatac ggcatttcga tgtaactgtt tccgtctttt gacgtaaagc    90660
tacggattgt tgggggatct gacagattaa aattcatctg caactggaga ttgcccgttt    90720
tctgaattaa aggcagcagg gtcatattga atccggtggt gatcatgccc ggcgttaatg    90780
ttgttgttgc tcctacatcc gtagtcgttg ttgttgctga ctgggcgacg taaaccgtct    90840
gatctgccat ctggataggt accggcgtca ggtttgtgac agtgctttct tgtgaagtca    90900
caacactgac atcgccctgt tcactcagcg ctttaatcag aagactggaa ccgctgaatt    90960
tggcggcatt ccctgttgcc gtatccagaa ttgatacgcc tgcagatgta gcgcctgtaa    91020
aatctccgct tgcattgttc aacgttgctc cggcggaatg tagcgattta taaacaaggt    91080
tccagtccag accgaactgt tcgtttctgg tattgctgac gctcagaacc tgtacgttca    91140
gggctacctg gcggttcata atactgtttt gttcgtccac atatcgtgcg acggcttcct    91200
ggacagctgg agtatcagtg acagtcagcg ttgagctcga tgcagataac cagtaacggc    91260 cttttctgg tgtcagcatt gcttcaatag ttttccggat gtcttcatac agatcgtatt     91320
cctgaccaac ggttgtgctc tgagaggacg ttgcatcacc ggatgctgag ttatcctggc    91380
ctcctgttgc ccccattgtg cttgttgagc cagagctgac actggaactg ctgctggttt    91440
tggtgttcag catatgaagt ggatacgttc tggtttcagt cagatagaat acaatccgac    91500
cattatccat gcgccagtac agaccactcc ggctggccat cagatccaaa agaccattga    91560
tatctccctg ccacatgagg ttattcagcg ttaatggctg agtggaggta gtcattgttg    91620
```

```
tgctgcccag gctgcttaac ggtagacgcc cattttcatc tggtgctggt agtgttcctg   91680
tcatctggcg ggtagcgcct ccttcaagag ttgaattggc tgcgtcaggc gtgatgatca   91740
cagggatgcc gcatacggca gtaatacgtt gccccagttc ctgcagagtg atctctcctt   91800
ttcttgcctg cgtgatgtag caggccgag ctgtttgttt tttctctctt gatacctgag    91860
cgaccggaac agggtttatc cattgattat cgagccaggt aagagcctgc gatttacggg   91920
ccgaaagggc tgatacccttt tcccgtgcat gtgctgagtc ttcctgtgct ttttctgca   91980 ttttgttgat ttcgctgaaa gtacatccgg agatggaaag agcgacggcg atcatgcagg   92040
ggagcaccgc cagcttcatt gaacgctggt gtgattttt catgaatata tccagattag    92100
ttaacgtaga cgacagaacc agcagtaatg cctgccgggg gtgtcagacc ggttgcagtt   92160
cctgatagcc aggtgagttg cccgttttgg aagatcccta ttagtgcaga accacgactt   92220
tttgaacgca aagtttcaac aagacctggt tgttcaggca tccatacccca cagacgcccc   92280 tgttgtaact gatgtttaat tcgggagtcc ggagtgacag ggagagccag tttatctgag   92340
gaaattactc cgtcctgctg gcctgatacg tatctgatat cattgattct gttagcaatc   92400
attagtatct gacttgccca tacagacgca cttgcatatt gctggcgtt tgtggtttca    92460 gacatcttct gattctggta gctaccagtg ataatcagaa tggtcaggcc gacggccatg   92520
accagccatc ccattagcga ccatctcttg tatcagaaac tgtaatgatg cactgcatgc   92580
gagaagcctg tgcgtataaa ggttttgcg cagtccgata taactcaaat acctgctcca    92640
tggttgattc aaatgatccc cggaacatta aggcgcatc cagacggtaa tcggttacag    92700
aaagtggcca tatgaccatc cagtgcgttg atgccatgct ttcgcatttt gtttcttctg   92760
cccacttgat aatgttctct cttaatgtgg tgcctgccgg cgcacgccac tctttaccct   92820
gagataccgg tttaacaggc gttccggtca tgagcgggat cgacttgact gtggagccgg   92880
ttggagtcgg ggtggcggcg ggcgttgacg aagatacgct gtttccctg aatggatttc    92940 gtggttttgtt ttggctatt gctgtcgttg gagattcagg gtaagtggat gtggttacca    93000
tggctgctgg cgagatagtg gttgccgtgt cctgtgccgg tgcagcagct gatgttgtga   93060
cggtcaacgt tttattattc cagtccagat ggccccagag gtgttgttct tccagcaacc   93120
ggttcagaga acgggtccac tgatcattgg cagaccatga aaccagtttg gtattcagct   93180
tgggcgtggc tgcattctct tgtctgaatt tccatccttc cggtagtaat gttttatcc    93240 actgactgac ggtccggtta cgggccgtcg gcgatagtgt tacaggggcg ctaccaggct   93300
tgcctgtaat gattaaccgg gagaaattct gacttattgt tggtgaaggt aacggtcggg   93360
attcgctaac aggctgtgct gttttttactg tctctggcac gctgactctc gggggggag    93420 ttattttagg tggagaaaga cgttgttgcg taagtgccag aacgccagca ctttcactga   93480
tttgtccgtc aacaaaaacc agagcaggcg tatctgatgg tgccacgtta ttgctgccgg   93540
aaattccggc acagccggac aataatgacg gcagtataag tgtcagacag tttttttca    93600 taacggagac tccgtgttcg tatatacgtg tttgttaatt ggtgtgaggc ggctggagag   93660
gacgaatgac gactgtcatt ccgtccgaat gcaaatgcgg gagagaccac tgaaataaga   93720
gatatacaaa aggaattgat aattttttcat acagacttgt tttccgtggg catgtaataa   93780
cagagaaatt caaaccataa gattccagtc tctttataag tttatttatt cttgcaggag   93840
taaagagatg tgaatgcata acaatggttt catcattatt aattgctttt gatatcagaa   93900
aaagtaacac atcccagtgt ttcctcattg actccgggca acgtgtatcg gcatagggc    93960
```

-continued

```
taagatgtat gcttgattct ttactgccat tttttttcgc aaagaatgtg aagttgtatt    94020
tagatacaga ccttacgata agaagcacgc atctgaaaag tagtggggaa aagcaaataa    94080
taaccactat acagaaatat aatatataag atagtgatat gtggtcagtg tatagataac    94140
ggaagtattg ccacggggta gtgatgtaca ggcaaaacgt acaccaaagt aaccatagat    94200
ataatggtac gttattattt ttcatgttag ttgatgccgg cgactaagat aacagagtaa    94260
gggggattaa ctgtttaatt ctttggaacg aaaaaatgca gttcctgaac atcacacacc    94320
attatttcca caggcttacc attttatcc agtaaatttg aattggtttc aaaagatttg     94380
cagttgtttt tacttttaaa tgaatcaagg tacagggtgt taatgtcaga ttcgtcatct    94440
gttgtttctc ttgaaataat actgttttct atcaccacat tttcatgtac ctcatttggc   94500
attttgtact gttgcaaata ttgttggcgg cggatgcgtg cctgttcact gctttctatg    94560
aacaccaccg tgatgattgc ccagtacatg ataatcagga aaacccagaa atcttttggt    94620
atcttccaaa aaagtgcgga cagttttgtta tctgatgaaa ttaaaatcgg aaaaaggatt   94680
gcaaagacaa tcaaaatcgc gatggttaat ttaaataaaa acgacatggt cccctcctgt    94740
tttgacgagg tcttttgttt ttgttgtttt tacgacagcc agtcctgcag gtgctgatgg    94800
cgggagcggc taccccttgcg ccagcggcag tggctaccgg gtgcacgttc caggcggaac  94860
agaaatcggt tgttgcatag taccaccaca aggcagttat ccggcgtgca gaagcgtcgg    94920
gcaagctcat cgggatctgt ctgtgttttc gttgaaaaca gcttgcgttt gcagtgcgtg    94980
tcgacgacca gtacctgtag tcgtccggga tgttgctgtg gcatcaaaga ctccttccgg    95040
aacggggaaa aaaagcagct gtaccgtcat aactgcaggt accggttgcg aaaaaaacgg    95100
cacaagcgag tggtgacaga aagaattccg gaaacggcag aaagggcggt acaggctgcg   95160 aagacggaa acgggttgtg ttgggaatta acgcacgtga ggtgtgatga gaacgacgcg     95220
cttttcgcca gctccgtctc cggtgaatcc attcacgaca agggactgtt ccggtctgag    95280
agaaatgctt tgttcaacag tctgttttcg tttctggtct gtggtcgaga gtcgcagagt    95340
gatatttccg ggcgcaccgt gaatatccgg tgatacctgc attctgacac cgggagagac    95400
atctgcagtg aaggtatccg gacctacgga cgttaccagt gattcaacac agggcgtatt    95460
ctgtatcatc ccgtggagcg tttcaggtgt cagcgtcagg ctgtcattaa aaaatgcact    95520
gcgtgaaata ctcccctgag caccggcaaa caggtccgga tggcgctcat taagaaggct    95580
tccgtatttt tccgccaggc agattgggtt gctggccgtt gtgtctgttc gcacggtatc    95640
gaccgtgaat gtcacctgcg ggtgatgttc cctgtggcct gtgcagccgg acagcagtgc   95700
ggcggctatc gtcatccaga gtagtggttg tttttttcatg ctgttaatttt cctctcaggg  95760 taaaaagaaa gactcgcacc gtcatgtcga tggggggccgc ttgcgaaaaa atggcacaag   95820
cgagtagtga cagaaagaat gtcggaaacg gcaggaaggg cggtacaggc tgcgaagact    95880
ggaaacgggg tatgccgggg attacacatc ctcagtgtaa tgtgatagtc gtctgctcct    95940
gtgttgcacc ccagacatct tctggcaggc tgggcagccc gataaatagg gtgtgaaaga    96000
gggtttctct gcgttcgatc ccgaattgat gttcgtatcc tctcaccacc tgaaatcctt    96060
cgtcggagaa tattaactct gccgtttcca gaagctgcat agttttgcgg tgtagtggag    96120
tgatcagctg caacgtaact ggtgccctca tatcgcctgt cggtagaaaa cactcttcgg    96180
tgcgacttag ttgtagcaga tgacgttcc cggaacaggc ccgttcaatg gattcattga     96240
acaccctctc aggccatggg cagacatatg tgcgccagcc tgctttctgt aatttaccca    96300
gtgcagcccg aaaacgaaac aacggacatt ccccgacagt ggcagagctg agaaagagcg    96360
```

```
tattcagcgt tccgatgatg ggaatattgc gatcttttc ggtcaatgct tttaacgcca   96420
tgatttcgcc agggagacta cggaactcag gatgtctgct ggcaccagaa agccattcaa   96480
gcaggtaatg ccgtaatccg gtttcactgg ttatattgtg gttttcctgt gccgttttca   96540
gggcattcag tgcacaccag agcaactggc gcacggatg ttctgtcgtg gtcatgcgaa    96600
tgtcctactg tgagatgaaa agaagaccgg tatccgctct ctccgccaca cgtgatggca   96660
cgggccggcc tttgataaaa cgaatcaata ctctggggtg aagcctttta tttctttcgc   96720
cattaagaaa tacacgattc catcaaaaga caggggagt ccatggtggg gatggcttcg    96780
tgcaggcttc actccagaat attctctgaa ttgaaaaaag cccggcccga aggccgggaa   96840
atactggcta tgggatgttt acaaggcgct ccataaagcc gtgatgttcg gcatttgata   96900
ccagttccag gagcagggat atcctcgact caggctggag agtattttcc attctgagga   96960
gatactgata ttgtgctttt gtcagccata tgctggaagc cgcattcagc tcttccctgg   97020
ctcccggatt tagcacaggg tccgggtaaa tcttcattaa tccatcaaca atatctttat   97080
tgacgggttt tatttcaccg ccaaacttca cgaaatcaat gaaggcgcta tggcgacgta   97140
atgccgatac tggttgaatg tcaaaattag ccagaataaa aaagtaccct ggaaaaatag   97200
cgaatattct ttcacggtaa cagcgcctgg agtctgcccg tcttatcttt cttgttatta   97260
atggagtcca tggtacgacg ttttgctcat tcagccatga gaataaagat tctctgtttt   97320
tgccggctgt attatattgc gcaagatacc agttccggtt attcaggtgt tctatattca   97380
cgaagttcaa cgctccgcgc aaaaccgatc catgatggac gattttgcga tgtcaggcga   97440
atatgctaaa tcatatgtct gaagcagtgt ccagcccata tctggataaa ctgcagttct   97500
gacaggcata taaccagcag actctagtac gttctgtatc ggtgatttgg cgaactcaca   97560
gataaagaac ggctaagcac taatatcagc aatacagtgg cacagtattg tgatacgcga   97620
aataaaacat cagcacgtca gttcagagta agatcgccat atatcgggca tgagccagat   97680
acaaataact gggacaccgt ctgaagtgat ttgctttatt aaagtaactt gtgcttggtg   97740
tttatgttta tcaatttggg atcgcctgta aagtgcaaaa tgcaatttcc atgaaagtgt   97800
cccctttaat ggggacacct gttcacattt tttcgttttc tttagctgta ttgctaatca   97860
tgaaaacgaa agttcgcatc agcacagcag agcgaagtgc atcatatcct tccagattta   97920
aattcttcag gcttcgcttc aggtaggttc gtaccgtttc gggagaaagc cgacagttct   97980
gagcaatggc gtcgtaagga acacccattg cgtaaaaaac gcagacttta agctggtttg   98040
ttgatagctc gggaaacatg ccttccaaca gagtgatggc cgggagtttc tgtatcagtt   98100
gaggtgacat agcaaaggtc tccgatgaca actaaaaacg ctatcaccga gttcctacgc   98160
tcattggtga tagcccagac gggggtagga ataccggcgt catcggaaac cggccaggct   98220
aatgcctgcc ccgcctgagc taccatagat gacgacaaga aatacaagtt cctgtcttta   98280
tggtatggca aaaacgacg ccaaatgaag aaattaactt ctgcgccgac gatgactacg    98340
cgggttccta cgcccgatca cagttttgcc tgtgaccagt aaagggtact tagtataacg   98400
caccgagtca actaacagct taaaaaacat acaaaaaagc gtcaaaactt aacgctccgc   98460
gccgaagcga tccaggcatg atgcttctgc tttgtggcgt tcgaacatgc tggtccatat   98520
gcacgaaacg gtgtctgacc ctcgcccaga caatccgcag ttctgacgaa catatgaaca   98580
aatatgctct tgtagaggct gttgttcacac aattggcggg ttgtgtaaca aatggtttta   98640
tcttctaaga attattctat ttacgatcga atgatctaca aaatgatttt ttaaaggttt   98700
```
tttagatcgt ttaattacat taaaacagaa tattattctg ttaggtggat cggttgtaag    98760
ataaatgatc gtgagtagga caaaagtcga tcttttaatc caaaagaag              98809

<210> SEQ ID NO 34
<211> LENGTH: 4773
<212> TYPE: DNA
<213> ORGANISM: Escherichia coli

<400> SEQUENCE: 34
tcacctcctg ttggggtgat tatttatatt atgagttctg gcaggtcgat atgttatttc      60
cgaaaagtga ccatctctca gatacagaac tctgtctgcg gatgctattg tttctggtcg     120
atgagctatt aacagaacag gaattccgag ttggcgtaat gtctggctta tttctatttc     180
actttccaca tcaagatgac tggttgcttc gtccagtaat aatagaccgg gttttttata     240
cagtgctctt gccagtagaa tacgttgctt ctgaccacct gaaagtcccc ctccggtttc     300
tccaagtaat gtttgatagc ccattggcat tgccataata tcactgtcta taagtgccag     360
acttgcgcat ttacgcatgt gttcatgatc tctaatttcg ctaaaaaaca ttatattatc     420
agctatagaa cctttgaaaa gatagtcatc ttgcaataca gtgccaattc gttgacgaac     480
ctgaaaataa tcagaatgtg tatgtggtat gccaaatgca ttaattcttc cttcacttgg     540
tgtatgaatt ccaagaataa gctttaccaa tgttgatttg ccacatcctg atttacctgt     600
tattgctaat atttctccag gaaagagcat tagtgacgcg ttatccaata tgggtttatc     660
tgcgccctta tggctaaatg ttattttttc gataagtaat ggtggatggg tattatcata     720
tttatgttct ctgtactggc ttgcagatat tgtttcatta tggtttgccc aatggtgctg     780
attctggtga ccttcctgtg gtgttagcac aatatcggca agtctctcgt tataaacatc     840
aagcatgcgc caggaaaaaa agttatcagt cagattgctt atactggatg aaaaacgcat     900
ctgataggat aagtaagcaa ccaacatacc cacggtaaat gtcccatcca gcacttctac     960
tgctccctgc cacaaaataa tggctgaaac tacactttcc gtcagtgtat gcgtcagttc    1020
atagctcatt tgtaaacgat tctggcgtag ctgtgtgttt ctgcgggtaa cgttgaggtt    1080
cagccaggcc gcttctctgt gaatagttac accgttgatt ctcagactct gaatgccgtt    1140
aagggtttcg agaaaatgcc ccgactcctt agttcctgca tcccagacat cttcaacaga    1200
ttgccgtaaa gccggatacc acaatgctct cagtgcgcca tatataatag ctgcaattac    1260
tgcgattaat gtcattcctg ggctatacaa cagcatcatg caaagagcag tcacaataag    1320
tagcatatcc agaatgcctt caagaacctg cgttgtcagc gcctgctgga ttatatctac    1380
tgcttcaaaa cgggcattaa tacttccttt acttcgggca tcgaaccatg caagagggag    1440
tcttacaaga tgatggaaaa ctctggcagt ccattgcatg ttaaaattga cggataaact    1500
gatcgttgcc cattgtcgtg ctagggagag taataattgt atgagtgata acaacagtag    1560
tgccactata atgacataca atagacttct gtctgctgcg accagaactt catcaattac    1620
cagttgatta agaagtggac cacctaaagc cagaatctca agggccagag caaaaataat    1680 aattttgtc attgatgcta aaagccccgg ggttttccct gtcagttgac gcaggtggat    1740 ttttttctc tcgttccggg gggtgaaatc actggctgga gttaattcca gtgccactcc    1800
tgtaaaatgc ttacctgcgt ccaacagact tattgtaatt tttcctctgt ccggatcatg    1860
gatgtataac cggtttcccc gaactttatg gagaacgacg aaatggttca tatcccagtg    1920
cagaatagat ggaagattaa gacacctcag atcttcgggt tccagacgaa ctgcacgtga    1980
tgataaatgg atggacgctg cacattcgat caacctttgt agcgtcattc cctgaatacc    2040

-continued

```
tatattgaaa cgttcccgta atgtcgataa atctgttttc agtccatgcc agcaggcaat    2100
catagccaga cacgccagac cgcattcagc tgattcggtt tgacggataa cgggtagttg    2160
tttccttact ttccagttta ttgattccat tacagatttc ctttcatgct ccatagggc    2220 tctgtcagcc attcccataa atgacgagta tcaaggttga cgtctccttc cagagtcatg    2280
cctggtctta gcggttcttt ttttccgtat gcaaatataa atgtattttc aggttcaaca    2340
ataacgcgat aatgcccttc gttttctttc catgtgacgg gtgaaactgg taataagtcg    2400
gaaggagcca gagtcgtatg actgatttta cgaattgtgc cgtactggat accaaatttc    2460
tgataaggga aggccgaaaa cttcagagat acccgttgac ctggtcggat aaaaccggct    2520
ttctggctgg tagcataaag ctcaatttgt aaatgagcat tatcgggaat gagagtcatg    2580
accggttcag atgctttcac agactgcccc tgtttgatca gtacagcagc aatagtcccg    2640
gatactggag ccctcagtgt aaattttct tgtccggcga gttcatcctg ttgttgtttt    2700
agcacctgca attgtctgtc gagttctgct ttacggcttt tcccctgaac aataagatga    2760
tttagttcat ctttggctgt gtccattgca gtatgtaact ggagaagccc ctgacgctga    2820
tcttcaacgt tttgttgagc ggcagaaaca tcaatttgtt tctgttggaa ttcgatatct    2880
gacacataat gcgtaccagc caattttta tagcgttcca tgacggatat agccagttct    2940
gcctgacgtt cagcaagctg aagtctttgt tctgcacttc ttatttgcgg ctcaagtgat    3000
atcatccttt gccgtatggc ttcctgttgt tgactattat ctcgcgactc aaaggattgc    3060
tgggaggcca acataatata ctgagtcttc agggaaatac tcatcgttgc taatgtgcca    3120
gttccgttac cgttataatg ttctccactt atatgataga gttgtgtccc tgcagttacg    3180
tgttctcctt cggatacagt cagttgtgtt acatatcctg catattgagg aattattttt    3240
accagtcctg atgagggcat gacgatacct gtaagatgcg ctttccttgt atagctaccg    3300
taatatatga atacagtcag acttaacata atgaataatg taactgttgc acatacggat    3360
aggctaaatg atgttggtaa aataatgtca ccatattcag tgtcattatg atgttctatt    3420
gcttcacttc tgaatatatt cattattttt aatacaataa gtaacctttc cgtcaacaag    3480
agggtttggt tgaataatat tgatatttga tatacatctg acctgtgtga tgttaaagtt    3540
ttatactata atatatttaa caatataaca aagccgttta ttcccgcatg taacagcatt    3600
ggatagaaaa tccccttact gcaaatcctt atattcaaca ataacattga cataataaac    3660
agaataattt gatcagccac attataatac tgcggatgca tcaggcagaa aaataaagat    3720
gtacacacgc aggggggtaaa taattctttt ttataagtcg tacatagaag accgaataga    3780
catgttcggt aaacaatttc ttcataatac ggaactgtca ggaccagtat aaatatttca    3840
atccaattaa gtgaagttga ttcactattg ttcaaattgt ctctataagc aaaaataagc    3900
agttgcatga gagcaatcac agcaaatgat attactaata gctttaatgt tttcgcattt    3960
gtctttatgg tgattttaca acctggtatt cttcttaagt aaaaaatata aaatgaagtt    4020
gacattaaaa tttcagtaat aaagacaaag gaaaatgcca gatccaaacc aatatattgt    4080
atggtgaatg ccggtgtgaa tatcacaact gttgatataa caacaagtag aagaaacgct    4140
atcgcattat ctttactata tttatatatg ttatcattca taatgctatt tcgcggagat    4200
tgttcttatt ttttctatga tatagtccat gaatcttgcc gtggaaaaaa gagtgatcag    4260
catgactaca atctttgaaa actcggaagg tagtgaaaac cagtataaat caataacaga    4320
ggagccactc aatagtgcaa atcccagtaa caaaccacat ataaggaaa gtaatttaat    4380
```

```
aaacatagta gcgccctcca ttatatctat ttatcggtta catgttccgc caacattatt    4440
acctgaacaa ctactggaac ttcctctgtt accacttcca tttccactac catgatctga    4500
gagacattga ccaacaacgg ctccaccaat ggtacctctt gccattccta tgggacctcc    4560
tttgatcgca ccaccaatca ttccactaaa tacagcgtta gcgcatttta cagtgcttgg    4620
atcactataa atatgagttg gtgcgtttcg acccagtgag ttacgagccc cactggaacg    4680
gtcattacgg gggccacctt caaagttgct gtttgcgttt cctccgctga caagcgttat    4740
ctcatctaaa gttaattctc ttatatttgc cat                                 4773
```

<210> SEQ ID NO 35  
<211> LENGTH: 102  
<212> TYPE: PRT  
<213> ORGANISM: Escherichia coli

<400> SEQUENCE: 35

```
Asn Ala Asn Ser Asn Phe Glu Gly Gly Pro Arg Asn Asp Arg Ser Ser
1               5                   10                  15

Gly Ala Arg Asn Ser Leu Gly Arg Asn Ala Pro Thr His Ile Tyr Ser
            20                  25                  30

Asp Pro Ser Thr Val Lys Cys Ala Asn Ala Val Phe Ser Gly Met Ile
        35                  40                  45

Gly Gly Ala Ile Lys Gly Gly Pro Ile Gly Met Ala Arg Gly Thr Ile
    50                  55                  60

Gly Gly Ala Val Val Gly Gln Cys Leu Ser Asp His Gly Ser Gly Asn
65                  70                  75                  80

Gly Ser Gly Asn Arg Gly Ser Ser Ser Cys Ser Gly Asn Asn Val
                85                  90                  95

Gly Gly Thr Cys Asn Arg
            100
```

<210> SEQ ID NO 36  
<211> LENGTH: 20  
<212> TYPE: DNA  
<213> ORGANISM: Artificial Sequence  
<220> FEATURE:  
<223> OTHER INFORMATION: Synthetic oligonucleotide primer

<400> SEQUENCE: 36

```
tgctgcgatg gaaaaacgtc                                                  20
```

<210> SEQ ID NO 37  
<211> LENGTH: 20  
<212> TYPE: DNA  
<213> ORGANISM: Artificial Sequence  
<220> FEATURE:  
<223> OTHER INFORMATION: Synthetic oligonucleotide primer

<400> SEQUENCE: 37

```
ttctggacgc ttgcgatctt                                                  20
```

<210> SEQ ID NO 38  
<211> LENGTH: 36  
<212> TYPE: DNA  
<213> ORGANISM: Artificial Sequence  
<220> FEATURE:  
<223> OTHER INFORMATION: Synthetic oligonucleotide primer

<400> SEQUENCE: 38

```
cttgcagacg tcttgcagtc ttaaggggac tggagc                                36
```

```
<210> SEQ ID NO 39
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 39
gccttgcggc ctgccctaag gcaagccgcc agacgt                              36

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 40
atcgctgtag gtctgggtct                                                20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 41
atgtcctgcc agcgttctac                                                20

<210> SEQ ID NO 42
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 42
aatatcagaa cgttaactaa atagaggcat tgtgct                              36

<210> SEQ ID NO 43
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 43
ctaccgtaat aaattcagac atcagccccT ccctcc                              36

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 44
agcggcagga tgcattatca                                                20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide primer
```

```
<400> SEQUENCE: 45
gggaagatta ctggctgcga                                               20

<210> SEQ ID NO 46
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 46
gtgaatattc acgggcttta tgtaatttac attgaa                             36

<210> SEQ ID NO 47
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 47
aattaacacc tatgtattaa tcggagagag tagatc                             36

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 48
caatggcaga tgaagcgagc                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 49
tgcaaatggg ctggatagca                                               20

<210> SEQ ID NO 50
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 50
aactgcgcac tctatgcata ttgcagggaa atgatt                             36

<210> SEQ ID NO 51
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 51
caggaaaaaa gcgctcccgc aggagcgctg aaggga                             36

<210> SEQ ID NO 52
```

<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 52
cgctatcagg gtaacgggag    20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 53
agcactttca cggtagcgaa    20

<210> SEQ ID NO 54
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 54
gttgtcagaa tcgatctggt tgatgatgta gtcaac    36

<210> SEQ ID NO 55
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 55
gtgatcgtcc ctgctctgtt agtagcaggt actgca    36

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 56
tgttgcgaac ctttgggagt    20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 57
agcaaggtga cgatgagcaa    20

<210> SEQ ID NO 58
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 58
gggcaaatga acttcgtggc gagaagcgca atcgcc                                    36

<210> SEQ ID NO 59
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 59
cttacaaatt gttgcgaacc tttgggagta caaaca                                    36

<210> SEQ ID NO 60
<211> LENGTH: 22
<212> TYPE: DNA
<213> ORGANISM: Artificial Sequence
<220> FEATURE:
<223> OTHER INFORMATION: Synthetic oligonucleotide primer site

<400> SEQUENCE: 60
tgtgtaggct ggagctgctt cg                                                  22

<210> SEQ ID NO 61
<211> LENGTH: 19
<212> TYPE: DNA
<213> ORGANISM: Artificial Sequence
<220> FEATURE:
<223> OTHER INFORMATION: Synthetic oligonucleotide primer site

<400> SEQUENCE: 61
catatgaata tcctcctta                                                      19

<210> SEQ ID NO 62
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 62
gaaaacatac aaattttttc acatatttac atttaatcac acaatttcac tttcattaca         60
tttttg                                                                    66

<210> SEQ ID NO 63
<211> LENGTH: 20
<212> TYPE: DNA
<213> ORGANISM: Artificial Sequence
<220> FEATURE:
<223> OTHER INFORMATION: Sythetic oligonucleotide F1

<400> SEQUENCE: 63
tttacttttg gttacatatt                                                     20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide F2

<400> SEQUENCE: 64
ttttcttttt gaaaccaaat                                                     20

<210> SEQ ID NO 65

```
<211> LENGTH: 20
<212> TYPE: DNA
<213> ORGANISM: Artificial Sequence
<220> FEATURE:
<223> OTHER INFORMATION: Synthetic oligonucleutide F3

<400> SEQUENCE: 65
ttatctttgt agcactttca                                             20

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide F4

<400> SEQUENCE: 66
gttacggaat attacattgc                                             20

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide C1

<400> SEQUENCE: 67
tttacatttt gaaacatcta                                             20

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide B1

<400> SEQUENCE: 68
tttacattta atcacacaat                                             20

<210> SEQ ID NO 69
<211> LENGTH: 19
<212> TYPE: DNA
<213> ORGANISM: Artificial Sequence
<220> FEATURE:
<223> OTHER INFORMATION: Synthetic oligonucleotide B2

<400> SEQUENCE: 69
ttcactttca ttacatttt                                              19

<210> SEQ ID NO 70
<211> LENGTH: 18
<212> TYPE: DNA
<213> ORGANISM: Artificial Sequence
<220> FEATURE:
<223> OTHER INFORMATION: Synthetic oligonucleotide B3

<400> SEQUENCE: 70
tacaaatttt ttcacata                                               18

<210> SEQ ID NO 71
<211> LENGTH: 120
<212> TYPE: PRT
<213> ORGANISM: Artificial Sequence
<220> FEATURE:
<223> OTHER INFORMATION: Synthetic McsS

<400> SEQUENCE: 71
```

-continued

```
Met Ser Asn Ile Arg Glu Leu Ser Phe Asp Glu Ile Ala Leu Val Ser
1               5                   10                  15

Gly Gly Asn Ala Asn Ser Asn Tyr Glu Gly Gly Ser Arg Ser Arg
                20                  25                  30

Asn Thr Gly Ala Arg Asn Ser Leu Gly Arg Asn Ala Pro Thr His Ile
            35                  40                  45

Tyr Ser Asp Pro Ser Thr Val Lys Cys Ala Asn Ala Val Phe Ser Gly
        50                  55                  60

Met Val Gly Gly Ala Ile Lys Gly Gly Pro Val Gly Met Thr Arg Gly
65                  70                  75                  80

Thr Ile Gly Gly Ala Val Ile Gly Gln Cys Leu Ser Gly Gly Asn
                85                  90                  95

Gly Asn Gly Gly Asn Arg Ala Gly Ser Ser Asn Cys Ser Gly Ser
            100                 105                 110

Asn Val Gly Gly Thr Cys Ser Arg
            115                 120

<210> SEQ ID NO 72
<211> LENGTH: 103
<212> TYPE: PRT
<213> ORGANISM: Artificial Sequence
<220> FEATURE:
<223> OTHER INFORMATION: Synthetic ColV

<400> SEQUENCE: 72

Met Arg Thr Leu Thr Leu Asn Glu Leu Asp Ser Val Ser Gly Gly Ala
1               5                   10                  15

Ser Gly Arg Asp Ile Ala Met Ala Ile Gly Thr Leu Ser Gly Gln Phe
                20                  25                  30

Val Ala Gly Gly Ile Gly Ala Ala Ala Gly Gly Val Ala Gly Gly Ala
            35                  40                  45

Ile Tyr Asp Tyr Ala Ser Thr His Lys Pro Asn Pro Ala Met Ser Pro
        50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
                85                  90                  95

Asn Leu Ser Asp Val Cys Leu
            100

<210> SEQ ID NO 73
<211> LENGTH: 105
<212> TYPE: PRT
<213> ORGANISM: Artificial Sequence
<220> FEATURE:
<223> OTHER INFORMATION: Synthetic MccL

<400> SEQUENCE: 73

Met Arg Glu Ile Thr Leu Asn Glu Met Asn Asn Val Ser Gly Ala Gly
1               5                   10                  15

Asp Val Asn Trp Val Asp Val Gly Lys Thr Val Ala Thr Asn Gly Ala
                20                  25                  30

Gly Val Ile Gly Gly Ala Phe Gly Ala Gly Leu Cys Gly Pro Val Cys
            35                  40                  45

Ala Gly Ala Phe Ala Val Gly Ser Ser Ala Ala Val Ala Ala Leu Tyr
        50                  55                  60

Asp Ala Ala Gly Asn Ser Asn Ser Ala Lys Gln Lys Pro Glu Gly Leu
```

```
                65                  70                  75                  80

Pro Pro Glu Ala Trp Asn Tyr Ala Glu Gly Arg Met Cys Asn Trp Ser
                85                  90                  95

Pro Asn Asn Leu Ser Asp Val Cys Leu
            100                 105

<210> SEQ ID NO 74
<211> LENGTH: 90
<212> TYPE: PRT
<213> ORGANISM: Artificial Sequence
<220> FEATURE:
<223> OTHER INFORMATION: Synthetic Mcc24

<400> SEQUENCE: 74

Met Tyr Met Arg Glu Leu Asp Arg Glu Glu Leu Asn Cys Val Gly Gly
1               5                   10                  15

Ala Gly Asp Pro Leu Ala Asp Pro Asn Ser Gln Ile Val Arg Gln Ile
            20                  25                  30

Met Ser Asn Ala Ala Trp Gly Pro Pro Leu Val Pro Glu Arg Phe Arg
        35                  40                  45

Gly Met Ala Val Gly Ala Ala Gly Val Thr Gln Thr Val Leu Gln
    50                  55                  60

Gly Ala Ala Ala His Met Pro Val Asn Val Pro Ile Pro Lys Val Pro
65                  70                  75                  80

Met Gly Pro Ser Trp Asn Gly Ser Lys Gly
                85                  90

<210> SEQ ID NO 75
<211> LENGTH: 99
<212> TYPE: PRT
<213> ORGANISM: Artificial Sequence
<220> FEATURE:
<223> OTHER INFORMATION: Synthetic MccE492

<400> SEQUENCE: 75

Met Arg Glu Ile Ser Gln Lys Asp Leu Asn Leu Ala Phe Gly Ala Gly
1               5                   10                  15

Glu Thr Asp Pro Asn Thr Gln Leu Leu Asn Asp Leu Gly Asn Asn Met
            20                  25                  30

Ala Trp Gly Ala Ala Leu Gly Ala Pro Gly Gly Leu Gly Ser Ala Ala
        35                  40                  45

Leu Gly Ala Ala Gly Gly Ala Leu Gln Thr Val Gly Gln Gly Leu Ile
    50                  55                  60

Asp His Gly Pro Val Asn Val Pro Ile Pro Val Leu Ile Gly Pro Ser
65                  70                  75                  80

Trp Asn Gly Ser Gly Ser Gly Tyr Asn Ser Ala Thr Ser Ser Ser Gly
                85                  90                  95

Ser Gly Ser

<210> SEQ ID NO 76
<211> LENGTH: 75
<212> TYPE: PRT
<213> ORGANISM: Artificial Sequence
<220> FEATURE:
<223> OTHER INFORMATION: Synthetic MchB

<400> SEQUENCE: 76

Met Arg Glu Ile Thr Glu Ser Gln Leu Arg Tyr Ile Ser Gly Ala Gly
1               5                   10                  15
```

-continued

```
Gly Ala Pro Ala Thr Ser Ala Asn Ala Ala Gly Ala Ala Ala Ile Val
             20                  25                  30

Gly Ala Leu Ala Gly Ile Pro Gly Gly Pro Leu Gly Val Val Val Gly
         35                  40                  45

Ala Val Ser Ala Gly Leu Thr Thr Ala Ile Gly Ser Thr Val Gly Ser
     50                  55                  60

Gly Ser Ala Ser Ser Ser Ala Gly Gly Gly Ser
65                  70                  75

<210> SEQ ID NO 77
<211> LENGTH: 84
<212> TYPE: PRT
<213> ORGANISM: Artificial Sequence
<220> FEATURE:
<223> OTHER INFORMATION: Synthetic cleaved mcpM

<400> SEQUENCE: 77

Arg Asn Ser Leu Gly Arg Asn Ala Pro Thr His Ile Tyr Ser Asp Pro
1               5                   10                  15

Ser Thr Val Lys Cys Ala Asn Ala Val Phe Ser Gly Met Ile Gly Gly
             20                  25                  30

Ala Ile Lys Gly Gly Pro Ile Gly Met Ala Arg Gly Thr Ile Gly Gly
         35                  40                  45

Ala Val Val Gly Gln Cys Leu Ser Asp His Gly Ser Gly Asn Gly Ser
     50                  55                  60

Gly Asn Arg Gly Ser Ser Ser Cys Ser Gly Asn Asn Val Gly Gly
65                  70                  75                  80

Thr Cys Asn Arg
```